US006696472B2

(12) United States Patent
Sikorski et al.

(10) Patent No.: US 6,696,472 B2
(45) Date of Patent: Feb. 24, 2004

(54) SUBSTITUTED N-PHENOXY-N-PHENYL AMINOALCOHOL COMPOUNDS USEFUL FOR INHIBITING CHOLESTERYL ESTER TRANSFER PROTEIN ACTIVITY

(75) Inventors: James A. Sikorski, Des Peres, MO (US); Richard C. Durley, Chesterfield, MO (US); Deborah A. Mischke, Defiance, MO (US); Emily J. Reinhard, Chesterfield, MO (US); Yvette M. Fobian, Labadie, MO (US); Michael B. Tollefson, O'Fallon, MO (US); Lijuan Wang, Wildwood, MO (US); Margaret L. Grapperhaus, Troy, IL (US); Brian S. Hickory, Wildwood, MO (US); Mark A. Massa, Ballwin, MO (US); Monica B. Norton, St. Louis, MO (US); William F. Vernier, St. Louis, MO (US); Barry L. Parnas, University City, MO (US); Michele A. Promo, Chesterfield, MO (US); Ashton T. Hamme, St. Louis, MO (US); Dale P. Spangler, Deerfield, IL (US); Melvin L. Rueppel, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/154,788

(22) Filed: May 23, 2002

(65) Prior Publication Data

US 2003/0125328 A1 Jul. 3, 2003

Related U.S. Application Data

(60) Continuation of application No. 09/990,645, filed on Nov. 14, 2001, now Pat. No. 6,451,823, which is a division of application No. 09/405,524, filed on Sep. 23, 1999, now abandoned.

(51) Int. Cl.[7] .................... A61C 31/133; C07C 239/20; C07C 233/00

(52) U.S. Cl. .................. 514/351; 514/150; 514/473; 514/615; 514/616; 514/617; 514/645; 514/646; 514/653; 546/300; 549/479; 552/8; 562/622; 564/149; 564/158; 564/184; 564/300; 564/310

(58) Field of Search .................. 564/149, 158, 564/184, 300, 310; 546/300; 549/479; 552/8; 562/622; 514/150, 351, 473, 575, 615, 616, 617, 645, 646, 653

(56) References Cited

U.S. PATENT DOCUMENTS

| 2,700,686 A | 1/1955 | Dickey | 260/633 |
| 4,333,952 A | 6/1982 | McDonald | 424/330 |
| 4,447,608 A | 5/1984 | Jones | 544/287 |

FOREIGN PATENT DOCUMENTS

| EP | 801060 | 10/1997 |
| EP | 818197 | 1/1998 |
| GB | 2305665 | 4/1997 |
| JP | 09078277 | 3/1997 |
| JP | 10287662 | 10/1998 |
| WO | 98/50029 | 11/1998 |
| WO | 99/14204 | 3/1999 |

OTHER PUBLICATIONS

J.–P. Begue et al., "A Versatile Synthesis of Amino Trifluoromethyl Ketones and Alcohols", Tetrahedron Letters, vol. 33, No. 14, pp. 1879–1882, 1992.

P. Bravo et al., "New Fluorinated Chiral Synthons", Tetrahedron:Assymmetry, vol. 5, No. 6, pp. 987–1004, 1994.

P. Dunn et al., "The Synthesis of Fluorine–containing Pterins", Tetrahedron, vol. 52, No. 40, pp. 13017–13206, 1996.

S. Furuta and T. Fuchigami "Electrolytic reactions of fluoroorganic compounds. 16*. Regioselective anodic methoxylation of 2–methoxy–2,3,3,3–tetrafluoropropylamines", Electrochimica Acta, vol. 43, Nos. 21–22, pp. 3183–3191, 1998.

L. Lebreton et al., "Structure–Immunosuppressive Activity Relationships of New Analogues of 15–Deoxyspergualin. 2. Structural Modifications of the Spermidine Moiety", J. Med. Chem., vol. 42, pp. 4749–4763, 1999.

T. Katagiri et al., "General Syntheses of Optically Active α–Trifluoromethylated Amines via Ring–Opening Reactions of N–Benzyl–2–trifluoromethylaziridine", J. Org. Chem., vol. 64, pp. 7323–7329, 1999.

(List continued on next page.)

Primary Examiner—Richard L. Raymond
(74) Attorney, Agent, or Firm—J. Timothy Keane

(57) ABSTRACT

The invention relates to substituted polycyclic aryl and heteroaryl tertiary-heteroalkylamine compounds useful as inhibitors of cholesteryl ester transfer protein (CETP; plasma lipid transfer protein-I) and compounds, compositions and methods for treating atherosclerosis and other coronary artery diseases. Preferred tertiary-heteroalkylamine compounds are substituted N-phenoxy-N-phenyl aminoalcohols. A preferred specific N-phenoxy-N-phenyl aminoalcohol is the compound:

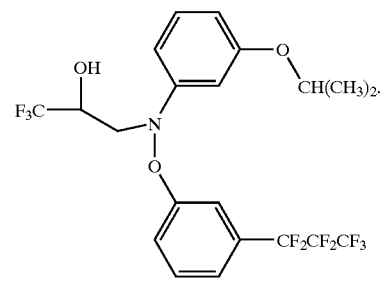

18 Claims, No Drawings

OTHER PUBLICATIONS

J. M. Concellon et al., "Iodomethylation of Chiral α–Amino Aldehydes by Means of Samarium–Diiodomethane. Application to the synthesis of Various Enantiomerically Pure Compounds", J. Org. Chem., vol. 62, pp. 8902–8906, 1997.

J. Barluenga et al., "Highly Diastereoselective Synthesis of *Threo or Erythro* Aminoalkyl Expoxides from α–Amino Acids", J. Org. Chem., vol. 60, pp. 6696–6699, 1995.

P. L. Beaulieu and D. Wernic, "Preparation of Aminoalkyl Chlorohydrin Hydrochlorides: Key Building Blocks for Hydroxyethylamine–Based HIV Protease Inhibitors", J. Org. Chem., vol. 61, No. 11, pp. 3635–3645, 1996.

J. M. Concellon et al., "Nucleophilic ring closure and opening of aminoiodohydrins", Tetrahedron Letters, vol. 41, pp. 1231–1234, 2000.

P. L. Beaulieu et al., "Large Scale Preparation of (2S, 3S)–N–Boc–3–Amino–1,2–Epoxy–4–Phenylbutane: A Key Building Block for HIV–Protease Inhibitors", Tetrahedron Letters, vol. 36, No. 19, pp. 3317–3320, 1995.

M.S. Kuo et al., "Discovery, Isolation, Structure Elucidation, and Biosynthesis of U–106305, a Cholesteryl Ester Transfer Protein Inhibitor from UC 11136", J. Am. Chem. Soc., vol. 117, 10629–10634, 1995.

A.G.M. Barrett et al., "Total Synthesis and Stereochemical Assignment of the Quinquecyclopropane–Containing Cholesteryl Ester Transfer Protein Inhibitor U–106305", J. Am. Chem. Soc., vol. 118, 7863–7864, 1997.

S.J. Coval et al., "Wiedendiol–A and –B Cholesteryl Ester Transfer Protein Inhibitors from the Marine Sponge *Xestospongla Wiedenmayer1*", Biorg. Med. Chem. Lett., vol. 5, 605–610, 1995.

T. Pietzonka et al., "Phosphonate–containing Analogs of Cholesteryl Ester as Novel Inhibitors of Cholesteryl Ester Transfer Protein", Biorg. Med. Chem. Lett., vol. 6, 1951–1954, 1996.

S.J. Busch and J.A.K. Harmony, "Cholesteryl Ester Analogs Inhibit Cholesteryl Ester but not Triglyceride Transfer Catalyzed by the Plasma Cholesteryl Ester–Triglyceride Transfer Protein", Lipids, vol. 25, 216–220, 1990.

J.C. Lee et al., "A Cholesteryl Ester Transfer Protein Inhibitor From an Insect–associated Fungus", J. Antibiot., vol. 49, 693–696, 1996.

R. E. Morton and D. B. Zilversmit, "Purification and Characterization of Lipid Transfer Protein(s) from Human Lipoprotein–deficient Plasma", J. Lipid Res., vol. 23, 1058–1067, 1982.

D.T. Connolly et al., "Inactivation of Cholesteryl Ester Transfer Protein by Cysteine Modification", Biochem. Biophys. Res Commun., vol. 223, 42–47, 1996.

C.L. Bisgaier et al., "Cholesteryl Ester Transfer Protein Inhibition by PD 140195", Lipids, vol. 29, 811–818, 1994.

Y. Xia et al., "Substituted 1,3,5–Triazines as Cholesteryl Ester Transfer Protein Inhibitors", Bioorg. Med. Chem. Lett., vol. 6, 919–922, 1996.

S. Kutkevicius and S. Rutkauskas "γ–Chloro–β–Hydroxypropyl Derivatives and their Reaction Products. VI. N–Mono– and N,N–Bis–β,γ–Epoxypropylamines", Lietuvos TSR Aukst. Mokyklu Mokslo Darbai, Chemija ir Chemine Technologija, vol. 8, pp. 99–104 (1967).

S. Kutkevicius and E. A. Samarskis, "γ–Chloro–β–Hydroxypropyl Derivatives of Aromatic Amines and their Reaction Products. XVII. 4–Methyldiphenylamine", Lietuvos TSR Aukst. Mokyklu Mokslo Darbai, Chemija ir Chemine Technologija, vol. 17, pp. 151–154 (1975).

S. Kutkevicius, B. Milukas, and E. A. Samarskis, "Products of Epichlorohydrin Reaction with Aromatic Amines. XVI. 4–Phenyl–1,2,3,4–tetrahydro [f] quinoline", Khim. Geterotsikl. Soedin. (Kaunas. Politekh. Inst., Kaunas, USSR), vol. 9, pp. 1228–1231 (1972).

S. Kutkevicius and E. A. Samarskis, "Products of Epichlorohydrin Reaction with Aromatic Amines. XVIII. N–Phenyl–1–Naphthylamine", Khim. Geterotsikl. Soedin. (Kaunas. Politekh. Inst., Kaunas, USSR), vol. 5, pp. 685–688 (1974).

M. Meguro et al., "Ytterbium Triflate and High Pressure–mediated Ring Opening of Epoxides with Amines", J. Chem. Soc., Perkin Trans. 1, vol. 18, pp. 2597–2601 (1994).

Y. Hayashi et al., "A Novel Chiral Super–Lewis Acidic Catalyst for Enantioselective Synthesis", J. Am. Chem. Soc., vol. 118(23), pp. 5502–5503 (1996).

SUBSTITUTED N-PHENOXY-N-PHENYL AMINOALCOHOL COMPOUNDS USEFUL FOR INHIBITING CHOLESTERYL ESTER TRANSFER PROTEIN ACTIVITY

RELATED APPLICATIONS

This is a continuation of pending U.S. patent application Ser. No. 09/990,645, filed Nov. 14, 2001, which issued as U.S. patent application Ser. No. 6,451,823 on Sep. 17, 2002, which is a divisional of U.S. patent application Ser. No. 09/405,524, filed Sep. 23, 1999, now abandoned.

FIELD OF THE INVENTION

This invention is in the field of treating cardiovascular disease, and specifically relates to compounds, compositions and methods for treating atherosclerosis and other coronary artery disease. More particularly, the invention relates to substituted polycyclic aryl and heteroaryl tertiary-heteroalkylamine compounds that inhibit cholesteryl ester transfer protein (CETP), also known as plasma lipid transfer protein-I.

BACKGROUND OF THE INVENTION

Numerous studies have demonstrated that a low plasma concentration of high density lipoprotein (HDL) cholesterol is a powerful risk factor for the development of atherosclerosis (Barter and Rye, *Atherosclerosis*, 121, 1–12 (1996)). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL) and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above 180 mg/dl) and low HDL cholesterol (below 35 mg/dl) have been shown to be important contributors to the development of atherosclerosis. Other diseases, such as peripheral vascular disease, stroke, and hypercholesterolaemia are negatively affected by adverse HDL/LDL ratios. Inhibition of CETP by the subject compounds is shown to effectively modify plasma HDL/LDL ratios, and to check the progress and/or formation of these diseases.

CETP is a plasma protein that facilitates the movement of cholesteryl esters and triglycerides between the various lipoproteins in the blood (Tall, *J. Lipid Res.*, 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile (McCarthy, *Medicinal Res. Revs.*, 13, 139–59 (1993); Sitori, *Pharmac. Ther.*, 67,443–47 (1995)). This exact phenomenon was first demonstrated by Swenson et al., (*J. Biol. Chem.*, 264, 14318 (1989)) with the use of a monoclonal antibody that specifically inhibited CETP. In rabbits, the antibody caused an elevation of the plasma HDL cholesterol and a decrease in LDL cholesterol. Son et al. (*Biochim. Biophys. Acta* 795, 743–480 (1984)), Morton et al. (*J. Lipid Res.* 35, 836–847 (1994)) and Tollefson et al. (*Am. J. Physiol.*, 255, (Endocrinol. Metab. 18, E894–E902 (1988))) describe proteins from human plasma that inhibit CETP. U.S. Pat. No. 5,519,001, issued to Kushwaha et al., describes a 36 amino acid peptide derived from baboon apo C-1 that inhibits CETP activity. Cho et al. (*Biochim. Biophys. Acta* 1391, 133–144(1998)) describe a peptide from hog plasma that inhibits human CETP. Bonin et al. (*J. Peptide Res.*, 51, 216–225 (1998)) disclose a decapeptide inhibitor of CETP. A depsipeptide fungal metabolite is disclosed as a CETP inhibitor by Hedge et al. in *Bioorg. Med. Chem. Lett.*, 8, 1277–80 (1998).

There have been several reports of non-peptidic compounds that act as CETP inhibitors. Barrett et al. (*J. Am. Chem. Soc.*, 188, 7863–63 (1996)) and Kuo et al. (*J. Am. Chem. Soc.*, 117, 10629–34 (1995)) describe cyclopropane-containing CETP inhibitors. Pietzonka et al. (*Bioorg. Med. Chem. Lett*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol-A and -B, and related sesquiterpene compounds as CETP inhibitors. Japanese Patent Application No. 10287662-A describes polycyclic, non-amine containing, polyhydroxylic natural compounds possessing CETP inhibition properties. Lee et al. (*J. Antibiotics*, 49, 693–96 (1996)) describe CETP inhibitors derived from an insect fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42–47 (1996)) describe other cysteine modification reagents as CETP inhibitors. Xia et al. describe 1,3,5-triazines as CETP inhibitors (*Bioorg. Med. Chem. Lett.*, 6, 919–22 (1996)). Bisgaier et al. (*Lipids*, 29, 811–8 (1994)) describe 4phenyl-5-tridecyl-4H-1,2,4-triazole-thiol as a CETP inhibitor. Oomura et al. disclose non-peptidic tetracyclic and hexacyclic phenols as CETP inhibitors in Japanese Patent Application No. 10287662. In WO Patent Application No. 09914204, Sikorski describes 1,2,4-triazolylthiols useful as chlolesteryl ester transfer protein inhibitors.

Some substituted heteroalkylamine compounds are known. In European Patent Application No. 796846, Schmidt et al. describe 2-aryl-substituted pyridines as cholesteryl ester transfer protein inhibitors useful as cardiovascular agents. One substitutent at C3 of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and artherosclerotic diseases. In European Patent Application No. 818448, Schmidt et al. describe tetrahydroquinoline derivatives as chlolesteryl ester transfer protein inhibitors. European Patent Application No. 818197, Schmek et al. describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In WO Patent Application No. 09839299, Muller-Gliemann et al. describe quinoline derivatives as cholesteryl ester transfer protein inhibitors. U.S. Pat. No. 2,700,686, issued to Dickey and Towne, describes N-(2-haloalkyl-2-hydroxyethyl)amines in which the amine is further substituted with either 1 to 2 aliphatic groups or one aromatic group and one aliphatic group. U.S. Pat. No. 2,700,686 further describes a process to prepare the N-(2-haloalkyl-2-hydroxyethyl)amines by reacting halogenated-1,2-epoxyalkanes with the corresponding aliphatic amines and N-alkylanilines and their use as dye intermediates.

SUMMARY OF THE INVENTION

The present invention provides compounds that can be used to inhibit cholesteryl ester transfer protein (CETP) activity and that have the general structure:

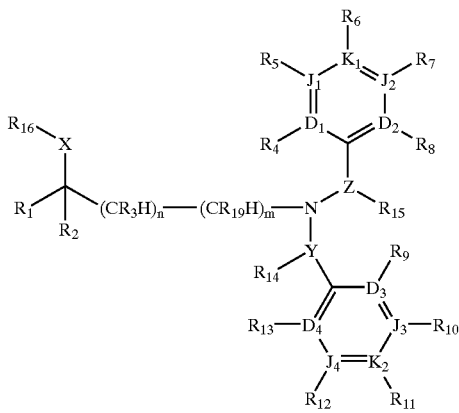

In another aspect, the present invention includes pharmaceutical compositions comprising a pharmaceutically effective amount of the compounds of this invention and a pharmaceutically acceptable carrier.

In another aspect, this invention relates to methods of using these inhibitors as therapeutic agents in humans to inhibit cholesteryl ester transfer protein (CETP) activity, thereby decreasing the concentrations of low density lipoprotein (LDL) and raising the level of high density lipoprotein (HDL), resulting in a therapeutically beneficial plasma lipid profile. The compounds and methods of this invention can also be used to treat dyslipidemia (hypoalphalipoproteinemia), hyperlipoproteinaemia (chylomicronemia and hyperapobetalipoproteinemia), peripheral vascular disease, hypercholesterolaemia, atherosclerosis, coronary artery disease and other CETP-mediated disorders. The compounds can also be used in prophylactic treatment of subjects who are at risk of developing such disorders. The compounds can be used to lower the risk of atherosclerosis. The compounds of this invention would be also useful in prevention of cerebral vascular accident (CVA) or stroke. Besides being useful for human treatment, these compounds are also useful for veterinary treatment of companion animals, exotic animals and farm animals such as primates, rabbits, pigs, horses, and the like.

DESCRIPTION OF THE INVENTION

The present invention relates to a class of compounds comprising substituted polycyclic aryl and heteroaryl tertiary-heteroalkylamines which are beneficial in the therapeutic and prophylactic treatment of coronary artery disease as given in Formula V-H (also referred to herein as generic substituted polycyclic aryl and heteroaryl tertiary omegaheteroalkylamines):

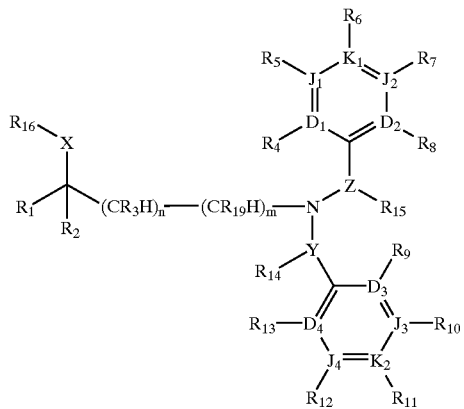

(V-H)

or a pharmaceutically acceptable salt thereof, wherein;
m is an integer selected from 0 through 5;
n is an integer selected from 0 through 5;
m plus n is an integer selected from 0 through 6;
$R_1$ is selected from the group consisting of haloalkyl, haloalkenyl, haloalkoxyalkyl, and haloalkenyloxyalkyl;
X is selected from the group consisting of O, H, F, S, S(O), NH, N(OH), N(alkyl), and N(alkoxy);
$R_{16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_4$, $R_8$, $R_9$, $R_{13}$, $R_{14}$, and $R_{15}$ to form a heterocyclyl ring having from 5 through 10 contiguous members with the provisos that said spacer moiety is other than a covalent single bond when $R_2$ is alkyl and there is no $R_{16}$ wherein X is H or F;
$D_1$, $D_2$, $J_1$, $J_2$ and $K_1$ are independently selected from the group consisting of C, N, O, S and a covalent bond with the provisos that no more than one of $D_1$, $D_2$, $J_1$, $J_2$ and $K_1$ can be a covalent bond, no more than one of $D_1$, $D_2$, $J_1$, $J_2$ and $K_1$ can be O, no more than one of $D_1$, $D_2$, $J_1$, $J_2$ and $K_1$ can be S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ can be N;
$D_3$, $D_4$, $J_3$, $J_4$ and $K_2$ are independently selected from the group consisting of C, N, O, S and a covalent bond with the provisos that no more than one of $D_3$, $D_4$, $J_3$, $J_4$ and $K_2$ can be a covalent bond, no more than one of $D_3$, $D_4$, $J_3$, $J_4$ and $K_2$ can be O, no more than one of $D_3$, $D_4$, $J_3$, $J_4$ and $K_2$ can be S, one of $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ can be N;

$R_2$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_2$ and $R_3$ can be taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_2$ and $R_{14}$ can be taken together to form a linear spacer moiety selected from the group consisting of a covalent bond and a linear spacer moiety having from 1 through 5 contiguous atoms to form a heterocyclyl ring having from 5 through 8 contiguous members with the proviso that said spacer group is other than —N═;

$R_2$ and $R_{15}$ can be taken together to form a linear spacer moiety selected from the group consisting of a covalent bond and a linear spacer moiety having from 1 through 5 contiguous atoms to form a heterocyclyl ring having from 5 through 8 contiguous members with the proviso that said spacer group is other than —N═;

$R_2$ and $R_{19}$ can be taken together to form a linear spacer moiety selected from the group consisting of a covalent single bond and a linear moiety having from 1 through 5 contiguous atoms to form a ring selected from the group consisting of a cycloalkyl having from 3 through 8 contiguous members, a cycloalkylenyl having from 5 through 8 contiguous members, and a heterocyclyl having from 4 through 8 contiguous members;

$R_2$ and $R_4$, $R_2$ and $R_8$, $R_2$ and $R_9$, and $R_2$ and $R_{13}$ can be independently selected to form spacer pairs wherein a spacer pair is taken together to form a linear spacer moiety wherein said linear spacer moiety is selected to form a heterocyclyl ring having from 5 through 10 contiguous members;

$R_3$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_3$ and $R_{14}$ can be taken together to form a linear spacer moiety selected from the group consisting of a covalent bond and a linear moiety having from 1 through 5 atoms to form a heterocyclyl ring having from 5 through 8 contiguous members;

$R_3$ and $R_{15}$ can be taken together to form a linear spacer moiety selected from the group consisting of a covalent bond and a linear moiety having from 1 through 5 atoms to form a heterocyclyl ring having from 5 through 8 contiguous members;

$R_3$ and $R_{19}$ can be taken together to form a linear spacer moiety selected from the group consisting of a covalent single bond and a linear moiety having a chain length of 1 to 5 atoms to form a ring selected from the group consisting of a cycloalkyl having from 3 through 8 contiguous members, a cycloalkylenyl having from 5 through 8 contiguous members, and a heterocyclyl having from 4 through 8 contiguous members;

$R_3$ and $R_4$, $R_3$ and $R_8$, $R_3$ and $R_9$, and $R_3$ and $R_{13}$ can be independently selected to form spacer pairs wherein a spacer pair is taken together to form a linear spacer moiety wherein said linear spacer moiety is selected to form a heterocyclyl ring having from 5 through 10 contiguous members;

Y is selected from a group consisting of a covalent single bond, $(C(R_{14})_2)_q$ wherein q is an integer selected from 1 through 4 and $(CH(R_{14}))_g$—W—$(CH(R_{14}))_p$ wherein g and p are integers independently selected from 0 through 2;

$R_{14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_9$ and $R_{13}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_4$ and $R_8$ to form a heterocyclyl having from 5 through 8 contiguous members with the proviso that, when Y is a covalent bond, an $R_{14}$ substituent is not attached to Y;

$R_{14}$ and $R_{15}$ can be taken together to form a spacer selected from a moiety having a chain length of 2 to 5 atoms to form a heterocyclyl ring having from 5 through 8 contiguous members;

$R_{14}$ and $R_{19}$ can be taken together to form a spacer selected from a moiety having a chain length of 2 to 5 atoms to form a heterocyclyl ring having from 5 through 8 contiguous members;

$R_{14}$ and $R_{14}$, when bonded to the different atoms, can be taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{14}$ and $R_{14}$, when bonded to the same atom can be taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

W is selected from the group consisting of O, C(O), C(S), C(O)N($R_{14}$), C(S)N($R_{14}$), ($R_{14}$)NC(O), ($R_{14}$)NC(S), S, S(O), S(O)$_2$, S(O)$_2$N($R_{14}$), ($R_{14}$)NS(O)$_2$, and N($R_{14}$) with the proviso that $R_{14}$ is selected from other than halo and cyano;

Z is independently selected from a group consisting of a covalent single bond, $(C(R_{15})_2)_q$ wherein q is an integer selected from 1 through 4, $(CH(R_{15}))_j$—W—$(CH(R_{15}))_k$ wherein j and k are integers independently selected from 0 through 2 with the proviso that, when Z is a covalent single bond, an $R_{15}$ substituent is not attached to Z;

$R_{15}$ is independently selected, when Z is $(C(R_{15})_2)_q$ wherein q is an integer selected from 1 through 4, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_4$ and $R_8$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_9$ and $R_{13}$ to form a heterocyclyl having from 5 through 8 contiguous members;

$R_{15}$ and $R_{19}$ can be taken together to form a spacer selected from the group consisting of a covalent single bond and a linear moiety having a chain length of 2 to 5 atoms to form a heterocyclyl ring having from 5 through 8 contiguous members;

$R_{15}$ and $R_{15}$, when bonded to the different atoms, can be taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{15}$ and $R_{15}$, when bonded to the same atom can be taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{15}$ is independently selected, when Z is $(CH(R_{15}))_j$—W—$(CH(R_{15}))_k$ wherein j and k are integers independently selected from 0 through 2, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_4$ and $R_8$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_9$ and $R_{13}$ to form a heterocyclyl ring having from 5 through 8 contiguous members;

$R_4$, $R_5$, $R_6$, $R_7$, $R_8$, $R_9$, $R_{10}$, $R_{11}$, $R_{12}$, and $R_{13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkyl, carboxamidoalkoxy, alkoxycarbonylalkoxy, alkoxycarbonylalkenyloxy, aralkanoylalkoxy, aralkenoyl, N-alkylcarboxanido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_4$, $R_5$, $R_6$, $R_7$, and $R_8$ present, that there are one to five non-hydrido ring substituents $R_9$, $R_{10}$, $R_{11}$, $R_{12}$, and $R_{13}$ present, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time;

$R_4$ and $R_9$, $R_4$ and $R_{13}$, $R_8$ and $R_9$, and $R_8$ and $R_{13}$ can be independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_4$ and $R_9$, $R_4$ and $R_{13}$, $R_8$ and $R_9$, and $R_8$ and $R_{13}$ can be used at the same time;

$R_5$ and $R_{10}$, $R_5$ and $R_{12}$, $R_7$ and $R_{10}$, and $R_7$ and $R_{12}$ can be independently selected to form a spacer pair wherein said spacer pair is taken together to form a linear moiety wherein said linear moiety forms a C8 to C13 heterocyclyl ring having from 8 through 13 contiguous members with the proviso that no more than one of the group consisting of spacer pairs $R_5$ and $R_{10}$, $R_5$ and $R_{12}$, $R_7$ and $R_{10}$, and $R_7$ and $R_{12}$ can be used at the same time;

$R_{19}$ is selected from the group consisting of hydrido, hydroxyalkyl, acyl, sulfhydryl, acylamido, alkoxy, alkylthio, arylthio, alkyl, alkenyl, alkynyl, aryl, aralkyl, aryloxyalkyl, aralkanoyl, heteroarylthio, aralkylthio, aroyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, and a spacer group selected from the group consisting of a covalent single bond and a linear moiety having a chain length of 2 to 5 atoms connected to a point of bonding selected from the group consisting of $R_4$, $R_8$, $R_9$, and $R_{13}$ to form a heterocyclyl ring having from 5 through 8 contiguous members.

In another embodiment, the compounds correspond to Formula V-H wherein m is an integer selected from 0 through 5; n is an integer selected from 0 through 5; the sum of m plus n is an integer selected from 0 through 6; $D_1$, $D_2$, $D_3$, $D_4$, $J_1$, $J_2$, $J_3$, $J_4$, $K_1$, and $K_2$ are each a carbon atom; and a terminal carbon atom of the $CH(R_3)$ moiety is directly connected by a covalent single bond to the nitrogen when m=0. Compounds of Formula V-H wherein m is an integer selected from 0 through 5, n is an integer selected from 0 through 5, the sum of m plus n is an integer selected from 0 through 6, and $D_1$, $D_2$, $D_3$, $D_4$, $J_1$, $J_2$, $J_3$, $J_4$, $K_1$, and $K_2$ are each a carbon atom, have the $CH(R_3)$ moiety directly connected by a covalent single bond to the nitrogen when m=0 and correspond to Formula V (also referred to herein as generic phenyl tertiary omegaheteroalkylamines):

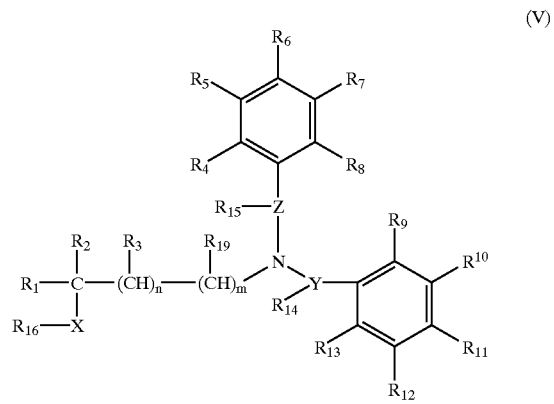

(V)

or a pharmaceutically acceptable salt thereof, wherein;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-H;

$D_1$, $D_2$, $D_3$, $D_4$, $J_1$, $J_2$, $J_3$, $J_4$, $K_1$, and $K_2$ are each carbon;

$R_{16}$ and $R_4$, $R_{16}$ and $R_8$, $R_{16}$ and $R_9$, $R_{16}$ and $R_{13}$, $R_2$ and $R_3$, $R_9$ and $R_{14}$, $R_{13}$ and $R_{14}$, $R_4$ and $R_{14}$, $R_8$ and $R_{14}$, $R_{14}$ and $R_{14}$, $R_4$ and $R_{15}$, $R_8$ and $R_{15}$, $R_9$ and $R_{15}$, $R_{13}$ and $R_{15}$, $R_{15}$ and $R_{15}$, $R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, $R_{12}$ and $R_{13}$, $R_4$ and $R_9$, $R_4$ and $R_{13}$, $R_8$ and $R_9$, $R_8$ and $R_{13}$, $R_{16}$ and $R_{14}$, $R_{16}$ and $R_{15}$, $R_2$ and $R_{14}$, $R_2$ and $R_{15}$, $R_2$ and $R_{19}$, $R_2$ and $R_4$, $R_2$ and $R_8$, $R_2$ and $R_9$, $R_2$ and $R_{13}$, $R_3$ and $R_{14}$, $R_3$ and $R_{15}$, $R_3$ and $R_{19}$, $R_3$ and $R_4$, $R_3$ and $R_8$, $R_3$ and $R_9$, $R_3$ and $R_{13}$, $R_{14}$ and $R_{19}$, $R_{14}$ and $R_{15}$, $R_{15}$ and $R_{19}$, $R_5$ and $R_{10}$, $R_5$ and $R_{12}$, $R_7$ and $R_{10}$, and $R_7$ and $R_{12}$ spacer pairs are as defined for the compounds of Formula V-H.

In another embodiment, the compounds correspond to Formula V-H wherein m is an integer selected from 0 through 5; n is an integer selected from 0 through 5; the sum of m plus n is an integer selected from 0 through 6; and a terminal carbon atom of the $CH(R_3)$ moiety is directly connected by a covalent single bond to the nitrogen when m=0. Compounds of Formula V-H wherein wherein m is the integer zero, and n is an integer selected from 0 through 5, have the $CH(R_3)$ moiety directly connected by a covalent single bond to the nitrogen when m=0 and correspond to Formula VII-H (also referred to herein as generic substituted polycyclic heteroaryl tertiary 2-heteroalkylamines):

(VII-H)

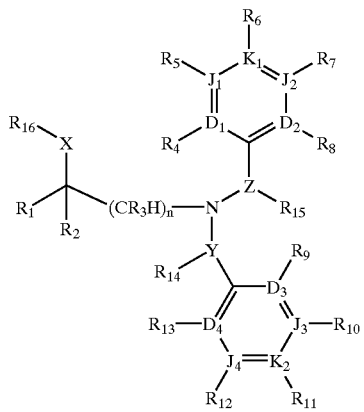

or a pharmaceutically acceptable salt thereof, wherein;
$R_1, R_2, R_3, R_4, R_5, R_6, R_7, R_8, R_9, R_{10}, R_{11}, R_{12}, R_{13}, R_{14}, R_{15}, R_{16}, D_1, D_2, D_3, D_4, J_1, J_2, J_3, J_4, K_1, K_2, X, Y,$ and $Z$ are as defined for the compounds of Formula V-H;
$R_{16}$ and $R_4$, $R_{16}$ and $R_8$, $R_{16}$ and $R_9$, $R_{16}$ and $R_{13}$, $R_2$ and $R_3$, $R_9$ and $R_{14}$, $R_{13}$ and $R_{14}$, $R_4$ and $R_{14}$, $R_8$ and $R_{14}$, $R_{14}$ and $R_{14}$, $R_4$ and $R_{15}$, $R_8$ and $R_{15}$, $R_9$ and $R_{15}$, $R_{13}$ and $R_{15}$, $R_{15}$ and $R_{15}$, $R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, $R_{12}$ and $R_{13}$, $R_4$ and $R_9$, $R_4$ and $R_{13}$, $R_8$ and $R_9$, and $R_8$ and $R_{13}$ spacer pairs are as defined for the compounds of Formula V-H;
$R_{19}$ and spacer pairs $R_{16}$ and $R_{14}$, $R_{16}$ and $R_{15}$, $R_2$ and $R_{14}$, $R_2$ and $R_{15}$, $R_2$ and $R_{19}$, $R_2$ and $R_4$, $R_2$ and $R_8$, $R_2$ and $R_9$, $R_2$ and $R_{13}$, $R_3$ and $R_{14}$, $R_3$ and $R_{15}$, $R_3$ and $R_{19}$, $R_3$ and $R_4$, $R_3$ and $R_8$, $R_3$ and $R_9$, $R_3$ and $R_{13}$, $R_{14}$ and $R_{19}$, $R_{14}$ and $R_{15}$, $R_{15}$ and $R_{19}$, $R_5$ and $R_{10}$, $R_5$ and $R_{12}$, $R_7$ and $R_{10}$, and $R_7$ and $R_{12}$ are not present.

In another embodiment of compounds of Formula VII-H, $D_1, D_2, J_1, J_2$ and $K_1$ are each carbon with the proviso that at least one of $D_3, D_4, J_3, J_4$ and $K_2$ is selected from the group consisting of O, S, and N, wherein $D_3, D_4, J_3, J_4$ and $K_2$ are independently selected from the group consisting of C, N, O, S and covalent bond with the provisos that no more than one of $D_3, D_4, J_3, J_4$ and $K_2$ can be a covalent bond, no more than one of $D_3, D_4, J_3, J_4$ and $K_2$ can be O, no more than one of $D_3, D_4, J_3, J_4$ and $K_2$ can be S, one of $D_3, D_4, J_3, J_4$ and $K_2$ must be a covalent bond when two of $D_3, D_4, J_3, J_4$ and $K_2$ are O and S, and no more than four of $D_3, D_4, J_3, J_4$ and $K_2$ can be N;

$D_1, D_2, J_1, J_2$ and $K_1$ can be selected from the group consisting of C, O, S, N and covalent bond with the provisos that $D_3, D_4, J_3, J_4$ and $K_2$ are each carbon and at least one of $D_1, D_2, J_1, J_2$ and $K_1$ is selected from the group consisting of O, S, and N wherein, when $D_1, D_2, J_1, J_2$ and $K_1$ are selected from the group consisting of C, O, S, covalent bond, and N, no more than one of $D_1, D_2, J_1, J_2$ and $K_1$ can be a covalent bond, no more than one of $D_1, D_2, J_1, J_2$ and $K_1$ can be O, no more than one of $D_1, D_2, J_1, J_2$ and $K_1$ can be S, one of $D_1, D_2, J_1, J_2$ and $K_1$ must be a covalent bond when two of $D_1, D_2, J_1, J_2$ and $K_1$ are O and S, and no more than four of $D_1, D_2, J_1, J_2$ and $K_1$ can be N;

n is an integer selected from 1 through 4;
X is oxy;
$R_{16}$ is selected from the group consisting of hydrido, acyl, aroyl, and trialkylsilyl;

$R_1$ is selected from the group consisting of haloalkyl, haloalkenyl, haloalkoxyalkyl, and haloalkenyloxyalkyl;

$R_2$ is selected from the group consisting of hydrido, hydroxy, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl;

$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Y is selected from the group consisting of covalent single bond and $(C(R_{14})_2)_q$ wherein q is an integer selected from 1 through 2;

$R_{14}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 2;

W is oxy;

$R_{15}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroarylsulfonyl, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, lower alkylamino, alkylthio, arylamino, aralkylamino, arylthio, arylthioalkyl, alkylsulfonyl, alkylsulfonamido, monoarylamidosulfonyl, arylsulfonyl, heteroarylthio, heterocyclylsulfonyl, heterocyclylthio, alkanoyl, alkenoyl, aroyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aralkyl, aryloxy, aralkoxy, saturated heterocyclyl, heteroaryl, heteroaryloxy, heteroaryloxyalkyl, arylalkyl, heteroarylalkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ spacer pairs can be independently selected from the group consisting of alkylene, alkenylene, alkylenedioxy, aralkylene, diacyl, haloalkylene, and aryloxylene with the provisos that no more than one of the group consisting of spacer pairs $R_4$ and $R_5$, $R_5$ and $R_6$, $R_6$ and $R_7$, and $R_7$ and $R_8$ can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In a more specific embodiment of compounds of Formula VII-H, $D_1$, $D_2$, $J_1$, $J_2$ and $K_1$ are each carbon;

$D_3$, $D_4$, $J_3$, $J_4$ and $K_2$ are independently selected from the group consisting of C, N, O, S and covalent bond with the provisos that at least one of $D_3$, $D_4$, $J_3$, $J_4$ and $K_2$ is selected from the group consisting of O, S, and N, wherein no more than one of $D_3$, $D_4$, $J_3$, $J_4$ and $K_2$ can be a covalent bond, no more than one of $D_3$, $D_4$, $J_3$, $J_4$ and $K_2$ can be O, no more than one of $D_3$, $D_4$, $J_3$, $J_4$ and $K_2$ can be S, one of $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ can be N;

n is an integer selected from 1 through 3;

X is oxy;

$R_1$ is selected from the group consisting of trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, and heptafluoropropyl;

$R_{16}$ is selected from the group consisting of acetyl, benzoyl, dimethyl tert-butylsilyl, hydrido, and trimethylsilyl;

$R_2$ is selected from the group consisting of hydrido, hydroxy, methyl, ethyl, propyl, butyl, isopropyl, isobutyl, vinyl, phenyl, trifluoromethyl, 4-trifluoromethylphenyl, 1,1,2,2-tetrafluoroethoxymethyl, chloromethyl, trifluoromethoxymethyl, fluoromethyl, difluoromethyl, chlorodifluoromethyl, pentafluoroethyl, 2,2,3,3,3-pentafluoropropyl, and heptafluoropropyl, pentafluorophenyl, and pentafluorophenoxymethyl;

$R_3$ is selected from the group consisting of hydrido, hydroxy, cyano, acetyl, methoxy, ethoxy, methyl, ethyl, propyl, vinyl, phenyl, methoxymethyl, 4-trifluoromethylphenyl, trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and pentafluorophenoxymethyl.

In a more specific embodiment of compounds of Formula VII-H, $D_3$, $D_4$, $J_3$, $J_4$ and $K_2$ are each carbon;

$D_1$, $D_2$, $J_1$, $J_2$ and $K_1$ are independently selected from the group consisting of C, N, O, S and covalent bond with the provisos that at least one of $D_1$, $D_2$, $J_1$, $J_2$ and $K_1$ is selected from the group consisting of O, S, and N, wherein no more than one of $D_1$, $D_2$, $J_1$, $J_2$ and $K_1$ can be a covalent bond, no more than one of $D_1$, $D_2$, $J_1$, $J_2$ and $K_1$ can be O, no more than one of $D_1$, $D_2$, $J_1$, $J_2$ and $K_1$ can be S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ can be N;

n is an integer selected from 1 through 3;

X is oxy;

$R_1$ is selected from the group consisting of trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, and heptafluoropropyl;

$R_{16}$ is selected from the group consisting of acetyl, benzoyl, dimethyl tert-butylsilyl, hydrido, and trimethylsilyl;

$R_2$ is selected from the group consisting of hydrido, hydroxy, methyl, ethyl, propyl, butyl, isopropyl, isobutyl, vinyl, phenyl, trifluoromethyl, 4-trifluoromethylphenyl, 1,1,2,2-tetrafluoroethoxymethyl, chloromethyl, trifluoromethoxymethyl, fluoromethyl, difluoromethyl, chlorodifluoromethyl, pentafluoroethyl, 2,2,3,3,3-pentafluoropropyl, and heptafluoropropyl, pentafluorophenyl, and pentafluorophenoxymethyl;

$R_3$ is selected from the group consisting of hydrido, hydroxy, cyano, acetyl, methoxy, ethoxy, methyl, ethyl, propyl, vinyl, phenyl, methoxymethyl, 4-trifluoromethylphenyl, trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and pentafluorophenoxymethyl.

In a preferred embodiment of compounds of Formula VII-H, the compounds correspond to the Formula VII (also referred to herein as generic phenyl tertiary 2-heteroalkylamines):

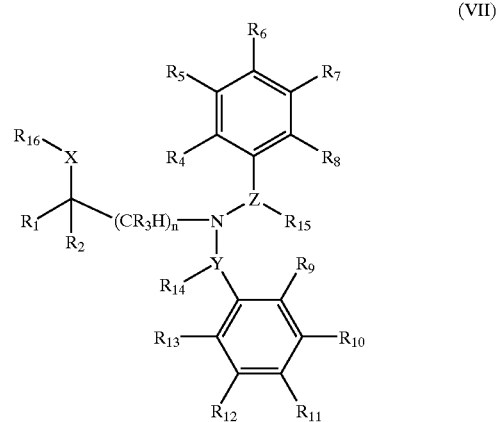

(VII)

or a pharmacuetically acceptable salt thereof, wherein;

n is an-integer selected from 0 through 4;

X is selected from the group consisting of O, H, F, S, S(O), NH, N(OH), N(alkyl), and N(alkoxy);

$R_{16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_4$, $R_8$, $R_9$, and $R_{13}$ to form a heterocyclyl ring having from 5 through 10 contiguous members with the proviso that said linear spacer moiety is other than covalent single bond when $R_2$ is alkyl;

$R_1$ is selected from the group consisting of haloalkyl, haloalkenyl, haloalkoxyalkyl, and haloalkenyloxyalkyl;

$R_2$ is selected from the group consisting of hydrido, hydroxy, hydroxyalkyl, aryl, aralkyl, alkyl, alkenyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, monocyanoalkyl, and dicyanoalkyl, carboalkoxycyanoalkyl;

$R_3$ is selected from the group consisting of hydrido, hydroxy, halo, cyano, hydroxyalkyl, aryl, aralkyl, acyl, alkoxy, alkyl, alkenyl, alkoxyalkyl, aroyl, heteroaroyl, alkenyloxyalkyl, haloalkyl, haloalkenyl, haloalkoxy, haloalkoxyalkyl, haloalkenyloxyalkyl, monocarboalkoxyalkyl, dicarboalkoxyalkyl, monocyanoalkyl, dicyanoalkyl, carboalkoxycyanoalkyl, carboxamide, and carboxamidoalkyl;

Y is selected from the group consisting of covalent single bond and $(C(R_{14})_2)_q$ wherein q is an integer selected from 1 through 2;

$R_{14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 2;

W is selected from the group consisting of O, C(O), C(S), C(O)N($R_{14}$), C(S)N($R_{14}$), ($R_{14}$)NC(O), ($R_{14}$)NC(S), S, S(O), S(O)$_2$, S(O)$_2$N($R_{14}$), ($R_{14}$)NS(O)$_2$, and N($R_{14}$) with the proviso that $R_{14}$ is other than cyano;

$R_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, heteroaralkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In a preferred embodiment of compounds of Formula VII, compounds have the Formula VII-2:

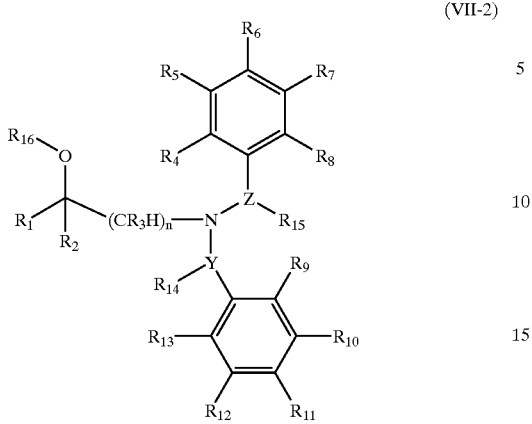

(VII-2)

wherein;

n is an integer selected from 1 through 4;

$R_{16}$ is selected from the group consisting of hydrido, acyl, aroyl, and trialkylsilyl;

$R_1$ is selected from the group consisting of haloalkyl, haloalkenyl, haloalkoxyalkyl, and haloalkenyloxyalkyl;

$R_2$ is selected from the group consisting of hydrido, hydroxy, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl;

$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Y is selected from the group consisting of covalent single bond and $(C(R_{14})_2)_q$ wherein q is an integer selected from 1 through 2;

$R_{14}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 2;

W is oxy;

$R_{15}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroarylsulfonyl, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, lower alkylamino, alkylthio, arylamino, aralkylamino, arylthio, arylthioalkyl, alkylsulfonyl, alkylsulfonamido, monoarylamidosulfonyl, arylsulfonyl, heteroarylthio, heterocyclylsulfonyl, heterocyclylthio, alkanoyl, alkenoyl, aroyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aralkyl, aryloxy, aralkoxy, saturated heterocyclyl, heteroaryl, heteroaryloxy, heteroaryloxyalkyl, arylalkyl, heteroarylalkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ spacer pairs can be independently selected from the group consisting of alkylene, alkenylene, alkylenedioxy, aralkylene, diacyl, haloalkylene, and aryloxylene with the provisos that no more than one of the group consisting of spacer pairs $R_4$ and $R_5$, $R_5$ and $R_6$, $R_6$ and $R_7$, and $R_7$ and $R_8$ can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In a more preferred embodiment of compounds of Formula VII-2, n is an integer selected from 1 through 2;

$R_1$ is selected from the group consisting of haloalkyl and haloalkoxyalkyl;

$R_{16}$ is hydrido;

$R_2$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl, and heteroaryl;

$R_3$ is selected from the group consisting of hydrido, aryl, alkyl, alkenyl, haloalkyl, and haloalkoxyalkyl;

Y is selected from the group consisting of a covalent single bond and alkylene;

Z is selected from the group consisting of a covalent single bond and alkylene;

$R_{14}$ is selected from the group consisting of hydrido, alkyl, and haloalkyl;

$R_{15}$ is selected from the group consisting of hydrido, alkyl, and haloalkyl;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamido-alkoxy, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl.

In an even more preferred embodiment of compounds of Formula VII-2, n is the integer 1;
$R_{16}$ is hydrido;
$R_1$ is haloalkyl;
$R_2$ is selected from the group consisting of hydrido, alkyl, haloalkyl, aryl, and haloalkoxy;
$R_3$ is selected from the group consisting of hydrido, alkyl, and haloalkyl;
Y is alkylene;
Z is covalent single bond;
$R_{14}$ is hydrido;
$R_4$, $R_8$, $R_9$, and $R_{13}$ are independently selected from the group consisting of hydrido and halo;
$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, and heteroaryloxyalkyl.

In an embodiment of compounds of Formula VII-2, n is an integer selected from 1 to 3;
$R_1$ is selected from the group consisting of trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, and heptafluoropropyl;
$R_{16}$ is selected from the group consisting of acetyl, benzoyl, dimethyl tert-butylsilyl, hydrido, and trimethylsilyl;
$R_2$ is selected from the group consisting of hydrido, hydroxy, methyl, ethyl, propyl, butyl, isopropyl, isobutyl, vinyl, phenyl, trifluoromethyl, 4-trifluoromethylphenyl, 1,1,2,2-tetrafluoroethoxymethyl, chloromethyl, trifluoromethoxymethyl, fluoromethyl, difluoromethyl, chlorodifluoromethyl, pentafluoroethyl, 2,2,3,3,3-pentafluoropropyl, and heptafluoropropyl, pentafluorophenyl, and pentafluorophenoxymethyl;
$R_3$ is selected from the group consisting of hydrido, hydroxy, cyano, acetyl, methoxy, ethoxy, methyl, ethyl, propyl, vinyl, phenyl, methoxymethyl, 4-trifluoromethylphenyl, trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and pentafluorophenoxymethyl.

In a preferred embodiment of compounds of Formula VII-2, n is the integer 1;
$R_{16}$ is hydrido;
$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;
$R_2$ is selected from the group consisting of hydrido, methyl, ethyl, propyl, butyl, vinyl, phenyl, 4-trifluoromethylphenyl, trifluoromethyl, 1,1,2,2-tetrafluoroethoxymethyl, trifluoromethoxymethyl, difluoromethyl, chlorodifluoromethyl, pentafluoroethyl, 2,2,3,3,3-pentafluoropropyl, and heptafluoropropyl;
$R_3$ is selected from the group consisting of hydrido, phenyl, 4-trifluoromethylphenyl, methyl, ethyl, vinyl, methoxymethyl, trifluoromethyl, trifluoromethoxymethyl, difluoromethyl, chlorodifluoromethyl, and pentafluoroethyl;

In a even more preferred embodiment of compounds of Formula VII-2, n is the integer 1;
$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;
$R_{16}$ is hydrido;
$R_2$ is selected from the group consisting of hydrido, methyl, ethyl, phenyl, 4-trifluoromethylphenyl, trifluoromethyl, trifluoromethoxymethyl, 1,1,2,2-tetrafluoroethoxymethyl, difluoromethyl, chlorodifluoromethyl, pentafluoroethyl, 2,2,3,3,3-pentafluoropropyl, and heptafluoropropyl;
$R_3$ is selected from the group consisting of hydrido, phenyl, 4-trifluoromethylphenyl, methyl, trifluoromethyl, difluoromethyl, and chlorodifluoromethyl;

In a most preferred embodiment of compounds of Formula VII-2, n is the integer 1;
$R_1$ is selected from the group consisting of trifluoromethyl and pentafluoroethyl;
$R_{16}$ is hydrido;
$R_2$ is selected from the group consisting of hydrido, phenyl, and trifluoromethyl;
$R_3$ is selected from the group consisting of hydrido, methyl, trifluoromethyl, and difluoromethyl;

In another embodiment of compounds of Formula VII, compounds have the Formula Cyclo-VII:

(Cyclo-VII)

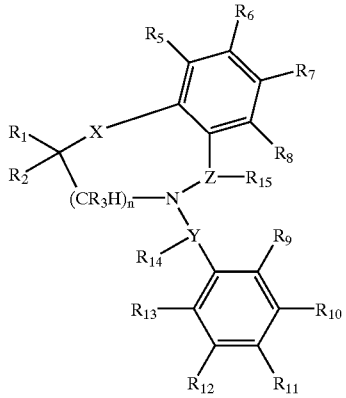

wherein:

R$_{16}$ is taken together with R$_4$, R$_8$, R$_9$ or R$_{13}$ to form a spacer selected from the group consisting of a covalent single bond and a linear spacer moiety having a chain length of 1 to 4 atoms to form a heterocyclyl ring having from 5 through 10 contiguous members with the proviso that said linear spacer moiety is other than covalent single bond when R$_2$ is alkyl;

n is an integer selected from 1 through 3;

X is selected from the group consisting of O, S, NH, N(alkyl), and N(alkoxy);

R$_1$ is selected from the group consisting of haloalkyl, haloalkenyl, haloalkoxyalkyl, and haloalkenyloxyalkyl;

R$_2$ is selected from the group consisting of hydrido, hydroxy, hydroxyalkyl, aryl, aralkyl, alkyl, alkenyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, monocyanoalkyl, and dicyanoalkyl, carboalkoxycyanoalkyl;

R$_3$ is selected from the group consisting of hydrido, hydroxy, halo, cyano, hydroxyalkyl, aryl, aralkyl, acyl, alkoxy, alkyl, alkenyl, alkoxyalkyl, aroyl, heteroaroyl, alkenyloxyalkyl, haloalkyl, haloalkenyl, haloalkoxy, haloalkoxyalkyl, haloalkenyloxyalkyl, monocarboalkoxyalkyl, dicarboalkoxyalkyl, monocyanoalkyl, dicyanoalkyl, carboalkoxycyanoalkyl, carboxamide, and carboxamidoalkyl;

Y is selected from the group consisting of covalent single bond and (C(R$_{14}$)$_2$)$_q$ wherein q is an integer selected from 1 through 2;

R$_{14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, carboxamidoalkyl;

Z is selected from the group consisting of covalent single bond, (C(R$_{15}$)$_2$)$_q$ wherein q is an integer selected from 1 through 2, and (CH(R$_{15}$))$_j$—W—(CH(R$_{15}$))$_k$ wherein j and k are integers independently selected from 0 through 2;

W is selected from the group consisting of O, C(O), S, S(O), and S(O)$_2$;

R$_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

R$_4$, R$_8$, R$_9$, and R$_{13}$ can be independently selected from the group consisting of hydrido, halo, haloalkyl, and alkyl;

R$_5$, R$_6$, R$_7$, R$_{10}$, R$_{11}$, and R$_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, heteroaralkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

R$_5$ and R$_6$, R$_6$ and R$_7$, R$_7$ and R$_8$, R$_9$ and R$_{10}$, R$_{10}$ and R$_{11}$, R$_{11}$ and R$_{12}$, and R$_{12}$ and R$_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_5$ and $R_6$, $R_6$ and $R_7$, and $R_7$ and $R_8$, can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In an embodiment of compounds of Formula Cyclo-VII, n is the integer 1;

X is selected from the group consisting of O, NH, and S;

$R_{16}$ is taken together with $R_4$, $R_8$, $R_9$ or $R_{13}$ to form a spacer selected from the group consisting of a covalent single bond, $CH_2$, $CH(CH_3)$, $CF_2$, $C(O)$, $C(S)$, and $SO_2$;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrido, phenyl, 4-trifluoromethylphenyl, vinyl, trifluoromethyl, pentafluoroethyl, 1,1,2,2-tetrafluoroethoxymethyl, trifluoromethoxymethyl, difluoromethyl, chlorodifluoromethyl, 2,2,3,3,3-pentafluoropropyl, and heptafluoropropyl;

$R_3$ is selected from the group consisting of hydrido, methyl, ethyl, vinyl, phenyl, 4-trifluoromethylphenyl, methoxymethyl, trifluoromethyl, trifluoromethoxymethyl, difluoromethyl, chlorodifluoromethyl, and pentafluoroethyl.

In another embodiment of compounds of Formula Cyclo-VII, compounds have the formula:

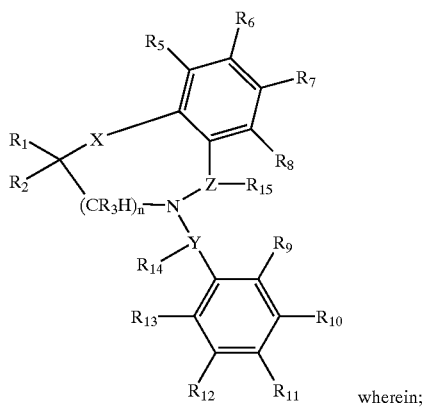

wherein;

n is the integer 1;

X is oxy;

$R_{16}$ and $R_4$ are taken together to form a covalent single bond;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is selected from the group consisting of hydrido, phenyl, 4-trifluoromethylphenyl, vinyl, trifluoromethyl, pentafluoroethyl, 1,1,2,2-tetrafluoroethoxymethyl, trifluoromethoxymethyl, difluoromethyl, chlorodifluoromethyl, 2,2,3,3,3-pentafluoropropyl, and heptafluoropropyl;

$R_3$ is selected from the group consisting of hydrido, methyl, ethyl, vinyl, phenyl, 4-trifluoromethylphenyl, methoxymethyl, trifluoromethyl, trifluoromethoxymethyl, difluoromethyl, chlorodifluoromethyl, and pentafluoroethyl.

In another embodiment of compounds of Formula VII, compounds have the Formula VII-3:

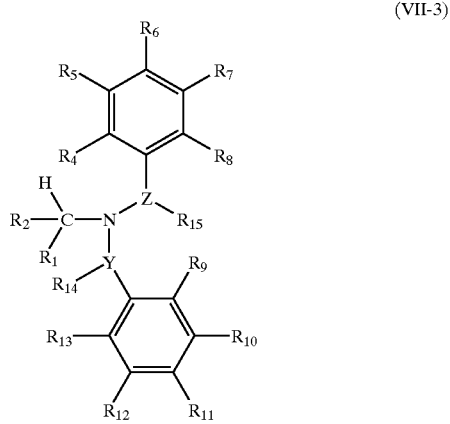

(VII-3)

or a pharmaceutically acceptable salt thereof, wherein:

$R_1$ is selected from the group consisting of haloalkyl, haloalkenyl, haloalkoxyalkyl and haloalkenyloxyalkyl;

$R_2$ is hydroxyalkyl;

Y is selected from the group consisting of covalent single bond and $(C(R_{14})_2)_q$ wherein q is an integer selected from 1 through 2;

$R_{14}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 2;

W is oxy;

$R_{15}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroarylsulfonyl, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, lower alkylamino, alkylthio, arylamino, aralkylamino, arylthio, arylthioalkyl, alkylsulfonyl, alkylsulfonamido, monoarylamidosulfonyl, arylsulfonyl, heteroarylthio, heterocyclylsulfonyl, heterocyclylthio, alkanoyl, alkenoyl, aroyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aralkyl, aryloxy, aralkoxy, saturated heterocyclyl, heteroaryl, heteroaryloxy, heteroaryloxyalkyl, arylalkyl, heteroarylalkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ spacer pairs can be independently selected from the group consisting of alkylene, alkenylene, alkylenedioxy, aralkylene, diacyl, haloalkylene, and aryldioxylene with the provisos that no more than one of the group consisting of spacer pairs $R_4$ and $R_5$, $R_5$ and $R_6$, $R_6$ and $R_7$, and $R_7$ and $R_8$ can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In an embodiment of compounds of Formula VII-3, $R_1$ is selected from the group consisting of trifluoromethyl, 1,1,2,2-tetrafluoroethoxymethyl, chloromethyl, trifluoromethoxymethyl, fluoromethyl, difluoromethyl, chlorodifluoromethyl, pentafluoroethyl, 2,2,3,3,3-pentafluoropropyl, heptafluoropropyl, and pentafluorophenoxymethyl;

$R_2$ is hydroxymethyl, 1-hydroxyethyl, and 1,2-dihydroxyethyl.

In another embodiment of compounds of Formula VII, compounds have the Formula VII-4:

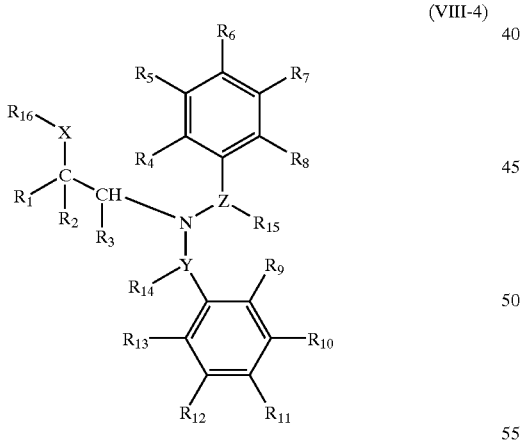

(VIII-4)

wherein;

X is oxy;

$R_1$ is selected from the group consisting of haloalkyl and haloalkoxyalkyl;

$R_{16}$ is hydrido;

$R_2$ and $R_3$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

Y is selected from the group consisting of a covalent single bond and alkylene;

Z is selected from the group consisting of a covalent single bond and alkylene;

$R_{14}$ is selected from the group consisting of hydrido, alkyl, and haloalkyl;

$R_{15}$ is selected from the group consisting of hydrido, alkyl, and haloalkyl;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl.

In an embodiment of compounds of Formula VII-4,

X is oxy;

$R_{16}$ is hydrido;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ and $R_3$ spacer pair is selected from the group consisting of —CH$_2$SCH$_2$—, —CH$_2$OCH$_2$—, —CH$_2$CH(R$_{17}$)—, —CH=C(R$_{17}$)—, —CH$_2$S(O)$_2$CH$_2$—, —CH$_2$CH$_2$CH(R$_{17}$)—,.—CH$_2$CH(R$_{17}$)CH$_2$—, —CH$_2$CH=C(R$_{17}$)—, —CH(R$_{17}$)CH=CH—, —CH$_2$C(R$_{17}$)=CH—, —CH(R$_{17}$)C(O)N(R$_{17}$)—, —C(O)N(R$_{17}$)CH(R$_{17}$)—, —CH(R$_{17}$)C(O)NHCH$_2$—, —CH$_2$C(O)NHCH(R$_{17}$)—, —CH(R$_{17}$)CH(R$_{17}$)C(O) NH—, —C(O)NHCH(R$_{17}$)CH(R$_{17}$)—, —CH$_2$CH (R$_{17}$)CH$_2$CH$_2$—, —CH(R$_{17}$)CH$_2$CH$_2$CH$_2$—, —CH$_2$CH=CHCH$_2$—, —CH=CHCH$_2$CH$_2$—, —CH=CHCH=CH—, —CH$_2$CH$_2$CH$_2$CH$_2$CH$_2$—, —CH$_2$CH$_2$CH=CHCH$_2$—, —(CH$_2$)$_2$O—, —(CH$_2$CHR$_{17}$)O—, —(CF$_2$)$_2$O—, —SCH$_2$CH$_2$—, —S(O)CH$_2$CH$_2$—, —CH$_2$S(O)CH$_2$—, —CH$_2$S(O) CH$_2$CH$_2$—, —S(O)$_2$CH$_2$—, —CH$_2$N(R$_{17}$)O—, —CH$_2$CH$_2$C(O)—, —CH$_2$C(O)NR$_{17}$—, and —CH$_2$NR$_{17}$CH$_2$— wherein R$_{17}$ is selected from the group consisting of H, CH$_3$, OCH$_3$, CF$_3$, CH$_2$CH$_3$, F, Cl, CH$_2$OH, and OH.

In an embodiment of compounds of Formulas VII-H, VII, VII-2, VII-3, VII-4, and Cyclo-VII, Y is selected from the group consisting of a covalent single bond, methylene, 2-fluoroethylidene, ethylidene, 2,2-difluoroethylidene, and 2,2,2-trifluoroethylidene;

Z is group selected from the group consisting of covalent single bond, oxy, methyleneoxy, methylene, ethylene, ethylidene, 2-fluoroethylidene, 2,2-difluoroethylidene, and 2,2,2-trifluoroethylidene;

$R_4$, $R_8$, $R_9$, and $R_{13}$ are independently selected from the group consisting of hydrido and fluoro;

$R_5$ and $R_{10}$ are independently selected from the group consisting of acetoxy, 3-acetamidophenoxy, 3-acetylphenoxy, 4acetylphenylsulfonyl, amino, 4acetylphenylthio, acetylthio, 3-aminobenzyloxy, 4-aminobenzyloxy, 4-aminophenoxy, 3-aminophenyl, benzoyl, benzoylamido, benzoylmethoxy, benzyl, N-benzylamidocarbonyl, benzylamino, 3-benzylimidazol-4-ylmethoxy, N-benzyl-N-methylamidocarbonyl, benzyloxy, 4-benzyloxybenzyloxy, 4-benzylphenoxy, 4-benzylpiperidinyl, bromo, 5-bromo-2-fluorophenoxy, 4-bromo-3-fluorophenoxy, bromomethyl, 4-bromo-2-nitrophenoxy, 2-bromobenzyloxy, 3-bromobenzyloxy, 4-bromobenzyloxy, 4-bromophenoxy, 5-bromopyrid-2-yloxy, 4-bromothiophen-3-ylthio, butoxy, 4-butoxyphenoxy, N-butylylcarboxamido, N-butyl-N-methylcarboxamido, N-butyl-4-ethoxycarbonylphenylamino, 4-butylphenoxy, carboxy, carboxamidomethoxy, 3-carboxybenzyloxy, 4-carboxybenzyloxy, 4carboxyphenyl, 5-carboxypyrid-3-yloxy, chloro, 3-chlorobenzyl, 2-chlorobenzyloxy, 3-chlorobenzyloxy, 4-chlorobenzyloxy, 2-chlorophenoxy, 4chlorophenoxy, 4-chloro-3-ethylphenoxy, 3-chloro-fluorobenzyl, 3-chloro-fluorophenyl, 3-chloro-2-fluorobenzyloxy, 3-chloro-2-hydroxypropoxy, 4-chloro-3-methylphenoxy, 4-chloro-3-methylbenzyl, 2-chloro-fluorophenoxy, 4-chlorophenoxy, 3-chloro-ethylphenoxy, 3-chloromethylphenoxy, 3-chloro-4-fluorophenoxy, 4chloro-3-fluorophenoxy, 4-chloro-2-fluorophenoxy, 3-chlorofluorophenylsulfonylamido, 4-chlorophenyl, 3-chlorophenylamino, 4-chlorophenylamino, 5-chlorophenylthiophen-3-ylmethoxy, 5-chloropyrid-3-yloxy, 4chlorothiophen-2-ylmethylthio, cyano, 3-cyanobenzyloxy, 4cyanobenzyloxy, 4-(2-cyano-2-ethoxycarbonylacetyl)phenylamino, N-(2-cyanoethyl)-methylphenylamino, 2-cyanopyrid-3-yloxy, 4cyanophenoxy, 4-cyanophenyl, 3-cyanophenylamino, 4cyanophenylamino, 3-cyanopropoxy, cyclobutoxy, cyclobutyl, cyclohexylamidocarbonyl, cyclohexoxy, cyclohexylmethoxy, cyclopentoxy, cyclopentyl, N-cyclopentylamidocarbonyl, cyclopentylcarbonyl, 4cyclopentylphenxoy, cyclopropyl, cyclopropylmethoxy, cyclopropoxy, 3,5-dichlorobenzyloxy, 3,5-dichloro4-methylphenoxy, 2,3-dichlorophenoxy, 2,4-dichlorophenoxy, 3,5-dichlorophenoxy, 2,4-dichlorophenyl, 3,5-dichlorophenyl, 3,5-dichloro4-methoxyphenyl, 3,5-dichlorobenzyl, 3,4-dichlorophenoxy, 3,4-dichlorophenyl, 3,4-difluorophenoxy, 2,4-difluorobenzyloxy, 2,5-difluorobenzyloxy, 3,5-difluorobenzyloxy, 2,6-difluorobenzyloxy, 3,5-difluorophenoxy, 3,4-difluorophenyl, 4-difluoromethoxybenzyloxy, 2,3-difluorophenoxy, 2,4-difluorophenoxy, 2,3-difluorophenoxy, 3,4-difluorobenzyloxy, difluoromethoxy, 2,5-difluorophenoxy, 3,5-difluorophenylamino, 3,5-dimethoxyphenoxy, dimethylamino, N,N-dimethylcarboxamido, 2-(N,N-dimethylamino)ethoxy, 3-dimethylaminophenoxy, 3,4-dimethylbenzyloxy, 3,5-dimethylbenzyloxy, 3,5-dimethylphenoxy, 3,4-dimethylphenoxy, 3,5-dimethyl4-(N,N-dimethylamino)phenyl, 3,4-dimethoxyphenylamino, 3,4-dimethylbenzyl, 3,4-dimethylbenzyloxy, 1,1-dimethylhydroxymethyl, 3,3-dimethyl-2-oxobutoxy, 2,2-dimethylpropoxy, 1,3-dioxan-2-yl, 1,4-dioxan-2-yl, 1,3-dioxolan-2-yl, ethoxy, ethoxycarbonyl, 3-ethoxycarbonylphenylamino, 4-ethoxycarbonylphenylamino, 1-ethoxycarbonylbutoxy, 4-ethoxyphenoxy, ethyl, 4,4-ethylenedioxypiperidinyl, N-ethyl-N-methylcarboxamido, 3-ethylphenoxy, 4-ethylaminophenoxy, 4-ethylbenzyloxy, 3-ethyl-5-methylphenoxy, N-ethyl-3-methylphenylamino, N-ethyl-methoxyphenylamino, fluoro, 4-fluorobenzylamino, 4-fluoro-3-methylbenzyl, 2-fluoro-3-methylbenzyloxy, 4-fluoro-3-methylphenyl, 4-fluorobenzoyl, 4-fluoro-3-methylbenzoyl, 3-fluorobenzyloxy, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 4-fluoro-2-trifluoromethylbenzyloxy, 4-fluoro-3-trifluoromethylbenzyloxy, 5-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamidocarbonylamido, 4-fluorophenylamino, 4-fluorobenzoylamido, 4-fluorobenzylamidocarbonyl, 2-fluoro4-trifluoromethylphenoxy, 4-fluoro-2-trifluoromethylphenoxy, 2-fluoro4-chloromethylphenoxy, 4-fluoropyrid-2-yloxy, 2-furyl, 3-furyl, N-(2,2,3,3,4,4,4-heptafluorobutyl) amidocarbonyl, heptafluoropropyl, 1,1,1,3,3,3-hexafluoropropyl, hydrazinocarbonyl, hydrido, hydroxy, 2-hydroxyethoxy, 1-hydroxyisobutyl, 3-hydroxy-2,2-dimethylpropoxy, hydroxymethyl, 3-hydroxymethylphenoxy, 4-hydroxyphenoxy, 3-hydroxypropoxy, 2-hydroxy-3,3,3-trifluoropropoxy, 4-imidazol-1-yl-phenoxy, indol-5-yloxy, iodo, 3-iodobenzyloxy, isobutylamino, isobutoxy, N-isobutoxycarbonylamido, isobutyl, isobutyryl, isobutyrylamido, 3-isoxazolyl, 4-isoxazolyl, 5-isoxazolyl, isopropoxy, isopropyl, isopropylamidocarbonyl, isopropylamidocarbonylamido, 4-isopropylbenzyloxy, N-isopropyl-N-methylamino, 3-isopropylphenoxy, 4-isopropylphenoxy, isopropylthio, 4-isopropyl-3-methylphenoxy, isopropylsulfonyl, isopropylsulfonylamido, isoquinolin-3-yloxy, 3-isothiazolyl, 4-isothiazolyl, 5-isothiazolyl, methoxy, 3-methoxybenzoylamido, 3-methoxybenzyl, methoxycarbonyl, 4-methoxycarbonylbutoxy, 3-methoxycarbonylbenzyloxy, 4-methoxycarbonylbenzyloxy, 2-methoxyethoxy, 3-methoxycarbonylmethoxy, 3-methoxycarbonylprop-2-enyloxy, methoxymethyl, N-methoxy-N-methylcarboxamido, 3-methoxyphenoxy, 4-methoxyphenoxy, 4-methoxy-3-methylphenyl, 3-methoxyphenyl, 4-methoxyphenyl, 3-methoxyphenylamino, 4-methoxyphenylamino, 3-methoxyphenylamidocarbonylamido, 4-methoxyphenylthio, methyl, N-methyl-4-methoxyphenylamino, 4-methylbenzyl, 3-methylbutyl, 3-methylphenoxy, 4-methylsulfonylphenyl, 3-methyl-4-methylthiophenoxy, 3-methylbenzyloxy, 4-methylbenzyloxy, 2-methyl-3-nitrophenoxy, 2-methyl-5-nitrophenoxy, 4-methylphenoxy, 4-methylphenyl, N-methyl-N-phenylamidocarbonyl, N-methyl -N-propylcarboxamido, 4-(5-(4-methylphenyl)-1,3,4-oxadiazol-2-yl)phenylamino, 3-methylphenylsulfonylamido, 4-methylpiperazin-1- ylcarbonyl, 1-methylpropoxy, 3-methylbut-2-enyloxy, 2-methylpyrid-6-yl, 3-methylpyrid-2-yl, 2-methylpyrid-3-yloxy, 2-methylpyrid-5-yloxy, N-methylpyrrol-2-yl, 4-methylsulfonylphenylsulfonyl, 4-methylsulfonylphenylthio, 4-methylthiophenoxy, 4-methylthiophenyl, 4-methylthiobenzyl, morpholin-4-ylcarbonyl, 2-naphthyloxy, N-neopentylamidocarbonyl, nitro, 3-nitrobenzyl, 3-nitrobenzyloxy, 4-nitrobenzyloxy, 2-nitrophenoxy, 3-nitrophenoxy, 4-nitrophenoxy, 3-nitrophenyl, 4-nitrophenylsulfonyl, 3-nitrophenylsulfonylamido, 4-nitrophenylthio, 2-oxazolyl, 4-oxazolyl, 5-oxazolyl, 2-oxobutoxy, 5-oxohexoxy, N-oxypyrid-3-ylmethylsulfonyl, 2,3,4,5,6-pentafluorobenzyloxy, pentafluoroethyl, pentafluoroethylthio, 4(2,3,4,5,6-pentafluorophenyl)-2,3,5,6-tetrafluorophenoxy, 2,2,3,3,3-pentafluoropropyl, 1,1,3,3,3-pentafluoropropyl, 1,1,2,2,3-pentafluoropropyl, phenoxy, 3-phenoxybenzyloxy, phenyl, phenylamidocarbonylamido, 1-(N-phenylcarboxamido)ethoxy, phenylamino, 4-phenylbenzyloxy, 1-phenylethoxy, phenylhydroxymethyl, 3-phenylphenoxy, 4-phenylphenoxy, phenylsulfonyl, phenylsulfonylamido, 2-phenylsulfonylethoxy, phenylthio, 1-piperidinyl, piperidin4-ylcarbonyl, piperidin-4-ylsulfonyl, piperidin4-ylthio, hexahydropyran-4-yloxy, 4-propanoyl, 4-propanoylphenoxy, propoxy, 4-propylphenoxy, 4-propylphenylamino, 4-propoxyphenoxy, pyrid-2-yl, pyrid-3-yl, pyrid-3-ylcarboxamido, pyrid-2-ylmethoxy, pyrid-3-ylmethoxy, pyrid-4-ylmethoxy, pyrid-2-yloxy, pyrid-3-yloxy, pyrid-2-ylmethylthio, pyrid-4ylthio, pyrimid-2-yl, pyrimid-2-yloxy, pyrimid-5-yloxy, pyrrolin-1-ylcarbonyl, 2-(pyrrolidin-1-yl)ethoxy, thiophen-3-yl, sec-butyl, 4-sec-butylphenoxy,tert-butoxy, N-tert-butylamidocarbonyl, 4-tert-butylbenzyl, 4-tert-butylbenzyloxy, 3-tert-butylphenoxy, 4-tert-butylphenoxy, 4-tert-butylphenyl, tetrazol-5-yl, 3-(1,1,2,2-tetrafluoroethoxy)benzylamino, 1,1,2,2-tetrafluoroethoxy, 2,3,5,6-tetrafluoro-4-methoxybenzyloxy, 2,3,5,6-tetrafluoro-4-trifluoromethylbenzyloxy, tetrahydrofuran-2-yl, 2-(5,6,7,8-tetrahydronaphthyloxy), thiazol-2-yl, thiazol-4-yl, thiazol-5-yl, thiol, 4-thiophenoxy, thiophen-2-yl, 2,3,5-trifluorobenzyloxy, 2,4,6-trifluorobenzyloxy, N-(4,4,4-trifluorobutyl)-4-methoxyphenylamino, 2,2,2-trifluoroethoxy, 2,2,2-trifluoroethyl, 3,3,3-trifluoro-2-hydroxypropyl, N-(2,2,2-trifluoroethyl)amidocarbonyl, trifluoromethoxy, 3-trifluoromethoxybenzyloxy, 3-trifluoromethoxybenzylamidocarbonyl, 3-trifluoromethoxybenzylamidocarbonylhydrazinocarbonyl, 4-trifluoromethoxybenzyloxy, 3-trifluoromethoxyphenoxy, 4-trifluoromethoxyphenoxy, 4-trifluoromethoxyphenylamino, trifluoromethyl, 3-trifluoromethylbenzylamine, 3-trifluoromethylbenzyloxy, 4-trifluoromethylbenzyloxy, 2,4-bis-trifluoromethylbenzyloxy, 3,4-bis-trifluoromethylbenzyloxy, 1,1-bis-trifluoromethyl-1-hydroxymethyl, 3,5-bis-trifluoromethylphenyl, 3-trifluoromethylbenzyl, 3,5-bis-trifluoromethylbenzyloxy, 4-trifluoromethylphenoxy, 3-trifluoromethylphenoxy, 2-trifluoromethylphenyl, 3-trifluoromethylphenyl, 4-trifluoromethylphenyl, 3-trifluoromethylphenylamidocarbonylamido, 4-trifluoromethylphenylamino, 3-trifluoromethylphenylsulfonylamido, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3,4,5-trimethoxyphenylamino, 3-trifluoromethylpyrid-2-yl, 3-trifluoromethylpyrid-2-yloxy, 5-trifluoromethylpyrid-2-yloxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of acetoxy, benzyloxy, bromo, butoxy, butoxycarbonyl, chloro, 4-chlorophenyl, 3,4-dichlorophenoxy, cyano, 2-cyanophenyl, difluoromethoxy, ethoxy, fluoro, hydrido, hydroxy, methoxy, methoxycarbonyl, methyl, methylsulfonyl, morpholin-4-yl, nitro, octyl, phenoxy, phenyl, phenylethenyl, phenylethynyl, propoxy, thiophen-2-yl, trifluoromethyl, pentafluoroethyl, 1,1,2,2-tetrafluoroethoxy, and trifluoromethoxy;

$R_7$ and $R_{12}$ are independently selected from the group consisting of benzyloxy, hydrido, fluoro, hydroxy, methoxy, and trifluoromethyl;

$R_5$ and $R_6$ can be taken together to form a spacer group selected from the group consisting of benzylidene, 5-bromobenzylidene, ethylene-1,2-dioxy, tetrafluoroethylene-1,2-dioxy, 1,4-butadienyl, methylene-1,1-dioxy, phenoxylidene, and propylene-1,3-dioxy;

$R_6$ and $R_7$ can be taken together to form a spacer group selected from the group consisting of benzylidene, 5-bromobenzylidene, ethylene-1,2-dioxy, tetrafluoroethylene-1,2-dioxy, 1,4-butadienyl, methylene-1,1-dioxy, phenoxylidene, and propylene-1,3-dioxy;

$R_{10}$ and $R_{11}$ can be taken together to form a spacer group selected from the group consisting of benzylidene, ethylene-1,2-dioxy, methylene-1,1-dioxy, phthaloyl, and tetrafluoroethylene-1,2-dioxy;

$R_{11}$ and $R_{12}$ can be taken together to form a spacer group selected from the group consisting of benzylidene, ethylene-1,2-dioxy, methylene-1,1-dioxy, phthaloyl, and tetrafluoroethylene-1,2-dioxy;

$R_{12}$ and $R_{13}$ can be the spacer group 1,4-butadienyl.

In a preferred embodiment of compounds of Formulas VII-H, VII, VII-2, VII-3, VII-4, and Cyclo-VII, Y is selected from the group consisting of methylene, ethylene, and ethylidene;

Z is covalent single bond;

$R_4$, $R_8$, $R_9$, and $R_{13}$ are independently selected from the group consisting of hydrido and fluoro;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3- methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;

$R_7$ and $R_{12}$ are independently selected from the group consisting of hydrido, fluoro, and trifluoromethyl.

In an even more preferred embodiment of compounds of Formulas VII-H, VII, VII-2, VII-3, VII-4, and Cyclo-VII, Y is methylene;

Z is covalent single bond;

$R_4$, $R_8$, $R_9$, and $R_{13}$ are independently selected from the group consisting of hydrido and fluoro;

$R_5$ and $R_{10}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, -4chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, and trifluoromethyl;

$R_7$ and $R_{12}$ are independently selected from the group consisting of hydrido, fluoro, and trifluoromethyl.

In a most preferred embodiment of compounds of Formulas VII-H, VII, VII-2, VII-3, VII-4, and Cyclo-VII, Y is methylene;

Z is covalent single bond;

$R_4$, $R_8$, $R_9$, and $R_{13}$ are independently selected from the group consisting of hydrido and fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

Definitions

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrogen atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 1 to about 8 carbon atoms and more preferably 1 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 2 to about 8 carbon atoms and more preferably 2 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical (=CH—), or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, ethylidene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene ($CH_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydoxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "lower alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated, partially saturated and unsaturated heteroatom-containing ring-shaped radicals having from 5 through ring members selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents as defined below. Preferred heterocyclic radicals include five to twelve membered fused or unfused radicals. Non-limiting examples of heterocyclic radicals include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxidiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazoyl, quinolinyl, tetraazolyl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above. The term "aminosulfonyl" denotes an amino radical attached to a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The terms alkylamino denotes "monoalkylamino" and "dialkylamino" containing one or two alkyl radicals, respectively, attached to an amino radical.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent $S(=O)$ atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent $S(=O)$ atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4chloro-3-ethylphenoxy, 4chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. Examples of such radicals include benzyloxy, 1-phenylethoxy, 3-trifluoromethoxybenzyloxy, 3-trifluoromethylbenzyloxy, 3,5-difluorobenzyloxy, 3-bromobenzyloxy, 4propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "lower heteroaralkoxy" radicals having heteroaryl radicals attached to lower alkoxy radical as described above.

The term "haloheteroaryloxyalkyl" embraces heteroaryloxyalkyl radicals, as defined above, wherein one to four halo radicals are attached to an heteroaryloxy group.

The term "heteroarylamino" embraces heterocyclyl radicals, as defined above, attached to an amino group. Examples of such radicals include pyridylamino.

The term "heteroarylaminoalkyl" embraces heteroarylamino radicals, as defined above, attached to an alkyl group. Examples of such radicals include pyridylmethylamino.

The term "heteroaryloxy" embraces heterocyclyl radicals, as defined above, attached to an oxy group. Examples of such radicals include 2thiophenyloxy, 2-pyrimidyloxy, 2-pyridyloxy, 3-pyridyloxy, and 4-pyridyloxy.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamide" embraces amino, monoalkylamino, dialkylamino, monocycloalkylamino, alkylcycloalkylamino, and dicycloalkylamino radicals, attached to one of two unshared bonds in a carbonyl group. The term "carboxamidoalkyl" embraces carboxamide radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl. The term "diacyl", alone or in combination, means having two or more carbonyl or thionocarbonyl groups bonded to a radical selected from, for example, alkylene, alkenylene, alkynylene, haloalkylene, alkoxyalkylene, aryl, heterocyclyl, heteroaryl, aralkyl, cycloalkyl, cycloalkylalkyl, and cycloalkenyl. Examples of "diacyl" are phthaloyl, malonyl, succinyl, adipoyl, and the like.

The term "benzylidenyl" radical denotes substituted and unsubstituted benzyl groups having attachment points for two covalent bonds. One attachment point is through the methylene of the benzyl group with the other attachment point through an ortho carbon of the phenyl ring. The methylene group is designated for attached to the lowest numbered position. Examples include the base compound benzylidene of structure:

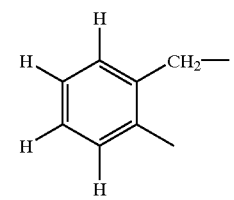

The term "phenoxylidenyl" radical denotes substituted and unsubstituted phenoxy groups having attachment points for two covalent bonds. One attachment point is through the oxy of the phenoxy group with the other attachment point through an ortho carbon of the phenyl ring. The oxy group is designated for attached to the lowest numbered position. Examples include the base compound phenoxylidene of structure:

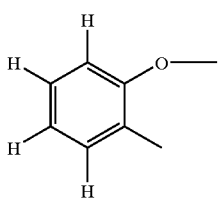

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

Said "alkyl", "alkenyl", "alkynyl", "alkanoyl", "alkylene", "alkenylene", "benzylidenyl", "phenoxylidenyl", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroarylaminoalkyl", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl" and "diacyl" groups defined above may optionally have 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 continous atoms. The spacer may have 1 to 7 atoms of a univalent or multi-valent chain. Univalent chains may be constituted by a radical selected from =C(H)—, =C($R_{17}$)—, —O—, —S—, —S(O)—, —S(O)$_2$—, —NH—, —N($R_{17}$)—, —N=, —CH(OH)—, =C(OH)—, —CH(O$R_{17}$)—, =C(O$R_{17}$)—, and —C(O)— wherein $R_{17}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: lower alkylene, lower alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$_{17}$)O—, —O(CH$_2$CHR$_{17}$)O—, —OCF$_2$O—, —O(CF$_2$)$_2$O—, —S—, —S(O)—, —S(O)$_2$—, —N(H)—, —N(H)O—, —N(R$_{17}$)O—, —N(R$_{17}$)—, —C(O)—, —C(O)NH—, —C(O)NR$_{17}$—, —N=, —OCH$_2$—, —SCH$_2$—, S(O)CH$_2$—, —CH$_2$C(O)—, —CH(OH)—, =C(OH)—, —CH(OR$_{17}$)—, =C(OR$_{17}$)—, S(O)$_2$CH$_2$—, and —NR$_{17}$CH$_2$— and many other radicals defined above or generally known or ascertained by one of skill-in-the art. Side chains may include substituents such as 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "F" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms.

Said amide carbonyl groups may be both oxo (C=O) and thiono (C=S) in type. Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The following general synthetic sequences are useful in making the present invention. Abbreviations used in the schemes are as follows: "AA" represents amino acids, "BINAP" represents 2,2'-bis(diphenylphosphino)-1,1'-binaphthyl, "Boc" represents tert-butyloxycarbonyl, "BOP" represents benzotriazol-1-yl-oxy-tris-(dimethylamino), "bu" represents butyl, "dba" represents dibenzylideneacetone, "DCC" represents 1,3-dicyclohexycarbodiimide, "DIBAH" represents diisobutylaluminum hydride, "DIPEA" represents diisopropylethylamine, "DMF" represents dimethylformamide, "DMSO" represents dimethylsulfoxide, "Fmoc" represents 9-fluorenylmethoxycarbonyl, "LDA" represents lithium diisopropylamide, "PHTH" represents a phthaloyl group, "pnZ" represents 4-nitrobenzyloxycarbonyl, "PTC" represents a phase transfer catalyst, "p-TsOH" represents para-toluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, and "Z" represents benzyloxycarbonyl.

Pharmaceutical Utility And Composition

The present invention comprises a pharmaceutical composition comprising a therapeutically-effective amount of a compound of Formulas V-H, V, VII-H, VII, VII-2, VII-3, VII-4, and Cyclo-VII, in association with at least one pharmaceutically-acceptable carrier, adjuvant or diluent.

The present invention also comprises a treatment and prophylaxis of coronary artery disease and other CETP-mediated disorders in a subject, comprising administering to the subject having such disorder a therapeutically-effective amount of a compound of Formula V-H:

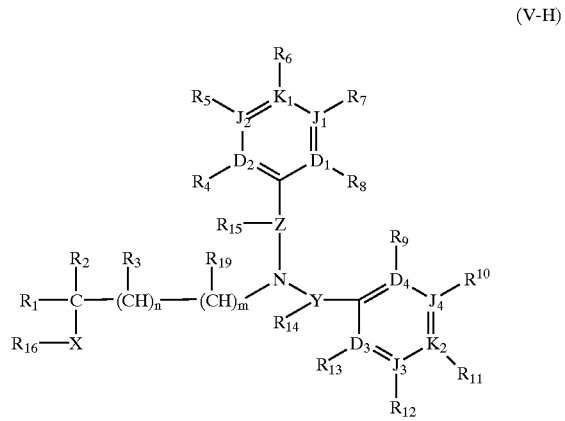

(V-H)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined above for the compounds of Formula V-H;

or a pharmaceutically-acceptable salt thereof.

As a further embodiment, compounds of the present invention of Formulas V-H, V, VII-H, VII, VII-2, VII-3, VII-4, and Cyclo-VII, or a pharmaceutically-acceptable salt thereof as defined above and further including those, wherein $R_{16}$ is a covalent single bond linked to a point of bonding of $R_4$ or $R_8$ when $R_2$ is alkyl, $R_2$ and $R_{14}$ are taken together to form a —N= spacer group, and $R_2$ and $R_{15}$ are taken together to form a —N= spacer group, comprise a treatment and prophylaxis of coronary artery disease and other CETP-mediated disorders in a subject, comprising administering to the subject having such disorder a therapeutically-effective amount of compounds of Formulas V-H, V, VII-H, VII, VII-2, VII-3, VII-4, and Cyclo-VII, of the present invention or a pharmaceutically-acceptable salt thereof.

Compounds of Formulas V-H, V, VII-H, VII, VII-2, VII-3, VII-4, and Cyclo-VII including those, wherein $R_{16}$ is a covalent single bond linked to a point of bonding of $R_4$ or $R_8$ when $R_2$ is alkyl, $R_2$ and $R_{14}$ are taken together to form a —N= spacer group, and $R_2$ and $R_{15}$ are taken together to form a —N= spacer group, are capable of inhibiting activity of cholesteryl ester transfer protein (CETP), and thus could be used in the manufacture of a medicament, a method for the prophylactic or therapeutic treatment of diseases mediated by CETP, such as peripheral vascular disease, hyperlipidaemia, hypercholesterolemia, and other diseases attributable to either high LDL and low HDL or a combination of both, or a procedure to study the mechanism of action of the cholesteryl ester transfer protein (CETP) to enable the design of better inhibitors. The compounds of Formulas V-H, V, VII-H, VII, VII-2, VII-3, VII-4, and Cyclo-VII would be also useful in prevention of cerebral vascular accident (CVA) or stroke.

Also included in the family of compounds of Formulas V-H, V, VII-H, VII, VII-2, VII-3, VII-4, and Cyclo-VII are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula V-H may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula V-H include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds of Formulas V-H, V, VII-H, VII, VII-2, VII-3, VII-4, and Cyclo-VII by reacting, for example, the appropriate acid or base with the compounds of Formulas V-H, V, VII-H, VII, VII-2, VII-3, VII-4, and Cyclo-VII.

Also embraced within this invention is a class of pharmaceutical compositions comprising the active compounds of Formula V-H in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner.

While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

General Synthetic Procedures

The compounds of the present invention can be synthesized, for example, according to the following procedures of Schemes 1 through 59 below, wherein the substituents are as defined for Formulas V-H, V, VII-H, VII, VII-2, VII-3, VII-4, and Cyclo-VII above except where further noted.

Synthetic Schemes 1 and 2 shows the preparation of compounds of formula XIII ("Generic Secondary Amines") which are intermediates in the preparation of the compounds of the present invention corresponding to Formula V-H ("Generic Substituted Polycyclic Aryl and Heteroaryl tertiary omegahydroxyalkylamines"), Formula V ("Generic Substituted Polycyclic Aryl tertiary omegahydroxyalkylamines"), Formula VII ("Generic Substituted Polycyclic Aryl tertiary-2-hydroxyalkylamines"), and Formula VII-H ("Generic Substituted Polycyclic Heteroaryl tertiary-2-hydroxyalkylamines") wherein A and Q are independently aryl and heteroaryl. Schemes 1 and 2, taken together, prepare tertiary oxyalkylamine compounds of the present invention by addition of a halogenated, oxygen containing precursor to a secondary amine to introduce an oxy containing alkyl group wherein the two groups making up the secondary amine both are made up of aromatic groups or both groups contain aromatic rings wherein said aromatic rings maybe 0 to 2 aryl rings and 0 to 2 heteroaryl rings.

The "Generic Imine" corresponding to Formula XII can be prepared through dehydration techniques generally known in the art and the preferred technique depending on the nature of "Generic Amine-1" of Formula X by reacting it with the "Generic Carbonyl Compound" of Formula XI. For example, when Z is a covalent bond, methylene, methine substituted with another subsitutent, ethylene, or another subsituent as defined in Formula V-H, the two reactants (X and XI) react by refluxing them in an aprotic solvent, such as hexane, toluene, cyclohexane, benzene, and the like, using a Dean-Stark type trap to remove water. After about 2–8 hours or until the removal of water is complete, the aprotic solvent is removed in vacuo to yield the "Generic Imine" of Formula XII. Alternately, when Z is an oxygen, the "Generic Imine" is an oxime derivative. Oxime type "Generic Imine" compounds are readily prepared from the corresponding O-substituted hydroxylamine and the appropriate aldehyde or ketone type "Generic Carbonyl Compound". Suitable procedures are described by Shriner, Fuson, and Curtin in The Systematic Indentification of Organic Compounds, 5th Edition, John Wiley & Sons and by Fieser and Fieser in Reagents for Organic Synthesis, Volume 1, John Wiley & Sons, which are incorporated herein by reference. Alternately, when Z is a nitrogen, the "Generic Imine" is a hydrazone derivative. Hydrazone type "Generic Imine" compounds are readily prepared from the corresponding hydrazine and the appropriate aldehyde or ketone type "Generic Carbonyl Compound". Suitable procedures for forming the hydrazone imines are also described by Shriner, Fuson, and Curtin in The Systematic Indentification of Organic Compounds, 5th Edition, John Wiley & Sons, and by Fieser and Fieser in Reagents for Organic Synthesis, Volume 1, John Wiley & Sons, which are incorporated herein by reference.

Scheme 1 shows the preparation of "Generic Imine" compounds in which the amine functionality is bonded to Z; Z is bonded to A; and Y is bonded to Q. One of skill in the art will recognize that A and Q as defined can be structurally interchanged to prepare "Generic Imine" compounds with similar, identical or different structures.

The "Generic Secondary Amines" of Formula XIII can be prepared from the corresponding "Generic Imine" of Formula XII in several ways.

For example, in one synthetic scheme (Reduction Method-1), which is preferred when Z is a nitrogen, the "Generic Imine" hydrazone of Formula XII is partially or completely dissolved in lower alkanols such as ethanol or like solvent containing sufficient organic acid such as acetic acid or mineral acid such as HCl or sulfuric acid to neutralize the hydrazone as described in WO Patent Application No.9738973, Swiss Patent CH 441366 and U.S. Pat. Nos. 3,359,316 and 3,334,017, which are incorporated herein by reference. The resulting mixture is then hydrogenated at 0–100° C., more preferrably 20–50° C., and most preferrably between 20–30° C. and pressures of 10–200 psi hydrogen or more preferrably between 50–70 psi hydrogen in the presence of a noble metal catalyst such as $PtO_2$. The mixture is cooled, and a base such as sodium carbonate or sodium hydroxide added until the solution is neutral to just alkaline (pH 6–8).

Isolation of the desired product can be accomplished, for example, by removing the ethanol, adding water, and extracting the aqueous-organic mixture twice with a solvent, such as diethyl ether or methylene chloride, that is immiscible with water. The combined solvent extract is washed with saturated brine, dried with a drying agent such as anhydrous magnesium sulfate, and concentrated in vacuo to yield the "Generic Secondary Amines" hydrazine of Formula XIII. If needed the "Generic Secondary Amines" hydrazine can be further purified by crystallization, distillation at reduced pressure, or liquid chromatography.

In another synthetic scheme (Reduction Method-2), which is preferrred when Z is a single bond or carbon, the "Generic Imine" of Formula XII is slurried in a lower alcohol such as ethanol, methanol or like solvent at 0–10° C. and solid sodium borohydride is added in batches over 5–10 minutes at 0–10° C. with stirring. The reaction mixture is stirred below 10° C. for 30–90 minutes and then is warrned gradually to 15–30° C. After about 1–10 hours, the mixture is cooled and acid is added until the aqueous layer was just acidic (pH 5–7).

Isolation of the desired product can be accomplished, for example, by extracting the aqueous layer twice with a solvent, such as diethyl ether or methylene chloride, that is immiscible with water. The combined solvent extract is washed with saturated brine, dried with a drying agent such as anhydrous MgSO4, and concentrated in vacuo to yield the "Generic Secondary Amines" amine, aniline, or amine of Formula XIII. If needed the "Generic Secondary Amines" amine, aniline, or amine derivative can be further purified by crystallization, distillation at reduced pressure, or liquid chromatography.

In yet another synthetic scheme (Reduction Method-3), which is preferrred when Z is an oxygen, the "Generic Imine" oxime of Formula XII is slurried in a lower alcohol solvent such methanol or like solvent at 0–10° C. and acidified to a pH less than 4. Solid sodium cyanoborohydride is added in batches over 30–90 minutes at 0–20° C. with stirring and addition of a suitable organic or mineral acid to keep the pH at or below 4. The reaction mixture is stirred and warmed gradually to about 20–25° C. After about 1–10 hours, the mixture is cooled and base added until the mixture was just slightly alkaline.

Isolation of the desired product can be accomplished, for example, by removing the methanol or other low boiling solvent in vacua. The residue is slurried with water and aqueous-organic mixture is extracted twice with a solvent, such as diethyl ether or methylene chloride, that is immiscible with water. The combined solvent extract is washed with saturated brine, dried with a drying agent such as anhydrous $MgSO_4$, and concentrated in vacuo to yield the "Generic Secondary Amines" hydroxylamine of Formula XIII. If needed the "Generic Secondary Amines" hydroxylamine can be further purified by crystallization, distillation at reduced pressure, or liquid chromatography.

The "Generic Secondary Amines" of Formula XIII can also be prepared, according to Scheme 1 by two alkylation procedures based on the nucleophilic substitution of bromides by amines. In one procedure, "Generic Amine-1" of Formula X is reacted with "Generic Bromide-1" of Formula XXI. In another alkylation procedure, "Generic Amine-2" of Formula XXII is reacted together with "Generic Bromide-2" of Formula XXIII.

In one synthetic alkylation scheme (Alkylation Method-1), a "Generic Amine-1" of Formula X is reacted with a "Generic Bromide-2" of Formula XXIII as described in Vogel's Textbook of Practical Organic Chemistry, Fifth Edition, 1989, pages 902 to 905 and references cited therein all of which are incorporated herein by reference. In this procedure, the "Generic Amine-1" is placed in a reaction vessel equipped with a reflux condenser with the capability to either cool or heat the vessel as dictated by the reaction. A suitable "Generic Amine-1" will be selected from primary amine and primary aromatic amine classes of compounds. Cooling may be needed and used should the reaction prove strongly exothermic. Heating may be needed and used to drive the reaction to completion. A suitable solvent may also be used to dissolve the "Generic Amine-1". Suitable solvents are hydrocarbons such as toluene, hexane, xylene, and cyclohexane, ethers, amides such as dimethylformamide, esters such as ethyl acetate, ketones such as acetone, and nitriles such as acetonitrile or mixtures of two or more of these solvents. A suitable base is also added to the reaction vessel. Suitable bases include cesium carbonate, calcium carbonate, sodium carbonate and sodium bicarbonate. The base will normally be added in at least a stoichmetric quantity compared to the "Generic Amine-1" so as to neutralize liberated acid as it forms.

The "Generic Bromide-1" of Formula XXI is then added to the reaction vessel in portions so as to minimize the rate of heat evolution and minimize the concentration of the "Generic Bromide-1". The "Generic Bromide-1" will be selected from primary and secondary organic alkyl and substituted alkyl halide compounds. The halide will preferrably be a bromide although iodides and chlorides may also be generally used. One of skill in the art will also be able to readily select and utilize organic alkyl and substituted alkyl compounds containing readily displaceable primary and secondary groups such as tosylates, mesylates, triflates, and the like. Alternately, the halides can be generally prepared from the corresponding alcohols by reaction with, for example, concentrated hydrohalic acids such as HBr or by reaction with phosphorus trihalides such as $PBr_3$ as described in Fieser and Fieser in Reagents for Organic Synthesis, Volume 1, John Wiley & Sons, which are incorporated herein by reference. The appropriate alcohols can be converted to tosylates, mesylates, and triflates using procedures described below.

Addition of the "Generic Bromide-1" is carried out over a period of a few minutes to several hours at temperatures between 0 and 150° C. Preferably, the addition will take 30–120 minutes at a temperature of 0 to 50° C. The reaction can be stirred until completion. Completion can be monitored, for example, spectroscopically using nuclear magnetic resonance or chromatographically using thin layer, liquid, or gas chromatographic procedures. If the reaction does not proceed to completion, the reactants may be heated until completion is obtained and verified.

Isolation of the desired product can be accomplished, for example, when a water immiscible solvent was used for the reaction, by adding water to the finished reaction. Additional base such as sodium carbonate can be added to ensure the reaction is basic (pH of 9 to 11). The organic layer containing the "Generic Secondary Amine" is washed with saturated brine, dried with a drying agent such as anhydrous MgSO$_4$, and concentrated in vacuo to yield the "Generic Secondary Amine" amine, aniline, or amine of Formula XIII. If needed the "Generic Secondary Amine" amine, aniline, or amine derivative can be further purified by crystallization, distillation at reduced pressure, or liquid chromatography.

In a second synthetic alkylation scheme (Alkylation Method-2), a "Generic Amine-2" of Formula XXII is reacted with a "Generic Bromide-2" of Formula XXIII in a method employing pallladium catalyzed carbon-nitrogen bond formation. Suitable procedures for this conversion are described in Wagaw and Buchwald, J. Org. Chem.(1996), 61, 7240–7241, Wolfe, Wagaw and Buchwald, J. Am. Chem. Soc. (1996), 118, 7215–7216, and Wolfe and Buchwald, Tetrahedron Letters (1997), 38(36), 6359–6362 and references cited therein all of which are incorporated herein by reference. The preferred "Generic Bromide-2" of Formula XXIII are generally aryl bromides, aryl triflates, and heteroaryl bromides.

The "Generic Amine-1" and "Generic Amine-2" amines, hydroxylamines, and hydrazines, the "Generic Carbonyl Compound" aldehydes, ketones, hydrazones, and oximes, and "Generic Bromide-1" and "Generic Bromide-2" halides, tosylates, mesylates, triflates, and precursor alcohols required to prepare the "Generic Secondary Amine" compounds are available from commercial sources, can be prepared by one skilled in the art from published procedures, and/or can be obtained using specific procedures shown in Schemes 42, 43, and 44. Commercial sources include but are not limited to Aldrich Chemical, TCI-America, Lancaster-Synthesis, Oakwood Products, Acros Organics, and Maybridge Chemical. Disclosed procedures for "Generic Amine" amines, hydroxylamines, and hydrazines include Sheradsky and Nov, J. Chem. Soc., Perkin Trans.1 (1980), (12), 2781–6; Marcoux, Doye, and Buchwald, J. Am. Chem. Soc. (1997), 119, 1053–9; Sternbach and Jamison, Tetrahedron Lett. (1981), 22(35), 33314; U.S. Pat. No. 5,306,718; EP No. 314435; WO No. 9001874; WO No. 9002113; JP No. 05320117; WO No. 9738973; Swiss Patent No. CH 441366; U.S. Pat. Nos. 3,359,316 and 3,334,017; and references cited therein which are incorporated herein by reference. Representative specific "Generic Secondary Amine" of Formula XIII compounds useful for the preparation of compounds of the present invention are listed in Tables 3, 4, and 5.

As summarized in the general Scheme 1 and specific descriptions above, Schemes 3, 4, 9, and 10 illustrate the principles of Scheme 1 for the preparation of specifically substituted "Secondary Heteroaryl Amines" (XIIIA-H) having 0 to 2 aryl groups and 0 to 2 aromatic heterocyclyl groups and "Secondary Phenyl Amines" (XIII-A) having two aryl groups.

Synthetic Scheme 2 shows the preparation of the class of compounds of the present invention corresponding to Formula V-H ("Generic Substituted Polycyclic Aryl and Heteroaryl tertiary omegahydroxyalkylamines"), Formula V ("Generic Substituted Polycyclic Aryl tertiary omegahydroxyalkylamines"), Formula VII ("Generic Substituted Polycyclic Aryl tertiary-2-hydroxyalkylamines"), and Formula VII-H ("Generic Substituted Polycyclic Heteroaryl tertiary-2-hydroxyalkylamines") wherein A and Q are independently aryl and heteroaryl.

Derivatives of "Generic Substituted Polycyclic Aryl and Heteroaryl tertiary omegahydroxyalkylamines" and "Generic Substituted Polycyclic Aryl tertiary omegahydroxyalkylamines", wherein A and Q are independently aryl and heteroaryl, in which the hetero atom (—O—) is attached to an alkyl group removed from the amine by three or more carbons are readily prepared by anion chemistry using Method B of Scheme 2. The anion of "Generic Secondary Amine" amines, hydroxylamines, and hydrazines of Formula XIII are readily formed by dissolving the specific amine, hydroxylamine, or hydrazine in an aprotic solvent, such as tetrahydrofuran, toluene, ether, dimethylformamide, and dimethylformamide, under anhydrous conditions. The solution is cooled to a temperature between −78 and 0° C., preferably between −78 and −60° C. and the anion formed by the addition of at least one equivalent of a strong, aprotic, non-nucleophillic base such as NaH or n-butyllithium under an inert atmosphere for each acidic group present. Maintaining the temperature between −78 and 0° C., preferably between −78 and −60° C., with suitable cooling, an appropriate alkyl

TABLE 3

Structure of "Secondary Phenyl Amine" Reagents.

(XIIIA)

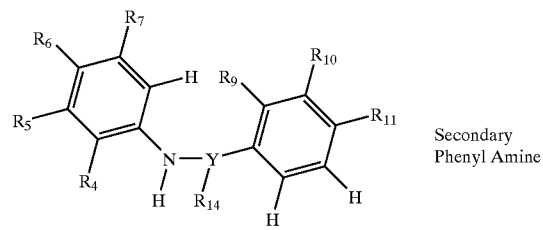

Secondary Phenyl Amine

| Reagent Number | R$_4$ | R$_5$ | R$_6$ | R$_7$ | R$_9$ | R$_{10}$ | R$_{11}$ | Y | R$_{14}$ |
|---|---|---|---|---|---|---|---|---|---|
| 1N | H | phenoxy | H | H | H | OCF$_2$CF$_2$H | H | CH | H |
| 2N | H | OCF$_3$ | H | H | H | OCF$_2$CF$_2$H | H | CH | H |
| 3N | F | H | H | F | H | OCF$_2$CF$_2$H | H | CH | H |
| 4N | H | F | H | H | H | OCF$_2$CF$_2$H | H | CH | H |
| 5N | H | phenoxy | H | H | H | OCF$_3$ | H | CH | H |

TABLE 3-continued

Structure of "Secondary Phenyl Amine" Reagents.

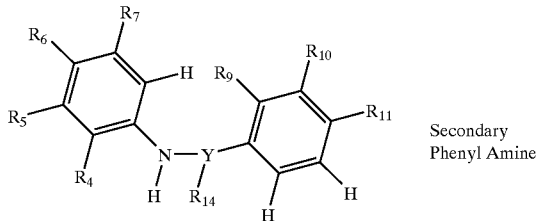

(XIIIA)

Secondary Phenyl Amine

| Reagent Number | $R_4$ | $R_5$ | $R_6$ | $R_7$ | $R_9$ | $R_{10}$ | $R_{11}$ | Y | $R_{14}$ |
|---|---|---|---|---|---|---|---|---|---|
| 6N | H | $OCF_3$ | H | H | H | $OCF_3$ | H | CH | H |
| 7N | H | H | phenyl | H | H | $OCF_3$ | H | CH | H |
| 8N | H | phenyl | H | H | H | $OCF_3$ | H | CH | H |
| 9N | H | H | H | H | H | $OCF_3$ | H | CH | H |
| 10N | H | Br | H | H | H | $OCF_3$ | H | CH | H |
| 11N | H | $CF_3$ | F | H | H | $CF_3$ | H | CH | H |
| 12N | H | $CH_3$ | H | H | H | $CF_3$ | H | CH | H |
| 13N | H | $CF_3$ | H | H | H | $CF_3$ | H | CH | H |
| 14N | H | $CH_3$ | H | H | H | $OCF_3$ | H | CH | H |
| 15N | H | F | F | H | H | $OCF_3$ | H | CH | H |
| 16N | H | Br | H | H | H | $CF_3$ | H | CH | H |
| 17N | H | $CF_3$ | F | H | H | $OCF_3$ | H | CH | H |
| 18N | H | F | H | H | H | $OCF_3$ | H | CH | H |
| 19N | H | Cl | H | H | H | $OCF_3$ | H | CH | H |
| 20N | H | F | H | H | H | $CF_3$ | H | CH | H |
| 21N | H | F | F | H | H | $CF_3$ | H | CH | H |
| 22N | H | Cl | H | H | H | $CF_3$ | H | CH | H |
| 23N | H | F | H | H | H | phenoxy | H | CH | H |
| 24N | H | $CF_3$ | Cl | H | H | $CH_3$ | H | CH | H |
| 25N | H | $CF_3$ | F | H | H | $CH_3$ | H | CH | H |
| 26N | H | H | H | H | H | $CF_3$ | H | CH | H |
| 27N | F | F | H | H | H | $CF_3$ | H | CH | H |
| 28N | H | H | $OCH_3$ | H | H | $CF_3$ | H | CH | H |
| 29N | H | F | F | H | H | $CH_3$ | H | CH | H |
| 30N | H | $OCH_3$ | H | H | H | $CH_3$ | H | CH | H |
| 31N | H | H | $CH_3$ | H | H | H | H | CH | H |
| 32N | H | Cl | H | H | H | H | H | CH | H |
| 33N | H | F | H | H | H | F | H | CH | H |
| 34N | H | H | $OCH_3$ | H | H | $CH_3$ | H | CH | H |
| 35N | H | H | H | H | H | H | H | CH | H |
| 36N | H | H | $CH_3$ | H | H | $CH_3$ | H | CH | H |
| 37N | H | H | Cl | H | H | H | H | CH | H |
| 38N | H | F | H | H | H | 3-$CF_3$-phenoxy | H | CH | H |
| 39N | H | F | H | H | H | 4-$CH_3$O-phenoxy | H | CH | H |
| 40N | H | F | H | H | H | 4-Cl-phenoxy | H | CH | H |
| 41N | H | F | H | H | H | H | H | CH | H |
| 42N | H | F | H | H | H | $CH_3$ | H | CH | H |
| 43N | H | F | H | F | H | $CH_3$ | H | CH | H |
| 44N | F | F | H | H | H | $CH_3$ | H | CH | H |
| 45N | H | Cl | H | H | H | $CH_3$ | H | CH | H |
| 46N | H | $CH_3$ | H | H | H | $CH_3$ | H | CH | H |
| 48N | H | H | $CH_3$ | H | H | $CF_3$ | H | CH | H |
| 51N | H | H | $CH_3$ | H | H | F | H | CH | H |
| 52N | H | $CF_3$ | H | H | H | F | H | CH | H |
| 53N | H | $CF_3$ | H | H | H | $CH_3$ | H | CH | H |
| 54N | H | $OCH_3$ | H | H | H | $CF_3$ | H | CH | H |
| 56N | H | H | $CH_3$ | H | H | $CF_3$ | H | CH | H |
| 57N | H | phenoxy | H | H | H | H | $OCF_3$ | CH | H |
| 58N | H | H | H | H | H | H | $OCF_3$ | CH | H |
| 59N | H | $OCF_3$ | H | H | H | H | $OCF_3$ | CH | H |
| 60N | H | $CF_3$ | F | H | H | H | $CF_3$ | CH | H |
| 61N | H | H | $OCH_3$ | H | H | H | $CF_3$ | CH | H |
| 62N | H | $CH_3$ | H | H | H | H | $CF_3$ | CH | H |
| 63N | H | Cl | H | H | H | H | $CF_3$ | CH | H |
| 64N | H | $CF_3$ | H | H | H | H | $OCF_3$ | CH | H |
| 65N | H | F | H | H | H | H | $OCF_3$ | CH | H |
| 66N | H | F | H | F | H | H | $OCF_3$ | CH | H |
| 67N | H | Br | H | H | H | H | $OCF_3$ | CH | H |
| 68N | H | Cl | H | H | H | H | $OCF_3$ | CH | H |
| 69N | H | F | F | H | H | H | $OCF_3$ | CH | H |
| 70N | H | F | H | H | H | H | phenyl | CH | H |

TABLE 3-continued

Structure of "Secondary Phenyl Amine" Reagents.

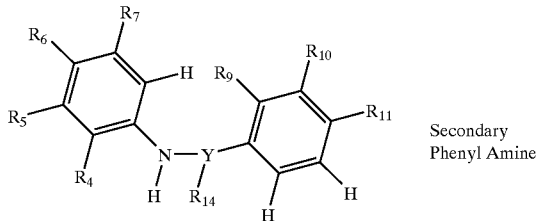

(XIIIA) Secondary Phenyl Amine

| Reagent Number | R$_4$ | R$_5$ | R$_6$ | R$_7$ | R$_9$ | R$_{10}$ | R$_{11}$ | Y | R$_{14}$ |
|---|---|---|---|---|---|---|---|---|---|
| 71N | H | CH$_3$ | H | H | H | H | OCF$_3$ | CH | H |
| 72N | H | F | F | H | H | H | CF$_3$ | CH | H |
| 73N | H | Cl | H | H | H | H | CH$_3$ | CH | H |
| 74N | H | OCH$_3$ | H | H | H | H | CH$_3$ | CH | H |
| 75N | H | F | H | H | H | H | CH$_3$ | CH | H |
| 76N | F | F | H | H | H | H | OCF$_3$ | CH | H |
| 78N | H | H | OCH$_3$ | H | H | H | CH$_3$ | CH | H |
| 79N | H | H | CH$_3$ | H | H | H | CH$_3$ | CH | H |
| 80N | H | CH$_3$ | H | H | H | H | CH$_3$ | CH | H |
| 82N | H | F | F | H | H | H | CH$_3$ | CH | H |
| 83N | H | F | H | F | H | H | CH$_3$ | CH | H |
| 84N | F | F | H | H | H | H | CH$_3$ | CH | H |
| 85N | F | CF$_3$ | H | H | H | H | CH$_3$ | CH | H |
| 86N | H | H | CH$_3$ | H | H | H | CF$_3$ | CH | H |
| 88N | H | CF$_3$ | H | H | H | H | CH$_3$ | CH | H |
| 90N | H | H | CF$_3$ | H | H | H | CH$_3$ | CH | H |
| 92N | H | CF$_3$ | F | H | H | H | CH$_3$ | CH | H |

TABLE 4

Structure of "Secondary Phenyl Amine" Reagents (Z is covalent bond; there is no R$_{15}$ substituent; R$_4$ and R$_{13}$ equal H).

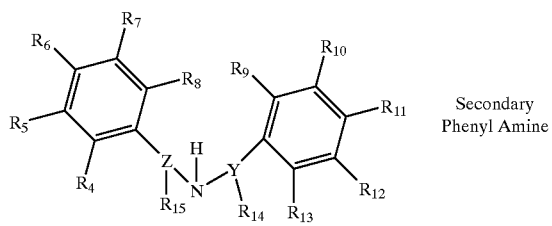

(XIII-A) Secondary Phenyl Amine

| Rgnt. No. | R$_5$ | R$_6$ | R$_7$ | R$_8$ | Y | R$_{14}$ | R$_9$ | R$_{10}$ | R$_{11}$ | R$_{12}$ | Spacer | Spacer Bond Points |
|---|---|---|---|---|---|---|---|---|---|---|---|---|
| 93N | Br | H | H | | CH | H | | H | H | OCF$_3$ | —O— | R$_8$ + R$_9$ |
| 94N | OCF$_3$ | H | H | | CH | H | | H | H | OCF$_3$ | — | R$_8$ + R$_9$ |
| 95N | Br | H | H | | C | | H | OCF$_3$ | H | H | =CH— | R$_8$ + R$_{14}$ |
| 96N | OH | OH | H | H | CH | H | H | C$_6$H$_5$O | H | H | none | none |
| 97N | C$_6$H$_5$O | H | H | H | CH | H | H | OH | OH | H | none | none |
| 98N | 3-pyridyl | H | H | H | CH | H | H | CF$_3$ | H | H | none | none |
| 99N | SO$_2$N(CH$_3$)$_2$ | H | H | H | CH | H | H | OCF$_3$ | H | H | none | none |
| 100N | SO$_2$CH$_3$ | H | H | H | CH | H | H | OCF$_3$ | H | H | none | none |
| 101N | C$_6$H$_5$O | H | H | H | CH | H | H | C$_6$H$_5$O | H | H | none | none |
| 102N | CF$_3$O | H | H | H | CH | H | H | C$_6$H$_5$O | H | H | none | none |
| 103N | C$_6$H$_5$ | H | H | H | CH | H | H | C$_6$H$_5$O | H | H | none | none |
| 104N | H | C$_6$H$_5$ | H | H | CH | H | H | C$_6$H$_5$O | H | H | none | none |
| 105N | C$_6$H$_5$O | H | H | H | CH | H | H | 4-Cl—C$_6$H$_4$O | H | H | none | none |
| 106N | CF$_3$O | H | H | H | CH | H | H | 4-Cl—C$_6$H$_4$O | H | H | none | none |
| 107N | C$_6$H$_5$O | H | H | H | CH | H | H | 3,4-Cl—C$_6$H$_3$O | H | H | none | none |
| 108N | CF$_3$O | H | H | H | CH | H | H | 3,4-Cl—C$_6$H$_3$O | H | H | none | none |
| 109N | CF$_3$O | H | H | H | CH | H | H | 3,5-Cl—C$_6$H$_3$O | H | H | none | none |
| 110N | CF$_3$O | H | H | H | CH | H | H | 3-CH$_3$O—C$_6$H$_4$O | H | H | none | none |

TABLE 4-continued

Structure of "Secondary Phenyl Amine" Reagents (Z is covalent bond; there is no $R_{15}$ substituent; $R_4$ and $R_{13}$ equal H).

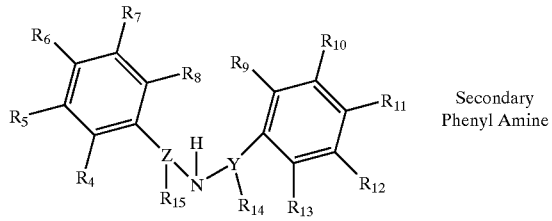

(XIII-A)

Secondary Phenyl Amine

| Rgnt. No. | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 111N | $CF_3O$ | H | H | H | CH | H | H | H | 3-$CH_3O$—$C_6H_4O$ | H | none | none |
| 112N | $CF_3O$ | H | H | H | CH | H | H | 3-$CF_3$—$C_6H_4O$ | H | H | none | none |
| 113N | $CF_3O$ | H | H | H | CH | H | H | $C_6H_5$—$CH_2O$ | H | H | none | none |
| 114N | $CF_3O$ | H | H | H | CH | H | H | $C_6H_5$—$CH_2O$ | $CH_3O$ | H | none | none |
| 115N | $CF_3O$ | H | H | H | CH | H | H | $C_6H_5$—$CH_2O$ | $C_6H_5$—$CH_2O$ | H | none | none |
| 116N | $CF_3O$ | H | H | H | CH | H | H | ethoxy | H | H | none | none |
| 117N | $CF_3O$ | H | H | H | CH | H | H | $CH_3CO_2$ | H | H | none | none |
| 118N | $CF_3O$ | H | H | H | CH | H | H | $HOCH_2$—$CH_2O$ | H | H | none | none |
| 119N | $CF_3O$ | H | H | H | CH | H | H | (glycidyloxy) | H | H | none | none |
| 120N | $CF_3O$ | H | H | H | CH | H | H | $R_{10} + R_{11} = OCH_2O$ | | H | none | none |
| 121N | $CF_3O$ | H | H | H | CH | H | H | $R_{10} = R_{11} = OCH_2CH_2O$ | | H | none | none |
| 122N | $CF_3O$ | H | H | H | CH | H | H | $CH_3O$ | $CH_3O$ | H | none | none |
| 123N | $CF_3O$ | H | H | H | CH | H | H | ethoxy | $CH_3O$ | H | none | none |
| 124N | $CF_3O$ | H | H | H | CH | H | H | ethoxy | ethoxy | H | none | none |
| 125N | $CF_3O$ | H | H | H | CH | H | H | $CH_3CO_2$ | $CH_3CO_2$ | H | none | none |
| 126N | $CF_3O$ | H | H | H | CH | H | H | $CH_3O$ | $CH_3CO_2$ | H | none | none |
| 127N | $CF_3O$ | H | H | H | CH | H | H | n-butoxy | H | H | none | none |
| 128N | $CF_3O$ | H | H | H | CH | H | H | $CH_3O$ | H | H | none | none |
| 129N | $CF_3O$ | H | H | H | CH | H | H | H | $CH_3O$ | H | none | none |
| 130N | $CH_3O$ | H | H | H | CH | H | H | $CH_3O$ | H | H | none | none |
| 131N | $CH_3O$ | H | H | H | CH | H | H | H | $CF_3O$ | H | none | none |
| 132N | $CF_3O$ | H | H | H | CH | H | H | H | ethoxy | H | none | none |
| 133N | $CF_3O$ | H | H | H | CH | H | H | H | n-propoxy | H | none | none |
| 134N | $C_6H_5$—$CH_2O$ | H | H | H | CH | H | H | $CF_3O$ | H | H | none | none |
| 135N | $C_6H_5$—$CH_2O$ | H | H | H | CH | H | H | $C_6H_5O$ | H | H | none | none |
| 136N | ethoxy | H | H | H | CH | H | H | $CF_3O$ | H | H | none | none |
| 137N | $R_5 + R_6 = OCH_2O$ | | H | H | CH | H | H | $CF_3O$ | H | H | none | none |
| 138N | $R_5 + R_6 = OCH_2O$ | | H | H | CH | H | H | $C_6H_5O$ | H | H | none | none |
| 139N | $R_5 + R_6 = OCH_2CH_2O$ | | H | H | CH | H | H | $CF_3O$ | H | H | none | none |
| 140N | $CH_3O$ | $CH_3O$ | H | H | CH | H | H | $CF_3O$ | H | H | none | none |
| 141N | $R_5 + R_6 = OCH_2CH_2CH_2O$ | | H | H | CH | H | H | $CF_3O$ | H | H | none | none |
| 142N | cyclo pentoxy | $CH_3O$ | H | H | CH | H | H | $CF_3O$ | H | H | none | none |
| 143N | H | $C_6H_5O$ | H | H | CH | H | H | $CF_3O$ | H | H | none | none |
| 144N | $CH_3O$ | $CH_3O$ | $CH_3O$ | H | CH | H | H | $CF_3O$ | H | H | none | none |
| 145N | H | $CF_3O$ | H | H | CH | H | H | $CF_3O$ | H | H | none | none |
| 146N | H | Benzyl | H | H | CH | H | H | $CF_3O$ | H | H | none | none |
| 147N | $C_6H_5O$ | H | H | H | CH | H | H | $R_{10} + R_{11} = OCH_2CH_2O$ | | H | none | none |
| 148N | H | $CF_3O$ | H | H | CH | H | H | $CF_3$ | H | H | none | none |
| 149N | $C_6H_5O$ | H | H | H | CH | H | H | $CF_3$ | H | H | none | none |
| 150N | $C_6H_5$ | H | H | H | CH | H | H | $CF_3$ | H | H | none | none |
| 151N | H | $C_6H_5$ | H | H | CH | H | H | $CF_3$ | H | H | none | none |
| 152N | CN | H | H | H | CH | H | H | $CF_3$ | H | H | none | none |
| 153N | H | $OCF_3$ | H | H | CH | H | H | $CF_3$ | H | H | none | none |
| 154N | $OCF_3$ | H | H | H | CH | H | H | H | $CF_3$ | H | none | none |
| 155N | $C_6H_5O$ | H | H | H | CH | H | H | H | $CF_3$ | H | none | none |
| 156N | $C_6H_5$ | H | H | H | CH | H | H | H | $CF_3$ | H | none | none |
| 157N | H | $C_6H_5$ | H | H | CH | H | H | H | $CF_3$ | H | none | none |
| 158N | CN | H | H | H | CH | H | H | H | $CF_3$ | H | none | none |
| 159N | $OCF_3$ | H | H | H | CH | H | H | H | $CF_3$ | H | none | none |
| 160N | $CF_3$ | H | H | H | CH | H | H | H | $C_6H_5$ | H | none | none |
| 161N | $CF_3$ | H | H | H | CH | H | H | 3-$CF_3$—$C_6H_5O$ | H | H | none | none |

TABLE 4-continued

Structure of "Secondary Phenyl Amine" Reagents (Z is covalent bond; there is no $R_{15}$ substituent; $R_4$ and $R_{13}$ equal H).

(XIII-A)

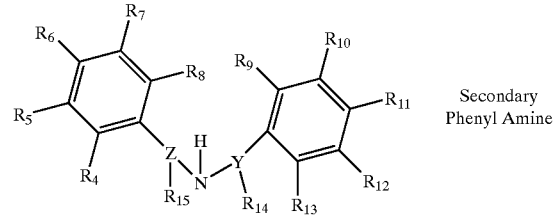

Secondary Phenyl Amine

| Rgnt. No. | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 162N | $CF_3$ | H | H | H | CH | H | H | $C_6H_5O$ | H | H | none | none |
| 163N | $CF_3$ | H | H | H | CH | H | H | $CF_3O$ | H | H | none | none |
| 164N | H | $CF_3$ | H | H | CH | H | H | H | $C_6H_5$ | H | none | none |
| 165N | H | $CF_3$ | H | H | CH | H | H | 3-$CF_3$—$C_6H_5O$ | H | H | none | none |
| 166N | H | $CF_3$ | H | H | CH | H | H | $CF_3O$ | H | H | none | none |
| 167N | H | $CF_3$ | H | H | CH | H | H | $C_6H_5O$ | H | H | none | none |
| 168N | $CF_3$ | H | $CF_3$ | H | CH | H | H | $CF_3O$ | H | H | none | none |
| 169N | $CF_3$ | H | $CF_3$ | H | CH | H | H | $C_6H_5O$ | H | H | none | none |
| 170N | $CF_3O$ | H | H | H | CH | H | H | $CF_3$ | H | $CF_3$ | none | none |
| 171N | $C_6H_5O$ | H | H | H | CH | H | H | $CF_3$ | H | $CF_3$ | none | none |
| 172N | H | $C_6H_5O$ | H | H | CH | H | H | $C_6H_5O$ | H | H | none | none |
| 173N | H | $CF_3O$ | H | H | CH | H | H | $CF_3O$ | H | H | none | none |
| 174N | H | $CF_3O$ | H | H | CH | H | H | H | $C_6H_5O$ | H | none | none |
| 175N | $C_6H_5O$ | H | H | H | CH | H | H | H | $C_6H_5O$ | H | none | none |
| 176N | H | $C_6H_5O$ | H | H | CH | H | H | H | $OCF_3$ | H | none | none |
| 177N | H | $C_6H_5O$ | H | H | CH | H | H | H | $C_6H_5O$ | H | none | none |
| 178N | $C_6H_5O$ | H | H | H | CH | H | H | H | CN | H | none | none |
| 179N | $C_6H_5O$ | H | H | H | CH | H | H | CN | H | H | none | none |
| 180N | $C_6H_5O$ | H | H | H | CH | H | H | $NO_2$ | H | H | none | none |
| 181N | $C_6H_5O$ | H | H | H | CH | H | H | H | $NO_2$ | H | none | none |
| 182N | $C_6H_5O$ | H | H | H | CH | H | H | H | $SO_2CH_3$ | H | none | none |
| 183N | $C_6H_5O$ | H | H | H | CH | H | H | H | 2-$NO_2$-4-Cl—$C_6H_3O$ | H | none | none |
| 184N | $C_6H_5O$ | H | H | H | CH | H | H | 4-Cl—$C_6H_4O$ | H | H | none | none |
| 185N | $C_6H_5O$ | H | H | H | CH | H | H | 3,4-Cl—$C_6H_3O$ | H | H | none | none |
| 186N | $C_6H_5O$ | H | H | H | CH | H | H | 3-$CF_3$—$C_6H_3O$ | H | H | none | none |
| 187N | $C_6H_5O$ | H | H | H | CH | H | H | 3,5-Cl—$C_6H_3O$ | H | H | none | none |
| 188N | $C_6H_5O$ | H | H | H | CH | H | H | H | $CH_3O$ | H | none | none |
| 189N | $C_6H_5O$ | H | H | H | CH | H | H | H | $CO_2CH_3$ | H | none | none |
| 190N | $C_6H_5O$ | H | H | H | CH | H | H | 3-$CH_3O$—$C_6H_5O$ | H | H | none | none |
| 191N | $C_6H_5O$ | H | H | H | CH | H | H | 4-$CH_3O$—$C_6H_5O$ | H | H | none | none |
| 193N | $C_6H_5O$ | H | H | H | CH | H | H | $CO_2CH_3$ | H | H | none | none |
| 194N | CN | H | H | H | CH | H | H | $OCF_3$ | H | H | none | none |
| 195N | $NO_2$ | H | H | H | CH | H | H | $OCF_3$ | H | H | none | none |
| 196N | H | CN | H | H | CH | H | H | $OCF_3$ | H | H | none | none |
| 197N | H | $NO_2$ | H | H | CH | H | H | $OCF_3$ | H | H | none | none |
| 198N | $SO_2CH_3$ | H | H | H | CH | H | H | $OCF_3$ | H | H | none | none |
| 199N | H | $SO_2CH_3$ | H | H | CH | H | H | $OCF_3$ | H | H | none | none |
| 200N | H | 4-F—$C_6H_5SO_2$ | H | H | CH | H | H | $OCF_3$ | H | H | none | none |
| 201N | $SO_2N(CH_3)_2$ | H | H | H | CH | H | H | $OCF_3$ | H | H | none | none |
| 202N | H | $SO_2N(CH_3)_2$ | H | H | CH | H | H | $OCF_3$ | H | H | none | none |
| 203N | H | $CONH_2$ | H | H | CH | H | H | $OCF_3$ | H | H | none | none |
| 204N | H | CONH—$C_6H_5$ | H | H | CH | H | H | $OCF_3$ | H | H | none | none |
| 205N | H | $CO_2CH_3$ | H | H | CH | H | H | $OCF_3$ | H | H | none | none |
| 206N | H | $CO_2C_4H_9$ | H | H | CH | H | H | $OCF_3$ | H | H | none | none |
| 207N | H | 4-Cl—$C_6H_5$ | H | H | CH | H | H | $C_6H_5O$ | H | H | none | none |
| 208N | H | 4-$CF_3O$—$C_6H_5$ | H | H | CH | H | H | $CF_3O$ | H | H | none | none |
| 209N | 4-F—$C_6H_4O$ | H | H | H | CH | H | H | $CF_3O$ | H | H | none | none |
| 210N | $C_6F_5O$ | H | H | H | CH | H | H | $CF_3O$ | H | H | none | none |
| 211N | H | 4-F—$C_6H_5$ | H | H | CH | H | H | $CF_3O$ | H | H | none | none |
| 212N | H | 4-CN—$C_6H_5$ | H | H | CH | H | H | $CF_3O$ | H | H | none | none |

TABLE 4-continued

Structure of "Secondary Phenyl Amine" Reagents (Z is covalent bond; there is no $R_{15}$ substituent; $R_4$ and $R_{13}$ equal H).

(XIII-A)

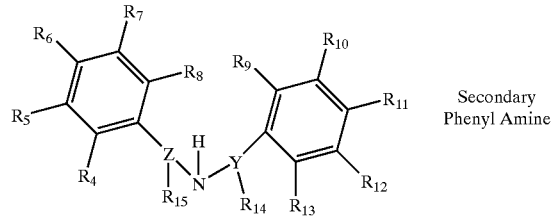

| Rgnt. No. | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 213N | H | 4-$C_6H_5$—$C_6H_5$ | H | H | CH | H | H | $CF_3O$ | H | H | none | none |
| 214N | $C_6H_5O$ | H | H | H | CH | $CH_3$ | H | $CF_3O$ | H | H | none | none |
| 215N | $C_6H_5O$ | H | H | H | CH | $CH_3$ | H | $NO_2$ | H | H | none | none |
| 216N | $C_6H_5O$ | H | H | H | CH | $CH_3$ | H | H | CN | H | none | none |
| 217N | $C_6H_5O$ | H | H | H | CH | 3-$CF_3$ $C_6H_5$ | H | $CF_3$ | H | H | none | none |
| 218N | $C_6H_5O$ | H | H | H | CH | $C_6H_5$ | H | H | $C_6H_5$ | H | none | none |
| 219N | $C_6H_5O$ | H | H | H | CH | $C_6H_5$ | H | $CF_3$ | H | H | none | none |
| 220N | $C_6H_5O$ | H | H | H | CH | $CH_3$ | H | F | H | H | none | none |
| 221N | $C_6H_5O$ | H | H | H | CH | $CF_3$ | H | H | H | H | none | none |
| 222N | bond to —O— of $R_6$ aryl group | (2-methyl phenoxy structure) | H | H | CH | H | H | $CF_3O$ | H | H | none | none |
| 223N | to $CH_2$ of $R_6$ aryl group | (bromo-ethyl-methyl phenyl structure) | H | H | CH | H | H | $CF_3O$ | H | H | none | none |
| 224N | $C_6H_5O$ | H | H | H | CH | H | H | $OCF_2CF_2H$ | H | H | none | none |
| 225N | 4-Cl—$C_6H_5O$ | H | H | H | CH | H | H | $OCF_2CF_2H$ | H | H | none | none |
| 226N | 4-F—$C_6H_5O$ | H | H | H | CH | H | H | $OCF_2CF_2H$ | H | H | none | none |
| 227N | 3,4-Cl—$C_6H_5O$ | H | H | H | CH | H | H | $OCF_2CF_2H$ | H | H | none | none |
| 228N | H | $C_6H_5$ | H | H | CH | H | H | $OCF_2CF_2H$ | H | H | none | none |
| 229N | H | 4-Cl—$C_6H_5$ | H | H | CH | H | H | $OCF_2CF_2H$ | H | H | none | none |
| 230N | H | 4-F—$C_6H_5$ | H | H | CH | H | H | $OCF_2CF_2H$ | H | H | none | none |
| 231N | H | 4-Br—$C_6H_5$ | H | H | CH | H | H | $OCF_2CF_2H$ | H | H | none | none |
| 232N | 4-Br—$C_6H_5O$ | H | H | H | CH | H | H | $OCF_2CF_2H$ | H | H | none | none |
| 233N | $C_6H_5O$ | H | H | H | CH | H | H | $OCF_2CF_3$ | H | H | none | none |
| 234N | 4-Cl—$C_6H_5O$ | H | H | H | CH | H | H | $OCF_2CF_3$ | H | H | none | none |
| 235N | 4-F—$C_6H_5O$ | H | H | H | CH | H | H | $OCF_2CF_3$ | H | H | none | none |
| 236N | 3,4-Cl—$C_6H_5O$ | H | H | H | CH | H | H | $OCF_2CF_3$ | H | H | none | none |
| 237N | H | $C_6H_5$ | H | H | CH | H | H | $OCF_2CF_3$ | H | H | none | none |
| 238N | H | 4-Cl—$C_6H_5$ | H | H | CH | H | H | $OCF_2CF_3$ | H | H | none | none |
| 239N | H | 4-F—$C_6H_5$ | H | H | CH | H | H | $OCF_2CF_3$ | H | H | none | none |
| 240N | H | 4-Br—$C_6H_5$ | H | H | CH | H | H | $OCF_2CF_3$ | H | H | none | none |
| 241N | 4-Br—$C_6H_5O$ | H | H | H | CH | H | H | $OCF_2CF_3$ | H | H | none | none |
| 242N | $C_6H_5O$ | H | H | H | CH | H | H | $OCCl_2CCl_2H$ | H | H | none | none |
| 243N | 4-Cl—$C_6H_5O$ | H | H | H | CH | H | H | $OCCl_2CCl_2H$ | H | H | none | none |
| 244N | 4-F—$C_6H_5O$ | H | H | H | CH | H | H | $OCCl_2CCl_2H$ | H | H | none | none |
| 245N | 3,4-Cl—$C_6H_5O$ | H | H | H | CH | H | H | $OCCl_2CCl_2H$ | H | H | none | none |

TABLE 4-continued

Structure of "Secondary Phenyl Amine" Reagents (Z is covalent bond; there is no $R_{15}$ substituent; $R_4$ and $R_{13}$ equal H).

(XIII-A)

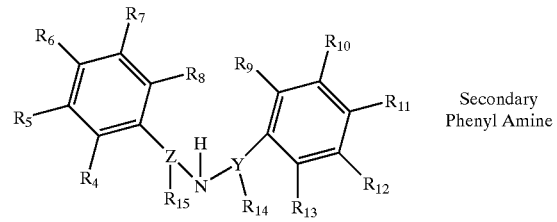

Secondary Phenyl Amine

| Rgnt. No. | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 246N | H | $C_6H_5$ | H | H | CH | H | H | $OCCl_2CCl_2H$ | H | H | none | none |
| 247N | H | 4-Cl—$C_6H_5$ | H | H | CH | H | H | $OCCl_2CCl_2H$ | H | H | none | none |
| 248N | H | 4-F—$C_6H_5$ | H | H | CH | H | H | $OCCl_2CCl_2H$ | H | H | none | none |
| 249N | H | 4-Br—$C_6H_5$ | H | H | CH | H | H | $OCCl_2CCl_2H$ | H | H | none | none |
| 250N | 4-Br—$C_6H_5$ | H | H | H | CH | H | H | $OCCl_2CCl_2H$ | H | H | none | none |
| 251N | $C_6H_5O$ | H | H | H | CH | H | H | $OCCl_2CCl_3$ | H | H | none | none |
| 252N | 4-Cl—$C_6H_5O$ | H | H | H | CH | H | H | $OCCl_2CCl_3$ | H | H | none | none |
| 253N | 4-F—$C_6H_5O$ | H | H | H | CH | H | H | $OCCl_2CCl_3$ | H | H | none | none |
| 254N | 3,4-Cl—$C_6H_5O$ | H | H | H | CH | H | H | $OCCl_2CCl_3$ | H | H | none | none |
| 255N | H | $C_6H_5$ | H | H | CH | H | H | $OCCl_2CCl_3$ | H | H | none | none |
| 256N | H | 4-Cl—$C_6H_5$ | H | H | CH | H | H | $OCCl_2CCl_3$ | H | H | none | none |
| 257N | H | 4-F—$C_6H_5$ | H | H | CH | H | H | $OCCl_2CCl_3$ | H | H | none | none |
| 258N | H | 4-Br—$C_6H_5$ | H | H | CH | H | H | $OCCl_2CCl_3$ | H | H | none | none |
| 259N | 4-Br—$C_6H_5O$ | H | H | H | CH | H | H | $OCCl_2CCl_3$ | H | H | none | none |
| 260N | $C_6H_5O$ | H | H | H | CH | H | H | $OCCl_2CF_3$ | H | H | none | none |
| 261N | 4-Cl—$C_6H_5O$ | H | H | H | CH | H | H | $OCCl_2CF_3$ | H | H | none | none |
| 262N | 4-F—$C_6H_5O$ | H | H | H | CH | H | H | $OCCl_2CF_3$ | H | H | none | none |
| 263N | 3,4-Cl—$C_6H_5O$ | H | H | H | CH | H | H | $OCCl_2CF_3$ | H | H | none | none |
| 264N | H | $C_6H_5$ | H | H | CH | H | H | $OCCl_2CF_3$ | H | H | none | none |
| 265N | H | 4-Cl—$C_6H_5$ | H | H | CH | H | H | $OCCl_2CF_3$ | H | H | none | none |
| 266N | H | 4-F—$C_6H_5$ | H | H | CH | H | H | $OCCl_2CF_3$ | H | H | none | none |
| 267N | H | 4-Br—$C_6H_5$ | H | H | CH | H | H | $OCCl_2CF_3$ | H | H | none | none |
| 268N | 4-Br—$C_6H_5O$ | H | H | H | CH | H | H | $OCCl_2CF_3$ | H | H | none | none |
| 269N | $C_6H_5O$ | H | H | H | CH | H | H | $OCF_2CCl_3$ | H | H | none | none |
| 270N | 4-Cl—$C_6H_5O$ | H | H | H | CH | H | H | $OCF_2CCl_3$ | H | H | none | none |
| 271N | 4-F—$C_6H_5O$ | H | H | H | CH | H | H | $OCF_2CCl_3$ | H | H | none | none |
| 272N | 3,4-Cl—$C_6H_5O$ | H | H | H | CH | H | H | $OCF_2CCl_3$ | H | H | none | none |
| 273N | H | $C_6H_5$ | H | H | CH | H | H | $OCF_2CCl_3$ | H | H | none | none |
| 274N | H | 4-Cl—$C_6H_5$ | H | H | CH | H | H | $OCF_2CCl_3$ | H | H | none | none |
| 275N | H | 4-F—$C_6H_5$ | H | H | CH | H | H | $OCF_2CCl_3$ | H | H | none | none |
| 276N | H | 4-Br—$C_6H_5$ | H | H | CH | H | H | $OCF_2CCl_3$ | H | H | none | none |
| 277N | 4-Br—$C_6H_5O$ | H | H | H | CH | H | H | $OCF_2CCl_3$ | H | H | none | none |
| 278N | $C_6H_5O$ | H | H | H | CH | H | H | $OCF_2CF_2H$ | $OCF_2CF_2H$ | H | none | none |
| 279N | 4-Cl—$C_6H_5O$ | H | H | H | CH | H | H | $OCF_2CF_2H$ | $OCF_2CF_2H$ | H | none | none |
| 280N | 4-F—$C_6H_5O$ | H | H | H | CH | H | H | $OCF_2CF_2H$ | $OCF_2CF_2H$ | H | none | none |
| 281N | 3,4-Cl—$C_6H_5O$ | H | H | H | CH | H | H | $OCF_2CF_2H$ | $OCF_2CF_2H$ | H | none | none |
| 282N | H | $C_6H_5$ | H | H | CH | H | H | $OCF_2CF_2H$ | $OCF_2CF_2H$ | H | none | none |
| 283N | H | 4-Cl—$C_6H_5$ | H | H | CH | H | H | $OCF_2CF_2H$ | $OCF_2CF_2H$ | H | none | none |
| 284N | H | 4-F—$C_6H_5$ | H | H | CH | H | H | $OCF_2CF_2H$ | $OCF_2CF_2H$ | H | none | none |
| 285N | H | 4-Br—$C_6H_5$ | H | H | CH | H | H | $OCF_2CF_2H$ | $OCF_2CF_2H$ | H | none | none |
| 286N | 4-Br—$C_6H_5O$ | H | H | H | CH | H | H | $OCF_2CF_2H$ | $OCF_2CF_2H$ | H | none | none |
| 287N | $C_6H_5O$ | H | H | H | CH | H | H | $OCF_3$ | $OCF_3$ | H | none | none |
| 288N | 4-Cl—$C_6H_5O$ | H | H | H | CH | H | H | $OCF_3$ | $OCF_3$ | H | none | none |
| 289N | 4-F—$C_6H_5O$ | H | H | H | CH | H | H | $OCF_3$ | $OCF_3$ | H | none | none |
| 290N | 3,4-Cl—$C_6H_5O$ | H | H | H | CH | H | H | $OCF_3$ | $OCF_3$ | H | none | none |
| 291N | H | $C_6H_5$ | H | H | CH | H | H | $OCF_3$ | $OCF_3$ | H | none | none |
| 292N | H | 4-Cl—$C_6H_5$ | H | H | CH | H | H | $OCF_3$ | $OCF_3$ | H | none | none |
| 293N | H | 4-F—$C_6H_5$ | H | H | CH | H | H | $OCF_3$ | $OCF_3$ | H | none | none |
| 294N | H | 4-Br—$C_6H_5$ | H | H | CH | H | H | $OCF_3$ | $OCF_3$ | H | none | none |
| 295N | 4-Br—$C_6H_5O$ | H | H | H | CH | H | H | $OCF_3$ | $OCF_3$ | H | none | none |

TABLE 4-continued

Structure of "Secondary Phenyl Amine" Reagents (Z is covalent bond; there is no $R_{15}$ substituent; $R_4$ and $R_{13}$ equal H).

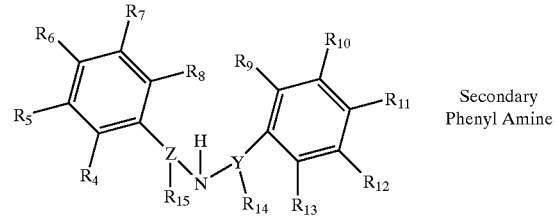

(XIII-A)

| Rgnt. No. | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 296N | $C_6H_5O$ | H | H | H | CH | H | H | $OCF_2H$ | $OCF_2H$ | H | none | none |
| 297N | 4-Cl—$C_6H_5O$ | H | H | H | CH | H | H | $OCF_2H$ | $OCF_2H$ | H | none | none |
| 298N | 4-F—$C_6H_5O$ | H | H | H | CH | H | H | $OCF_2H$ | $OCF_2H$ | H | none | none |
| 299N | 3,4-Cl—$C_6H_5O$ | H | H | H | CH | H | H | $OCF_2H$ | $OCF_2H$ | H | none | none |
| 300N | H | $C_6H_5$ | H | H | CH | H | H | $OCF_2H$ | $OCF_2H$ | H | none | none |
| 301N | H | 4-Cl—$C_6H_5$ | H | H | CH | H | H | $OCF_2H$ | $OCF_2H$ | H | none | none |
| 302N | H | 4-F—$C_6H_5$ | H | H | CH | H | H | $OCF_2H$ | $OCF_2H$ | H | none | none |
| 303N | H | 4-Br—$C_6H_5$ | H | H | CH | H | H | $OCF_2H$ | $OCF_2H$ | H | none | none |
| 304N | 4-Br—$C_6H_5O$ | H | H | H | CH | H | H | $OCF_2H$ | $OCF_2H$ | H | none | none |
| 305N | $C_6H_5O$ | H | H | H | CH | H | H | $R_{10} + R_{11} = OCF_2CF_2O$ | | H | none | none |
| 306N | 4-Cl—$C_6H_5O$ | H | H | H | CH | H | H | $R_{10} + R_{11} = OCF_2CF_2O$ | | H | none | none |
| 307N | 4-F—$C_6H_5O$ | H | H | H | CH | H | H | $R_{10} + R_{11} = OCF_2CF_2O$ | | H | none | none |
| 308N | 3,4-Cl—$C_6H_5O$ | H | H | H | CH | H | H | $R_{10} + R_{11} = OCF_2CF_2O$ | | H | none | none |
| 309N | H | $C_6H_5$ | H | H | CH | H | H | $R_{10} + R_{11} = OCF_2CF_2O$ | | H | none | none |
| 310N | H | 4-Cl—$C_6H_5$ | H | H | CH | H | H | $R_{10} + R_{11} = OCF_2CF_2O$ | | H | none | none |
| 311N | H | 4-F—$C_6H_5$ | H | H | CH | H | H | $R_{10} + R_{11} = OCF_2CF_2O$ | | H | none | none |
| 312N | H | 4-Br—$C_6H_5$ | H | H | CH | H | H | $R_{10} + R_{11} = OCF_2CF_2O$ | | H | none | none |
| 313N | 4-Br—$C_6H_5O$ | H | H | H | CH | H | H | $R_{10} + R_{11} = OCF_2CF_2O$ | | H | none | none |
| 314N | $C_6H_5O$ | H | H | H | CH | H | H | $R_{10} + R_{11} = OCCl_2CCl_2O$ | | H | none | none |
| 315N | 4-Cl—$C_6H_5O$ | H | H | H | CH | H | H | $R_{10} + R_{11} = OCCl_2CCl_2O$ | | H | none | none |
| 316N | 4-F—$C_6H_5O$ | H | H | H | CH | H | H | $R_{10} + R_{11} = OCCl_2CCl_2O$ | | H | none | none |
| 317N | 3,4-Cl—$C_6H_5O$ | H | H | H | CH | H | H | $R_{10} + R_{11} = OCCl_2CCl_2O$ | | H | none | none |
| 318N | H | $C_6H_5$ | H | H | CH | H | H | $R_{10} + R_{11} = OCCl_2CCl_2O$ | | H | none | none |
| 319N | H | 4-Cl—$C_6H_5$ | H | H | CH | H | H | $R_{10} + R_{11} = OCCl_2CCl_2O$ | | H | none | none |
| 320N | H | 4-F—$C_6H_5$ | H | H | CH | H | H | $R_{10} + R_{11} = OCCl_2CCl_2O$ | | H | none | none |
| 321N | H | 4-Br—$C_6H_5$ | H | H | CH | H | H | $R_{10} + R_{11} = OCCl_2CCl_2O$ | | H | none | none |
| 322N | 4-Br—$C_6H_5O$ | H | H | H | CH | H | H | $R_{10} + R_{11} = OCCl_2CCl_2O$ | | H | none | none |
| 323N | H | H | H | H | CH | H | H | OH | H | H | none | none |
| 324N | H | H | H | H | CH | H | H | OH | OH | H | none | none |
| 325N | H | H | H | H | CH | H | H | H | OH | H | none | none |
| 326N | H | H | H | H | CH | H | H | $OCH_2CF_3$ | H | H | none | none |
| 327N | H | H | H | H | CH | H | H | H | $OCH_2CF_3$ | H | none | none |
| 328N | H | H | H | H | CH | H | H | $OCH_2CF_2CF_3$ | H | H | none | none |
| 329N | H | H | H | H | CH | H | H | $OCH_2CH_2CF_3$ | H | H | none | none |
| 330N | H | H | H | H | CH | H | H | $OCH(CF_3)_3$ | H | H | none | none |
| 331N | H | 4-F—$C_6H_5O$ | H | H | CH | H | H | H | H | H | none | none |
| 332N | 4-F—$C_6H_5O$ | H | H | H | CH | H | H | H | H | H | none | none |
| 333N | H | cyclo-hexoxy | H | H | CH | H | H | H | H | H | none | none |
| 334N | cyclo-hexoxy | H | H | H | CH | H | H | H | H | H | none | none |
| 335N | H | $C(CH_3)_3$ | H | H | CH | H | H | H | H | H | none | none |
| 336N | F | H | H | H | CH | H | H | 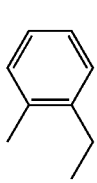 | bond to indicated phenyl carbon of $R_{10}$ subst. | H | none | none |

TABLE 5

Structure of "Secondary Phenyl Amine" Reagents (Y and Z each equal CH; $R_7$, $R_8$, $R_{12}$, $R_{13}$, $R_{14}$, and $R_{15}$ each equal H).

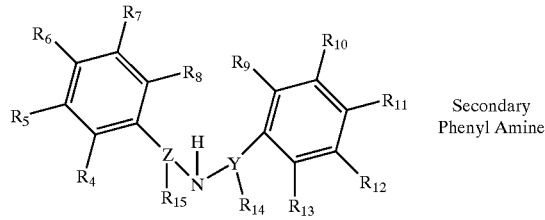

(XIII-A)    Secondary Phenyl Amine

| Reagent Number | $R_4$ | $R_5$ | $R_6$ | $R_9$ | $R_{10}$ | $R_{11}$ |
|---|---|---|---|---|---|---|
| 1DB | H | $OCF_3$ | H | H | $OCF_3$ | H |
| 2DB | H | Cl | H | H | H | $CF_3$ |
| 3DB | H | Br | H | H | $OCF_3$ | H |
| 4DB | H | Cl | H | H | $OCF_3$ | H |
| 5DB | H | Cl | H | H | $CF_3$ | H |
| 6DB | H | H | Cl | H | $CF_3$ | H |
| 7DB | H | F | H | H | $OCF_3$ | H |
| 8DB | H | H | Cl | H | H | $CF_3$ |
| 9DB | H | F | H | H | H | $CF_3$ |
| 10DB | H | H | F | H | H | $CF_3$ |
| 11DB | F | H | H | H | H | $CF_3$ |
| 12DB | H | Cl | H | $CF_3$ | H | H |
| 13DB | H | H | Cl | $CF_3$ | H | H |
| 14DB | Cl | H | H | $CF_3$ | H | H |
| 15DB | H | F | H | $CF_3$ | H | H |
| 16DB | H | H | F | H | H | $CH_3$ |
| 17DB | H | F | H | H | $CH_3$ | H |
| 18DB | F | H | H | $CH_3$ | H | H |
| 19DB | H | H | F | H | $CH_3$ | H |
| 20DB | F | H | H | H | H | $CH_3$ |
| 21DB | F | H | H | H | $CF_3$ | H |
| 22DB | Cl | H | H | H | $CF_3$ | H |
| 23DB | H | F | H | $CF_3$ | H | H |
| 24DB | H | H | F | $CF_3$ | H | H |
| 25DB | H | F | H | H | $CF_3$ | H |
| 26DB | H | H | F | H | $CF_3$ | H |
| 27DB | H | $OCF_3$ | H | H | H | $OCF_3$ | halide, alkyl benzenesulfonate such as a alkyl tosylate, alkyl mesylate, alkyl triflate or similar alkylating reagent of the general structure,

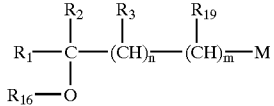

(XXX)

where M is a readily displaceable group such as chloride, bromide, iodide, tosylate, triflate, and mesylate. After allowing the reaction mixture to warm to room temperature, the reaction product is added to water, neutralized if necessary, and extracted with a water-immiscible solvent such as diethyl ether or methylene chloride. The combined aprotic solvent extract is washed with saturated brine, dried over drying agent such as anhydrous MgSO4 and concentrated in vacuo to yield crude Formula V-H ("Generic Substituted Polycyclic Aryl and Heteroaryl tertiary omegahydroxyalkylamines") and Formula V ("Generic Substituted Polycyclic Aryl tertiary omegahydroxyalkylamines"), wherein A and Q are independently aryl and heteroaryl. This material is purified, for example, by eluting through silica gel with 5–40% of a medium polar solvent such as ethyl acetate in a non-polar solvent such as hexanes to yield Formula V-H ("Generic Substituted Polycyclic Aryl and Heteroaryl tertiary omegahydroxyalkylamines") and Formula V ("Generic Substituted Polycyclic Aryl tertiary omegahydroxyalkylamines"). Products are tested for purity by HPLC. If necessary, Formula V-H ("Generic Substituted Polycyclic Aryl and Heteroaryl tertiary omegahydroxyalkylamines") and Formula V ("Generic Substituted Polycyclic Aryl tertiary omegahydroxyalkylamines") compounds are purified by additional chromatography or recrystallization. Products are structurally confirmed by low and high resolution mass spectrometry and NMR. Examples of specific Formula V-H ("Generic Substituted Polycyclic Aryl and Heteroaryl tertiary omegahydroxyalkylamines") and Formula V ("Generic Substituted Polycyclic Aryl tertiary omegahydroxyalkylamines") compounds prepared are summarized in Tables 6 and 7.

TABLE 6

Structure of Substituted Phenyl tertiary- omega-Hydroxyalkylamines (Y is CH; $R_8$, $R_9$, $R_{12}$, $R_{13}$, $R_{14}$, and $R_{19}$ are each H; Z is covalent bond and $R_{15}$ is absent).

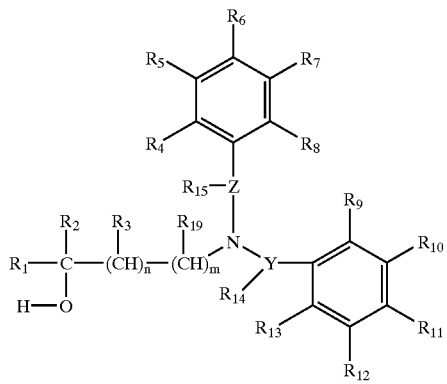

Inhibitor Number
Column 1 + Column 2

| Reagent | Reagent | $R_1$ | n | m | $R_2$ | $R_3$ | $R_4$ | $R_5$ | $R_6$ | $R_7$ | $R_{10}$ | $R_{11}$ |
|---|---|---|---|---|---|---|---|---|---|---|---|---|
| 1A | 1N | $CF_3$ | 1 | 2 | H | H | H | $C_6H_5O$ | H | H | $OCF_2CF_2H$ | H |
| 1A | 2N | $CF_3$ | 1 | 2 | H | H | H | $OCF_3$ | H | H | $OCF_2CF_2H$ | H |

TABLE 6-continued

Structure of Substituted Phenyl tertiary- omega-Hydroxyalkylamines (Y is CH; $R_8$, $R_9$, $R_{12}$, $R_{13}$, $R_{14}$, and $R_{19}$ are each H; Z is covalent bond and $R_{15}$ is absent).

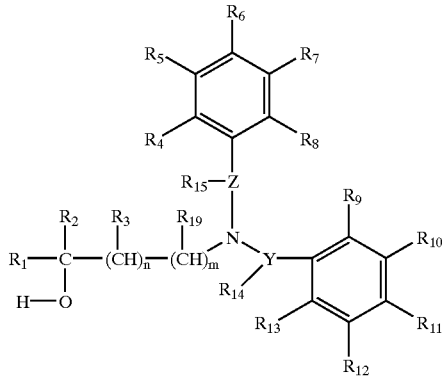

Inhibitor Number
Column 1 + Column 2

| Reagent | Reagent | $R_1$ | n | m | $R_2$ | $R_3$ | $R_4$ | $R_5$ | $R_6$ | $R_7$ | $R_{10}$ | $R_{11}$ |
|---|---|---|---|---|---|---|---|---|---|---|---|---|
| 1A | 3N | $CF_3$ | 1 | 2 | H | H | F | H | H | F | $OCF_2CF_2H$ | H |
| 1A | 4N | $CF_3$ | 1 | 2 | H | H | H | F | H | H | $OCF_2CF_2H$ | H |
| 1A | 5N | $CF_3$ | 1 | 2 | H | H | H | $C_6H_5O$ | H | H | $OCF_3$ | H |
| 1A | 6N | $CF_3$ | 1 | 2 | H | H | H | $OCF_3$ | H | H | $OCF_3$ | H |
| 1A | 7N | $CF_3$ | 1 | 2 | H | H | H | H | phenyl | H | $OCF_3$ | H |
| 1A | 8N | $CF_3$ | 1 | 2 | H | H | H | phenyl | H | H | $OCF_3$ | H |
| 1A | 9N | $CF_3$ | 1 | 2 | H | H | H | H | H | H | $OCF_3$ | H |
| 1A | 10N | $CF_3$ | 1 | 2 | H | H | H | Br | H | H | $OCF_3$ | H |
| 1A | 11N | $CF_3$ | 1 | 2 | H | H | H | $CF_3$ | F | H | $CF_3$ | H |
| 1A | 12N | $CF_3$ | 1 | 2 | H | H | H | $CH_3$ | H | H | $CF_3$ | H |
| 1A | 13N | $CF_3$ | 1 | 2 | H | H | H | $CF_3$ | H | H | $CF_3$ | H |
| 1A | 14N | $CF_3$ | 1 | 2 | H | H | H | $CH_3$ | H | H | $OCF_3$ | H |
| 1A | 15N | $CF_3$ | 1 | 2 | H | H | H | F | F | H | $OCF_3$ | H |
| 1A | 16N | $CF_3$ | 1 | 2 | H | H | H | Br | H | H | $CF_3$ | H |
| 1A | 17N | $CF_3$ | 1 | 2 | H | H | H | $CF_3$ | F | H | $OCF_3$ | H |
| 1A | 18N | $CF_3$ | 1 | 2 | H | H | H | F | H | H | $OCF_3$ | H |
| 1A | 19N | $CF_3$ | 1 | 2 | H | H | H | Cl | H | H | $OCF_3$ | H |
| 1A | 20N | $CF_3$ | 1 | 2 | H | H | H | F | H | H | $CF_3$ | H |
| 1A | 21N | $CF_3$ | 1 | 2 | H | H | H | F | F | H | $CF_3$ | H |
| 1A | 22N | $CF_3$ | 1 | 2 | H | H | H | Cl | H | H | $CF_3$ | H |
| 1A | 23N | $CF_3$ | 1 | 2 | H | H | H | F | H | H | phenoxy | H |
| 1A | 24N | $CF_3$ | 1 | 2 | H | H | H | $CF_3$ | Cl | H | $CH_3$ | H |
| 1A | 25N | $CF_3$ | 1 | 2 | H | H | H | $CF_3$ | F | H | $CH_3$ | H |
| 1A | 26N | $CF_3$ | 1 | 2 | H | H | H | H | H | H | $CF_3$ | H |
| 1A | 27N | $CF_3$ | 1 | 2 | H | H | F | F | H | H | $CF_3$ | H |
| 1A | 28N | $CF_3$ | 1 | 2 | H | H | H | H | $OCH_3$ | H | $CF_3$ | H |
| 1A | 29N | $CF_3$ | 1 | 2 | H | H | H | F | F | H | $CH_3$ | H |
| 1A | 30N | $CF_3$ | 1 | 2 | H | H | H | $OCH_3$ | H | H | $CH_3$ | H |
| 1A | 31N | $CF_3$ | 1 | 2 | H | H | H | H | $CH_3$ | H | H | H |
| 1A | 32N | $CF_3$ | 1 | 2 | H | H | H | Cl | H | H | H | H |
| 1A | 33N | $CF_3$ | 1 | 2 | H | H | H | F | H | H | F | H |
| 1A | 34N | $CF_3$ | 1 | 2 | H | H | H | H | $OCH_3$ | H | $CH_3$ | H |
| 1A | 35N | $CF_3$ | 1 | 2 | H | H | H | H | H | H | H | H |
| 1A | 36N | $CF_3$ | 1 | 2 | H | H | H | H | $CH_3$ | H | $CH_3$ | H |
| 1A | 37N | $CF_3$ | 1 | 2 | H | H | H | H | Cl | H | H | H |
| 1A | 38N | $CF_3$ | 1 | 2 | H | H | H | F | H | H | 3-$CF_3$-phenoxy | H |
| 1A | 39N | $CF_3$ | 1 | 2 | H | H | H | F | H | H | 4-$CH_3O$-phenoxy | H |
| 1A | 40N | $CF_3$ | 1 | 2 | H | H | H | F | H | H | 4-Cl-phenoxy | H |
| 1A | 41N | $CF_3$ | 1 | 2 | H | H | H | F | H | H | H | H |
| 1A | 42N | $CF_3$ | 1 | 2 | H | H | H | F | H | H | $CH_3$ | H |
| 1A | 43N | $CF_3$ | 1 | 2 | H | H | H | F | H | F | $CH_3$ | H |
| 1A | 44N | $CF_3$ | 1 | 2 | H | H | F | F | H | H | $CH_3$ | H |
| 1A | 45N | $CF_3$ | 1 | 2 | H | H | H | Cl | H | H | $CH_3$ | H |

TABLE 6-continued

Structure of Substituted Phenyl tertiary- omega-Hydroxyalkylamines (Y is CH; $R_8$, $R_9$, $R_{12}$, $R_{13}$, $R_{14}$, and $R_{19}$ are each H; Z is covalent bond and $R_{15}$ is absent).

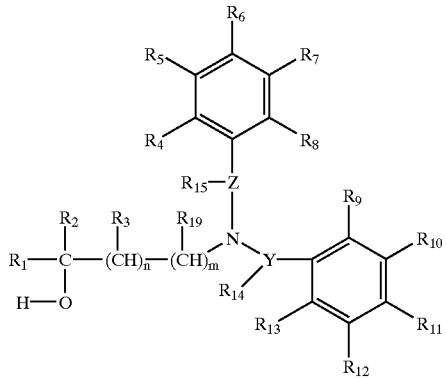

Inhibitor Number
Column 1 + Column 2

| Reagent | Reagent | $R_1$ | n | m | $R_2$ | $R_3$ | $R_4$ | $R_5$ | $R_6$ | $R_7$ | $R_{10}$ | $R_{11}$ |
|---|---|---|---|---|---|---|---|---|---|---|---|---|
| 1A | 46N | $CF_3$ | 1 | 2 | H | H | H | $CH_3$ | H | H | $CH_3$ | H |
| 1A | 48N | $CF_3$ | 1 | 2 | H | H | H | H | $CH_3$ | H | $CF_3$ | H |
| 1A | 51N | $CF_3$ | 1 | 2 | H | H | H | H | $CH_3$ | H | F | H |
| 1A | 52N | $CF_3$ | 1 | 2 | H | H | H | $CF_3$ | H | H | F | H |
| 1A | 53N | $CF_3$ | 1 | 2 | H | H | H | $CF_3$ | H | H | $CH_3$ | H |
| 1A | 54N | $CF_3$ | 1 | 2 | H | H | H | $OCH_3$ | H | H | $CF_3$ | H |
| 1A | 56N | $CF_3$ | 1 | 2 | H | H | H | H | $CH_3$ | H | $CF_3$ | H |
| 1A | 57N | $CF_3$ | 1 | 2 | H | H | H | $C_6H_5O$ | H | H | H | $OCF_3$ |
| 1A | 58N | $CF_3$ | 1 | 2 | H | H | H | H | H | H | H | $OCF_3$ |
| 1A | 59N | $CF_3$ | 1 | 2 | H | H | H | $OCF_3$ | H | H | H | $OCF_3$ |
| 1A | 60N | $CF_3$ | 1 | 2 | H | H | H | $CF_3$ | F | H | H | $CF_3$ |
| 1A | 61N | $CF_3$ | 1 | 2 | H | H | H | H | $OCH_3$ | H | H | $CF_3$ |
| 1A | 62N | $CF_3$ | 1 | 2 | H | H | H | $CH_3$ | H | H | H | $CF_3$ |
| 1A | 63N | $CF_3$ | 1 | 2 | H | H | H | Cl | H | H | H | $CF_3$ |
| 1A | 64N | $CF_3$ | 1 | 2 | H | H | H | $CF_3$ | H | H | H | $OCF_3$ |
| 1A | 65N | $CF_3$ | 1 | 2 | H | H | H | F | H | H | H | $OCF_3$ |
| 1A | 66N | $CF_3$ | 1 | 2 | H | H | H | F | H | F | H | $OCF_3$ |
| 1A | 67N | $CF_3$ | 1 | 2 | H | H | H | Br | H | H | H | $OCF_3$ |
| 1A | 68N | $CF_3$ | 1 | 2 | H | H | H | Cl | H | H | H | $OCF_3$ |
| 1A | 69N | $CF_3$ | 1 | 2 | H | H | H | F | F | H | H | $OCF_3$ |
| 1A | 70N | $CF_3$ | 1 | 2 | H | H | H | F | H | H | H | phenyl |
| 1A | 71N | $CF_3$ | 1 | 2 | H | H | H | $CH_3$ | H | H | H | $OCF_3$ |
| 1A | 72N | $CF_3$ | 1 | 2 | H | H | H | F | F | H | H | $CF_3$ |
| 1A | 73N | $CF_3$ | 1 | 2 | H | H | H | Cl | H | H | H | $CH_3$ |
| 1A | 74N | $CF_3$ | 1 | 2 | H | H | H | $OCH_3$ | H | H | H | $CH_3$ |
| 1A | 75N | $CF_3$ | 1 | 2 | H | H | H | F | H | H | H | $CH_3$ |
| 1A | 76N | $CF_3$ | 1 | 2 | H | H | F | F | H | H | H | $OCF_3$ |
| 1A | 78N | $CF_3$ | 1 | 2 | H | H | H | H | $OCH_3$ | H | H | $CH_3$ |
| 1A | 79N | $CF_3$ | 1 | 2 | H | H | H | H | $CH_3$ | H | H | $CH_3$ |
| 1A | 80N | $CF_3$ | 1 | 2 | H | H | H | $CH_3$ | H | H | H | $CH_3$ |
| 1A | 82N | $CF_3$ | 1 | 2 | H | H | H | F | F | H | H | $CH_3$ |
| 1A | 83N | $CF_3$ | 1 | 2 | H | H | H | F | H | F | H | $CH_3$ |
| 1A | 84N | $CF_3$ | 1 | 2 | H | H | F | F | H | H | H | $CH_3$ |
| 1A | 85N | $CF_3$ | 1 | 2 | H | H | F | $CF_3$ | H | H | H | $CH_3$ |
| 1A | 86N | $CF_3$ | 1 | 2 | H | H | H | H | $CH_3$ | H | H | $CF_3$ |
| 1A | 88N | $CF_3$ | 1 | 2 | H | H | H | $CF_3$ | H | H | H | $CH_3$ |
| 1A | 90N | $CF_3$ | 1 | 2 | H | H | H | H | $CF_3$ | H | H | $CH_3$ |
| 1A | 92N | $CF_3$ | 1 | 2 | H | H | H | $CF_3$ | F | H | H | $CH_3$ |

TABLE 7

Structure of Substituted Phenyltertiary- omega-Heteroalkylamines
(Z and Y are each CH; $R_7$, $R_8$, $R_{12}$, $R_{13}$, $R_{14}$, $R_{15}$ and $R_{19}$ are each H).

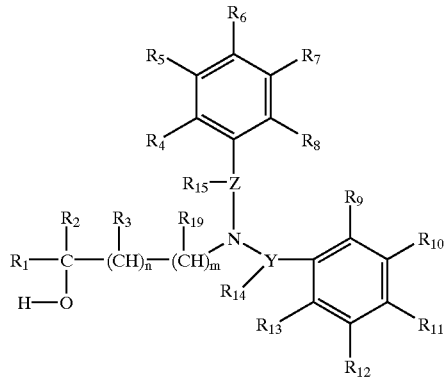

Inhibitor Number
Column 1 + Column 2

| Reagent | Reagent | $R_1$ | n | m | $R_2$ | $R_3$ | $R_4$ | $R_5$ | $R_6$ | $R_9$ | $R_{10}$ | $R_{11}$ |
|---|---|---|---|---|---|---|---|---|---|---|---|---|
| 1A | 1DB | $CF_3$ | 1 | 2 | H | H | H | $OCF_3$ | H | H | $OCF_3$ | H |
| 1A | 2DB | $CF_3$ | 1 | 2 | H | H | H | Cl | H | H | H | $CF_3$ |
| 1A | 3DB | $CF_3$ | 1 | 2 | H | H | H | Br | H | H | $OCF_3$ | H |
| 1A | 4DB | $CF_3$ | 1 | 2 | H | H | H | Cl | H | H | $OCF_3$ | H |
| 1A | 5DB | $CF_3$ | 1 | 2 | H | H | H | Cl | H | H | $CF_3$ | H |
| 1A | 6DB | $CF_3$ | 1 | 2 | H | H | H | H | Cl | H | $CF_3$ | H |
| 1A | 7DB | $CF_3$ | 1 | 2 | H | H | H | F | H | H | $OCF_3$ | H |
| 1A | 8DB | $CF_3$ | 1 | 2 | H | H | H | H | Cl | H | H | $CF_3$ |
| 1A | 9DB | $CF_3$ | 1 | 2 | H | H | H | F | H | H | H | $CF_3$ |
| 1A | 10DB | $CF_3$ | 1 | 2 | H | H | H | H | F | H | H | $CF_3$ |
| 1A | 11DB | $CF_3$ | 1 | 2 | H | H | F | H | H | H | H | $CF_3$ |
| 1A | 12DB | $CF_3$ | 1 | 2 | H | H | H | Cl | H | $CF_3$ | H | H |
| 1A | 13DB | $CF_3$ | 1 | 2 | H | H | H | H | Cl | $CF_3$ | H | H |
| 1A | 14DB | $CF_3$ | 1 | 2 | H | H | Cl | H | H | $CF_3$ | H | H |
| 1A | 15DB | $CF_3$ | 1 | 2 | H | H | H | F | H | $CH_3$ | H | H |
| 1A | 16DB | $CF_3$ | 1 | 2 | H | H | H | H | F | H | H | $CH_3$ |
| 1A | 17DB | $CF_3$ | 1 | 2 | H | H | H | F | H | H | $CH_3$ | H |
| 1A | 18DB | $CF_3$ | 1 | 2 | H | H | F | H | H | $CH_3$ | H | H |
| 1A | 19DB | $CF_3$ | 1 | 2 | H | H | H | H | F | $CH_3$ | H | H |
| 1A | 20DB | $CF_3$ | 1 | 2 | H | H | F | H | H | H | H | $CH_3$ |
| 1A | 21DB | $CF_3$ | 1 | 2 | H | H | F | H | H | H | $CF_3$ | H |
| 1A | 22DB | $CF_3$ | 1 | 2 | H | H | Cl | H | H | H | $CF_3$ | H |
| 1A | 23DB | $CF_3$ | 1 | 2 | H | H | H | F | H | $CF_3$ | H | H |
| 1A | 24DB | $CF_3$ | 1 | 2 | H | H | H | H | F | $CF_3$ | H | H |
| 1A | 25DB | $CF_3$ | 1 | 2 | H | H | H | F | H | H | $CF_3$ | H |
| 1A | 26DB | $CF_3$ | 1 | 2 | H | H | H | H | F | H | $CF_3$ | H |
| 1A | 27DB | $CF_3$ | 1 | 2 | H | H | H | $OCF_3$ | H | H | H | $OCF_3$ |

Compounds of Formula (XXX), which can be used to prepare the "Generic Substituted Polycyclic Aryl tertiary omegahydroxyalkylamines" compounds of Tables 6 and 7, are given in Table 2. Reagents 1a and 2a in Table 2 are prepared from the corresponding alcohols. The tosylates are readily obtained by reacting the corresponding alcohol with tosyl chloride using procedures found in House's Modem Synthetic Reactions, Chapter 7, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons, which are incorporated herein by reference.

A preferred procedure for Formula VII ("Generic Substituted Polycyclic Aryl tertiary 2-heteroalkylamine") and Formula VII-H ("Generic Substituted Polycyclic Heteroaryl tertiary-2-heteroalkylamines") compounds, wherein the 2-hetero group is a hydroxyl, is Method A of Scheme 2. Oxirane reagents useful in Method A are exemplified, but not limited to those in Table 1. Formula VII ("Generic Substituted Polycyclic Aryl tertiary 2-hydroxyalkylamine") and Formula VII-H ("Generic Substituted Polycyclic Heteroaryl tertiary-2-hydroxyalkylamines") compounds are prepared by using "Generic Secondary Amine" amines, hydroxylamines, and hydrazines of Formula XIII prepared above with oxiranes of the type listed in Table 1 and represented by the general structure:

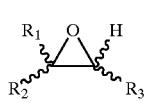
(XX)

In some cases, the oxiranes are prepared by reaction of epoxidation reagents such as MCPBA and similar type reagents readily selectable by a person of skill-in-the-art with alkenes. Fieser and Fieser in Reagents for Organic Synthesis, John Wiley & Sons provides, along with cited references, numerous suitable epoxidation reagents and reaction conditions, which are incorporated herein by reference.

Formula VII ("Generic Substituted Polycyclic Aryl tertiary 2-heteroalkylamine") and Formula VII-H ("Generic Substituted Polycyclic Heteroaryl tertiary-2-heteroalkylamines") compounds, wherein the 2-hetero group is an amino, substituted amino, or thiol, can be prepared by using appropriate aziridines and thirranes according to Method A of Scheme 2. Aziridine and thiirane reagents useful in Method A are exemplified, but not limited to those in Table 1. These Formula VII ("Generic Substituted Polycyclic Aryl tertiary 2-heteroalkylamine") and Formula VII-H ("Generic Substituted Polycyclic Heteroaryl tertiary-2-heteroalkylamines") compounds, wherein the 2-hetero group is an amino, substituted amino, or thiol, can be prepared by using "Generic Secondary Amine" amines, hydroxylamines, and hydrazines of Formula XIII prepared above with aziridines and thiiranes of the type listed in Table 1 and represented by the general structure:

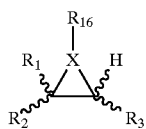
(XX)

wherein X is selected from N and S and $R_{16}$ is hydrogen or another suitable group when X is N.

TABLE 1

Structure of Oxirane, Aziridine, and Thiirane Reagents.

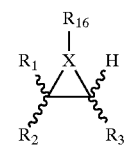
(XX)

| Rgnt No. | $R_{16}$ | X | $R_1$ | $R_2$ | $R_3$ |
|---|---|---|---|---|---|
| 1 | — | O | $CF_3$ | H | H |
| 2 | — | O | $CCl_3$ | H | H |
| 3 | — | O | $CF_3$ | $CH_3$ | H |
| 4 | — | O | $CF_3CF_2$ | H | H |
| 5 | — | O | $CF_3CF_2CF_2$ | H | H |
| 6 | — | O | $CF_3OCF_2CF_2$ | H | H |
| 7 | — | O | $CF_3CH_2$ | H | H |
| 8 | — | O | $CF_3$ | $CHF_2$ | H |
| 9 | — | O | $CF_3$ | H | $CF_3$ |
| 10 | — | O | $CF_3$ | $CF_3$ | H |
| 11 | — | O | $CF_3$ | $C_6H_5$ | H |
| 12 | — | O | $CCl_3$ | $C_6H_5$ | H |
| 13 | — | O | $CCl_3$ | Cyclopropyl | H |
| 14 | — | O | $CCl_3$ | $CH_3$ | H |
| 15 | — | O | $CCl_3$ | $(CH_3)_2CH$ | H |
| 16 | — | O | $CHCl_2$ | H | H |
| 17 | — | O | $CHCl_2$ | Cl | H |
| 18 | — | O | $CF_3$ | H | $CH_3$ |
| 19 | H | N | $CF_3$ | $CF_3$ | H |
| 20 | H | N | $CF_3$ | H | H |
| 21 | Benzyl | N | $CF_3$ | H | H |
| 22 | $CH_3O$ | N | $CF_3$ | H | H |
| 23 | $CH_3$ | N | $CF_3$ | H | H |
| 24 | Benzyloxy | N | $CF_3$ | H | H |
| 25 | — | S | $CF_3$ | H | H |
| 26 | — | S | $CF_3CF_2$ | H | H |
| 27 | — | O | $CCl_3CH_2$ | H | H |
| 28 | — | O | $CBr_3CH_2$ | H | H |
| 29 | — | O | $CHBr_2CH_2$ | H | H |
| 30 | — | O | $CBrCl_2$ | H | H |
| 31 | — | O | $CClF_2$ | H | H |
| 32 | — | O | $CCl_2F$ | H | H |
| 33 | — | O | $CCl_3CCl_2$ | H | H |
| 43 | — | O | $FCH_2$ | H | H |
| 46 | — | O | $CF_3$ | $R_2 + R_3 = (CH_2)_3$ | |
| 47 | — | O | $CF_3$ | $R_2 + R_3 = (CH_2)_4$ | |
| 48 | — | O | $CHF_2$ | $R_2 + R_3 = (CH_2)_4$ | |
| 56 | — | O | $CBrF_2CClFCH_2$ | H | H |
| 57 | — | O | $HCF_2CF_2OCH_2$ | H | H |

TABLE 2

Structure and Source of Alcohol Reagents.

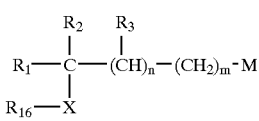
(XXX)

| Reagent Number | $R_1$ | n | M | m | $R_2$ | $R_3$ | $X—R_{16}$ | Source of Reagent |
|---|---|---|---|---|---|---|---|---|
| 1A | $CF_3$ | 1 | OTs | 2 | H | H | OH | Tosylation of alcohol from Justus Liebigs Ann. Chem. (1969), 720, 81–97. |
| 2A | $CF_3CH_2CH_2$ | 1 | OTs | 1 | H | H | OH | Tosylation of alcohol from Z. Naturforsch., B: Chem. Sci. (1997), 52 (3). 413–418 |

A mixture of a "Generic Secondary Amine" amine, hydroxylamine, or hydrazine of Formula XIII and an oxirane of Formula XX are stirred and heated to 40–90° C. for 5 to 48 hours in a tightly capped or contained reaction vessel. A Lewis acid such as ytterbium triflate in acetonitrile may be added to speed up reaction and improve yield. When a Lewis acid is used, the reaction should be carried out under inert, anhydrous conditions using a blanket of dry nitrogen or argon gas. After cooling to room temperature and testing the reaction mixture for complete reaction by thin layer chromatography or high pressure liquid chromatography (hplc), the reaction product is added to water and extracted with a water immiscible solvent such as diethyl ether or methylene chloride. (Note: If the above analysis indicates that reaction is incomplete, heating should be resumed until complete with the optional addition of more of the oxirane). The combined aprotic solvent extract is washed with saturated brine, dried over drying agent such as anhydrous $MgSO_4$ and concentrated in vacuo to yield crude Formula VII ("Generic Substituted Polycyclic Aryl tertiary 2-hydroxyalkylamine") and Formula VII-H ("Generic Substituted Polycyclic Heteroaryl tertiary-2-hydroxyalkylamine") compounds. This material is purified by eluting through silica gel with 5–40% of a medium polar solvent such as ethyl acetate in a non-polar solvent such as hexanes to yield the Formula VII ("Generic Substituted Polycyclic Aryl tertiary 2-hydroxyalkylamine") and Formula VII-H ("Generic Substituted Polycyclic Heteroaryl tertiary-2-hydroxyalkylamine"). Products are tested for purity by HPLC. If necessary, the Formula VII ("Generic Substituted Polycyclic Aryl tertiary 2-hydroxyalkylamine") and Formula VII-H ("Generic Substituted Polycyclic Heteroaryl tertiary-2-hydroxyalkylamine") compounds are purified by additional chromatography or recrystallization. Products are structurally confirmed by low and high resolution mass spectrometry and NMR. Examples of specific Formula VII ("Generic Substituted Polycyclic Aryl tertiary 2-hydroxyalkylamine") compounds prepared are summarized in Example Tables 1 through 54.

Specific Formula VII ("Generic Substituted Polycyclic Aryl tertiary 2-heteroalkylamine") analogs of the "Polycyclic Aryl tertiary -2-hydroxyalkylamine" compounds summarized in Example Tables 1 through 54, wherein the hydroxyl or oxy group are replaced with an amino, substituted amino, aza, or thiol, can be prepared by using the appropriate aziridine reagents or thiirane reagents readily by adapting the procedures in the numerous specific Examples and Schemes disclosed in the present invention. Similarly, intermediates, in which the hydroxyl or oxy group of said intermediates are replaced with an amino, substituted amino, aza, or thiol, can be converted using the numerous specific Examples and Schemes disclosed in the present invention to other Formula VII ("Generic Substituted Polycyclic Aryl tertiary 2-heteroalkylamine") analogs of the "Polycyclic Aryl tertiary -2-hydroxyalkylamine" compounds.

As summarized in the general Scheme 2 and specific descriptions above, Schemes 5, 6, 7, and 11 illustrate the principles of Scheme 2 for the preparation of specifically substituted "Generic Substituted Polycyclic Aryl Tertiary OmegaHydroxyalkylamines" (V) having 2 aryl groups, "Generic Substituted Polycyclic Aryl and Heteroaryl Tertiary OmegaHydroxyalkylamines" (V-H) having two aromatic substituents made up of 0 to 2 aryl groups and 0 to 2 aromatic heterocyclyl groups, "Generic Substituted Polycyclic Heteroaryl Tertiary 2-Hydroxyalkylamines" (VII-H) having two aromatic substituents made up of 0 to 2 aryl groups and 0 to 2 aromatic heterocyclyl groups, and "Generic Substituted Polycyclic Aryl Tertiary 2-Hydroxyalkylamines" (Vil) having two aryl groups.

Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") can further be prepared in an alternate manner to procedures disclosed above and in Schemes 1 to 7 and 9 to 11. Schemes 45 to 50 detail such procedures to prepare tertiary oxyalkylamine compounds of the present invention by initial formation of an halogenated, oxygen containing primary alkylamine XVL ("Generic Substituted Alkylamine"). Said halogenated, oxygen containing primary alkylamine XVL, formed in Schemes 45 and 48, is itself converted to secondary amines, VLX-H ("Heteroaryl Alkyl Amine) and VLX ("Phenyl Alkyl Amine"), using procedures disclosed above. Primary alkylamine XVL is first reacted with an aldehydic or ketonic carbonyl compound, XI-AH ("Heteroaryl Carbonyl") and XI-A ("Phenyl Carbonyl") with azeotropic distillation to form imines, VL-H ("Heteroaryl Imine") and VL ("Phenyl Imine"). Said imines VL-H and VL are then reduced with or without prior isolation by Reduction Methods 1, 2 or 3 as disclosed above and in Schemes 1, 3, and 9 to yield secondary amines, VLX-H ("Heteroaryl Alkyl Amine) and VLX ("Phenyl Alkyl Amine"). Said secondary amine VLX-H can be converted according to Schemes 46 and 47 to VII-H ("Generic Substituted Polycyclic Heteroaryl Tertiary 2-hydroxyalkylamines"). Using Schemes 49 and 50, VLX can be converted to VII ("Generic Substituted Polycyclic Phenyl Tertiary 2-hydroxyalkylamines"). Compounds of this invention in which one aromatic substituent is aryl and the other aromatic substitutent is heteroaryl can be readily prepared by reacting VLX-H with an aryl bromide or aralkyl bromide instead of using an heteroaryl bromide or heteroaralkyl bromide as described in Schemes 46 and 47. Similarly, compounds of this invention in which one aromatic substituent is aryl and the other aromatic substitutent is heteroaryl can be readily prepared by reacting VLX with an heteroaryl bromide or heteroaralkyl bromide instead of using an aryl bromide or aralkyl bromide as described in Schemes 49 and 50.

Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") can further be prepared in an alternate manner to procedures disclosed above and in Schemes 1 to 7, 9 to 11, and 45 to 50. Schemes 56,58, and 59 detail alternate procedures to prepare tertiary oxyalkylamine compounds of the present invention by initial formation of an halogenated, oxygen containing secondary alkylamines VLX and VLXX ("Phenyl Alkylamines") and VLXX-O ("Phenyl Oxy Alkylamines"). Said secondary alkylamines VLX and VLXX ("Phenyl Alkylamines") and VLXX-O ("Phenyl Oxy Alkylamines") can be converted according to Schemes 56,58 and 59 to VII ("Generic Substituted Polycyclic Aryl Tertiary 2-hydroxyalkylamines") and VII-H ("Generic Substituted Polycyclic Heteroaryl Tertiary 2-hydroxyalkylamines") by reaction with appropriate aromatic halides such as aryl bromides and heteroaryl bromides as desired.

Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") can further be prepared in an alternate manner to procedures disclosed above and in Schemes 1 to 7, 9 to 11, 45 to 50, 56, 58, and 59. Scheme 57 details another alternate procedure to prepare tertiary oxyalkylamine compounds of the present invention by reacting secondary amines XIII-A ("Secondary Phenyl Amine") and XIIIA-H ("Secondary Heteroaryl Amine") with a diazo ester. The intermediate glycinate tertiary amine can then be reduced, partially reoxidized to an aldehyde, and converted using a perfluoroalkyl trimethylsilyl compound (for example, trifluoromethyl-TMS) to the desired product, VII ("Generic Substituted Polycyclic Aryl Tertiary 2-hydroxyalkylamines") and VII-H ("Generic Substituted Polycyclic Heteroaryl Tertiary 2-hydroxyalkylamines").

Formula V ("Generic Substituted Polycyclic Aryl tertiary-3-hydroxyalkylamines") and Formula V-H ("Generic Substituted Polycyclic Heteroaryl tertiary-3-hydroxyalkylamines"), in which the halogenated oxy containing alkyl side chain has three carbons between the amine and oxy group, can be prepared in a manner similar to procedures disclosed above and in Schemes 45 to 50. Schemes 30 to 35 detail such procedures to prepare tertiary 3-oxyalkylamine compounds of the present invention by initial formation of an halogenated, oxygen containing primary alkylamine XL ("Generic Substituted Alkylamine"). Said halogenated, oxygen containing primary alkylamine XL, formed in Schemes 30 and 33, is itself converted to secondary amines, LX-H ("Heteroaryl Alkyl Amine) and LX ("Phenyl Alkyl Amine"), using procedures disclosed above. Primary alkylamine XL is first reacted with an aldehydic or ketonic carbonyl compound, XI-AH ("Heteroaryl Carbonyl") and XI-A ("Phenyl Carbonyl") with azeotropic distillation to form imines, L-H ("Heteroaryl Imine") and L ("Phenyl Imine"). Said imines L-H and L are then reduced with or without prior isolation by Reduction Methods 1, 2 or 3 as disclosed above and in Schemes 1, 3, and 9 to yield secondary amines, LX-H ("Heteroaryl Alkyl Amine) and LX ("Phenyl Alkyl Amine"). Said secondary amine LX-H can be converted according to Schemes 31 and 32 to V-H ("Generic Substituted Polycyclic Heteroaryl Tertiary 3-hydroxyalkylamines"). Using Schemes 34 and 35, LX can be converted to V ("Generic Substituted Polycyclic Phenyl Tertiary 3-hydroxyalkylamines"). Compounds of this invention in which one aromatic substituent is aryl and the other aromatic substitutent is heteroaryl can be readily prepared by reacting LX-H with an aryl bromide instead of using an heteroaryl bromide as described in Schemes 31 and 32. Similarly, compounds of this invention in which one aromatic substituent is aryl and the other aromatic substituent is heteroaryl can be readily prepared by reacting LX with an heteroaryl bromide instead of using an aryl bromide as described in Schemes 34 and 35.

A particularly useful procedure to prepare Formula V-H ("Generic Substituted Polycyclic Heteroaryl tertiary-3-hydroxyalkylamines") and VII-H ("Generic Substituted Polycyclic Heteroaryl Tertiary 2-hydroxyalkylamines") compounds of the present invention in which the heteroaryl group is directly bonded is disclosed in Schemes 51 to 54. An halogenated, oxygen containing primary alkylamine XVL ("Generic Substituted Alkylamine") formed in Schemes 45 and 48 is itself converted by reaction with LXXI-AH ("Heteroaryl Halide") to afford secondary amine VLXX-H ("Heteroaryl Secondary Amine) using procedures disclosed in Scheme 51 and above. VLXX-H is converted to VII-H ("Generic Substituted Polycyclic Phenyl Heteroaryl Tertiary 2-hydroxyalkylamine") by alkylation chemistry with an aralkyl bromide or aralkyloxyalkyl bromide using either of two procedures disclosed in Scheme 52. Isolation and purification is effected as disclosed previously. An halogenated, oxygen containing primary alkylamine XL ("Generic Substituted Alkylamine") formed in Schemes 30 and 33 is itself also converted by reaction with LXXI-AH ("Heteroaryl Halide") to afford secondary amine LXX-H ("Heteroaryl Secondary Amine) using procedures disclosed in Scheme 53 and above. LXX-H is converted to V-H ("Generic Substituted Polycyclic Phenyl Heteroaryl Tertiary 3-hydroxyalkylamine") by alkylation chemistry disclosed in Scheme 54 and previously and as given above with reference to Scheme 52. Isolation and purification of V-H and VII-H are effected as disclosed previously.

Formula V-H ("Generic Substituted Polycyclic Aryl and Heteroaryl tertiary omegahydroxyalkylamines"), Formula V ("Generic Substituted Polycyclic Aryl tertiary omegahydroxyalkylamines"), Formula VII ("Generic Substituted Polycyclic Aryl tertiary-2-hydroxyalkylamines"), and Formula VII-H ("Generic Substituted Polycyclic Heteroaryl tertiary-2-hydroxyalkylamines") can themselves serve as intermediates for conversion to additional compounds of this invention. Compounds of Formula VII and the present invention useful as intermediates include those in which the $R_7$ position substituent in Formula VII ("Generic Substituted Polycyclic Aryl Tertiary 2-hydroxyalkylamine") is a bromo group, hydroxyl group, sulfhydryl group, bromomethyl or other bromoalkyl groups, nitro group, amino group, methoxy carbonyl or other alkoxy carbonyl groups, cyano group, or acyl groups. Other preferred compounds of Formula VII and the present invention useful as intermediates include those in which the $R_{10}$ position substituent in Formula VII is a bromo group, hydroxyl group, sulfhydryl group, bromomethyl or other bromoalkyl groups, nitro group, amino group, methoxy carbonyl or other alkoxy carbonyl groups, cyano group, or acyl groups. Other compounds of Formula VII and the present invention useful as intermediates include those in which one or more of $R_6$, $R_7$, $R_{11}$, and $R_{12}$ substituents in Formula VII is a bromo group, hydroxyl group, sulfhydryl group, bromomethyl or other bromoalkyl groups, nitro group, amino group, methoxy carbonyl or other alkoxy carbonyl groups, cyano group, or acyl groups.

Scheme 8 discloses the conversion of a 3-bromo substituent at the $R_7$ position in Formula VII ("Generic Substituted Polycyclic 3-Bromoaryl Tertiary 2-hydroxyalkylamine") by reaction with a phenol to afford, after isolation and purification as described above for Schemes 2, 5, 6, 7, and 11, additional compounds of the present invention of Formula VII ("Generic Substituted Polycyclic 3-Phenoxyaryl Tertiary 2-Hydroxyalkylamine").

Scheme 12 discloses the conversion of a 3-bromo substituent at the $R_7$ position in Formula VII-H ("Generic Substituted Polycyclic 3-Bromoheteroaryl Tertiary 2-hydroxyalkylamine") by reaction with a phenol to afford, after isolation and purification as described above for Schemes 2, 5, 6, 7, and 11, additional compounds of the present invention of Formula VII-H ("Generic Substituted Polycyclic 3-Aryloxyaryl, 3-Heteroaryloxyaryl, 3-Heteroaryloxyheteroaryl, and 3-Aryloxyheteroaryl Tertiary 2-Hydroxyalkylamines").

Scheme 22 discloses the conversion of a 3-bromo substituent at the $R_7$ position in Formula VII ("Generic Substituted Polycyclic 3-Bromoaryl Tertiary 2-hydroxyalkylamine") by reaction with an aryl borinate to afford, after isolation and purification as described above for Schemes 2, 5, 6, 7, and 11, additional compounds of the present invention of Formula VII ("Generic Substituted Polycyclic 3-Phenylaryl Tertiary 2-Hydroxyalkylamine").

Scheme 23 discloses the conversion of a 3-bromo substituent at the $R_7$ position in Formula VII ("Generic Substituted Polycyclic 3-Bromoaryl Tertiary 2-hydroxyalkylamine") by reaction with a primary or secondary amine to afford, after isolation and purification as described above for Schemes 2, 5, 6, 7, and 11, additional compounds of the present invention of Formula VII ("Generic Substituted Polycyclic 3-$R_{22}$aminoaryl Tertiary 2-Hydroxyalkylamine").

Scheme 40 discloses the conversion of a 3-bromo substituent at the $R_{10}$ position in Formula VII ("Generic Substituted Polycyclic 3-Bromoaryl Tertiary 2-hydroxyalkylamine") by reaction with an aryl borinate to afford, after isolation and purification as described above for Schemes 2, 5, 6, 7, and 11, additional compounds of the present invention of Formula VII ("Generic Substituted Polycyclic 3-Phenylaryl Tertiary 2-Hydroxyalkylamine").

Scheme 41 discloses the conversion of a 3-bromo substituent at the $R_{10}$ position in Formula VII ("Generic Substituted Polycyclic 3-Bromoaryl Tertiary 2-hydroxyalkylamine") by reaction with a heteroaryl dibutyl tin compound to afford, after isolation and purification as described above for Schemes 2, 5, 6, 7, and 11, additional compounds of the present invention of Formula VII ("Generic Substituted Polycyclic 3-Heteroarylaryl Tertiary 2-Hydroxyalkylamine").

Scheme 21 discloses the conversion of a 3-bromomethyl substituent at the $R_7$ position in Formula VII ("Generic Substituted Polycyclic 3-Bromomethylaryl Tertiary 2-hydroxyalkylamine") by reaction with an aryl borinate to afford, after isolation and purification as described above for Schemes 2, 5, 6, 7, and 11, additional compounds of the present invention of Formula VII ("Generic Substituted Polycyclic 3-Arylmethylaryl Tertiary 2-Hydroxyalkylamine").

Scheme 13 discloses the conversion of a 3-hydroxyl substituent at the $R_7$ position in Formula VII-H ("Generic Substituted Polycyclic 3-Hydroxyheteroaryl Tertiary 2-hydroxyalkylamine") by reaction with an aryl bromide or heteroaryl bromide to afford, after isolation and purification as described above for Schemes 2, 5, 6, 7, and 11, additional compounds of the present invention of Formula VII-H ("Generic Substituted Polycyclic 3-Aryloxyaryl, 3-Heteroaryloxyaryl, 3-Heteroaryloxyheteroaryl, and 3-Aryloxyheteroaryl Tertiary 2-Hydroxyalkylamines").

Scheme 14 discloses the conversion of a 3-hydroxyl substituent at the $R_7$ position in Formula VII ("Generic Substituted Polycyclic 3-Hydroxyaryl Tertiary 2-hydroxyalkylamine") by reaction with an aryl bromide to afford, after isolation and purification as described above for Schemes 2, 5, 6, 7, and 11, additional compounds of the present invention of Formula VII ("Generic Substituted Polycyclic 3-Phenoxyaryl Tertiary 2-Hydroxyalkylamine").

Scheme 15 discloses the conversion of a 3-hydroxyl substituent at the $R_7$ position in Formula VII-H ("Generic Substituted Polycyclic 3-Hydroxyheteroaryl Tertiary 2-hydroxyalkylamine") by reaction with an aralkyl bromide or heteroaralkyl bromide to afford, after isolation and purification as described above for Schemes 2, 5, 6, 7, and 11, additional compounds of the present invention of Formula VII-H ("Generic Substituted Polycyclic 3-Aralkyloxyaryl, 3-Heteroaralkyloxyaryl, 3-Heteroaralkyloxyheteroaryl, and 3-Aralkyloxyheteroaryl Tertiary 2-Hydroxyalkylamines").

Scheme 16 discloses the conversion of a 3-hydroxyl substituent at the $R_7$ position in Formula VII ("Generic Substituted Polycyclic 3-Hydroxyaryl Tertiary 2-hydroxyalkylamine") by reaction with an aralkyl bromide to afford, after isolation and purification as described above for Schemes 2, 5, 6, 7, and 11, additional compounds of the present invention of Formula VII ("Generic Substituted Polycyclic 3-Aralkyloxyaryl Tertiary 2-Hydroxyalkylamine").

Scheme 20 discloses the conversion of a 3-hydroxyl substituent at the $R_7$ position in Formula VII ("Generic Substituted Polycyclic 3-Hydroxyaryl Tertiary 2-hydroxyalkylamine") by reaction with an $R_{17}$-bromide to afford, after isolation and purification as described above for Schemes 2, 5, 6, 7, and 11, additional compounds of the present invention of Formula VII ("Generic Substituted Polycyclic 3-$R_{17}$-oxyaryl Tertiary 2-Hydroxyalkylamine").

Scheme 19 discloses the conversion of a 3-thio substituent at the $R_7$ position in Formula VII ("Generic Substituted Polycyclic 3-thioaryl Tertiary 2-hydroxyalkylamine") by reaction with an $R_{17}$-bromide to afford, after isolation and purification as described above for Schemes 2, 5, 6, 7, and 11, additional compounds of the present invention of Formula VII ("Generic Substituted Polycyclic 3-$R_{17}$thiaaryl Tertiary 2-Hydroxyalkylamine"). "Generic Substituted Polycyclic 3-$R_{17}$thiaaryl Tertiary 2-Hydroxyalkylamines" can be oxidized to sulfonyl compounds of Formula VII ("Generic Substituted Polycyclic 3-$R_7$sulfonylaryl Tertiary 2-Hydroxyalkylamine").

Scheme 24 discloses the conversion of a 3-nitro substituent at the $R_7$ position in Formula VII ("Generic Substituted Polycyclic 3-Nitroaryl Tertiary 2-hydroxyalkylamine") by hydrogenation to afford, after isolation and purification as described above for Schemes 2, 5, 6, 7, and 11, additional compounds of the present invention of Formula VII ("Generic Substituted Polycyclic 3-Aminoaryl Tertiary 2-Hydroxyalkylamine"). "Generic Substituted Polycyclic 3-Aminoaryl Tertiary 2-Hydroxyalkylamines" can be acylated to acyl amide compounds of Formula VII ("Generic Substituted Polycyclic 3-Acylaminoaryl Tertiary 2-Hydroxyalkylamine").

Schemes 25 and 26 disclose the conversion of a 3-amino substituent at the $R_7$ position in Formula VII ("Generic Substituted Polycyclic 3-Aminoaryl Tertiary 2-hydroxyalkylamine") by reaction with carbonyl compounds to afford, after isolation and purification as described above for Schemes 2, 5, 6, 7, and 11, additional compounds of the present invention of Formula VII ("Generic Substituted Polycyclic 3-(Saturated Nitrogen Heterocycl-1yl)aryl Tertiary 2-Hydroxyalkylamine" and "Generic Substituted Polycyclic 3-(Unsaturated Nitrogen Heterocycl-1yl)aryl Tertiary 2-Hydroxyalkylamine", respectively).

Scheme 27 discloses the conversion of a 3-methoxycarbonyl substituent at the $R_7$ position in Formula VII ("Generic Substituted Polycyclic 3-Carbomethoxyaryl Tertiary 2-hydroxyalkylamine") by reaction with amination reagents to afford, after isolation and purification as described above for Schemes 2, 5, 6, 7, and 11, additional compounds of the present invention of Formula VII ("Generic Substituted Polycyclic 3-Carboxamidoaryl Tertiary 2-Hydroxyalkylamine").

Scheme 28 discloses the conversion of a 3-cyano substituent at the $R_7$ position in Formula VII ("Generic Substituted Polycyclic 3-Cyanoaryl Tertiary 2-hydroxyalkylamine") by reaction with organometallic reagents to afford, after isolation and purification as described above for Schemes 2, 5, 6, 7, and 11, additional compounds of the present invention of Formula VII ("Generic Substituted Polycyclic 3-Acylaryl Tertiary 2-Hydroxyalkylamine"). Said "Generic Substituted Polycyclic 3-Acylaryl Tertiary 2-Hydroxyalkylamines", according to Scheme 29 can be reduced to hydroxyl compounds of Formula VII ("Generic Substituted Polycyclic 3-Hydroxysubstitutedmethylaryl Tertiary 2-Hydroxyalkylamine").

Scheme 36 discloses the conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with amination reagents to afford, after isolation and purification as described above for Schemes 2, 5, 6, 7, and 11, additional compounds of the present invention of Formula VII ("Generic Substituted Polycyclic 3-Carboxamidoaryl Tertiary 2-Hydroxyalkylamine").

Scheme 37 discloses the conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with an organometallic reagent to afford, after isolation and purification as described above for Schemes 2, 5, 6, 7, and 11, additional compounds of the present invention of Formula VII ("Generic Substituted Polycyclic 3-(bis-$R_{20}$-hydroxymethyl)aryl Tertiary 2-Hydroxyalkylamine").

Scheme 38 discloses the conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with lithium aluminum hydride to afford, after isolation and purification as described above for Schemes 2, 5, 6, 7, and 11, additional compounds of the present invention of Formula VII ("Generic Substituted Polycyclic 3-Hydroxymethylaryl Tertiary 2-Hydroxyalkylamine").

Scheme 39 discloses the conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with an alkylation reagent to afford, after isolation and purification as described above for Schemes 2, 5, 6, 7, and 11, additional compounds of the present invention of Formula VII ("Generic Substituted Polycyclic 3-(bis-$R_{21}$-hydroxymethyl)aryl Tertiary 2-Hydroxyalkylamine").

Scheme 55 discloses the conversion of a 3-methoxycarbonyl substituent at the $R_{10}$ position in Formula VII ("Generic Substituted Polycyclic 3-Carbomethoxyaryl Tertiary 2-hydroxyalkylamine") by reaction intially with an amidation reagent and then an $R_{20}$-organometallic reagent to afford, after isolation and purification as described above for Schemes 2, 5, 6, 7, and 11, additional compounds of the present invention of Formula VII ("Generic Substituted Polycyclic 3-($R_{20}$-carbonyl) aryl Tertiary 2-Hydroxyalkylamine").

Formula V-H ("Generic Substituted Polycyclic Aryl and Heteroaryl tertiary omegahydroxyalkylamines"), Formula V ("Generic Substituted Polycyclic Aryl tertiary omegahydroxyalkylamines"), Formula VII ("Generic Substituted Polycyclic Aryl tertiary-2-hydroxyalkylamines"), Formula VII-H ("Generic Substituted Polycyclic Heteroaryl tertiary-2-hydroxyalkylamines") and other compounds of this invention poss-sessing hydroxyl, thiol, and amine functional groups can be converted to a wide variety derivatives. The hydroxyl group X, wherein $R_{16}$ is a hydrogen, of compounds of Formulas V, V-H, VII, and VII-H can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. In like manner, compounds of Formulas V, V-H, VII, VII-H, and Cyclo-VII that have at least one hydroxyl group present in the form of an alcohol or phenol can be acylated to its corresponding esters. Similarly, carbamic acid esters (urethans) can be obtained by reacting any hydroxyl group with isocyanates and carbamoyl chlorides. Sulfonate, phosphonate, and phosphate esters can be prepared using the corresponding acid chloride and similar reagents. Compounds of Formulas V, V-H, VII, VII-H, and Cyclo-VII that have at least one thiol group present can be converted to the corresponding thioesters derivatives analogous to those of alcohols and phenols using the same reagents and comparable reaction conditions. Compounds of Formulas V, V-H, VII, VII-H, and Cyclo-VII that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formulas V, V-H, VII, VII-H, and Cyclo-VII are available from commerical sources or the references cited above, which are incorporated herein by reference.

Formula V-H ("Generic Substituted Polycyclic Aryl and Heteroaryl tertiary omegahydroxyalkylamines"), Formula V ("Generic Substituted Polycyclic Aryl tertiary omegahydroxyalkylamines"), Formula VII ("Generic Substituted Polycyclic Aryl tertiary-2-hydroxyalkylamines"), Formula VII-H ("Generic Substituted Polycyclic Heteroaryl tertiary-2-hydroxyalkylamines") and other compounds of this invention poss-sessing hydroxyl, thiol, and amine functional groups can be alkylated to a wide variety derivatives. The hydroxyl group X, wherein $R_{16}$ is a hydrogen, of compounds of Formulas V, V-H, VII, and VII-H can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents, amine catalyst such as pyridine in an inert solvent. In like manner, compounds of Formulas V, V-H, VII, VII-H, and Cyclo-VII that have at least one hydroxyl group present in the form of an alcohol or phenol can be alkylated to their corresponding ethers. Compounds of Formulas V, V-H, VII, VII-H, and Cyclo-VII that have at least one thiol group present can be converted to the corresponding thioether derivatives analogous to those of alcohols and phenols using the same reagents and comparable reaction conditions. Compounds of Formulas V, V-H, VII, VII-H, and Cyclo-VII that have at least one primary, secondary or tertiary amine group present can be converted to the corresponding quaternary ammonium derivatives. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Tertiary amines can be preparedfrom the corresponding primary or secondary amine by reductive alkylation with aldehydes and ketones using reduction methods 1, 2, or 3 as shown in Scheme 3. Suitable procedures and methods for preparing these derivatives can be found in House's Modem Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formulas V, V-H, VII, VII-H, and Cyclo-VII are available from commerical sources or the references cited above, which are incorporated herein by reference.

Formula V-H ("Generic Substituted Polycyclic Aryl and Heteroaryl tertiary omegahydroxyalkylamines"), Formula V ("Generic Substituted Polycyclic Aryl tertiary omegahydroxyalkylamines"), Formula VII ("Generic Substituted Polycyclic Aryl tertiary-2-hydroxyalkylamines"), Formula VII-H ("Generic Substituted Polycyclic Heteroaryl tertiary-2-hydroxyalkylamines") and certain other compounds of this invention can be converted, according to Schemes 17 and 18, to the corresponding cyclic derivatives represented by the general designation "Tricyclic teriary-oxyalkylamines" exmplified by Formula Cyclo-VII ("Substituted Tri cyclic Phenyl teirtiay-2-oxyalkylamines"). The hydroxyl group X, wherein $R_{16}$ is a hydrogen of compounds of Formulas V, V-H, VII, and VII-H can be cyclized to corresponding cyclic ethers. Compounds suitable for cyclization will normally have at least one leaving group within 5 to 10 continuous atoms of the hydroxyl group X wherein $R_{16}$ is a hydrogen. Most preferrably the leaving group will be within 5 to 7 atoms of the hydroxyl group X so as to form a 5 to 7 membered ring heteroatom containing ring. When the leaving group is part of an aromatic ring system, the leaving group will be preferrably in an ortho position. Suitable leaving groups generally include halides, sulfates, sulfonates, trisubsituted amino, disubstituted sulfonium, diazonium, and like, and, in the case of aromatic systems, also includes nitro, alkoxy, aryloxy, heteroaryloxy, and alkylthio. When X-$R_{16}$ is a thiol, amino, or substituted amino, the corresponding analogous sulfur and nitrogen analogs, Cyclo-VII ("Substituted Tricyclic Phenyl tertiary-2-thioalkylamines and tertiary-2-azaalkylamines"), of Formula Cyclo-VII ("Substituted Tricyclic Phenyl tertiary-2-oxyalkylamines") can be obtained.

The cyclization reaction to form "Tricyclic tertaiy-oxyalkylamines" can be accomplished by aromatic and aliphatic nucleophilic substitution reactions such as those disclosed in March's Advanced Organic Chemistry, 4th Edition, John Wiley & Sons, especially at pages 293–412 and 649–658 and the references cited therein, which are incorporated herein by reference. Hydroxyl containing suitably substituted compounds can be converted to a cyclic analog by heating a suitably substituted compound under anhydrous conditions in a suitable solvent, such as dimethylformamide, dimethylsulfoxide, N-methylpyrrolidone, tetraglyme, or hexamethylphosphoramide, in the presence of a suitable base such as potassium carbonate, cesium carbonate, sodium hydroxide, potassium tertiary-butoxide, or lithium diisopropylamide. Alternately, sodium amide in anhydrous ammonia solvent can be used. Temperatures in the range of −20° C. to 200° C. can be used for time periods of 30 minutes to more than 24 hours. The preferred temperature can be selected by standard synthetic chemical technique balancing maximum yield, maximum purity, cost, ease of isolation and operation, and time required. Isolation of the "Tricyclic teniay-oxyalkylamines" can be effected as described above for other tertiary-oxyalkylamines. Representative "Tricyclic tertiary-oxyalkylamines" prepared using the methodology described above are included in Table 8.

The following examples are provided to illustrate the present invention and are not intended to limit the scope thereof. Those skilled in the art will readily understand that known variations of the conditions and processes of the following preparative procedures can be used to prepare these compounds.

TABLE 8

Structure of Substituted Tricyclictertiary-2-oxyalkylamines.

Cyclo-VII

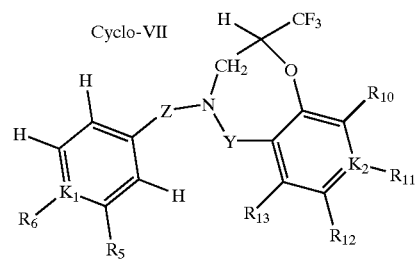

| Y | Z | $R_5$ | $K_1$—$R_6$ | $R_{10}$ | $K_2$—$R_{11}$ | $R_{12}$ | $R_{13}$ |
|---|---|---|---|---|---|---|---|
| $CH_2$ | — | 4-chloro-3-ethylphenoxy | C—H | H | C—$CF_3$ | H | H |
| $CH_2$ | — | 4-chloro-3-ethylphenoxy | N | H | C—$CF_3$ | H | H |

TABLE 8-continued

Structure of Substituted Tricyclictertiary-2-oxyalkylamines.

| | | | | | | | |
|---|---|---|---|---|---|---|---|
| $CH_2$ | — | 4-chloro-3-ethylphenoxy | C—H | H | C—H | $CF_3$ | H |
| $CH_2$ | — | 4-chloro-3-ethylphenoxy | N | H | C—H | $CF_3$ | H |
| $CH_2$ | — | 4-chloro-3-ethylphenoxy | C—H | H | N | $CF_3$ | H |
| — | — | 4-chloro-3-ethylphenoxy | C—H | H | C—$CF_3$ | H | H |
| — | — | 4-chloro-3-ethylphenoxy | N | H | C—$CF_3$ | H | H |
| — | — | 4-chloro-3-ethylphenoxy | C—H | H | C—H | $CF_3$ | H |
| — | — | 4-chloro-3-ethylphenoxy | N | H | C—H | $CF_3$ | H |
| — | — | 4-chloro-3-ethylphenoxy | C—H | H | N | $CF_3$ | H |

Cyclo-VII

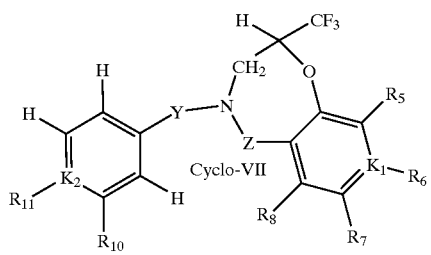

| Y | Z | $R_7$ | $K_1$—$R_6$ | $R_{10}$ | $K_2$—$R_{11}$ | $R_5$ | $R_8$ |
|---|---|---|---|---|---|---|---|
| $CH_2$ | — | 4-chloro-3-ethylphenoxy | C—H | $OCF_2CF_2H$ | C—H | H | H |
| $CH_2$ | — | 4-chloro-3-ethylphenoxy | N | $OCF_2CF_2H$ | C—H | H | H |
| $CH_2$ | — | 4-chloro-3-ethylphenoxy | C—H | $OCF_2CF_2H$ | N | H | H |
| $CH_2$ | — | phenoxy | C—H | $OCF_2CF_2H$ | C—H | H | H |
| $CH_2$ | — | phenoxy | N | $OCF_2CF_2H$ | C—H | H | H |
| $CH_2$ | — | phenoxy | C—H | $OCF_2CF_2H$ | N | H | H |
| $CH_2$ | — | 4-chloro-3-ethylphenoxy | C—H | $CF_2CF_3$ | C—H | H | H |
| $CH_2$ | — | 4-chloro-3-ethylphenoxy | N | $CF_2CF_3$ | C—H | H | H |
| $CH_2$ | — | 4-chloro-3-ethylphenoxy | C—H | $CF_2CF_3$ | N | H | H |
| $CH_2$ | — | phenoxy | C—H | $CF_2CF_3$ | C—H | H | H |
| $CH_2$ | — | phenoxy | N | $CF_2CF_3$ | C—H | H | H |
| $CH_2$ | — | phenoxy | C—H | $CF_2CF_3$ | N | H | H |
| $CH_2$ | — | 4-chloro-3-ethylphenoxy | C—H | $CF_3$ | C—H | H | H |
| $CH_2$ | — | 4-chloro-3-ethylphenoxy | N | $CF_3$ | C—H | H | H |
| $CH_2$ | — | 4-chloro-3-ethylphenoxy | C—H | $CF_3$ | N | H | H |
| $CH_2$ | — | phenoxy | C—H | $CF_3$ | C—H | H | H |
| $CH_2$ | — | phenoxy | N | $CF_3$ | C—H | H | H |
| $CH_2$ | — | phenoxy | C—H | $CF_3$ | N | H | H |
| $CH_2$ | — | 4-chloro-3-ethylphenoxy | C—H | $OCF_2CF_2H$ | C—H | H | F |
| $CH_2$ | — | 4-chloro-3-ethylphenoxy | N | $OCF_2CF_2H$ | C—H | H | F |
| $CH_2$ | — | 4-chloro-3-ethylphenoxy | C—H | $OCF_2CF_2H$ | N | H | F |
| $CH_2$ | — | 4-chloro-3-ethylphenoxy | C—H | 2-furyl | C—H | H | H |
| $CH_2$ | — | 4-chloro-3-ethylphenoxy | N | 2-furyl | C—H | H | H |
| $CH_2$ | — | 4-chloro-3-ethylphenoxy | C—H | 2-furyl | N | H | H |
| $CH_2$ | — | 4-chloro-3-ethylphenoxy | C—H | $SCF_3$ | C—H | H | H |
| $CH_2$ | — | 4-chloro-3-ethylphenoxy | N | $SCF_3$ | C—H | H | H |

Scheme 1
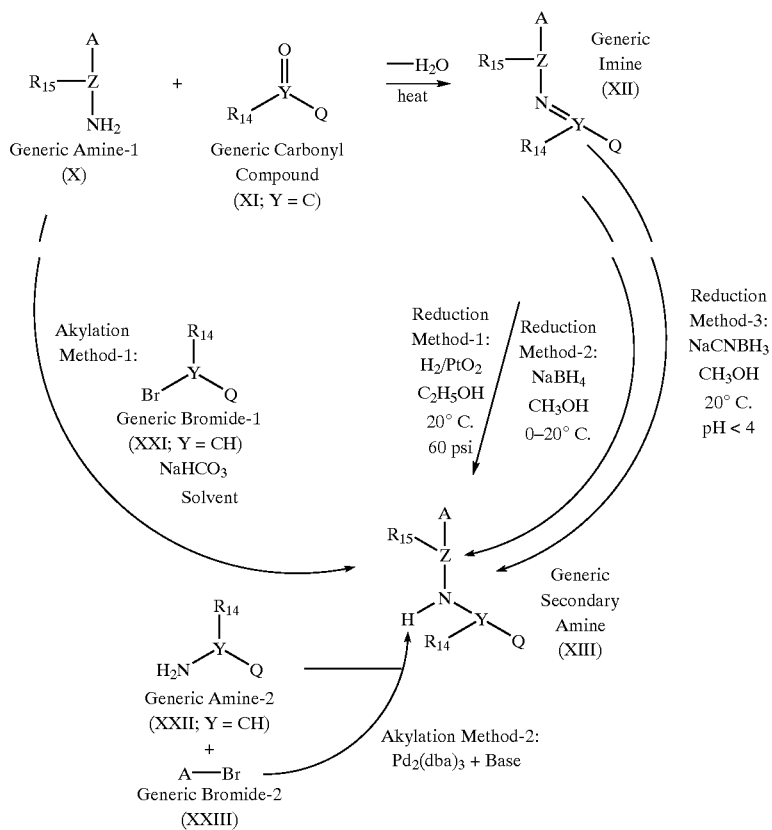
Scheme 2
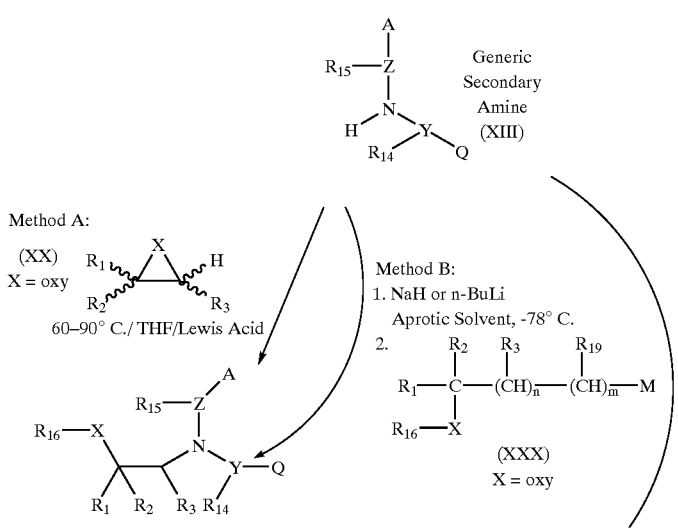

VII: (Generic Substituted Polycyclic Aryl
   Tertiary 2-Hydroxyalkylamine)
VII-H: (Generic Substituted Polycyclic
   Heteroaryl Tertiary
   2-Hydroxyalkylamine)

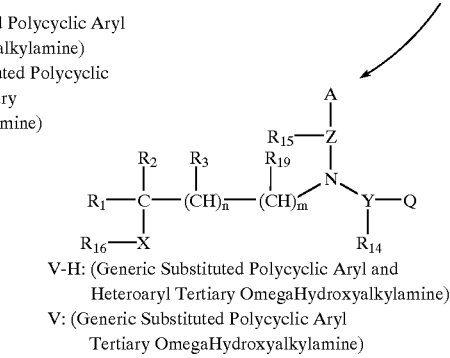

V-H: (Generic Substituted Polycyclic Aryl and
   Heteroaryl Tertiary OmegaHydroxyalkylamine)
V: (Generic Substituted Polycyclic Aryl
   Tertiary OmegaHydroxyalkylamine)

Scheme 3

Heteroaryl Amine (X-AH)

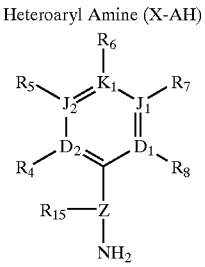

Heteroaryl Carbonyl (XI-AH)

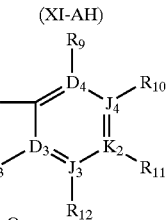

Heteroaryl Bromide (XXI-AH)

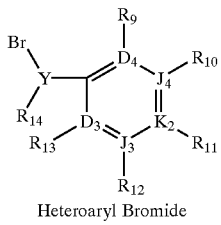

Akylation
Method-1:
Solvent
NaHCO₃

Diheteroaryl Imine (XII-AH)

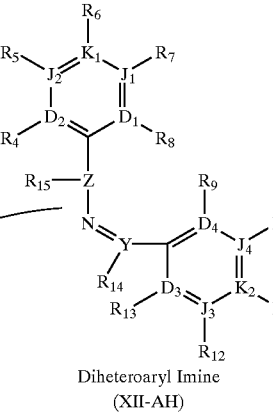

Reduction
Method-1:
H₂/PtO₂
C₂H₅OH
20° C.
60 psi

Reduction
Method-2:
NaBH₄
CH₃OH
0–20° C.

Reduction
Method-3:
NaCNBH₃
CH₃OH/20° C./pH < 4

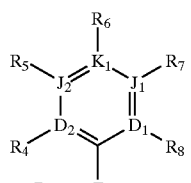

Secondary
Heteroaryl Amine
(XIIIA-H)

Scheme 4
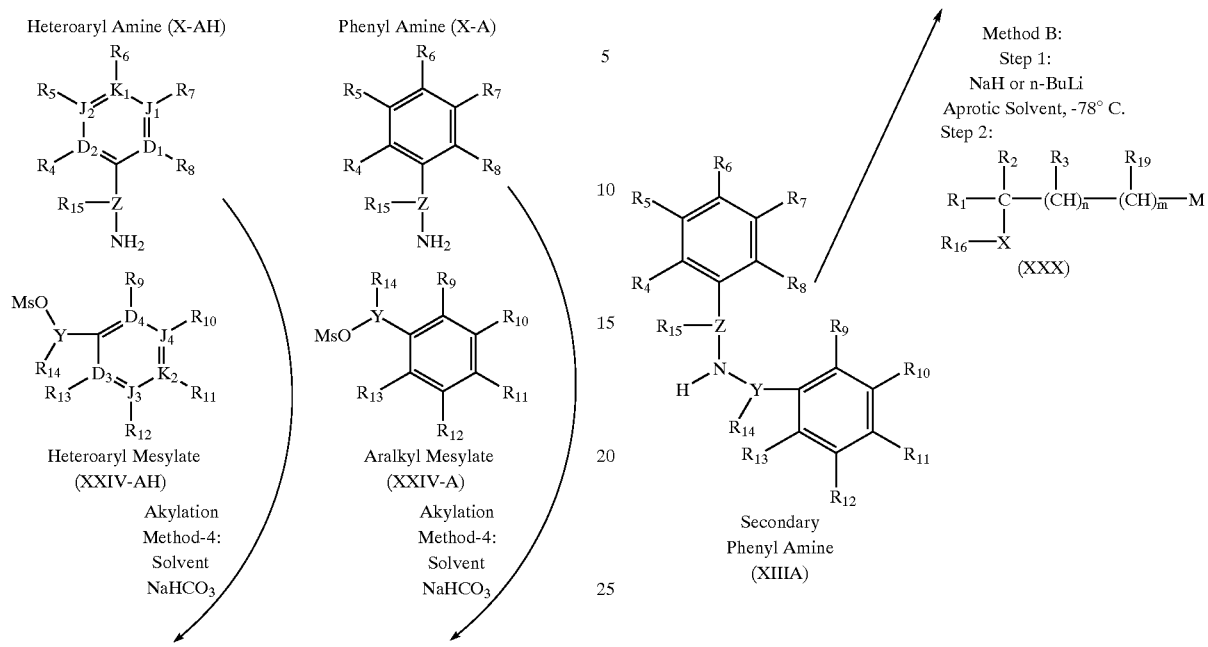
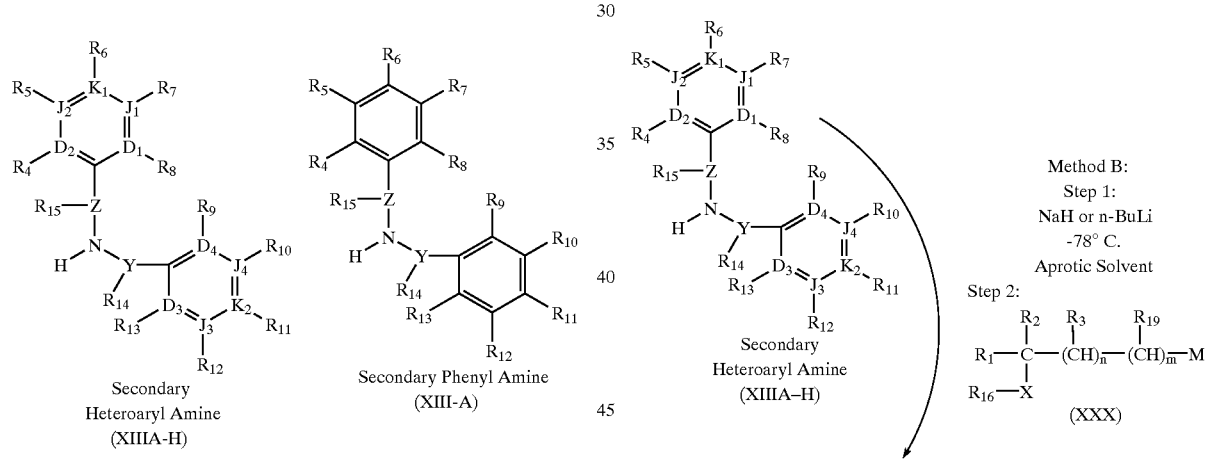
Scheme 5
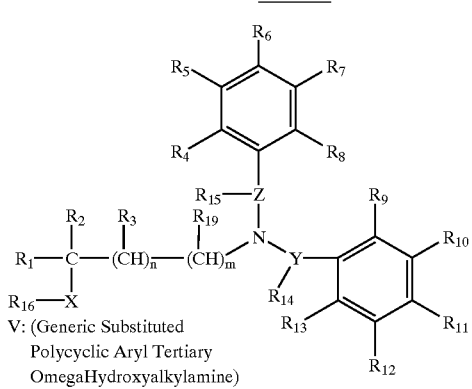
Scheme 6
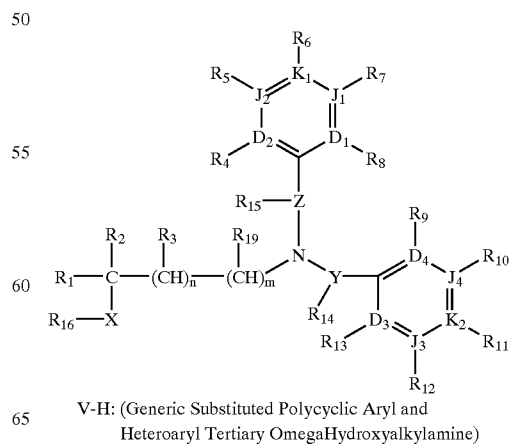

Scheme 7

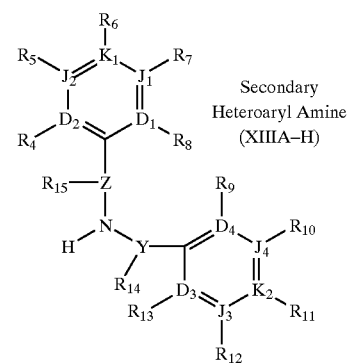

Secondary Heteroaryl Amine (XIIIA–H)

Method A:
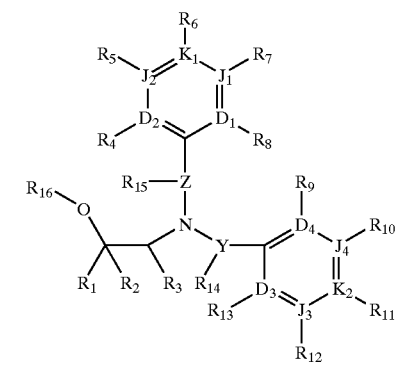
(XX)
60–90° C.
Acetonitrile
Lewis Acid

Method B:
1. NaH or n-BuLi
   Aprotic Solvent
   -78° C.
2. (XX)

VII-H: (Generic Substituted polycyclic Heteroaryl Tertiary 2-Hydroxyalkylamine)

Scheme 8

VII: (Generic Substituted Polycyclic 3-Phenoxyaryl Tertiary 2-Hydroxyalkylamine)

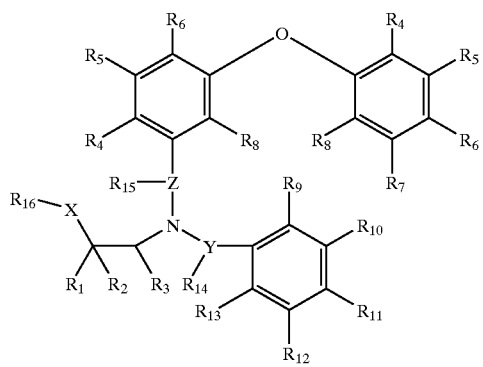

↑ Cu$_2$(triflate)$_2$•Benzene
2 equivalents of a phenol
2.5 equiv. Cs$_2$CO$_3$
2.5 equiv. 1-Naphthoic Acid
4A Molecular Sieves
Dimethylacetamide/toluene
105° C./10–14 Days

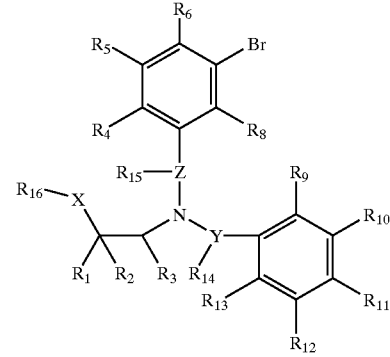

VII: (Generic Substituted Polycyclic 3-Bromoaryl Tertiary 2-Hydroxyalkylamine)

Scheme 9

Phenyl Amine (X-A)

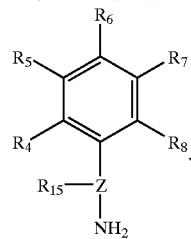

Phenyl Carbonyl (XI-A)

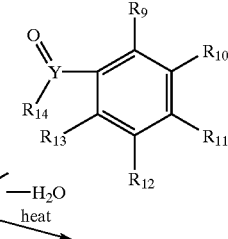

—H$_2$O
heat

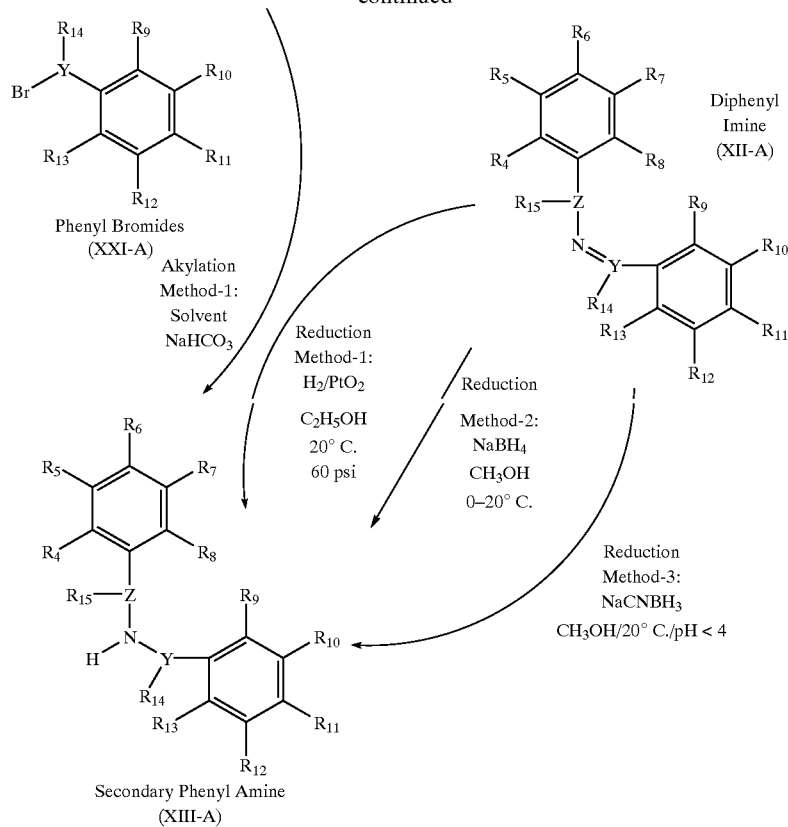
Scheme 10
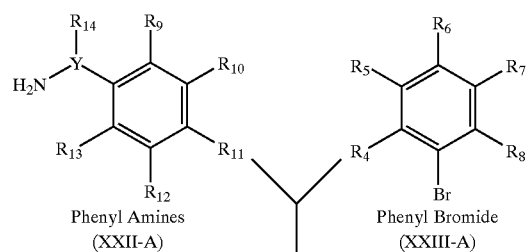
Scheme 11
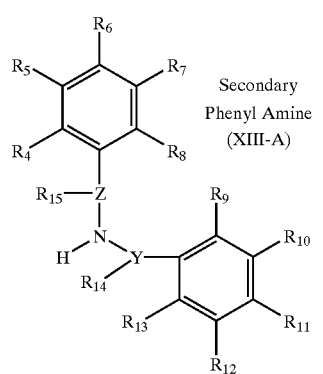
Method A:
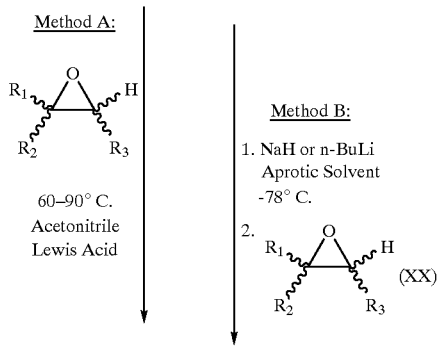
Method B:
1. NaH or n-BuLi
   Aprotic Solvent
   −78° C.
2.

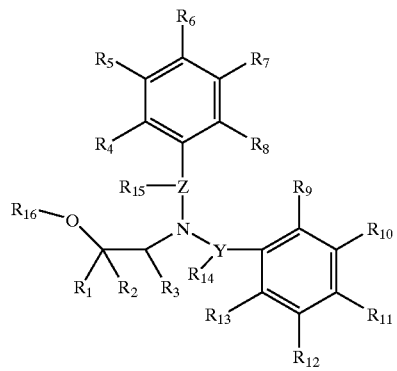

VII: (Generic Substituted Polycyclic Aryl
Tertiary 2-Hydroxyalkylamine)

Scheme 12

VII-H: (Generic Substituted Polycyclic
3-Aryloxyaryl, 3-Heteroaryloxyaryl,
3-Heteroaryloxyheteroaryl, 3-Aryloxyheteroaryl,
3-Arylthioaryl, 3-Heteroarylthioaryl,
3-Heteroarylthioheteroaryl, 3-Arylthioheteroaryl,
Tertiary 2-Hydroxyalkylamine)

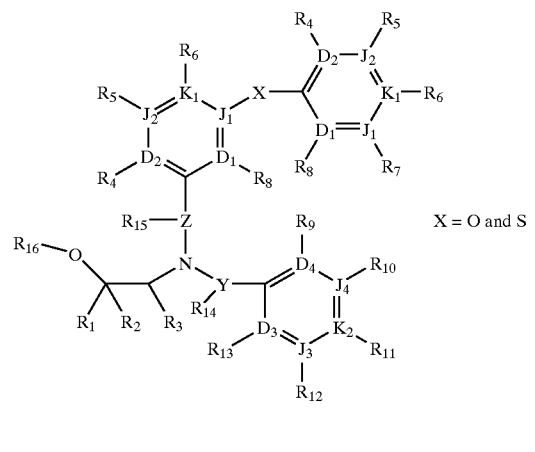

X = O and S

↑ Cu₂ (triflate)₂•Benzene
2 equivalents of Aryl—OH,
Aryl—SH, Heteroaryl—OH,
or Heteroaryl—SH
2.5 eqv. Cs₂CO₃
2.5 eqv. 1-Naphthoic Acid
4A Molecular Sieves
Dimethylacetamide/toluene
105° C./10–14 Days

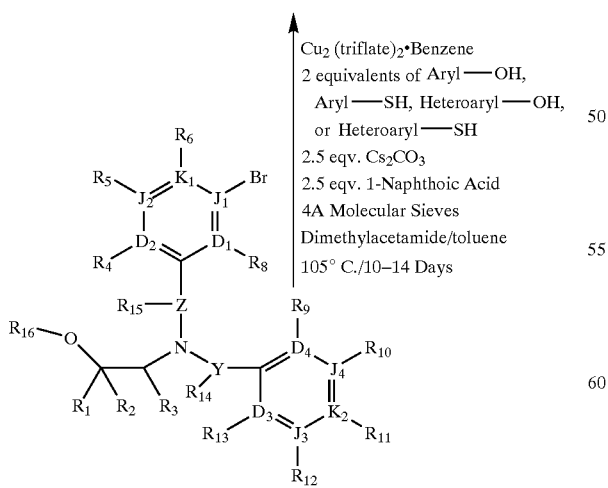

VII-H: (Generic Substituted Polycyclic
3-Bromoheteroaryl Tertiary 2-Hydroxyalkylamine)

Scheme 13

VII-H: (Generic Substituted Polycyclic
3-Aryloxyaryl, 3-Heteroaryloxyaryl
3-Aryloxyheteroaryl, or
3-Heteroaryloxyheteroaryl
Tertiary 2-Hydroxyalkylamine)

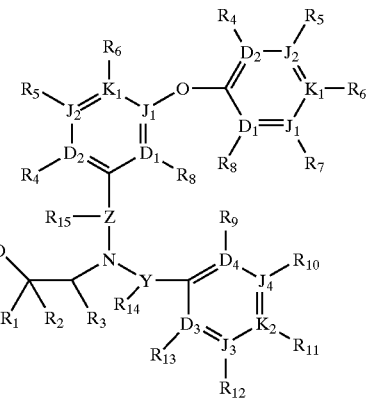

↑ Cu₂ (triflate)₂•Benzene
1 equiv. of aryl bromide
or heteroaryl bromide
1.4 equiv. Cs₂CO₃
Ethyl acetate/toluene
105° C./3–10 Days

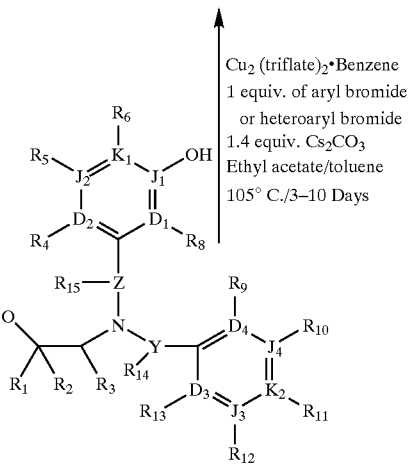

VII-H: (Generic Substituted Polycyclic
3-Hydroxyheteroaryl Tertiary
2-Hydroxyalkylamine)

Scheme 14

VII: (Generic Substituted Polycyclic 3-Phenoxyaryl
Tertiary 2-Hydroxyalkylamine)

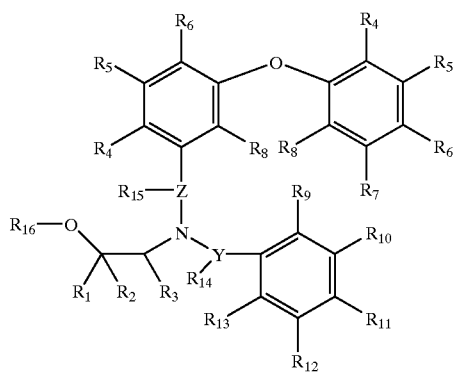

105

-continued

Cu₂(triflate)₂•Benzene
1 equiv. of aryl bromide
   or heteroaryl bromide
1.4 equiv. Cs₂CO₃
Ethyl acetate/toluene
105° C./3–10 Days

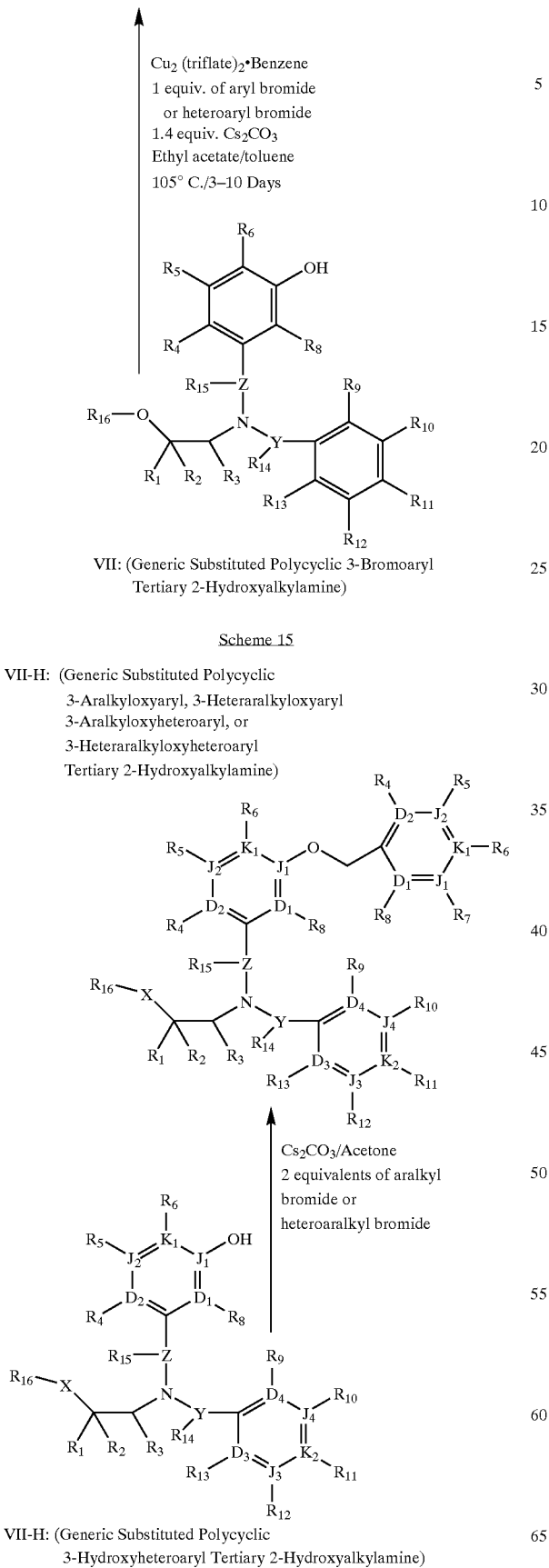

VII: (Generic Substituted Polycyclic 3-Bromoaryl Tertiary 2-Hydroxyalkylamine)

Scheme 15

VII-H: (Generic Substituted Polycyclic
3-Aralkyloxyaryl, 3-Heteraralkyloxyaryl
3-Aralkyloxyheteroaryl, or
3-Heteraralkyloxyheteroaryl
Tertiary 2-Hydroxyalkylamine)

Cs₂CO₃/Acetone
2 equivalents of aralkyl bromide or heteroaralkyl bromide

VII-H: (Generic Substituted Polycyclic 3-Hydroxyheteroaryl Tertiary 2-Hydroxyalkylamine)

106

Scheme 16

VII: (Generic Substituted Polycyclic 3-Aralkyloxyaryl Tertiary 2-Hydroxyalkylamine)

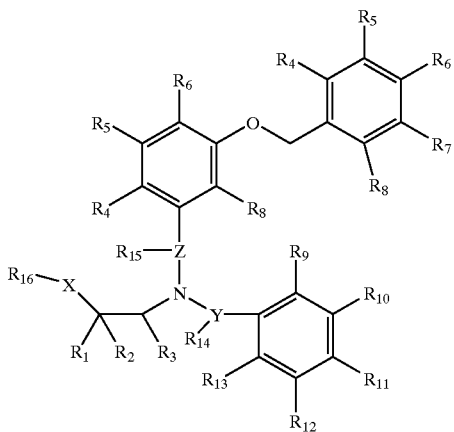

Cs₂CO₃/Acetone
2 equivalents aralkyl bromide

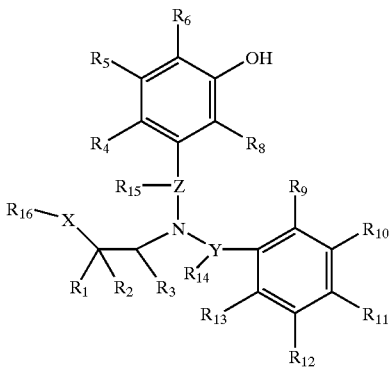

VII: (Generic Substituted Polycyclic 3-Hydroxyaryl Tertiary 2-Hydroxyalkylamine)

Scheme 17

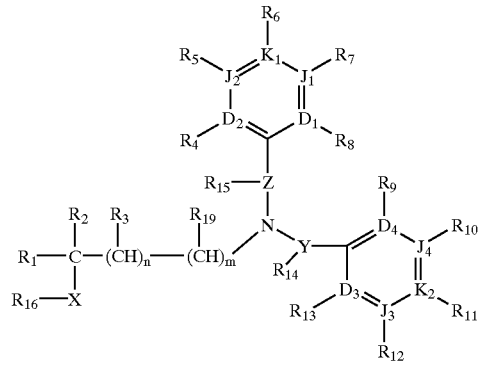

V-H: Generic Polycyclic Heteroaryl and Aryl Tertiary OmegaHydroxyalkylamines ($R_{16}$ = H)

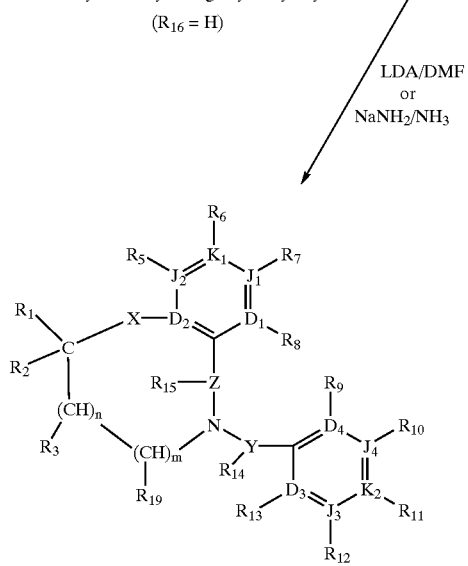

Heteroaryl Cyclo-VII: Substituted Tricyclic Heteroaryl and Aryl tertiary-2-oxyalkylamines Scheme 18

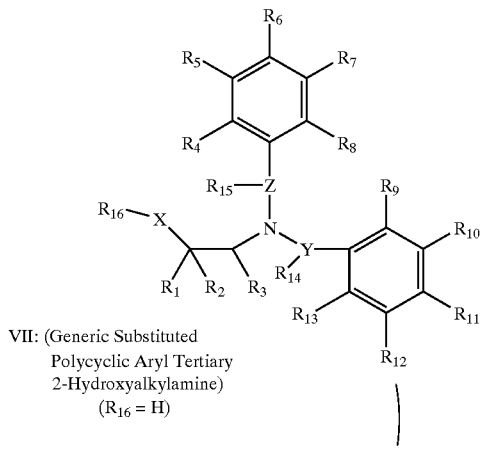

VII: (Generic Substituted Polycyclic Aryl Tertiary 2-Hydroxyalkylamine) ($R_{16}$ = H)

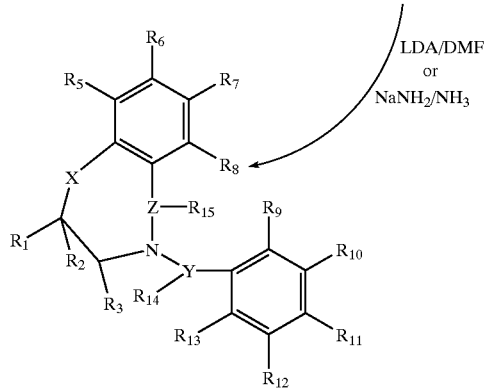

Phenyl Cyclo-VII: Substituted Tricyclic Phenyl tertiary-2-oxyalkylamines

Scheme 19

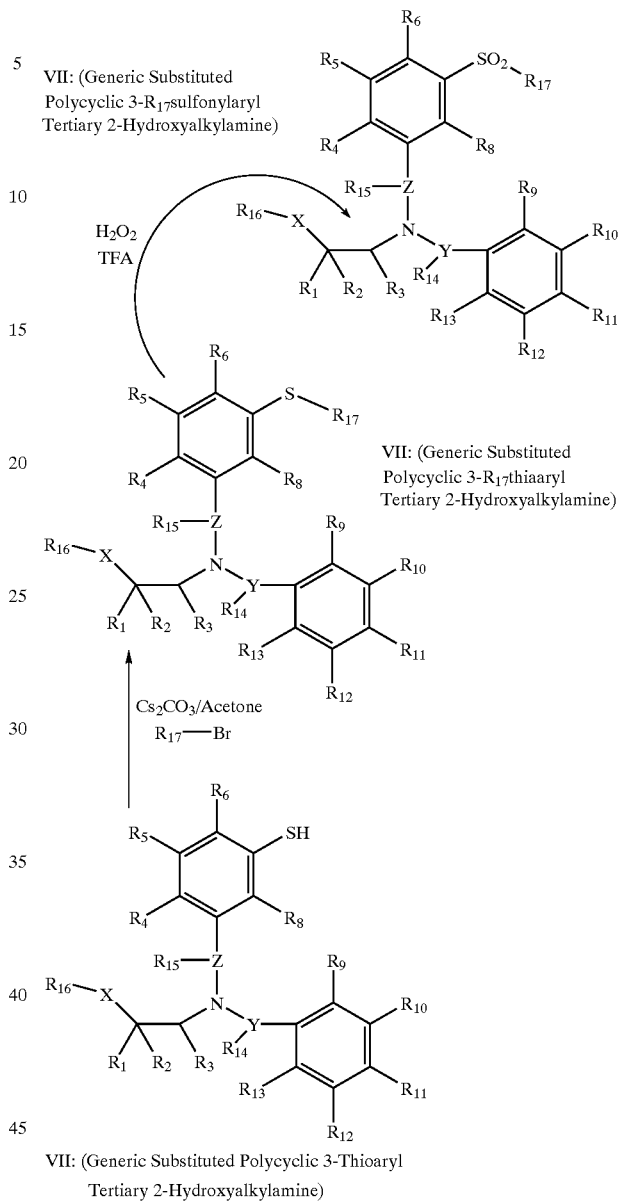

VII: (Generic Substituted Polycyclic 3-$R_{17}$sulfonylaryl Tertiary 2-Hydroxyalkylamine)

VII: (Generic Substituted Polycyclic 3-$R_{17}$thiaaryl Tertiary 2-Hydroxyalkylamine)

VII: (Generic Substituted Polycyclic 3-Thioaryl Tertiary 2-Hydroxyalkylamine)

Scheme 20

VII: (Generic Substituted Polycyclic 3-$R_{17}$-oxyaryl Tertiary 2-Hydroxyalkylamine)

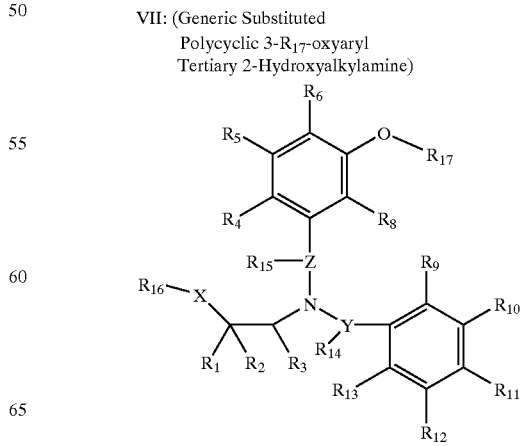

Cs₂CO₃/Acetone
R₁₇—Br

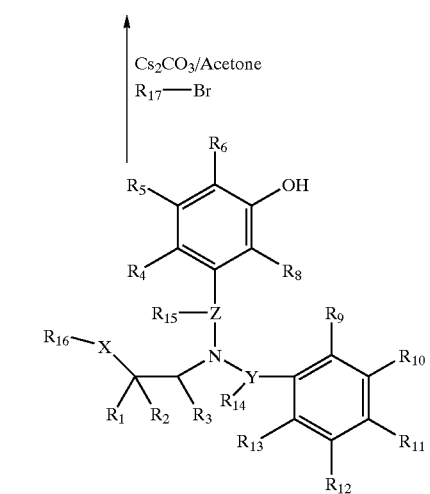

VII: (Generic Substituted Polycyclic 3-Hydroxyaryl Tertiary 2-Hydroxyalkylamine)

Scheme 21

VII: (Generic Substituted Polycyclic 3-Arylmethylaryl Tertiary 2-Hydroxyalkylamine)

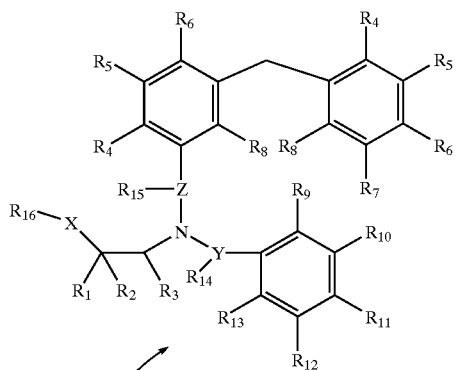

Pd (triphenylphospine)₄
Aryl-B(OH)₂
Toluene
2 M Na₂CO₃
Ethanol

NOTE: Use of Heteroaryl-B(OH)₂ will give the heteroarylmethyl analog of VII.

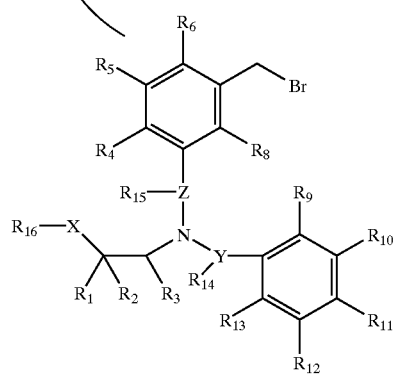

VII: (Generic Substituted Polycyclic 3-Bromomethylaryl Tertiary 2-Hydroxyalkylamine

Scheme 22

VII: (Generic Substituted Polycyclic 3-Arylaryl Tertiary 2-Hydroxyalkylamine)

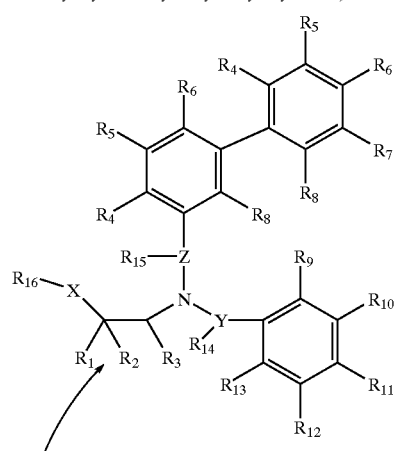

LiCl
Heat
PdCl₂(Ph₃P)₂
Aryl-Sn(n-Bu)₄
Toluene

Pd(Ph₃P)₄
Aryl-B(OH)₂
Toluene
2 M Na₂CO₃
Ethanol

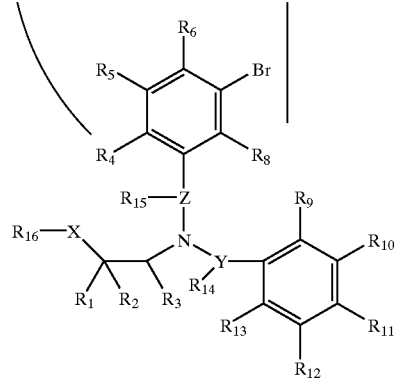

VII: (Generic Substituted Polycyclic 3-Bromoaryl Tertiary 2-Hydroxyalkylamine)

NOTE: Use of Heteroaryl-B(OH)₂ will give the heteroarylmethyl analog of VII.

Scheme 23

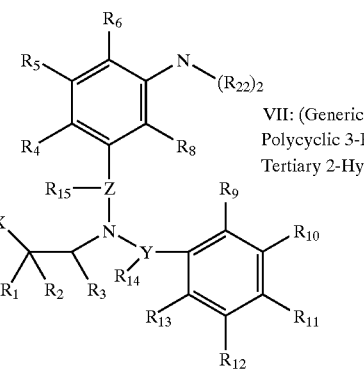

VII: (Generic Substituted Polycyclic 3-R₂₂-aminoaryl Tertiary 2-Hydroxyalkylamine)

-continued

R$_{22}$-primary or secondary amine
Pd(dba)$_3$/R-(+)-BINAP
2.5 equiv. Cs$_2$CO$_3$
Toluene/100° C./1–2 Days

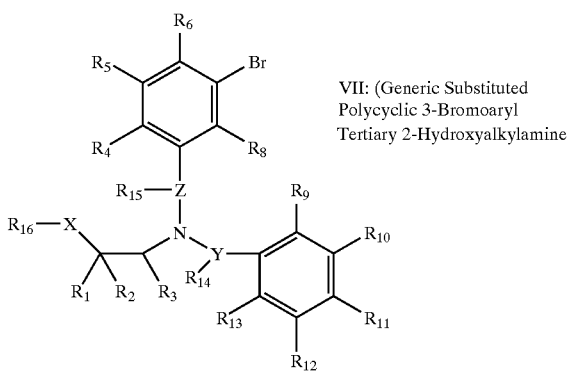

VII: (Generic Substituted Polycyclic 3-Bromoaryl Tertiary 2-Hydroxyalkylamine

Scheme 24

VII: (Generic Substituted Polycyclic 3-Acylaminoaryl Tertiary 2-Hydroxyalkylamine; R$_{16}$ = H)

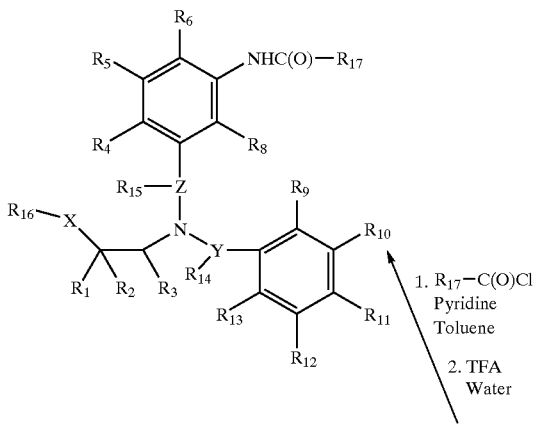

1. R$_{17}$—C(O)Cl
   Pyridine
   Toluene
2. TFA
   Water

VII: (Generic Substituted Polycyclic 3-aminoaryl Tertiary 2-Hydroxyalkylamine; R$_{16}$ = Trialkylsilyl)

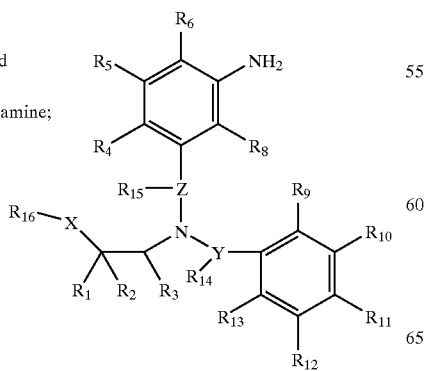

-continued

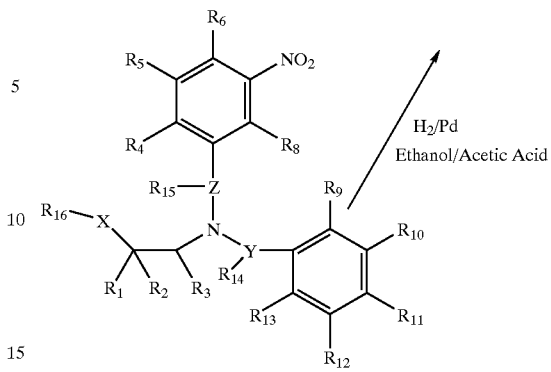

H$_2$/Pd
Ethanol/Acetic Acid

VII: (Generic Substituted Polycyclic 3-Nitroaryl Tertiary 2-Hydroxyalkylamine; R$_{16}$ = trialkylsilyl)

R$_{22}$ selected independently from any or two of the following groups: hydrido, hydroxy, aryloxy, alkyl, alkenyl, alkynyl, aryl, aralkyl, aryloxyalkyl, alkoxyalkyl, aralkoxyalkyl, alkylsulfinylalkyl, haloalkyl, haloalkenyl, halocycloalkyl, halocycloalkoxy, halocycloalkoxyalkyl, arylsulfinylalkyl, arylsulfonylalkyl, alkylamino cycloalkylsulfinylalky, cycloalkylsufonylalkyl, heteroarylsulfonylalkyl, heteroarylsulfinyl-sulfinylalkyl, aralkylsulfinylalkyl, aralkylsulfonylalkyl, hydroxyalkyl, amino, alkoxy, alkylsulfonylalkyl, aralkylthioalkyl, heteroaralkylthioalkyl, heteroaryloxyalkyl, alkenyloxyalkyl, haloalkoxy, haloalkoxyalkyl, haloalkenyloxyalkyl, heteroaryl, halocycloalkenyloxyalkyl, heteroarylalkyl, halocycloalkenyl, and heteroarylthioalkyl.

Scheme 25

VII: (Generic Substituted Polycyclic 3-(Saturated nitrogen heterocycl-1-yl) aryl Tertiary 2-Hydroxyalkylamine; R$_{16}$ = H)

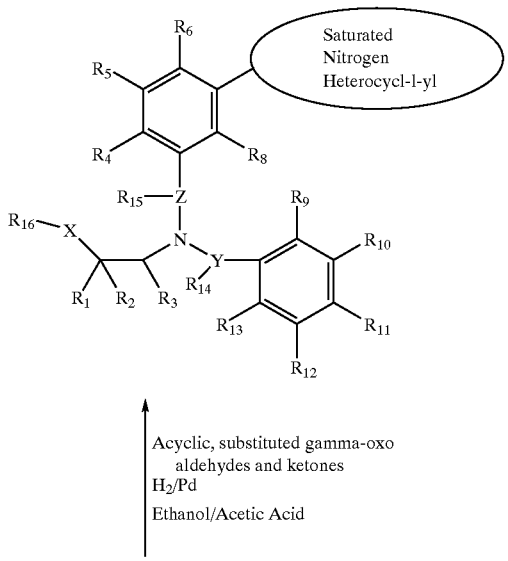

Acyclic, substituted gamma-oxo aldehydes and ketones
H$_2$/Pd
Ethanol/Acetic Acid

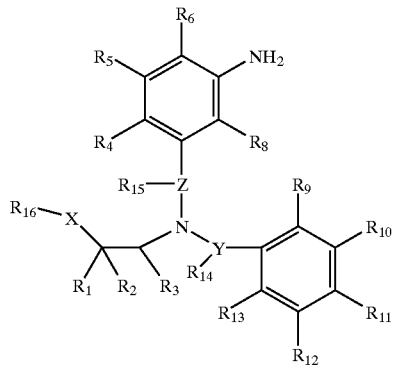

VII: (Generic Substituted Polycyclic 3-aminoaryl Tertiary 2-Hydroxyalkylamine; $R_{16}$ = H))

Scheme 26

VII: (Generic Substituted Polycyclic 3-(Unsaturated nitrogen heterocycl-1-yl) aryl Tertiary 2-Hydroxyalkylamine; $R_{16}$ = H)

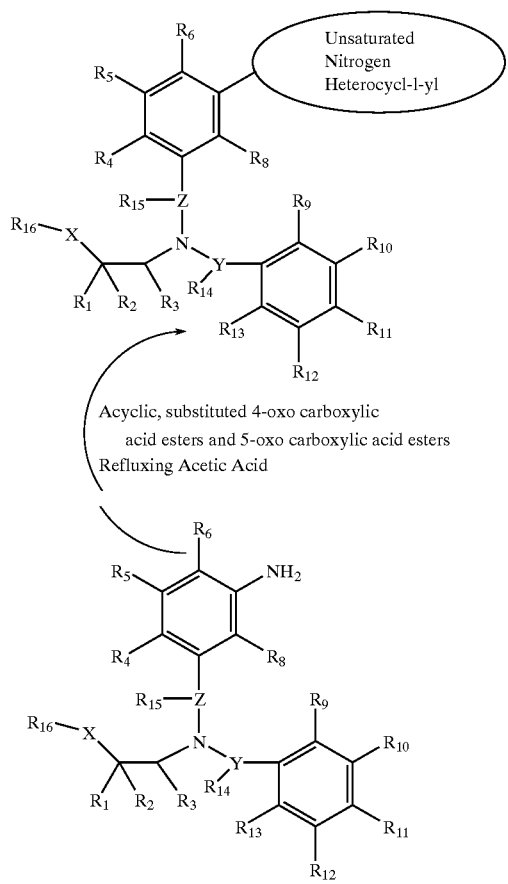

VII: (Generic Substituted Polycyclic 3-aminoaryl Tertiary 2-Hydroxyalkylamine; $R_{16}$ = H)

Scheme 27

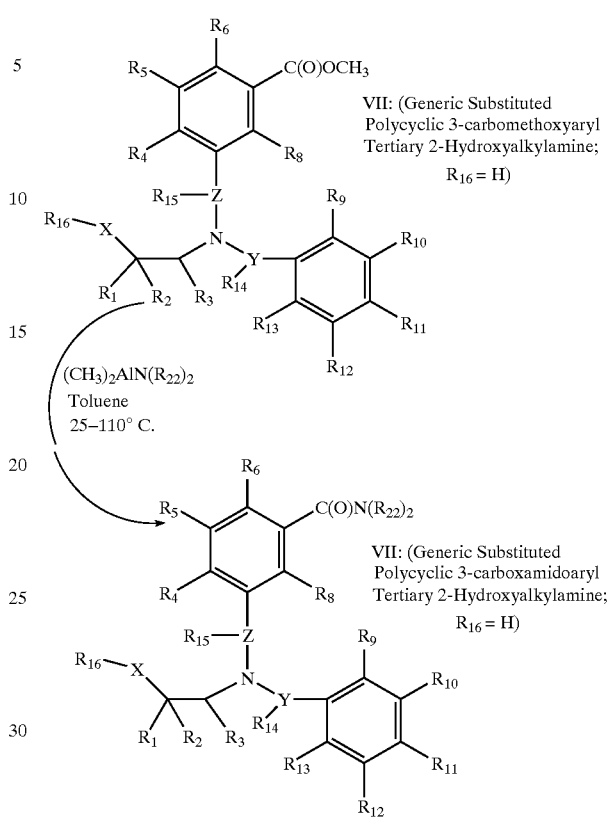

Scheme 28

VII: (Generic Substituted Polycyclic 3-cyanoaryl Tertiary 2-Hydroxyalkylamine; $R_{16}$ = H)

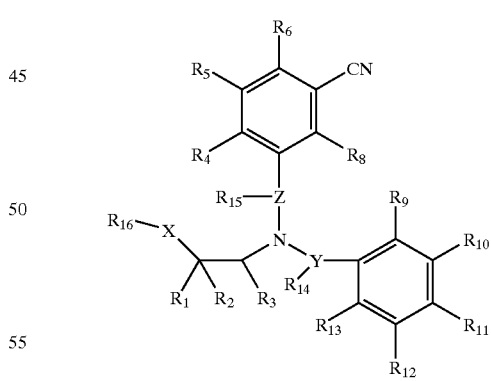

Method 1:
1. 2–5 equiv.
   $R_{17}$—MgBr/ether
2. HCl/$H_2O$

Method 2:
1. 2 equiv.
   $R_{17}$—Li
   hydrocarbon solvent
2. HCl/$H_2O$

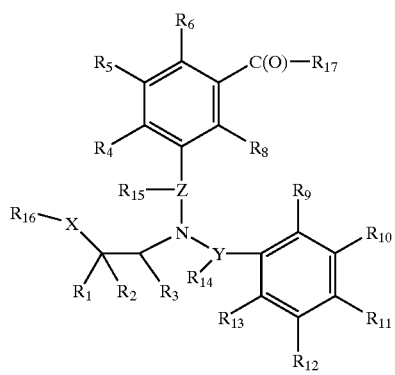

VII: (Generic Substituted Polycyclic 3-Acylaryl Tertiary 2-Hydroxyalkylamine; $R_{16}$ = H)

$R_{22}$ selected independently from any or two of the following groups: hydrido, hydroxy, aryloxy, alkyl, alkenyl, alkynyl, aryl, aralkyl, aryloxyalkyl, alkoxyalkyl, aralkoxyalkyl, alkylsulfinylalkyl, haloalkyl, haloalkenyl, halocycloalkyl, halocycloalkoxy, halocycloalkoxyalkyl, heteroaryl, arylsulfinylalkyl, arylsulfonylalkyl, alkylamino cycloalkylsulfinylalky, cycloalkylsufonylalkyl, heteroarylsulfonylalkyl, heteroarylsulfinylalkyl, aralkylsulfinylalkyl, aralkylsulfonylalkyl, hydroxyalkyl, amino, alkoxy, alkylsulfonylalkyl, aralkylthioalkyl, heteroaralkylthioalkyl, heteroaryloxyalkyl, alkenyloxyalkyl, haloalkoxy, haloalkoxyalkyl, haloalkenyloxyalkyl, halocycloalkenyl, halocycloalkenyloxyalkyl, heteroarylalkyl, and heteroarylthioalkyl.

Scheme 29

VII: (Generic Substituted Polycyclic 3-Hydroxysubstituted-methylarly Tertiary 2-Hydroxyalkylamine; $R_{16}$ = H)

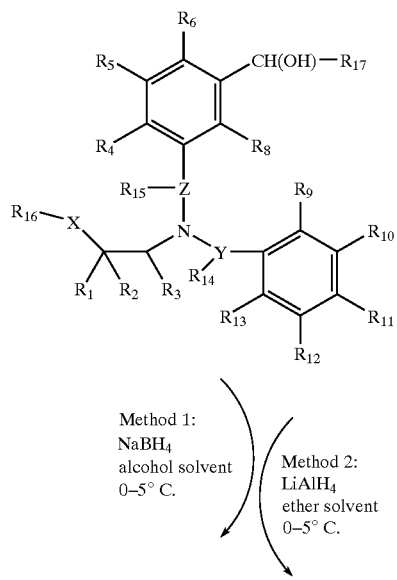

Method 1:
NaBH$_4$
alcohol solvent
0–5° C.

Method 2:
LiAlH$_4$
ether solvent
0–5° C.

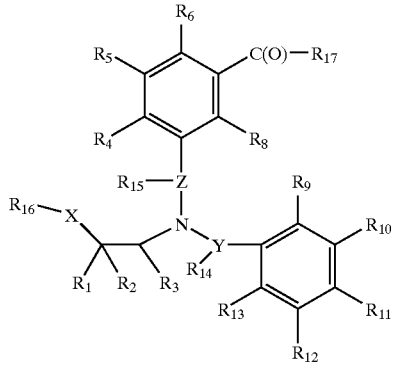

VII: (Generic Substituted Polycyclic 3-Acylaryl Tertiary 2-Hydroxyalkylamine; $R_{16}$ = H)

$R_{17}$ is selected from alkyl, alkenyl, alkynyl, aryl, aryloxyalkyl, aralkoxyalkyl, aralkylthioalkyl, heteroaryloxyalkyl, alkenyloxyalkyl, alkylthioalkyl, cycloalkyl, cycloalkylalkyl, cycloalkylalkenyl, heteroaryl, heteroarylalkyl, heteroarylthioalkyl, heteroaralkylthioalkyl, heteroaralkylthioalkyl, alkoxyalkyl, cycloalkenylalkyl, arylthioalkyl, aralkyl, and cycloalkenyl.

Scheme 30

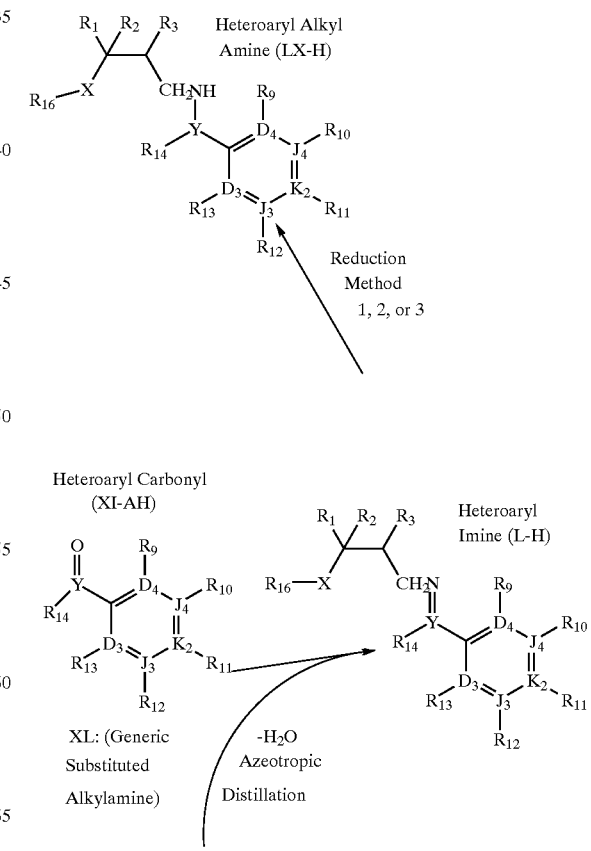

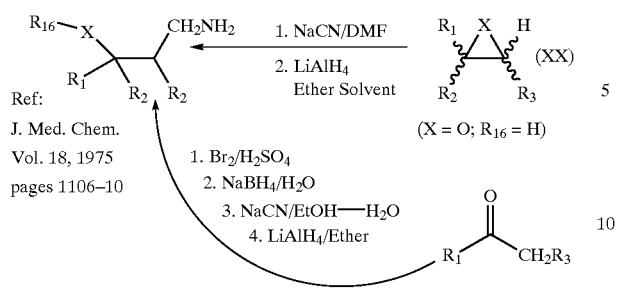

Ref:
J. Med. Chem.
Vol. 18, 1975
pages 1106–10

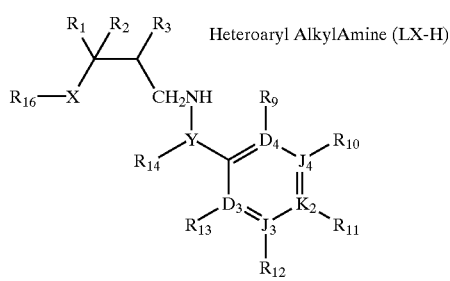

$R_{17}$ is selected from alkyl, alkenyl, alkynyl, aryl, aryloxyalkyl, aralkoxyalkyl, aralkylthioalkyl, heteroaryloxyalkyl, alkenyloxyalkyl, alkylthioalkyl, cycloalkyl, cycloalkylalkyl, cycloalkylalkenyl, heteroaryl, heteroarylalkyl, heteroarylthioalkyl, aralkyl, heteroaralkylthioalkyl, heteroaralkylthioalkyl, alkoxyalkyl, cycloalkenylalkyl, arylthioalkyl, and cycloalkenyl.

Scheme 31

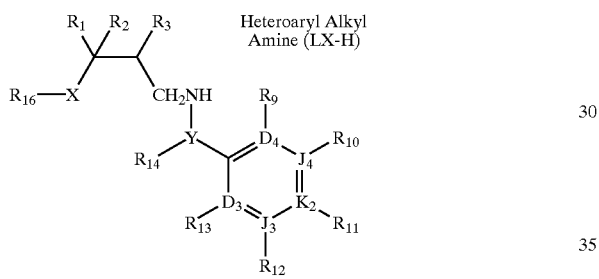

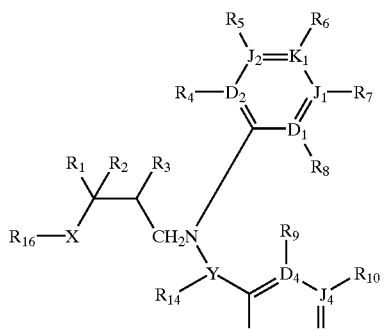

Scheme 32

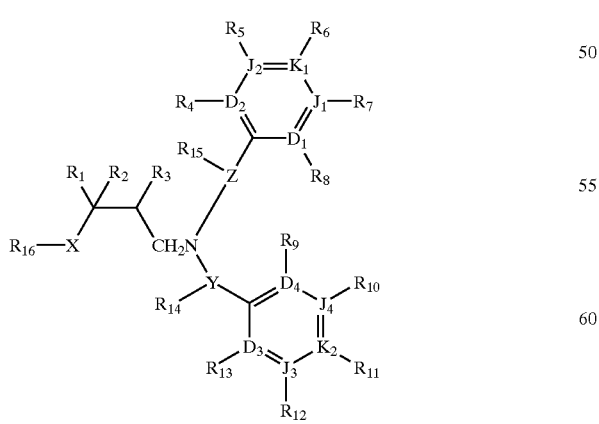

V-H: (Generic Substituted Polycyclic Heteroaryl Tertiary 3-hydroxyalkylamine; $R_{19}$ = H)

Scheme 33

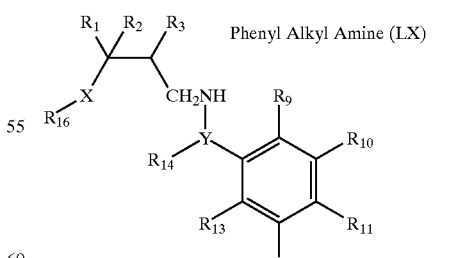

V-H: (Generic Substituted Polycyclic Heteroaryl Tertiary 3-hydroxyalkylamine; $R_{19}$ = H)

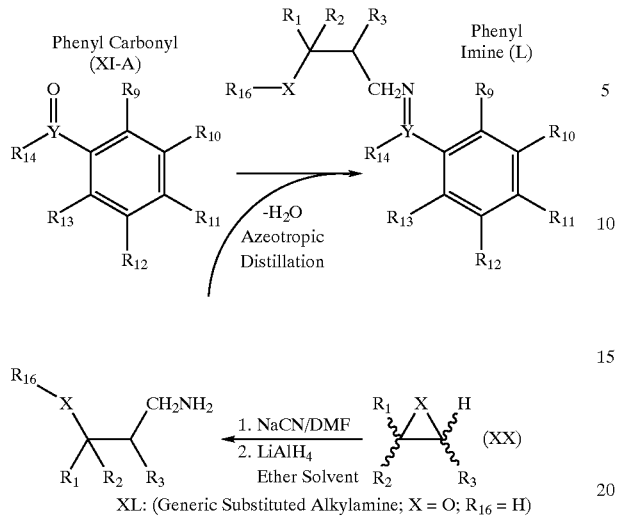
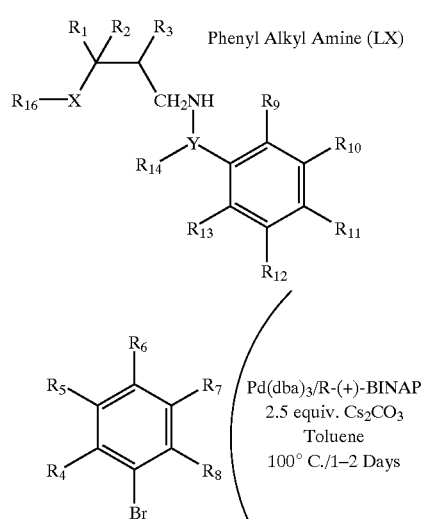
Scheme 35
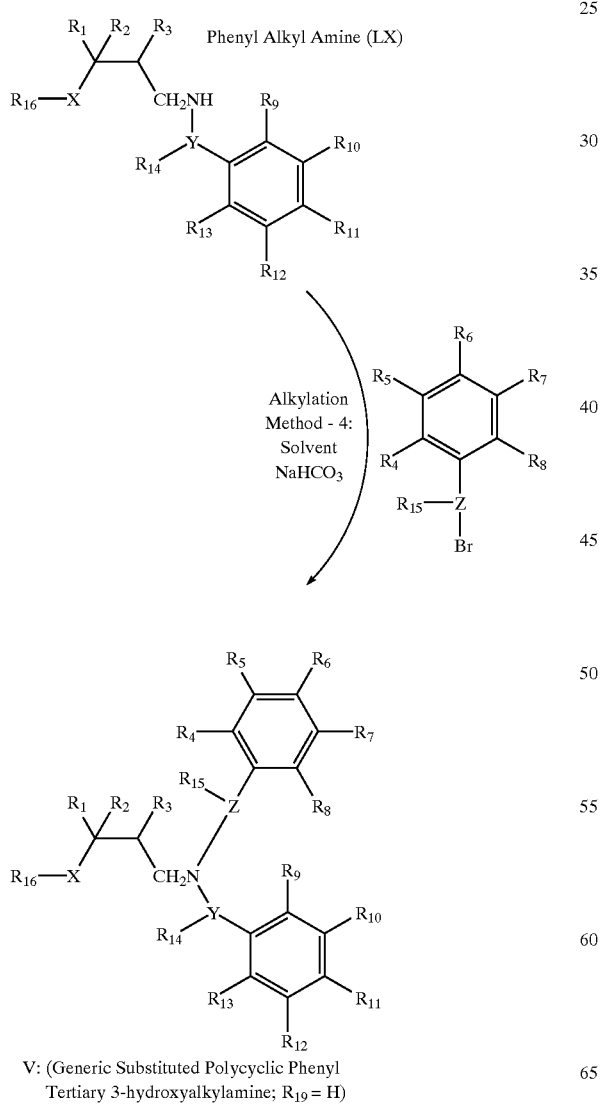
Scheme 34
Alkylation Method - 4: Solvent NaHCO₃
V: (Generic Substituted Polycyclic Phenyl Tertiary 3-hydroxyalkylamine; R₁₉ = H)
V: (Generic Substituted Polycyclic Phenyl Tertiary 3-hydroxyalkylamine; R₁₉ = H)
Scheme 36
VII: (Generic Substituted Polycyclic 3-Carbomethoxyaryl Tertiary 2-Hydroxyalkylamine; R₁₆ = H)
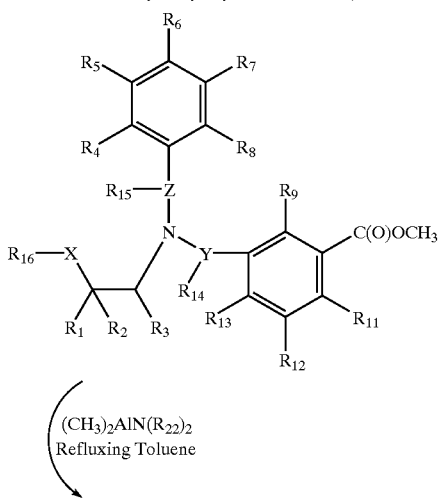

-continued

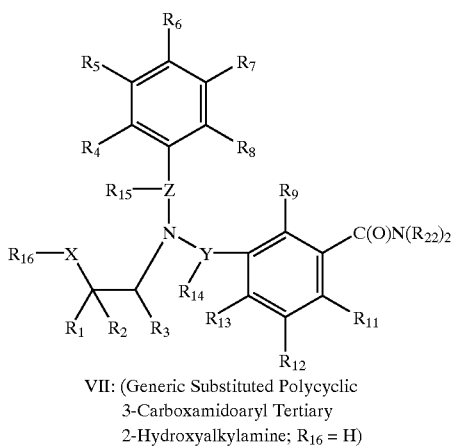

VII: (Generic Substituted Polycyclic
3-Carboxamidoaryl Tertiary
2-Hydroxyalkylamine; $R_{16}$ = H)

NOTE: $R_{22}$ is as defined in Scheme 27

Scheme 37

VII: (Generic Substituted Polycyclic
3-carbomethoxyarylTertiary
2-Hydroxyalkylamine; $R_{16}$ = H)

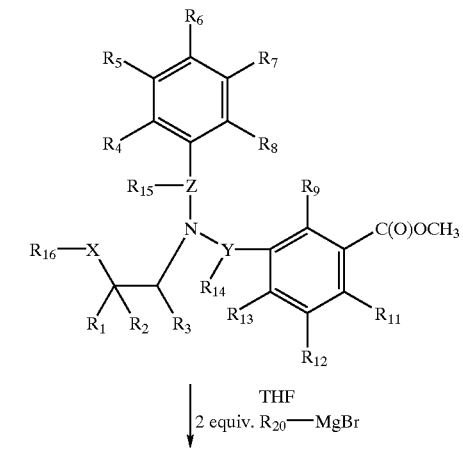

↓ THF
2 equiv. $R_{20}$—MgBr

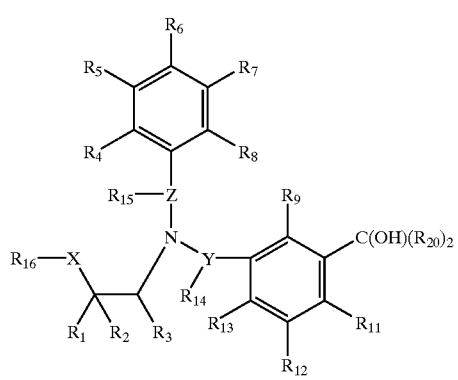

VII: (Generic Substituted Polycyclic
3-(bis-$R_{20}$-hydroxymethyl)aryl Tertiary
2-Hydroxyalkylamine; $R_{16}$ = H)

Scheme 38

VII: (Generic Substituted Polycyclic
3-carbomethoxyaryl Tertiary
2-Hydroxyalkylamine; $R_{16}$ = H)

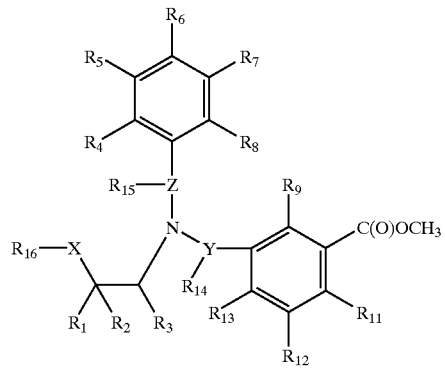

↓ THF
LiAlH$_4$

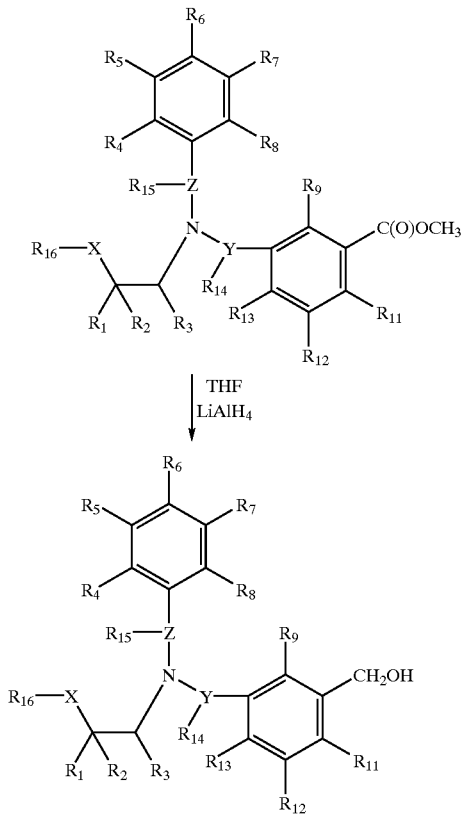

VII: (Generic Substituted Polycyclic
3-hydroxymethylaryl Tertiary
2-Hydroxyalkylamine; $R_{16}$ = H)

$R_{20}$ is selected from alkyl, alkenyl, alkynyl, aryloxyalkyl, aralkoxyalkyl, aralkylthioalkyl, heteroaryloxyalkyl, alkenyloxyalkyl, aryl, cycloalkyl, cycloalkylalkyl, cycloalkylalkenyl, heteroaryl, heteroarylalkyl, heteroarylthioalkyl, heteroaralkylthioalkyl, heteroaralkylthioalkyl, cycloalkenylalkyl, arylthioalkyl, aralkyl, alkoxyalkyl, alkylthioalkyl, and cycloalkenyl.

Scheme 39

VII: (Generic Substituted Polycyclic
3-carbomethoxyaryl Tertiary
2-Hydroxyalkylamine; $R_{16}$ = H)

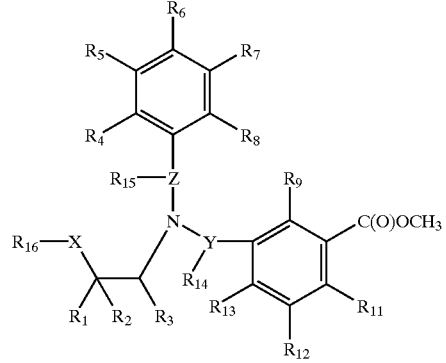

-continued

TBAF
excess R$_{21}$—TMS
refluxing toluene

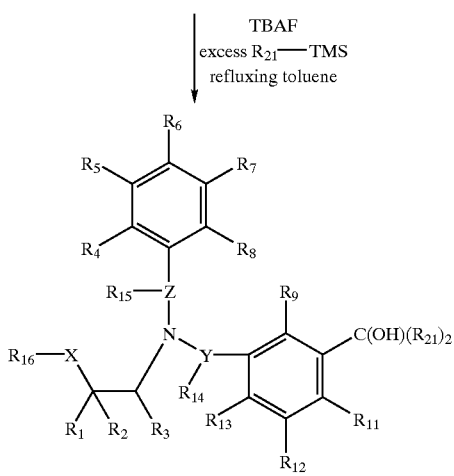

VII: (Generic Substituted Polycyclic
3-(bis)-R$_{21}$-hydroxymethyl)aryl Tertiary
2-Hydroxyalkylamine; R$_{16}$ = H)

Scheme 40

VII: (Generic Substituted Polycyclic
3-Arylaryl Tertiary
2-Hydroxyalkylamine)

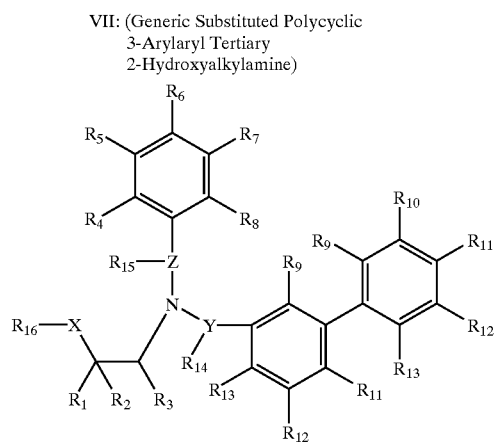

↑ Pd(triphenylphosphine)$_4$
Aryl—B(OH)$_2$
K$_2$CO$_3$, toluene, DMF

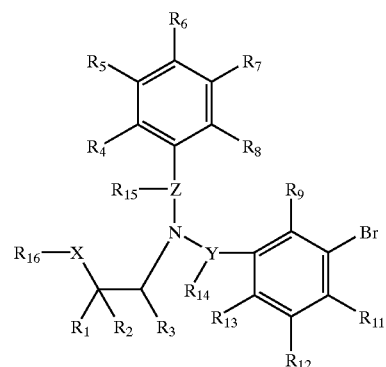

VII: (Generic Substituted Polycyclic
3-Bromoaryl Tertiary
2-Hydroxyalkylamine)

R$_{21}$ is selected from perfluoroalkyl, perfluoroalkenyl, perfluorocycloalkyl, perfluorocycloalkylalkyl, perfluoroaralkyl, perfluoroalkoxyalkyl, Scheme 41

VII: (Generic Substituted Polycyclic
3-Heteroarylaryl Tertiary 2-Hydroxyalkylamine)

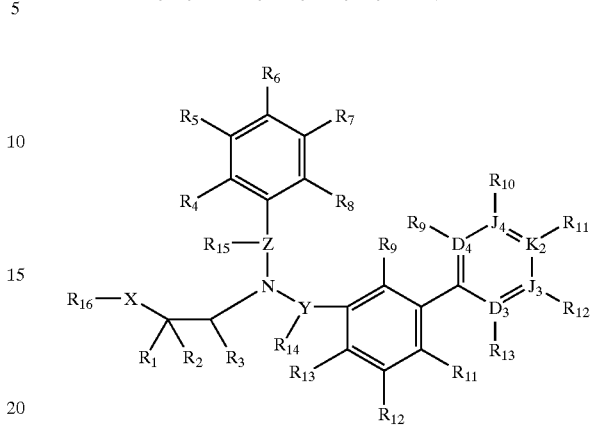

↑ Pd(triphenylphosphine)$_2$Cl$_2$
Heteroaryl-SnBu$_3$
Dioxane

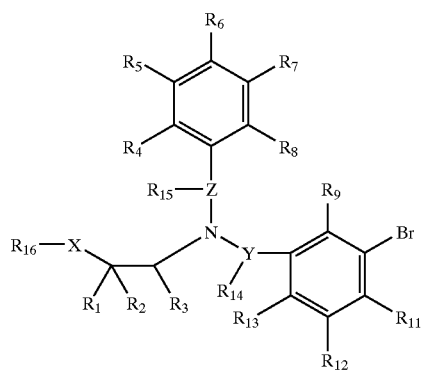

VII: (Generic Substituted Polycyclic
3-Bromaryl Tertiary 2-Hydroxyalkylamine)

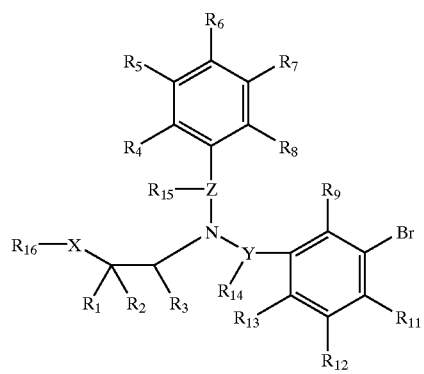

VII: (Generic Substituted Polycyclic
3-Bromaryl Tertiary 2-Hydroxyalkylamine)

Scheme 42

3-Bromo Phenyl Carbonyl (XI-A)

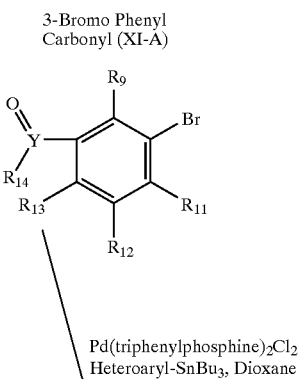

Pd(triphenylphosphine)$_2$Cl$_2$
Heteroaryl-SnBu$_3$, Dioxane

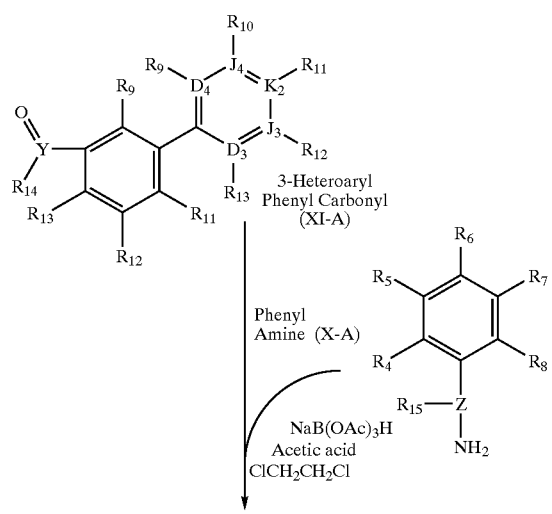

3-Heteroaryl Phenyl Carbonyl (XI-A)

Phenyl Amine (X-A)

NaB(OAc)$_3$H
Acetic acid
ClCH$_2$CH$_2$Cl

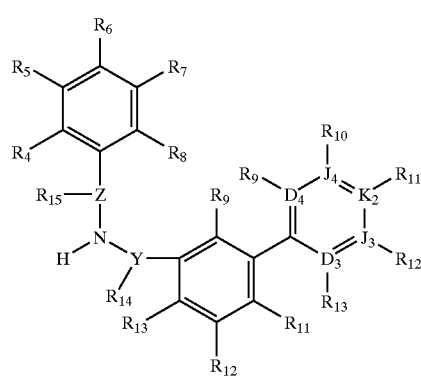

Secondary 3-Heteroarylphenyl Amine (XIII-A)

Scheme 43

3-Bromo Phenyl Carbonyl (XI-A)

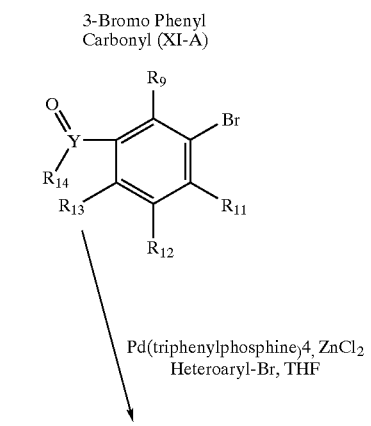

Pd(triphenylphosphine)$_4$, ZnCl$_2$
Heteroaryl-Br, THF

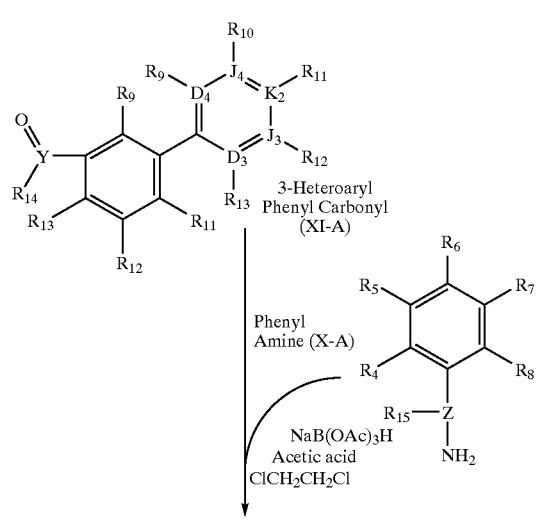

3-Heteroaryl Phenyl Carbonyl (XI-A)

Phenyl Amine (X-A)

NaB(OAc)$_3$H
Acetic acid
ClCH$_2$CH$_2$Cl

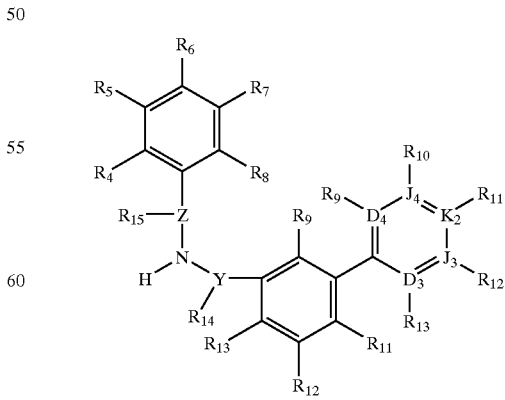

Secondary 3-Heteroarylphenyl Amine (XIII-A)

Scheme 44
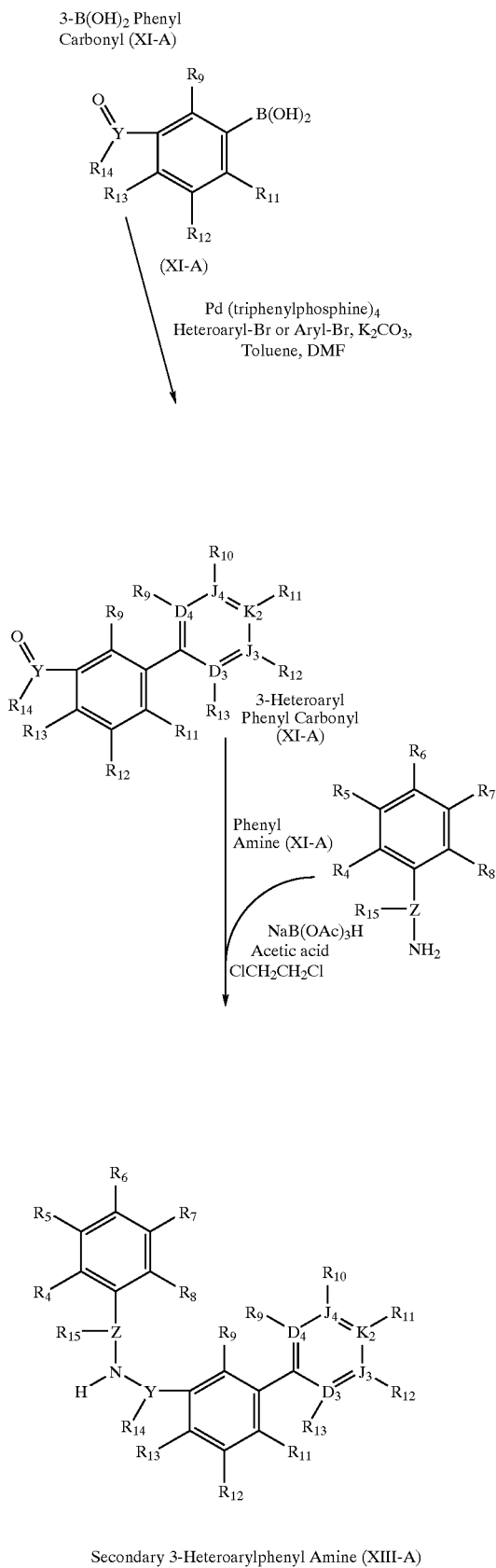
Scheme 45
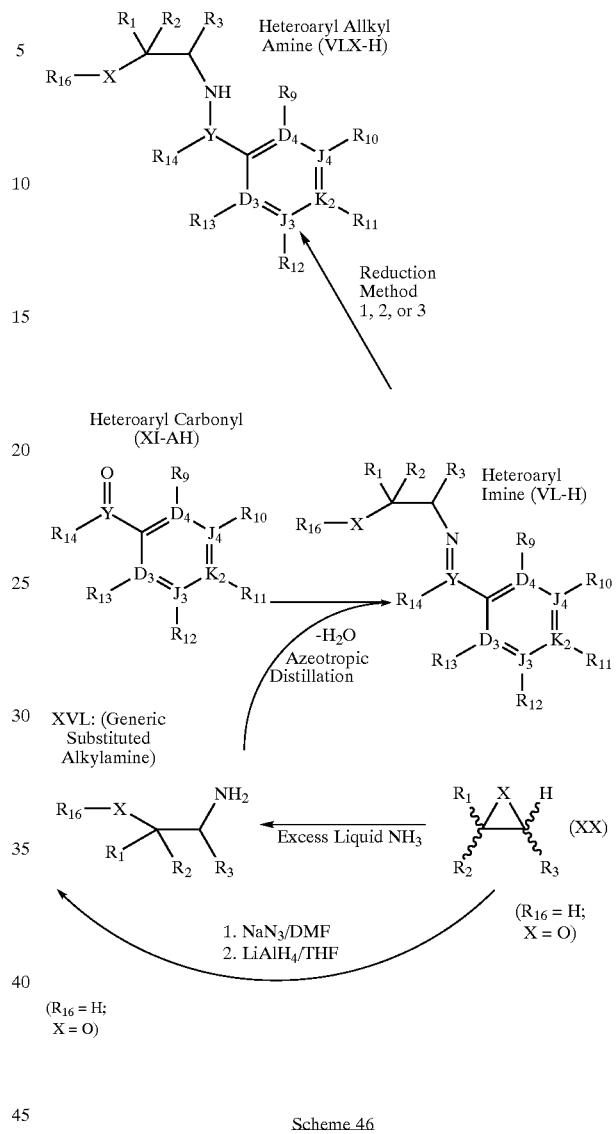
Scheme 46
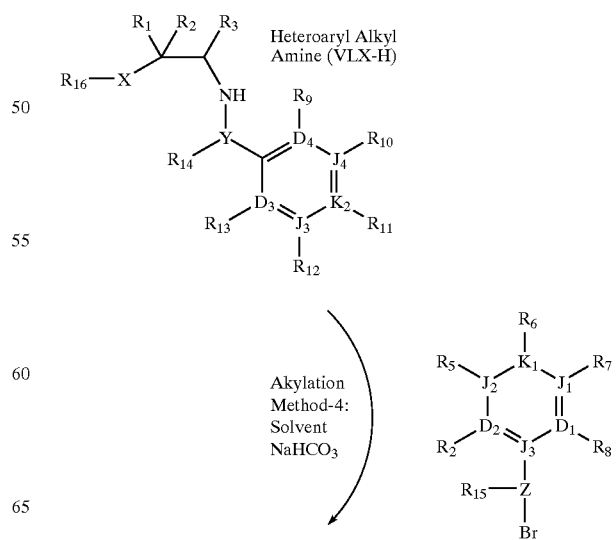

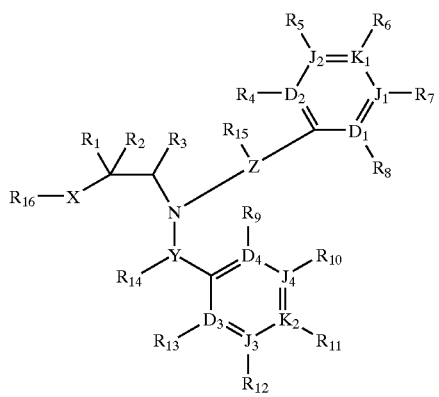

VII-H: (Generic Substituted Polycyclic Heteroaryl Tertiary 2-hydroxyalkylamine)

Scheme 47

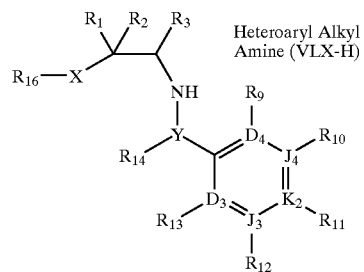

Heteroaryl Alkyl Amine (VLX-H)

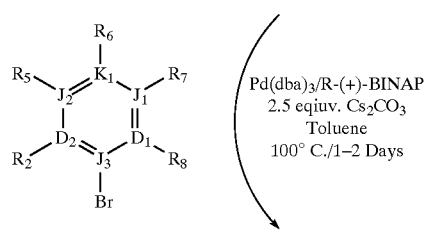

Pd(dba)$_3$/R-(+)-BINAP
2.5 eqiuv. Cs$_2$CO$_3$
Toluene
100° C./1–2 Days

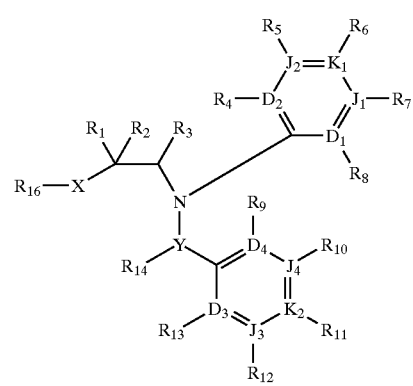

VII-H: (Generic Substituted Polycyclic Heteroaryl Tertiary 2-hydroxyalkylamine)

Scheme 48

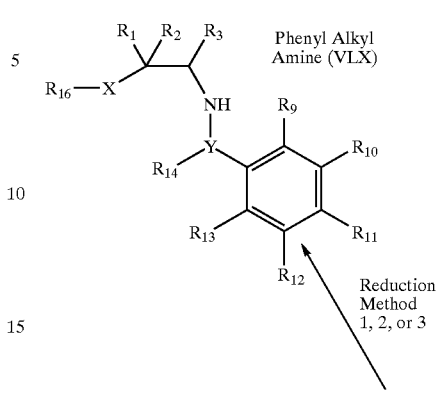

Phenyl Alkyl Amine (VLX)

Reduction Method 1, 2, or 3

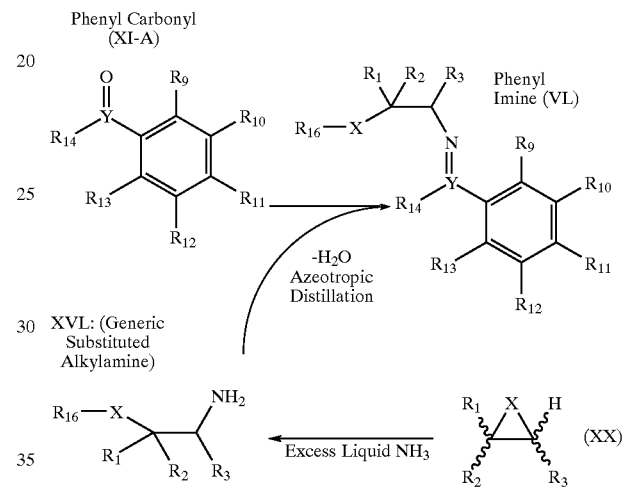

Phenyl Carbonyl (XI-A)

Phenyl Imine (VL)

−H$_2$O Azeotropic Distillation

XVL: (Generic Substituted Alkylamine)

Excess Liquid NH$_3$ (XX)

(X = O; R$_{16}$ = H)

Scheme 49

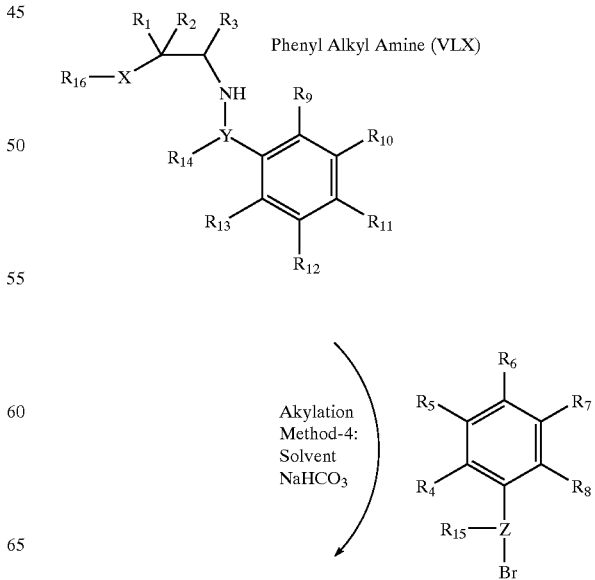

Phenyl Alkyl Amine (VLX)

Akylation Method-4:
Solvent
NaHCO$_3$

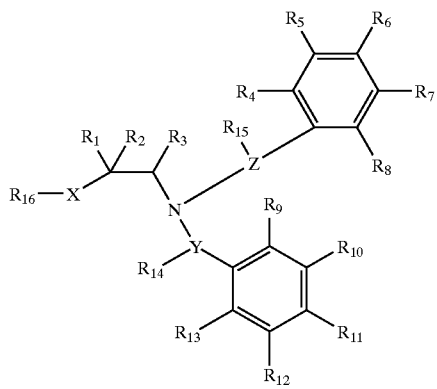
VII: (Generic Substituted Polycyclic Phenyl Tertiary 2-hydroxyalkylamine)
Scheme 50
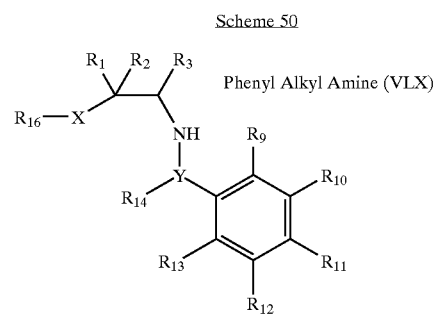
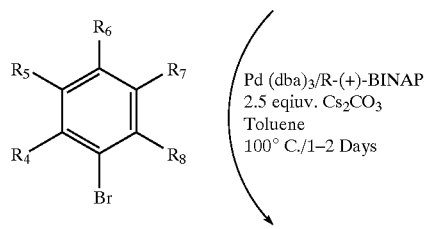
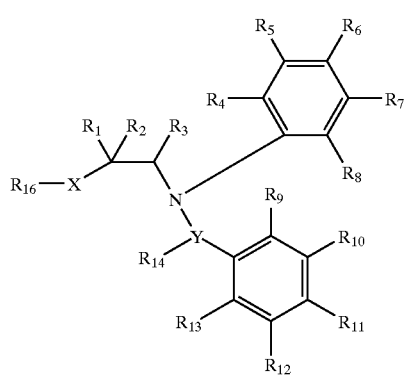
VII: (Generic Substituted Polycyclic Phenyl Tertiary 2-hydroxyalkylamine)
Scheme 51
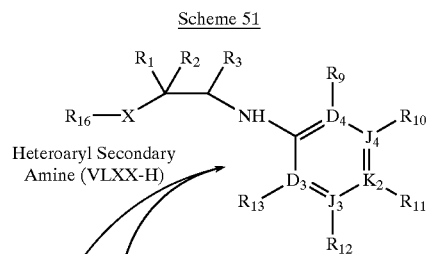
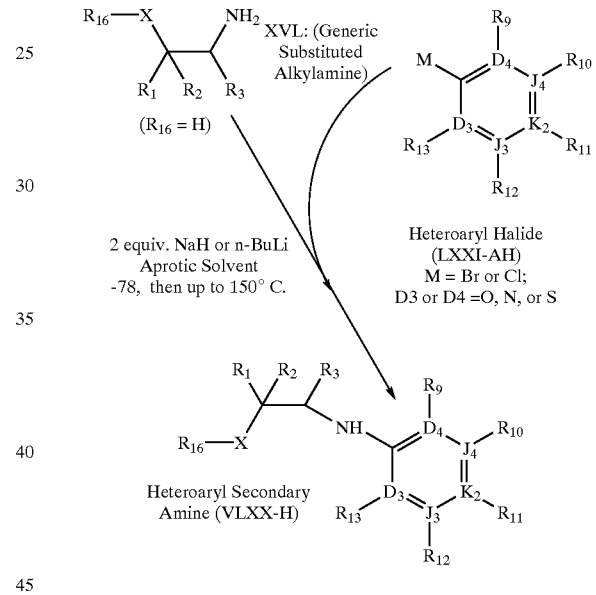
Scheme 52
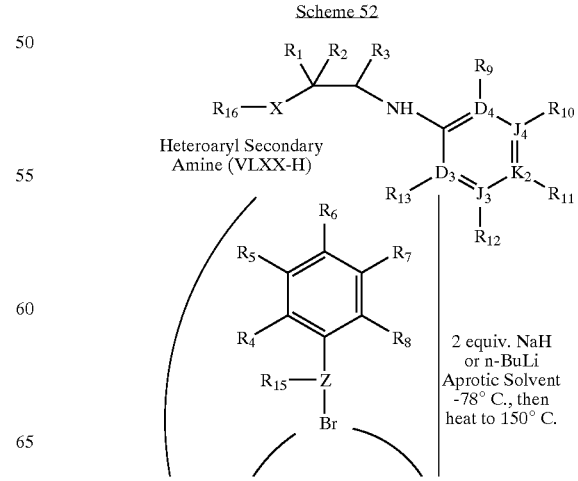

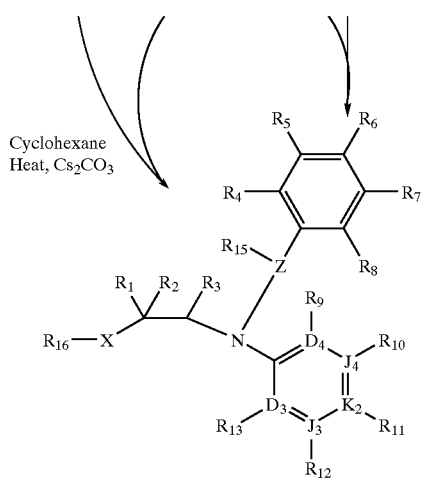

VII-H: (Generic Substituted Polycyclic Phenyl Heteroaryl Tertiary 2-hydroxyalkylamine)

Scheme 53

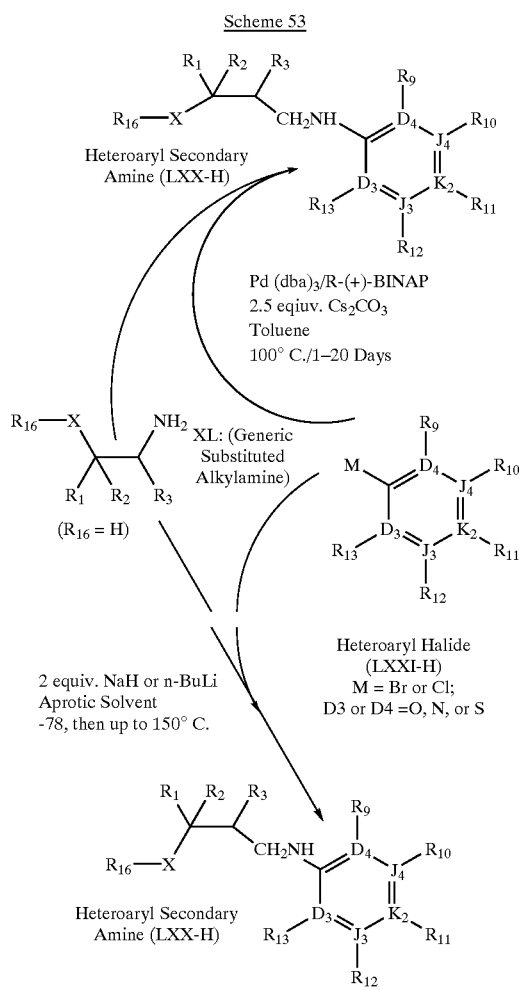

Scheme 54

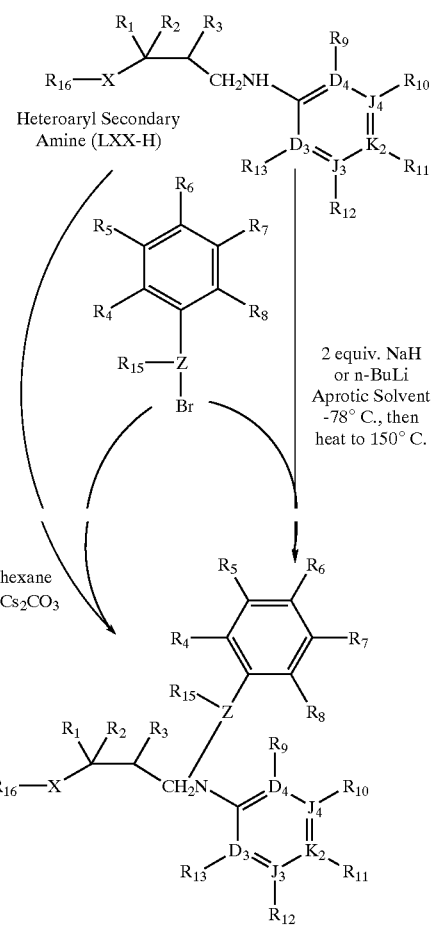

V-H: (Generic Substituted Polycyclic Phenyl Heteroaryl Tertiary 3-hydroxyalkylamine)

Scheme 55

VII: (Generic Substituted Polycyclic 3-carbomethoxyaryl Tertiary 2-Hydroxyalkylamine: $R_{16}$ = H)

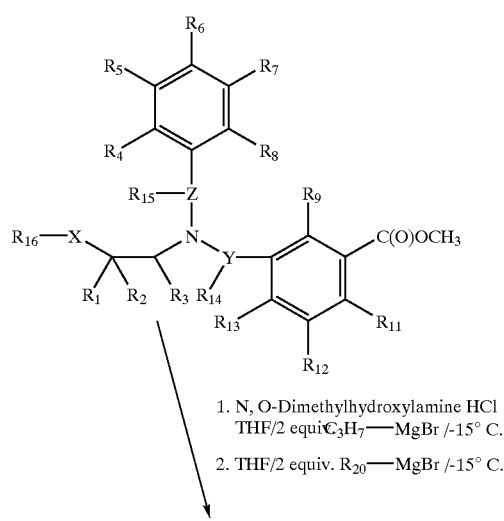

1. N, O-Dimethylhydroxylamine HCl THF/2 equiv. $C_3H_7$—MgBr /-15° C.
2. THF/2 equiv. $R_{20}$—MgBr /-15° C.

135

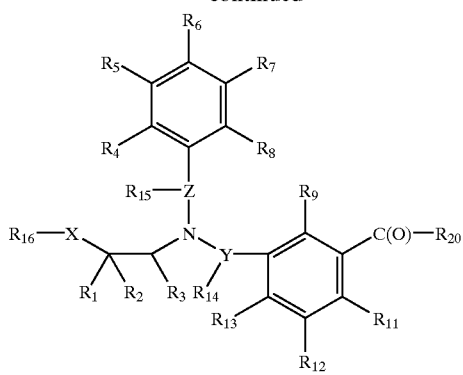

VII: (Generic Substituted Polycyclic 3- ($R_{20}$—carbonyl) Aryl Tertiary 2-Hydroxyalkylamine; $R_{16}$ = H)

Scheme 56

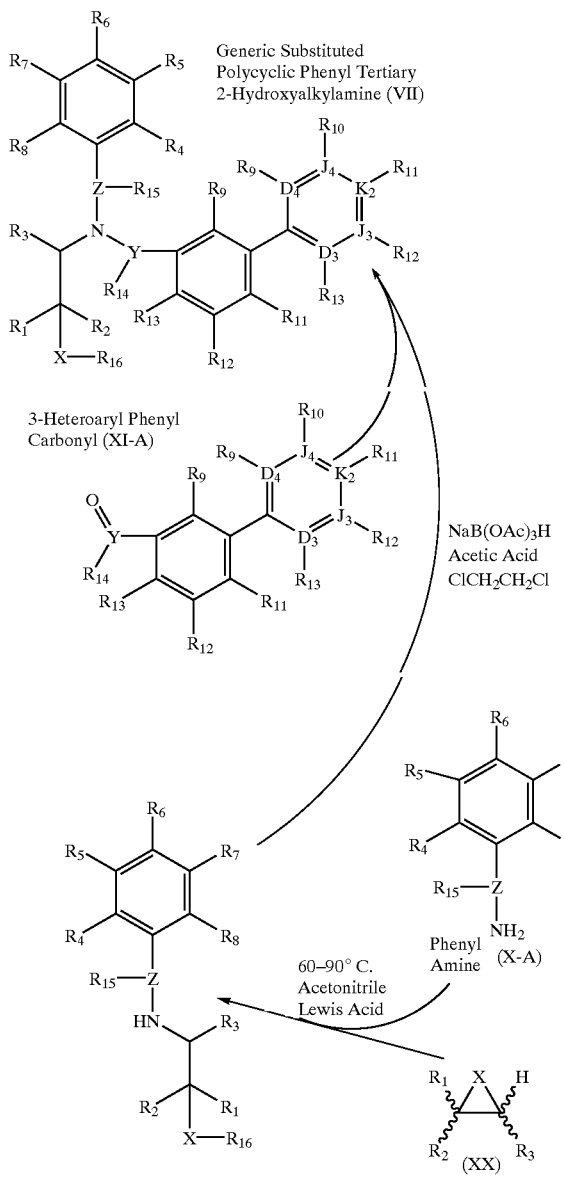

Phenyl Alkyl Amine (VLX)
NOTE: Heteroaryl Analogs Can Be Prepared Using Heteroaryl Analogs of X-A, VLX, and XI-A.

136

$R_{20}$ is selected from alkyl, alkenyl, alkynyl, aryl, aryloxyalkyl, aralkoxyalkyl, aralkylthioalkyl, heteroaryloxyalkyl, alkenyloxyalkyl, alkylthioalkyl, cycloalkyl, cycloalkylalkyl, cycloalkylalkenyl, heteroaryl, heteroarylalkyl, heteroarylthioalkyl, heteroaralkylthioalkyl, heteroaralkylthioalkyl, cycloalkenylalkyl, arylthioalkyl, aralkyl, alkoxyalkyl, and cycloalkenyl.

Scheme 57

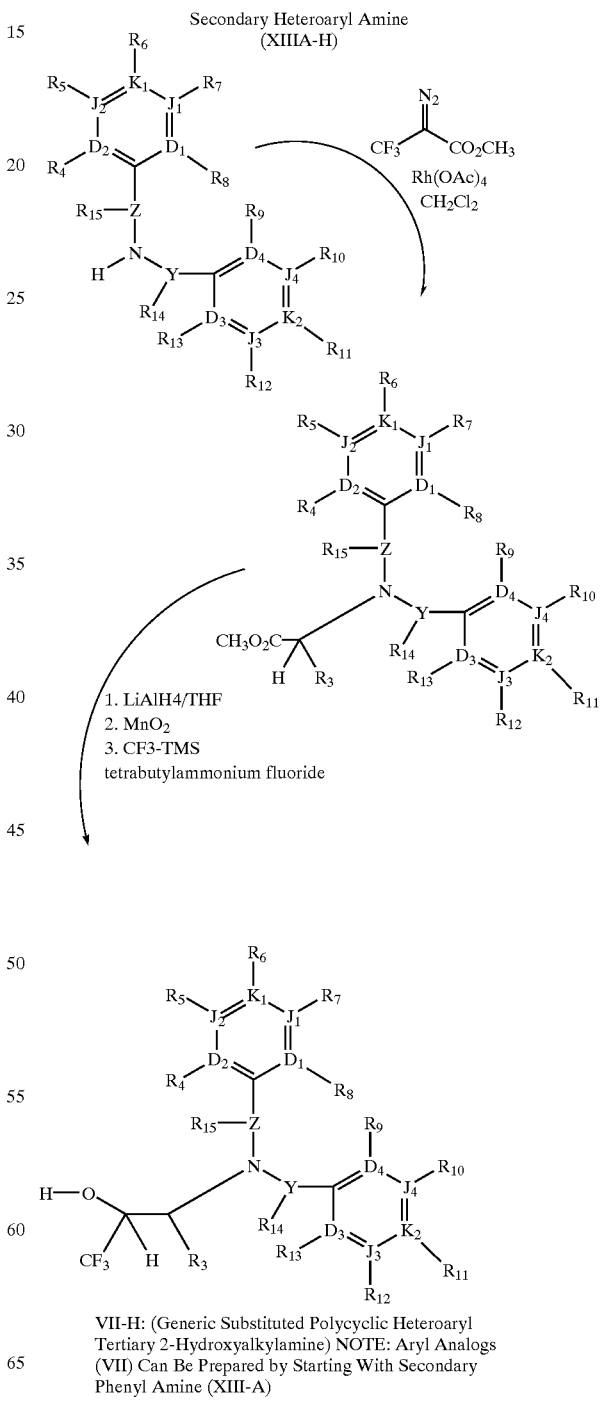

VII-H: (Generic Substituted Polycyclic Heteroaryl Tertiary 2-Hydroxyalkylamine) NOTE: Aryl Analogs (VII) Can Be Prepared by Starting With Secondary Phenyl Amine (XIII-A)

Scheme 58

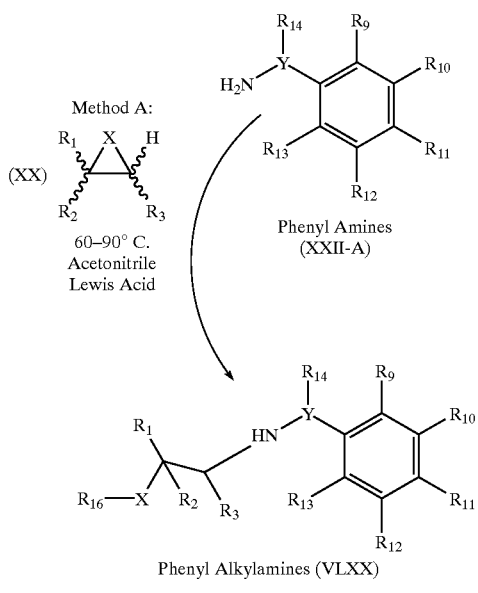

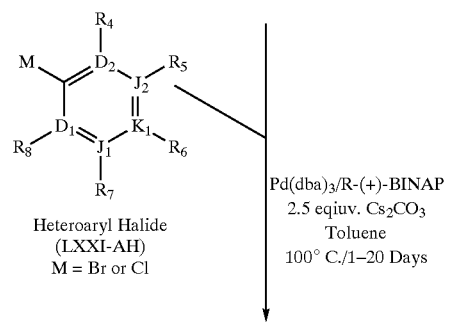

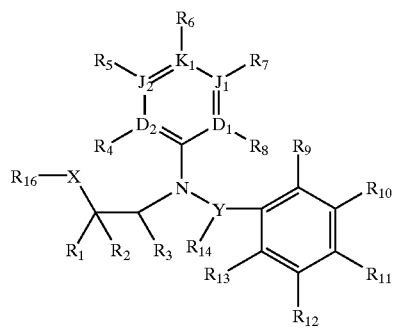

VII-H: (Generic Substituted Polycyclic
Phenyl Heteroaryl Tertiary 2-Hydroxyalkyl-
amine when $R_{16}$—X equals HO) NOTE: Aryl Analogs
(VII) of (VII-H) Can Be Prepared by Starting
With Aryl Bromide Analogs of (LXXI-AH).

Scheme 59

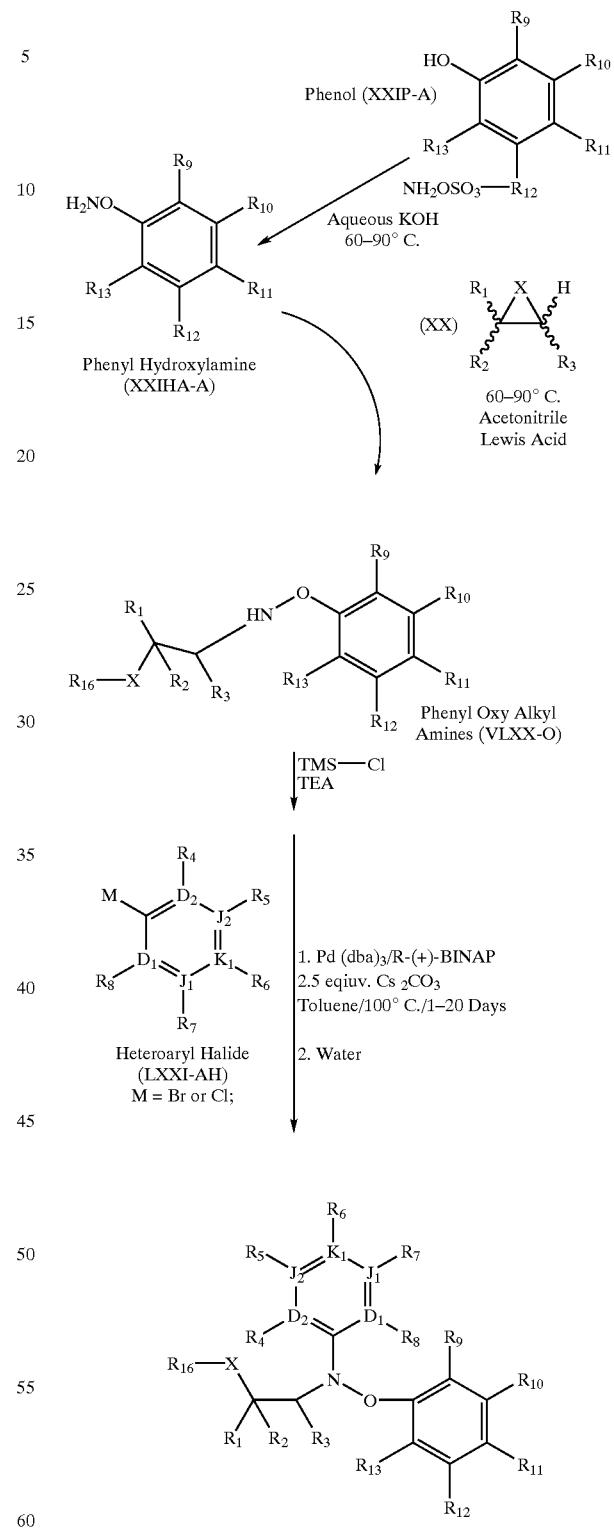

VII-H: (Generic Substituted Polycyclic Phenyl
Heteroaryl Tertiary 2-Hydroxyalkylamine when
$R_{16}$—X = HO and Y = O) NOTE: Diaryl and
Diheteroaryl Analogs Can Be Prepared by Using
Aryl Bromide and Heteroaryl-OH, respectively.

The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR and mass spectrometry. These compounds also may be formed in vivo.

The following examples contain detailed descriptions of the methods of preparation of compounds of Formula V-H. These detailed descriptions fall within the scope and are presented for illustrative purposes only and are not intended as a restriction on the scope of the invention. All parts are by weight and temperatures are Degrees centigrade unless otherwise indicated.

EXAMPLE 1

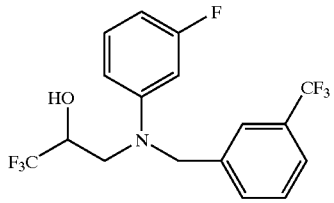

3-[(3-fluorophenyl)-[[3-(trifluoromethyl)phenyl]methyl]amino]-1,1,1-trifluoro-2-propanol EX-1A) A solution of 3-fluoroaniline (1.92 mL, 0.02 mol) and trifluoro-m-tolualde-hyde (2.68 mL, 0.02 mol) in 30 mL of cyclohexane was refluxed using a Dean-Stark trap to remove water. After 4 hours, the cyclohexane was removed in vacuo to yield 5.4 g (100%) of the desired imine product as an amber oil. MS m/z=267 [M$^+$]. $^1$H NMR (CDCl$_3$) δ8.50 (s, 1H), 8.22 (s, 1H), 8.09 (d, 1H), 7.78 (d, 1H), 7.63 (t, 1H), 7.39 (dq, 1H), 6.99 (m, 3H). This imine (5.34 g, 0.02 mol) was then slurried in 30 mL of methanol at 0° C. Solid NaBH$_4$ (1.32 g, 0.0349 mol) was added in batches over 3 minutes at 0° C. The reaction was stirred below 10° C. for 30 minutes and then warmed gradually to 15° C. After 1 hour, the solution was cooled, and 3% aq. HCl solution was added until the aqueous layer was acidic. The aqueous solution was extracted twice with diethyl ether. The combined ether extracts were washed 3 times with brine, dried (MgSO$_4$), and concentrated in vacuo to yield 4.45 g (82%) of the desired N-(3-fluorophenyl)-[[3-(trifluoromethyl)phenyl]methyl]amine product as a light amber oil. MS m/z=269 [M$^+$]. $^1$H NMR (CDCl$_3$) δ7.57 (m, 4H), 7.14 (dq, 1H), 6.45 (m, 2H), 6.33 (dt,1H), 4.41 (s, 2H), 4.27 (br, 1H).

The amine product EX-1A (2.69 g, 0.01 mol) was mixed with 3,3,3-trifluoro-1,2-epoxypropane (1.34 g, 0.012 mol), and the mixture was heated to 90° C. for 40 hours in a tightly capped vessel. After cooling to room temperature, the reaction product was purified by eluting through silica gel with 10% ethyl acetate in hexanes to yield 2.54 g (67%) of the desired aminopropanol as a light yellow oil, 100% pure product by GC and reverse phase HPLC. HRMS calcd. for C$_{17}$H$_{14}$F$_7$NO: 382.1042 [M+H]$^+$, found: 382.1032. $^1$H NMR (CDCl$_3$) δ7.47 (m, 4H), 7.19 (q, 1H), 6.50 (m, 3H), 4.50 (ABq, 2H), 4.39 (m,1H), 3.93 (dd, 1H), 3.60 (dd, 1H), 2.51 (d, 1H).

Additional substituted 3-[(N-aryl)-[[aryl]methyl]amino]-halo-2-propanols can be prepared by one skilled in the art using similar methods, as shown in Example Tables 1, 43, 46, and 47. Substituted 3-[(N-aralkyl)-[[aralkyl]amino]-halo-2-propanols can also be prepared by one skilled in the art using similar methods, as shown in Example Tables 2, 3, 44, and 45. Substituted 3-[(N-aryl)-[[aralkyl]amino]-halo-2-propanols can be prepared by one skilled in the art using similar methods, as shown in Example Table 4. Substituted 3-[(N-aryl or N-aralkyl)-[[aryl]methyl]amino]-haloalkoxy-2-propanols can be prepared by one skilled in the art using similar methods, as shown in Example Tables 5 and 48.

EXAMPLE TABLE 1

3-[N-(aryl)-[(aryl)methyl]amino]-1,1,1-trifluoro-2-propanols.

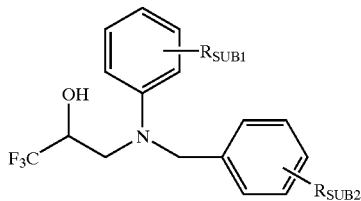

| Ex. No. | R$_{SUB1}$ | R$_{SUB2}$ | Calc.* Mass [M$^+$] | Obs.* Mass [M$^+$] |
|---|---|---|---|---|
| 2 | H | H | 295.1184 | 295.1180 |
| 3 | 3-OCH$_3$ | 3-CH$_3$ | 339.1446 | 339.1449 |
| 4 | 3-OCH$_3$ | 4-CH$_3$ | 339.1446 | 339.1444 |
| 5 | 4-CH$_3$ | 3-CH$_3$ | 323.1497 | 323.1491 |
| 6 | 4-OCH$_3$ | 4-CH$_3$ | 339.1446 | 339.1440 |
| 7 | 4-Cl | H | 329.0794 | 329.0783 |
| 8 | 4-CH$_3$ | 4-CH$_3$ | 323.1497 | 323.1495 |
| 9 | 3-Cl | 3-CH$_3$ | 343.0951 | 343.0950 |
| 10 | 3-F | H | 313.1090 | 313.1086 |
| 11 | 3-CH$_3$ | 3-CH$_3$ | 323.1497 | 323.1509 |
| 12 | 3-CH$_3$ | 4-CH$_3$ | 323.1497 | 323.1504 |
| 13 | 2-CH$_3$ | 4-CH$_3$ | 323.1497 | 323.1483 |
| 14 | 4-CH$_3$ | H | 309.1340 | 309.1331 |
| 15 | 2-CH$_3$ | H | 309.1340 | 309.1337 |
| 16 | 3-Cl | H | 329.0794 | 329.0794 |
| 17 | 3-F, 4-F | 3-CH$_3$ | 345.1152 | 345.1143 |
| 18 | 3-F | 3-F | 331.0996 | 331.0984 |
| 19 | 3-F, 4-F | 3-CF$_3$ | 399.0869 | 399.0827 |
| 20 | 4-CH$_3$ | 3-CF$_3$ | 377.1214 | 377.1180 |
| 21 | 2-CH$_3$ | 3-CF$_3$ | 377.1214 | 377.1176 |
| 22 | 3-F, 4-F | 4-CF$_3$ | 399.0869 | 399.0822 |
| 23 | 4-OCH$_3$ | 4-CF$_3$ | 393.1163 | 393.1159 |
| 24 | 3-F, 4-F | 4-CH$_3$ | 345.1152 | 345.1136 |
| 25 | 3-CH$_3$ | 3-CF$_3$ | 377.1214 | 377.1231 |
| 26 | 3-OCH$_3$ | 4-CF$_3$ | 393.1163 | 393.1179 |
| 27 | 2-CH$_3$ | 3-CH$_3$ | 323.1497 | 323.1486 |
| 28 | 4-OCH$_3$ | 3-CH$_3$ | 339.1446 | 339.1435 |
| 29 | 3-F, 5-F | 4-CH$_3$ | 345.1152 | 345.1159 |
| 30 | 3-Br | 3-CF$_3$ | 441.0163 | 441.0135 |
| 31 | 3-F | 3-OCF$_3$ | 397.0913 | 397.0894 |
| 32 | 4-CH$_3$ | 3-F | 327.1246 | 327.1291 |
| 33 | 3-F | 4-CH$_3$ | 328.1324 | 328.1333 |
| 34 | 3-Cl | 4-CH$_3$ | 344.1029 | 345.1045 |
| 35 | H | 3-CF$_3$ | 364.1136 | 364.1122 |
| 36 | 3-Br | 3-OCF$_3$ | 458.0190 | 458.0145 |
| 37 | 4-CH$_3$ | 4-CF$_3$ | 378.1292 | 378.1259 |
| 38 | 3-Cl | 3-CF$_3$ | 398.0746 | 398.0727 |
| 39 | 3-CH$_3$ | 4-CF$_3$ | 378.1292 | 378.1274 |
| 40 | 2-CH$_3$ | 4-CF$_3$ | 378.1292 | 378.1259 |
| 41 | 3-Cl | 3-OCF$_3$ | 414.0695 | 414.0699 |

EXAMPLE TABLE 1-continued

3-[N-(aryl)-[(aryl)methyl]amino]-1,1,1-trifluoro-2-propanols.

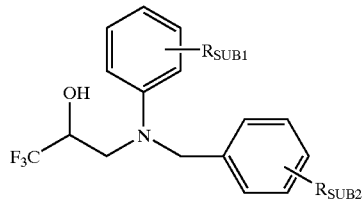

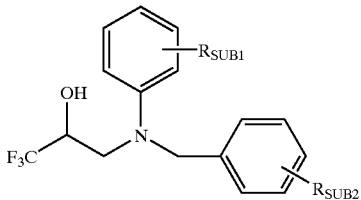

| Ex. No. | $R_{SUB1}$ | $R_{SUB2}$ | Calc.* Mass [M⁺] | Obs.* Mass [M⁺] |
|---|---|---|---|---|
| 42 | 3-CF₃ | 3-OCF₃ | 448.0959 | 448.0961 |
| 43 | 3-F | 3-OCF₂CF₂H | 430.1053 | 430.1042 |
| 44 | 3-I | 3-OCF₂CF₂H | 538.0114 | 538.0077 |
| 45 | 3-CF₃ | 4-CH₃ | 378.1292 | 378.1296 |
| 46 | 3-CF₃ | 3-F | 382.1042 | 382.1073 |
| 47 | 3-CF₃ | 3-CF₃ | 432.1010 | 432.1026 |
| 48 | 3-OCH₃ | 3-CF₃ | 394.1241 | 394.1227 |
| 49 | 3-F | 3-CH₃ | 328.1324 | 328.1300 |
| 50 | 3-Cl | 4-CF₃ | 398.0746 | 398.0731 |
| 51 | 4-OCH₃ | 3-CF₃ | 394.1241 | 394.1237 |
| 52 | 3-CF₃, 4-F | 3-CF₃ | 450.0915 | 450.0913 |
| 53 | 3-CF₃, 4-F | 4-CH₃ | 396.1198 | 396.1179 |
| 54 | 3-CF₃ | 4-OCF₃ | 448.0959 | 448.0967 |
| 55 | 3-Cl | 4-OCF₃ | 414.0695 | 414.0690 |
| 56 | 3-F, 4-F | 4-OCF₃ | 416.0886 | 416.0904 |
| 57 | 3-F | 4-OCF₃ | 398.0991 | 398.0975 |
| 58 | 3-CF₃, 4-F | 3-CH₃ | 396.1197 | 396.1178 |
| 59 | H | 4-OCF₃ | 380.1085 | 380.1077 |
| 60 | 3-OCF₃ | 4-OCF₃ | 464.0908 | 464.0877 |
| 61 | 3-CH₃ | 4-OCF₃ | 394.1241 | 394.1248 |
| 62 | 3-Br | 4-OCF₃ | 458.0189 | 458.0189 |
| 63 | 3-phenoxy | 4-OCF₃ | 472.1347 | 472.1344 |
| 64 | 3-F | 3-phenoxy | 406.1430 | 406.1418 |
| 65 | 3-F | 4-phenyl | 390.1481 | 390.1468 |
| 66 | 3-phenyl | 3-OCF₃ | 456.1397 | 456.1395 |
| 67 | 3-CF₃, 4-Cl | 3-CH₃ | 412.0903 | 412.0892 |
| 68 | 3-F, 5-F | 4-OCF₃ | 416.0896 | 416.0895 |
| 69 | 2-F, 3-F | 3-CF₃ | 400.0941 | 416.0956 |
| 70 | 2-F, 5-F | 3-OCF₂CF₂H | 448.0959 | 448.0940 |
| 71 | 3-OCF₃ | 3-OCF₂CF₂H | 496.0971 | 496.0959 |
| 72 | 3-CH₃ | 3-OCF₃ | 394.1241 | 394.1244 |
| 73 | H | 3-OCF₃ | 380.1085 | 380.1075 |
| 74 | 3-OCF₃ | 3-OCF₃ | 464.0908 | 464.0898 |
| 75 | 3-CF₃, 4-F | 4-CF₃ | 450.0915 | 450.0906 |
| 76 | 3,4-(CH=CH)₂— | 3-OCF₃ | 430.1241 | 430.1253 |
| 77 | 3-phenoxy | 3-OCF₃ | 472.1347 | 472.1342 |
| 78 | 3-F, 4-F | 3-OCF₃ | 416.0896 | 416.0884 |
| 79 | 4-phenyl | 3-OCF₃ | 456.1398 | 456.1368 |
| 80 | 2-F, 3-F | 4-OCF₃ | 416.0897 | 416.0885 |
| 81 | 3-F, 5-F | 3-CH₃ | 346.1230 | 346.1246 |
| 82 | 3-OCF₃ | 3-phenoxy | 472.1347 | 472.1342 |
| 83 | 3-OCF₃ | 3-benzyloxy | 486.1504 | 486.1503 |
| 84 | 3-phenoxy | 3-phenoxy | 480.1786 | 480.1772 |
| 85 | 2-phenyl | 3-phenoxy | 464.1837 | 464.1821 |
| 86 | 4-phenyl | 3-phenoxy | 464.1837 | 464.1836 |
| 87 | 4-phenyl | 3-OCF₂CF₂H | 488.1460 | 488.1443 |
| 88 | 4-n-octyl | 3-OCF₃ | 492.2337 | 492.2341 |
| 89 | 3,4-(OCF₂CF₂O) | 3-OCF₃ | 510.0763 | 510.0747 |
| 90 | 4-F | 3-OCF₃ | 398.0991 | 398.1023 |
| 91 | 3-phenoxy | 3-ethoxy | 432.1787 | 432.1770 |
| 92 | 3-phenoxy | 3-(4-Cl-phenoxy) | 514.1397 | 514.1426 |
| 93 | 3-OCF₃ | 3-(4-Cl-phenoxy) | 506.0958 | 506.0971 |
| 94 | 3-phenoxy | 3-(3,4-Cl₂—C₆H₃O) | 548.1007 | 548.1002 |
| 95 | 3-OCF₃ | 3-(3,4-Cl₂—C₆H₃O) | 540.0568 | 540.0555 |
| 96 | 3-OCF₃ | 3-(3,5-Cl₂—C₆H₃O) | 540.0568 | 540.0568 |
| 97 | 3-OCF₃ | 4-OCH₃ | 502.1453 | 502.1466 |
| 98 | 3-OCF₃ | 3-CF₃ | 540.1221 | 540.1248 |
| 99 | 3-OCF₃ | 3-benzyloxy, 4-OCH₃ | 516.161 | 516.1626 |
| 100 | 3-OCF₃ | 3,4-dibenzyloxy | 592.1922 | 592.1915 |
| 101 | 3-OCF₃ | 3-OCH₂CH₃ | 424.1347 | 424.1331 |
| 102 | 3-OCF₃ | 3-acetoxy | 438.114 | 438.1142 |
| 103 | 3-OCF₃ | 3-(2-OH-ethoxy) | 440.1297 | 440.1302 |
| 104 | 3-OCF₃ | 3-[(3-Cl, 2-OH)-n-propoxy] | 488.1063 | 488.1050 |
| 105 | 3-OCF₃ | 3,4-(OCH₂CH₂O) | 438.114 | 438.1142 |
| 106 | 3-OCF₃ | 4-benzyloxy, 3-OCH₃ | 516.1609 | 516.1608 |
| 107 | 3-OCF₃ | 3,5-dibenzyloxy | 592.1922 | 592.1903 |
| 108 | 3-CF₃ | 3-(3-CF₃-phenoxy) | 524.1372 | 524.1281 |
| 109 | 3-CF₃ | 3-phenoxy | 456.1398 | 456.1421 |
| 110 | 4-CF₃ | 3-(3-CF₃-phenoxy) | 524.1272 | 524.1259 |
| 111 | 4-CF₃ | 3-phenoxy | 456.1398 | 456.1415 |
| 112 | 4-CF₃ | 3-OCF₃ | 424.1347 | 424.1331 |
| 113 | 3-phenoxy | 3-nitro | 433.1375 | 433.1379 |
| 114 | 3-phenoxy | 3-(3,5-Cl₂—C₆H₃O) | 548.1007 | 548.1016 |
| 115 | 3-phenoxy | 3-(3-CF₃-phenoxy) | 548.166 | 548.1639 |
| 116 | 3-OCF₃ | 3,4-dimethoxy | 440.1296 | 420.1294 |
| 117 | 3-OCF₃ | 3-OCH₂CH₃, 4-OCH₃ | 454.1453 | 454.1458 |
| 118 | 3-OCF₃ | 3,4-diacetoxy | 496.1194 | 496.1183 |
| 119 | 3-OCF₃ | 4-acetoxy, 3-OCH₃ | 468.1245 | 468.1239 |
| 120 | 3-OCF₃ | 4-n-butoxy | 452.1584 | 452.1614 |
| 121 | 3-OCF₃ | 3-OCH₃ | 410.1191 | 410.1179 |
| 122 | 3-OCF₃ | 4-OCH₃ | 410.1191 | 410.1177 |
| 123 | 3-OCH₃ | 3-OCH₃ | 356.1473 | 356.1469 |
| 124 | 3-OCH₃ | 3-OCF₃ | 410.1191 | 410.1158 |
| 125 | 3-OCF₃ | 4-n-propoxy | 438.1503 | 438.1517 |
| 126 | 3-benzyloxy | 3-OCF₃ | 486.1504 | 486.1524 |
| 127 | 3-benzyloxy | 3-phenoxy | 494.1947 | 494.1956 |
| 128 | 3-ethoxy | 3-OCF₃ | 424.1347 | 424.1363 |
| 129 | 3,4-(OCH₂O) | 3-OCF₃ | 424.0983 | 424.0990 |
| 130 | 3,4-(OCH₂O) | 3-phenoxy | 432.1424 | 432.1432 |
| 131 | 3,4-(O(CH₂)₂O) | 3-OCF₃ | 438.1140 | 438.1165 |
| 132 | 3,4-dimethoxy | 3-OCF₃ | 440.1296 | 440.1319 |
| 133 | 4-phenoxy | 3-OCF₃ | 472.1347 | 472.1334 |
| 134 | 4-OCF₃ | 3-OCF₃ | 464.0908 | 464.0923 |
| 135 | 4-n-butoxy | 3-OCF₃ | 452.1660 | 452.1624 |
| 136 | 4-benzyl | 3-OCF₃ | 470.1554 | 470.1148 |
| 137 | 3-phenoxy | 3,4-(OCH₂CH₂O) | 446.1579 | 446.1583 |
| 138 | 3-OCF₃ | 3,4-diethoxy | 468.1609 | 468.1638 |
| 139 | 3,4-(O(CH₂)₃O) | 3-OCF₃ | 452.1297 | 452.1307 |
| 140 | 3-OCF₃ | 4-CF₃ | 448.0959 | 448.0985 |
| 141 | 4-phenyl | 4-CF₃ | 440.1449 | 440.1451 |
| 142 | 3-cyano | 4-CF₃ | 389.1089 | 389.1097 |
| 143 | 3-CF₃ | 4-phenyl | 440.1449 | 440.1444 |
| 144 | 4-CF₃ | 4-phenyl | 440.1449 | 440.1457 |
| 145 | 3-phenoxy | 3-CF₃, 5-CF₃ | 524.1272 | 524.1285 |
| 146 | 3-phenoxy | 4-cyano | 413.1477 | 413.149 |
| 147 | 3-phenoxy | 3-cyano | 413.1477 | 413.1493 |
| 148 | 3-phenoxy | 4-nitro | 433.1375 | 433.1398 |
| 149 | 3-phenoxy | 3-CF₃ | 456.1398 | 456.1414 |
| 150 | 3-phenoxy | 4-CF₃ | 456.1398 | 456.1394 |
| 151 | 4-phenoxy | 3-phenoxy | 480.1786 | 480.1794 |
| 152 | 3-OCF₃ | 4-phenoxy | 472.1347 | 472.1347 |
| 153 | 3-phenoxy | 4-phenoxy | 480.1786 | 480.1780 |
| 154 | 4-phenoxy | 4-phenoxy | 480.1786 | 480.1298 |
| 155 | 4-phenoxy | 4-OCF₃ | 472.1347 | 472.1338 |
| 156 | 3-phenoxy | 4-SO₂CH₃ | 466.1298 | 466.1253 |
| 157 | 3-phenoxy | 4-CO₂CH₃ | 446.1579 | 446.1569 |
| 158 | 3-OCF₃ | 4-ethoxy | 424.1347 | 424.1317 |
| 159 | 3-cyclopentoxy 4-methoxy | 3-OCF₃ | 494.1766 | 494.1771 |
| 160 | 3,4,5-trimethoxy | 3-OCF₃ | 470.1402 | 470.1408 |
| 161 | 3-phenoxy | 3-(OC₆H₄-4-OCH₃) | 510.1892 | 510.1881 |
| 162 | 3-cyano | 3-OCF₃ | 405.1038 | 405.1021 |

EXAMPLE TABLE 1-continued

3-[N-(aryl)-[(aryl)methyl]amino]-1,1,1-trifluoro-2-propanols.

| Ex. No. | $R_{SUB1}$ | $R_{SUB2}$ | Calc.* Mass [M+] | Obs.* Mass [M+] |
|---|---|---|---|---|
| 163 | 4-cyano | 3-OCF$_3$ | 405.1038 | 405.104 |
| 164 | 4-CO$_2$-n-C$_4$H$_9$ | 3-OCF$_3$ | 480.161 | 480.1594 |
| 165 | 4-(4-Cl-phenoxy) | 3-phenoxy | 514.1397 | 514.1407 |
| 166 | 3-(4-F-phenoxy) | 3-OCF$_3$ | 490.1253 | 490.1211 |
| 167 | 4-(4-CN—C$_6$H$_4$) | 3-OCF$_3$ | 481.135 | 481.1354 |
| 168 | 3-phenoxy | 4-(OC$_6$H$_4$-4-OCH$_3$) | 510.1892 | 510.1919 |

*Note:
Calculated (Calc.) and Observed (Obs.) masses measured for Example Numbers 33 through 168 are [M + H]+.

EXAMPLE TABLE 2

3-[N-[(aryl)methyl]-[(aryl)methyl]amino]-1,1,1-trifluoro-2-propanols.

| Ex. No. | $R_{SUB1}$ | $R_{SUB2}$ | Calc.* Mass [M+] | Obs.* Mass [M+] |
|---|---|---|---|---|
| 169 | 3-F | 4-CF$_3$ | 395.1120 | 395.1107 |
| 170 | 4-F | 4-CF$_3$ | 395.1120 | 395.1113 |
| 171 | 2-F | 4-CF$_3$ | 395.1120 | 395.1102 |
| 172 | 3-Cl | 4-CF$_3$ | 411.0825 | 411.0779 |
| 173 | 4-Cl | 4-CF$_3$ | 411.0825 | 411.0756 |
| 174 | 2-Cl | 4-CF$_3$ | 411.0825 | 411.0779 |
| 175 | 3-Cl | 2-CF$_3$ | 411.0825 | 411.0753 |
| 176 | 4-Cl | 2-CF$_3$ | 411.0825 | 411.0754 |
| 177 | 2-Cl | 2-CF$_3$ | 411.0825 | 411.0760 |
| 178 | 3-F | 4-CH$_3$ | 341.1403 | 341.1384 |
| 179 | 4-F | 4-CH$_3$ | 341.1403 | 341.1369 |
| 180 | 3-F | 3-CH$_3$ | 341.1403 | 341.1372 |
| 181 | 2-F | 4-CH$_3$ | 341.1403 | 341.1391 |
| 182 | 4-F | 3-CH$_3$ | 341.1403 | 341.1365 |
| 183 | 2-F | 3-CH$_3$ | 341.1403 | 341.1359 |
| 184 | 2-F | 3-CF$_3$ | 395.1120 | 395.1094 |
| 185 | 3-Cl | 3-CF$_3$ | 411.0825 | 411.0767 |
| 186 | 4-Cl | 3-CF$_3$ | 411.0825 | 411.0770 |
| 187 | 2-Cl | 3-CF$_3$ | 411.0825 | 411.0759 |
| 188 | 3-F | 2-CF$_3$ | 395.1120 | 395.1071 |
| 189 | 4-F | 2-CF$_3$ | 395.1120 | 395.1119 |
| 190 | 3-F | 3-CF$_3$ | 395.1120 | 395.1096 |
| 191 | 4-F | 3-CF$_3$ | 395.1120 | 395.1124 |
| 192 | 3-OCF$_3$ | 3-OCF$_3$ | 478.1064 | 478.0157 |
| 193 | 3-Cl | 3-OCF$_3$ | 428.0852 | 428.0878 |
| 194 | 3-Br | 3-OCF$_3$ | 472.0346 | 472.0366 |
| 195 | 3-phenoxy | 3-OCF$_3$ | 486.1503 | 486.1507 |
| 196 | 4-phenyl | 3-OCF$_3$ | 470.1554 | 470.1566 |
| 197 | 3-nitro | 3-OCF$_3$ | 439.1092 | 439.1051 |

*Note:
Calculated (Calc.) and Observed (Obs.) masses measured for Example Numbers 192 through 197 are [M + H]+.

EXAMPLE TABLE 3

3-[N-(aralkyl)-N-(aralkyl)amino]-1,1,1-trifluoro-2-propanols.

| Ex. No. | $R_{SUB1}$ | $R_{SUB2}$ | Calculated Mass [M + H] | Observed Mass [M + H] |
|---|---|---|---|---|
| 198 | 2-(3-F-phenyl)-ethyl | 3-(OCF$_2$CF$_2$H)-benzyl | 458.1364 | 458.1384 |

EXAMPLE TABLE 4

3-[N-(aryl)-N-(aralkyl)amino]-1,1,1-trifluoro-2-propanols.

| Ex. No. | $R_{SUB1}$ | $R_{SUB2}$ | Calculated Mass [M + H] | Observed Mass [M + H] |
|---|---|---|---|---|
| 199 | 3-F-phenyl | 2-fluorenylmethyl | 402.1481 | 402.1501 |
| 200 | 3-F-phenyl | 1-(4-OCH$_3$-naphthyl)methyl | 390.1430 | 390.1415 |
| 201 | 2-fluorenyl | 3-OCF$_3$-benzyl | 468.1398 | 468.1375 |
| 202 | 3-phenoxyphenyl | 1-(4-CN-phenyl)-ethyl | 427.1633 | 427.1627 |
| 203 | 3-phenoxyphenyl | 1-(3-F-phenyl)-ethyl | 420.1587 | 420.1584 |
| 204 | 2-(7-bromo-fluorenyl) | 3-OCF$_3$-benzyl | 546.0503 | 546.0531 |
| 205 | 3-phenoxyphenyl | 1-(3-nitro-phenyl)ethyl | 447.1531 | 447.1554 |
| 206 | 3-phenoxyphenyl | 1-(3-OCF$_3$-phenyl)ethyl | 486.1503 | 486.151 |
| 207 | 3-dibenzofuryl | 3-(OCF$_2$CF$_2$H) benzyl | 502.1253 | 502.1241 |

EXAMPLE TABLE 5

3-[N-(aryl or aralkyl)-N-(aralkyl)amino]-1-haloalkoxy-2-propanols.

| Ex. No. | $R_{SUB1}$ | $R_{SUB2}$ | Calculated Mass [M + H] | Observed Mass [M + H] |
|---|---|---|---|---|
| 208 | 3-OCF$_3$-benzyl | 3-OCF$_3$ | 540.1232 | 540.1219 |
| 209 | 3-OCF$_3$-phenyl | 3-OCF$_3$ | 526.1076 | 526.1049 |
| 210 | 3-phenoxy-phenyl | 3-OCF$_3$ | 534.1473 | 534.1515 |
| 211 | 3-phenoxy-phenyl | isopropoxy | 508.2111 | 508.2112 |

EXAMPLE TABLE 5-continued

3-[N-(aryl or aralkyl)-N-(aralkyl)amino]-1-haloalkoxy-2-propanols.

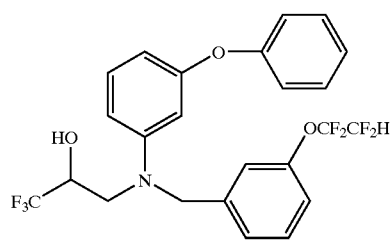

| Ex. No. | $R_{SUB1}$ | $R_{SUB2}$ | Calculated Mass [M + H] | Observed Mass [M + H] |
|---|---|---|---|---|
| 212 | 3-phenoxy-phenyl | 3-OCF$_2$CF$_2$H | 566.1577 | 566.1604 |
| 213 | 3-phenoxy-phenyl | 3-ethoxy | 494.1954 | 494.1982 |

EXAMPLE 214

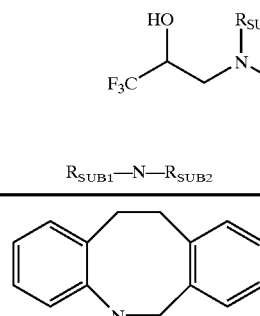

3-[(3-phenoxyphenyl)[[3-(1,1,2,2-tetrafluoroethoxy) phenyl]methyl]amino]-1,1,1-trifluoro-2-propanol EX-214A) A solution of 3-(phenoxy)aniline (2.78 g, 15 mmol) and 3-(1,1,2,2-tetrafluoroethoxy)benzaldehyde (3.33 g, 15 mmol) was prepared in 60 mL of dichloroethane. Acetic acid (0.92 mL, 16.05 mmol) and solid NaBH(OAc)$_3$ (4.13 g, 19.5 mmol) were added. The mixture was stirred at room temperature for 3 hours, then acidified with 1 N aqueous HCl. After neutralizing to pH 7.5 with 2.5 N sodium hydroxide, the mixture was extracted with methylene chloride. The organic layer was washed with brine and water, then dried over anhydrous MgSO$_4$, and evaporated to give 5.00 g (85%) of the desired N-(3-phenoxyphenyl)-[[3-(1,1,2,2-tetrafluoroethoxy)-phenyl]methyl]amine product as a brown oil, which was greater than 90% pure by reverse phase HPLC analysis. MS m/z=391.

Amine product EX-214A (3.13 g, 8 mmol) and 3,3,3-trifluoromethyl-1,2-epoxypropane (1.34 g, 12 mmol) were dissolved in 1.5 mL of acetonitrile. Ytterbium (III) trifluoromethanesulfonate (0.25 g, 0.4 nmmol) was added, and the stirred solution was warmed to 50° C. for 1 hour under an atmosphere of nitrogen, at which time HPLC analysis indicated that no secondary amine starting material remained. The reaction was quenched with water and extracted with ether. The ether layer was washed with water and brine, then dried over MgSO$_4$. The crude product was purified by flash column chromatography on silica gel eluting with ethyl acetate:hexane (1:16) to give 2.85 g (71%) of the desired aminopropanol product as a light amber oil, 99% pure by HPLC analysis. $^1$H NMR (CDCl$_3$) δ7.30 (m, 3H), 7.27 (t, 1H), 7.20 (m, 3H), 7.02 (s, 1H), 6.96 (m, 2H), 6.48 (dd, 1H), 6.41 (dd, 1H), 6.37 (m, 1H), 5.89 (tt, 1H), 4.64 (ABq, 2H), 4.34 (m, 1H), 3.87 (dd, 1H), 3.55(dd, 1H), 2.41 (bs, 1H). $^{19}$F NMR (CDCl$_3$) δ−79.3 (d, 3F), −88.6 (m, 2F), −137.2 (dt, 2F).

HRMS calcd. for $C_{24}H_{21}O_3NF_7$: 504.1410 [M+H]$^+$, found: 504.1425.

Additional examples of 3-[N-(aryl)-[(aryl)methyl] amino]-1,1,1-trifluoro-2-propanols are prepared by one skilled in the art using similar methods, as shown in Example Tables 6 and 7.

EXAMPLE TABLE 6

3-[N-(aryl)-[(aryl)methyl]amino]-1,1,1-trifluoro-2-propanols.

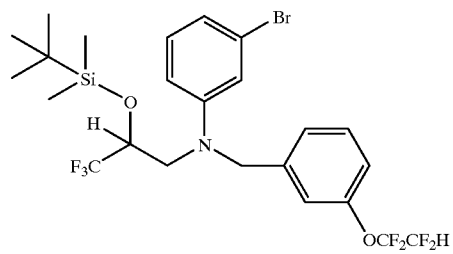

| Ex. No. | $R_{SUB1}$ | $R_{SUB2}$ | Calculated Mass [M + H] | Observed Mass [M + H] |
|---|---|---|---|---|
| 215 | 3-OCH$_3$, 5-CF$_3$ | 3-CF$_3$ | 462.1115 | 462.1115 |
| 216 | 3-phenoxy | 3-SCF$_3$ | 488.1119 | 488.1116 |
| 217 | 3-phenoxy | H | 388.1524 | 388.1558 |
| 218 | 3-SO$_2$-phenyl | 3-OCF$_2$CF$_2$H | 552.1080 | 552.1095 |

EXAMPLE TABLE 7

3-[N-(aryl)-[(aryl)methyl]amino]-1,1,1-trifluoro-2-propanols.

| Ex. No. | $R_{SUB1}$—N—$R_{SUB2}$ | Calculated Mass [M + H] | Observed Mass [M + H] |
|---|---|---|---|
| 219 | (dibenzazocine structure) | 322.1419 | 322.1426 |

EXAMPLE 220

N-(3-bromophenyl)-N-[2-[[(1,1-dimethylethyl) dimethylsilyl]oxy]-3,3,3-trifluoropropyl]-3-(1,1,2,2-tetrafluoroethoxy)-benzenemethanamine EX-220A) To a 1,2-dichloroethane (30 mL) solution of 3-(1,1,2,2-tetrafluoroethoxy)-benzaldehyde (2.00 g, 9.0 mmol) was added 3-bromoaniline (0.98 mL, 9.0 mmol), NaB(OAc)$_3$H (2.48 g, 11.7 mmol) and acetic acid (0.57 mL, 10 mmol). The cloudy mixture was stirred at room temperature for 1 hour. The reaction mixture was poured into water and extracted with dichloromethane. The organic layer was washed with saturated NaHCO₃ and brine, dried (MgSO₄) and evaporated to yield 3.27 g (96%) of the desired N-(3-bromophenyl)-[[3-(1,1,2,2-tetrafluoroethoxy)phenyl]methyl]amine product as a brown oil which was used without further purification. MS m/z=377 [M⁺].

EX-220B) To a dichloromethane (9 mL) solution of the EX-220A amine (3.27 g, 8.65 mmol) was added 1,1,1-trifluoro-2,3-epoxypropane (0.968 mL, 11.3 mmol) and Yb(OTf)₃ (0.536 g, 0.86 mmol). The cloudy mixture was stirred at room temperature for 24 hours, then diluted with diethyl ether. The organic layer was washed with water and brine, dried (MgSO₄) and evaporated to yield 4.20 g (99%) of the desired 3-[(3-bromophenyl)-[[3-(1,1,2,2-tetrafluoroethoxy)phenyl]methyl]amino]-1,1,1-trifluoro-2-propanol product as a pale brown oil which can be used without further purification. The formation of the desired product was confirmed by the presence of the alcohol peak (δ1.5, d) in the ¹H NMR spectrum (C₆D₆). An analytical sample was purified by silica gel chromatography eluting with 20% ethyl acetate in hexane to give the desired pure product as a yellow oil. FABMS m/z=491 [M+H]⁺. ¹H NMR (CDCl₃) δ3.55–3.63 (m, 1H), 3.88 (dd, 1H), 4.36 (m, 1H), 4.69 (s, 2H), 5.914 (tt, 1H), 6.66 (dd, 1H), 6.92 (m, 2H), 7.06 (s, 1H), 7.09 (m, 3H), 7.36 (t, 1H).

To a dichloromethane (10 mL) solution of EX-220B aminopropanol (4.20 g, 8.57 mmol) was added tert-butyldimethylsilyl trifluoromethanesulfonate (3.0 mL, 13.1 mmol) and triethylamine (2.40 mL, 17.3 mmol). The resulting solution was stirred at room temperature for 4 hours. The reaction mixture was diluted with dichloromethane, and washed with saturated NaHCO₃ and brine. The organic layer was dried (MgSO₄) and evaporated to an oil. Purification by flash chromatography on silica eluting with 2.5% EtOAc in hexane gave 3.0 g (58%) of the desired N-(3-bromophenyl)-N-[2-[[(1,1-dimethylethyl)dimethylsilyl]oxy]-3,3,3-trifluoropropyl]-3-(1,1,2,2-tetrafluoroethoxy)benzenemethanamine product as a colorless oil. HRMS calcd for C₂₄H₂₉BrF₇NO₂Si: 606.1098 [M+H]⁺, found 606.1118. ¹H NMR (C₆D₆) δ–0.19 (s, 3H), –0.06 (s, 3H), 0.88 (s, 9H), 3.38 (m, 2H), 4.11 (s, 2H), 4.12 (q, 1H), 5.10 (tt, 1H), 6.33 (dd, 1H), 6.61 (d, 1H), 6.68 (t, 1H), 6.81 (m, 2H), 6.89 (m, 2H), 6.97 (t, 1H).

EXAMPLE 221

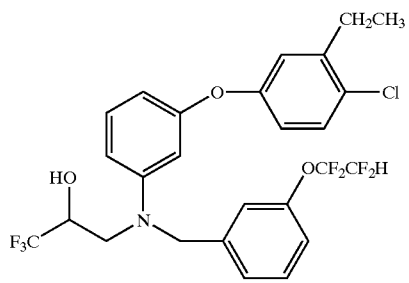

3-[[3-(4-chloro-3-ethylphenoxy)phenyl]-[[3-(1,1,2,2-tetrafluoroethoxy)phenyl]methyl]amino]-1,1,1-trifluoro-2-propanol A solution of N-(3-bromophenyl)-N-[2-[[(1,1-dimethylethyl)dimethylsilyl]oxy]-3,3,3-trifluoropropyl]-3-(1,1,2,2-tetrafluoroethoxy)benzenemethanamine (75 mg, 0.124 mmol), cesium carbonate (81 mg, 0.248 mmol), 4-chloro-3-ethylphenol (44 mg, 0.358 mmol), copper triflate benzene complex (6.24 mg, 10 mol %), 1-naphthoic acid (43 mg, 0.248 mmol) in 2:1 toluene-:dimethylacetamide (3.0 mL) was heated at 105° C. for 96 hours. The reaction mixture was filtered through celite, and the solvent was evaporated. The residue was purified by reverse phase chromatography eluting with 50–90% acetonitrile in water to afford 16.2 mg (23%) of the desired 3-[[3-(4chloro-3-ethylphenoxy)phenyl]-[[3-(1,1,2,2-tetrafluoroethoxy)phenyl]methyl]amino]-1,1,1-trifluoro-2-propanol product as an orange oil. HRMS calcd. for C₂₆H₂₃ClF₇NO₃: 566.1332 [M+H]⁺, found: 566.1332. ¹H NMR (CDCl₃) δ1.18 (t, 3H), 2.69 (q, 2H), 3.50–3.61 (m, 1H), 3.87 (dd, 1H), 4.28–4.39 (m, 1H), 4.63 (s, 2H), 5.88 (tt, 1H), 6.32–6.40 (m, 2H), 6.48 (dd, 1H), 6.69 (dd, 1H), 6.87 (d, 1H), 7.0–7.34 (m, 5H).

Additional examples of 3-((3-aryloxyphenyl and heteroaryloxyphenyl)[[3-(1,1,2,2-tetrafluoroethoxy)phenyl]methyl]amino]-1,1,1-trifluoro-2-propanols are prepared by one skilled in the art using similar methods, as shown in Example Tables 8 and 9. Additional examples of 3-[(3-arylthiophenyl)-[[3-(1,1,2,2-tetrafluoroethoxy)phenyl]-methyl]amino]-1,1,1-trifluoro-2-propanols are prepared by one skilled in the art using similar methods, as shown in Example Table 10.

EXAMPLE TABLE 8

3-[(3-Aryloxyphenyl)-[[3-(1,1,2,2-tetrafluoroethoxy)phenyl]-methyl]amino]-1,1,1-trifluoro-2-propanols.

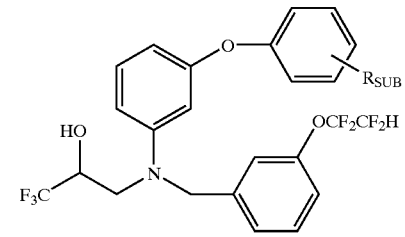

| Ex. No. | R_SUB | Calculated Mass [M + H]⁺ | Observed Mass [M + H]⁺ |
|---|---|---|---|
| 222 | 2-chloro | 538.1019 | 538.1021 |
| 223 | 2-fluoro | 522.1315 | 522.1310 |
| 224 | 2-fluoro, 4-CF₃ | 590.1189 | 590.1155 |
| 225 | 2,3,5-trifluoro | 558.1127 | 558.1109 |
| 226 | 3-N,N-dimethylamino | 547.1831 | 547.1844 |
| 227 | 2-fluoro, 3-CF₃ | 590.1189 | 590.1184 |
| 228 | 3-NHCOCH₃ | 561.1624 | 561.1590 |
| 229 | 2,3-dichloro | 572.0630 | 572.0653 |
| 230 | 2-chloro, 4-fluoro | 556.0925 | 556.0891 |
| 231 | 2-chloro, 4-chloro | 572.0630 | 572.0667 |
| 232 | 3-methyl, 5-ethyl | 546.1879 | 546.1899 |
| 233 | 3-ethyl | 532.1722 | 532.1706 |
| 234 | 3,5-dimethyl | 532.1722 | 532.1705 |
| 235 | 2,5-difluoro | 540.1221 | 540.1255 |
| 236 | 4-(perfluorophenyl)-2,3,5,6-tetrafluoro-phenyl | 741.0796 | 741.0799 |
| 237 | 2,3,4-trifluoro | 558.1127 | 558.1161 |
| 238 | 2,3-difluoro | 540.1221 | 540.1182 |
| 239 | 3-acetyl | 546.1515 | 546.1549 |
| 240 | 3-fluoro | 522.1315 | 522.1337 |
| 241 | 3,5-difluoro | 540.1221 | 540.1217 |
| 242 | 4-fluoro, 3-methyl | 536.1471 | 536.1480 |
| 243 | 4-propoxy | 562.1828 | 562.1803 |
| 244 | 3-trifluoromethoxy | 588.1232 | 588.1236 |
| 245 | 3-chloro, 4-fluoro | 556.0925 | 556.0932 |
| 246 | 4-chloro, 3-fluoro | 556.0925 | 556.0933 |
| 247 | 3,4,5-trimethyl | 546.1879 | 546.1901 |

EXAMPLE TABLE 8-continued

3-[(3-Aryloxyphenyl)-[[3-(1,1,2,2-tetrafluoroethoxy)phenyl]-methyl]amino]-1,1,1-trifluoro-2-propanols.

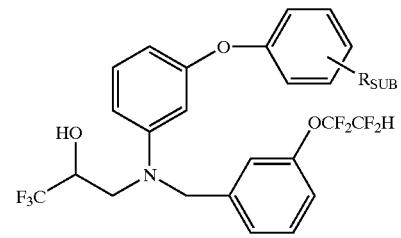

| Ex. No. | $R_{SUB}$ | Calculated Mass $[M + H]^+$ | Observed Mass $[M + H]^+$ |
| --- | --- | --- | --- |
| 248 | 3-trifluoromethyl | 572.1283 | 572.1265 |
| 249 | 3-isopropyl | 546.1879 | 546.1878 |
| 250 | 4-isopropyl | 546.1879 | 546.1899 |
| 251 | 4-butoxy | 576.1958 | 576.1969 |
| 252 | 3-tert-butyl | 560.2035 | 560.2055 |
| 253 | 4-isopropyl, 3-methyl | 560.2035 | 560.2035 |
| 254 | 4-sec-butyl | 560.2035 | 560.2051 |
| 255 | 4-(1,1-dimethyl-propyl) | 574.2192 | 574.2208 |
| 256 | 3,4-dichloro | 572.0630 | 572.0630 |
| 257 | 4-cyclopentyl | 572.2035 | 572.2029 |
| 258 | 3,4-$(CH_2)_4$ | 558.1879 | 558.1881 |
| 259 | 4-benzyl | 594.1879 | 594.1906 |
| 260 | 4-phenyl | 580.1722 | 580.1741 |
| 261 | 4-n-butyl | 560.2036 | 560.2033 |
| 262 | 4-ethoxy | 548.1672 | 548.1674 |
| 263 | 4-mercapto | 536.1130 | 536.1163 |
| 264 | 3-phenyl | 580.1723 | 580.1772 |
| 265 | 4-chloro, 2-fluoro | 556.0926 | 556.0954 |
| 266 | 4-n-propyl | 546.1879 | 546.1878 |
| 267 | 4-methylthio | 550.1209 | 550.1251 |
| 268 | 3,5-dimethoxy | 564.1623 | 564.1617 |
| 269 | 4-bromo | 582.0716 | 582.0473 |
| 270 | 3-hydoxymethyl | 564.1621 | 564.1617 |
| 271 | 3-methyl, 4-methylthio | 564.1443 | 564.1476 |
| 272 | 4-chloro, 3,5-dimethyl | 552.1176 | 552.1185 |
| 273 | 4-methoxy | 533.1437 | 533.1458 |
| 274 | 3-methoxy | 533.1437 | 533.1450 |
| 275 | 4-chloro | 537.0942 | 537.0944 |
| 276 | 4-(imidazo-1-yl) | 569.1549 | 569.1552 |
| 277 | 3,4-dimethyl | 531.1644 | 531.1649 |
| 278 | 3-methyl | 517.1488 | 517.1493 |
| 279 | 4-chloro, 3-methyl | 551.1098 | 551.1101 |
| 280 | 4-ethoxy | 547.1594 | 547.1594 |
| 281 | 4-methyl | 517.1488 | 517.1495 |

EXAMPLE TABLE 9

3-[(3-Aryloxy and Heteroaryloxyphenyl)-[[3-(1,1,2,2-tetrafluoroethoxy) phenyl]methyl]amino]-1,1,1-trifluoro-2-propanols.

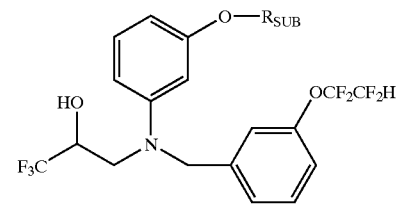

| Ex. No. | $R_{SUB}$ | Calculated Mass $[M + H]^+$ | Observed Mass $[M + H]^+$ |
| --- | --- | --- | --- |
| 282 | 6-methyl-3-pyridyl | 518.1440 | 518.1452 |
| 283 | 2-pyridyl | 504.1284 | 504.1284 |

EXAMPLE TABLE 9-continued

3-[(3-Aryloxy and Heteroaryloxyphenyl)-[[3-(1,1,2,2-tetrafluoroethoxy) phenyl]methyl]amino]-1,1,1-trifluoro-2-propanols.

| Ex. No. | $R_{SUB}$ | Calculated Mass $[M + H]^+$ | Observed Mass $[M + H]^+$ |
| --- | --- | --- | --- |
| 284 | 3-isoquinolyl | 555.1518 | 555.1513 |
| 285 | 2-naphthyl | 554.1566 | 554.1578 |
| 286 | 3-pyridyl | 505.1362 | 505.1369 |
| 287 | 5-chloro-3-pyridyl | 539.0972 | 539.1002 |
| 288 | 5-indolyl | 543.1519 | 543.1630 |
| 289 | 2-methyl-3-pyridyl | 519.1518 | 519.1517 |

EXAMPLE TABLE 10

3-[(3-Arylthiophenyl)-[[3-(1,1,2,2-tetrafluoroethoxy)phenyl]-methyl]amino]-1,1,1-trifluoro-2-propanols.

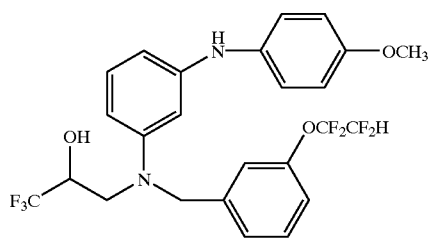

| Ex. No. | $R_{SUB}$ | Calculated Mass $[M + H]^+$ | Observed Mass $[M + H]^+$ |
| --- | --- | --- | --- |
| 290 | H | 519.1518 | 519.1119 |
| 291 | 4-methoxy | 549.1209 | 549.1216 |

EXAMPLE 292

3-[[3-[(4-methoxyphenyl)amino]phenyl]-[[3-(1,1,2,2-tetrafluoroethoxy)phenyl]methyl]amino]-1,1,1-trifluoro-2-propanol A mixture containing N-(3-bromophenyl)-N-[2-[[(1,1-dimethylethyl)dimethylsilyl]oxy]-3,3,3-trifluoropropyl]-3-(1,1,2,2-tetrafluoroethoxy)benzenemethanamine (75 mg, 0.124 mmol), cesium carbonate (57.5 mg, 0.176 mmol), 4-methoxyaniline (18.6 mg, 0.151 mmol) tris (dibenzylideneacetone)dipalladium(0) (4.6 mg, 0.005 mmol), R-(+)-2,2'-bis(diphenylphosphino)-1,1'-binaphthyl (4.7 mg, 0.0075 mmol) and toluene (2.5 mL) was heated to 95° C. in a sealed vial for 48 h. Tetrabutylammonium fluoride (1 M, THF, 0.372 mL, 0.372 mmol) was added, and the reaction was stirred at 23° C. for 1.5 h. The reaction mixture was filtered through celite, and the solvent was evaporated. The residue was purified by silica gel chromatography eluting with 20% ethyl acetate in hexane to give 49 mg (73%) of the desired 3-[[3-[(4-methoxyphenyl)amino]phenyl]-[[3-(1,1,2,2-tetrafluoroethoxy)phenyl]methyl]amino]-1,1,1-trifluoro-2-propanol product as an orange oil. HRMS calcd for $C_{25}H_{23}F_7N_2O_3$: 532.1597, found: 532.1592 [M]$^+$. $^1$H NMR (CDCl$_3$) δ3.48–3.57 (m, 1H), 3.77 (s, 3H), 3.83 (dd, 1H), 4.33 (m, 1H), 4.59 (s, 2H), 5.87 (tt, 1H), 6.27 (m, 1H), 6.33 (bd, 1H), 6.86 (dd, 4H), 7.02–7.12 (m, 4H), 7.31 (t, 1H), 7.41 (m, 1H), 7.60 (m, 1H). $^{19}$F NMR (CDCl$_3$) δ−137.201 (d, 2F), −88.515 (s, 2F), −79.120 (s, 3F).

Additional examples of 3-[[3-(N-arylamino and N-alkyl-N-arylamino)phenyl]-[[3-(1,1,2,2-tetrafluoroethoxy)phenyl]methyl]amino]-1,1,1-trifluoro-2-propanols are prepared by one skilled in the art using similar methods, as shown in Example Tables 11 and 12. Additional examples of 3-[[3-(piperidino)-phenyl]-[[3-(1,1,2,2-tetrafluoroethoxy)phenyl]methyl]amino]-1,1,1-trifluoro-2-propanols are prepared by one skilled in the art using similar methods, as shown in Example Table 13.

EXAMPLE TABLE 11

3-[[3-(Arylamino)phenyl]-[[3-(1,1,2,2-tetrafluoroethoxy)phenyl]-methyl]amino]-1,1,1-trifluoro-2-propanols.

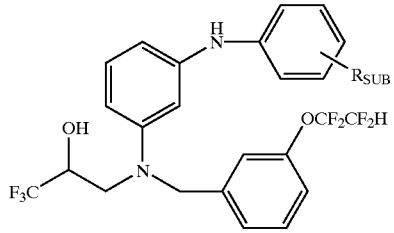

| Ex. No. | R$_{SUB}$ | Calculated Mass [M]$^+$ | Observed Mass [M]$^+$ |
|---|---|---|---|
| 293 | 4-fluoro | 520.1397 | 520.1389 |
| 294 | H | 502.1491 | 502.1473 |
| 295 | 4-trifluoromethyl | 570.1365 | 570.1335 |
| 296 | 4-chloro | 536.1102 | 536.1125 |
| 297 | 4-cyano | 527.1444 | 527.1452 |
| 298 | 4-CO$_2$CH$_2$CH$_3$ | 574.1703 | 574.1703 |
| 299 | 4-n-propyl | 544.1961 | 544.1959 |
| 300 | 4-[[3-(4-methyl-phenyl)]-1,2,4-oxadiazol-5-yl] | 660.1971 | 660.1969 |
| 301 | 4-]COCH(CN)—CO$_2$CH$_2$CH$_3$] | 641.1761 | 641.1755 |
| 302 | 3-cyano | 527.1444 | 527.1448 |
| 303 | 3-CO$_2$CH$_2$CH$_3$ | 574.1703 | 574.1668 |
| 304 | 3-chloro | 536.1102 | 536.1102 |
| 305 | 3-methoxy | 532.1597 | 532.1593 |
| 306 | 3,4,5,-trimethoxy | 592.1703 | 592.1703 |
| 307 | 3,5-difluoro | 538.1303 | 538.1329 |
| 308 | 4-trifluoromethoxy | 586.1314 | 586.1314 |
| 309 | 3,4-dimethoxy | 562.1703 | 562.1713 |
| 310 | 3-trifluoromethyl | 570.1365 | 570.1332 |

EXAMPLE TABLE 12

3-[[3-(N-alkyl-N-Arylamino)phenyl]-[[3-(1,1,2,2-tetrafluoroethoxy)phenyl]-methyl]amino]-1,1,1-trifluoro-2-propanols.

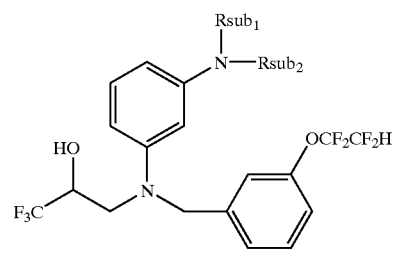

| Ex. No. | Rsub$_1$ | Rsub$_2$ | Calculated Mass [M]$^+$ | Observed Mass [M]$^+$ |
|---|---|---|---|---|
| 311 | H | 3-trifluoromethyl-benzyl | 584.1522 | 584.1518 |
| 312 | —CH$_2$CH$_3$ | 3-methyl-phenyl | 544.1961 | 544.1959 |
| 313 | n-C$_4$H$_9$ | 4-CO$_2$CH$_2$CH$_3$-phenyl | 630.2329 | 630.2329 |
| 314 | —(CH$_2$)$_2$CN | 4-methyl-phenyl | 569.1913 | 569.1920 |

EXAMPLE TABLE 13

3-[[3-(N-piperidino)phenyl]-[[3-(1,1,2,2-tetrafluoroethoxy)phenyl]-methyl]amino]-1,1,1-trifluoro-2-propanols.

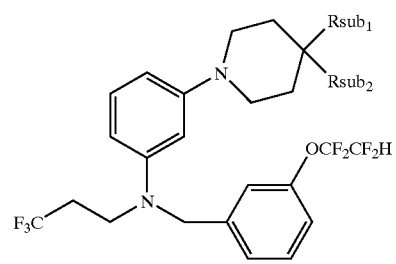

| Ex. No. | Rsub$_1$ | Rsub$_2$ | Calculated Mass [M]$^+$ | Observed Mass [M]$^+$ |
|---|---|---|---|---|
| 315 | H | H | 494.1804 | 494.1804 |
| 316 | H | benzyl | 584.2274 | 584.2280 |
| 317 | —OCH$_2$CH$_2$O— | | 552.1859 | 552.1863 |

EXAMPLE 318

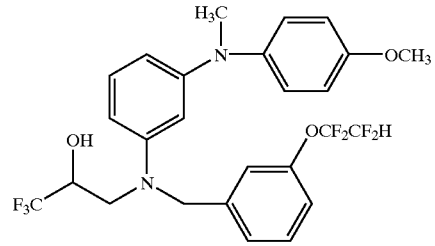

3-[[3-[(4-methoxyphenyl)methylamino]phenyl][[3-(1,1,2,2-tetrafluoroethoxy)phenyl]methyl]amino]-1,1,1-trifluoro-2-propanol To a solution of 3-[[3-[(4-methoxyphenyl)amino]phenyl]-[[3-(1,1,2,2-tetrafluoroethoxy)phenyl]methyl]amino]-1,1,1-trifluoro-2-propanol (44.3 mg, 0.083 mmol) in tetrahydrofuran (1.0 mL), methyl iodide (6.21 μL, 0.099 mmol) and cesium carbonate (36.6 mg, 0.112 mmol) were added. The dark solution was stirred at 23° C. for 2 h, then heated to 55° C. for 12 h. The reaction mixture was filtered through celite, and the residue was purified by silica gel chromatography eluting with 20% ethyl acetate in hexane to give 25.2 mg (55%) of the desired 3-[[3-[(4-methoxyphenyl)methylamino]-phenyl][[3-(1,1,2,2-tetrafluoroethoxy)phenyl]methyl]amino]-1,1,1-trifluoro-2-propanol product as an orange oil. HRMS calcd for $C_{26}H_{25}F_7N_2O_3$: 546.1753, found: 546.1750 $[M]^+$. $^1H$ NMR (CDCl$_3$), δ3.54 (m, 1H), 3.38 (s, 3H), 3.65–3.80 (m, 4H 4.59 (s, 2H), 5.90 (tt, 1H), 6.20 (d, 1H), 6.37 (d, 1H), 6.68 (s, 1H), 6.76 (d, 2H), 6.90–7.15 (m, 6H), 7.31 (t, 1H). $^{19}F$ NMR (CDCl$_3$), δ–137.21 (d, 2F), –88.52 (s, 2F), –78.79 (s, 3F).

Additional examples of 3-[[3-[(4-methoxyphenyl) alkylamino and haloalkylamino)phenyl]-[[3-(1,1,2,2-tetrafluoroethoxy)phenyl]methyl]amino]-1,1,1-trifluoro-2-propanols are prepared by one skilled in the art using similar methods, as shown in Example Table 14.

EXAMPLE TABLE 14

3-[[3-[(4-methoxyphenyl)alkylamino and haloalkylamino)phenyl]-[[3-(1,1,2,2-tetrafluoroethoxy)phenyl]methyl]amino]-1,1,1-trifluoro-2-propanols.

| Ex. No. | $R_{sub}$ | Calculated Mass $[M]^+$ | Observed Mass $[M]^+$ |
|---|---|---|---|
| 319 | ethyl | 560.1910 | 560.1910 |
| 320 | —(CH$_2$)$_3$CF$_3$ | 642.1940 | 642.1920 |

EXAMPLE 321

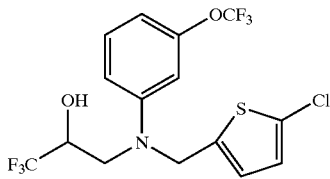

3-[[(5-chloro-2-thienyl)methyl][(3-trifluoromethoxy)phenyl]amino]-1,1,1-trifluoro-2-propanol EX-321A) 3-Trifluoromethoxyaniline (23.81 g, 134.4 mmol) and 3,3,3-trifluoro-1,2-epoxypropane (3.76 g, 33.6 mmol) were placed into a sealed tube and heated to 80° C. for 24 h. The excess aniline was removed by distillation (70° C. at 16.2 Torr) to give 8.6 g (88%) of the desired 3-[(3-trifluoromethoxyphenyl)amino]-1,1,1-trifluoro-2-propanol product as a light yellow oil. $^1H$ NMR (CDCl$_3$) δ3.29–3.37 (m, 1H), 3.55 (dd, 1H), 4.20 (m, 1H), 6.48–6.63 (m, 3H), 7.12 (t, 1H). F NMR (CDCl$_3$) δ–79.36 (s, 3F), –58.44 (s, 3F).

EX-321B) The aminopropanol (18.68 g, 64.6 mmol) from EX-321A and imidazole (10.99 g, 0.162 mmol) were dissolved in dimethylformamide (40.0 mL) and t-butyl-dimethylsilyl chloride (11.69 g, 77.6 mmol) was added in 3.0 g portions over 15 min. The reaction was stirred at 23° C. for 18 h. The reaction solution was diluted with ethyl acetate and washed with water and brine. The organic layer was dried (MgSO$_4$) and concentrated in vacuo. The residue was purified by silica gel chromatography eluting with 25% ethyl acetate in hexane to afford 17.08 g (66%) of the desired silylated N-(3-trifluoromethoxyphenyl)-N-[2-[[(1,1-dimethylethyl)dimethylsilyl]oxy]-3-3,3,3-trifluoro-propylamine product as a light golden oil. FABMS m/z=404 $[M+H]^+$. $^1H$ NMR (CDCl$_3$) δ0.042 (s, 3H), 0.085 (s, 3H), 0.91 (s, 9H), 3.25–3.35 (m, 1H), 3.50 (dd, 1H), 4.10 (m, 1H), 6.40 (bs, 1H), 6.50 (dd, 1H), 6.59 (d, 1H), 7.17 (t, 1H).

EX-321C) The silylated aminopropanol (0.157 g, 0.40 mmol) from EX-321B was dissolved in tetrahydrofuran (150 μL) and cooled to 0° C. Potassium tert-butoxide (1.0 M, THF, 0.60 mL, 0.60 mmol) was added in one portion via syringe. The dark solution was stirred at 0° C. for five minutes. 2-Chloro-5-bromomethyl-thiophene (73.5 mg, 0.44 mmol) was added in one portion to the cooled solution. The reaction mixture was stirred at 0° C. for 15 minutes then warmed to 23° C. for 16 h. Tetrabutyl-ammonium fluoride (1.0 M, THF, 1.2 mL, 1.2 mmol) was added to the dark reaction mixture and stirring followed for 2 h at 23° C. The solution was diluted with ethyl acetate and washed with water and brine. The organic layer was dried (MgSO$_4$) and concentrated in vacuo. The residue was purified by silica gel chromatography eluting with 0–20% ethyl acetate in hexane to afford 63.4 mg (39%) of the desired 3-[[(5-chloro-2-thienyl)methyl][(3-trifluoromethoxy)phenyl]amino-1,1,1-tifluoro-2-propanol product as a light golden oil. HRMS calcd. for $C_{15}H_{12}ClF_6NO_2S$: 419.1518, found: 419.1527 $[M]^+$. $^1H$ NMR (CDCl$_3$) δ3.50–3.56 (m, 1H), 3.77 (dd, 1H), 4.28 (m, 1H), 4.67 (s, 2H), 6.62–6.75 (m, 5H), 7.24 (t, 1H). $^{19}F$ NMR (CDCl$_3$) δ–79.24 (s, 3F), –58.04 (s, 3F).

Additional examples of 3-[[(aralkyl and heteroaralkyl)][(3-trifluoromethoxy)-phenyl]amino]-1,1,1,-trifluoro-2-propanols are prepared by one skilled in the art using similar methods, as shown in Example Table 15.

EXAMPLE TABLE 15

3-[[(aralkyl and heteroaralkyl)][(3-trifluoromethoxy)-phenyl]amino]-1,1,1-trifluoro-2-propanols.

| Ex. No. | $R_{SUB}$ | Calc. Mol. Wt. | Obs. Mass $[M]^+$ |
|---|---|---|---|
| 322 | 3-iodo-benzyl | 505 | 506 |
| 323 | 4-difluoromethoxy-benzyl | 445 | 446 |
| 324 | 4-(2-cyanophenyl)-benzyl | 480 | 481 |
| 325 | 3-CO$_2$CH$_3$-benzyl | 437 | 438 |
| 326 | 2,3,5,6-tetrafluoro-4-methoxy-benzyl | 481 | 482 |
| 327 | 3-cyano-benzyl | 404 | 405 |
| 328 | 3,5-difluoro-benzyl | 415 | 416 |
| 329 | 2,4-difluoro-benzyl | 415 | 416 |
| 330 | 2,6-difluoro-benzyl | 415 | 416 |
| 331 | 4-nitro-benzyl | 424 | 425 |
| 332 | (1-napthyl)methyl | 429 | 430 |

EXAMPLE TABLE 15-continued

3-[[(aralkyl and heteroaralkyl)][(3-trifluoro-methoxy)-phenyl]amino]-1,1,1-trifluoro-2-propanols.

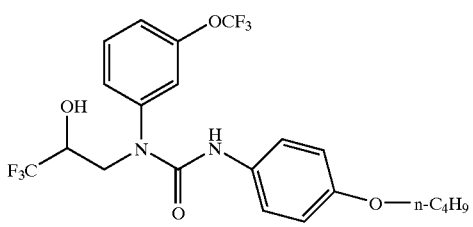

| Ex. No. | $R_{SUB}$ | Calc. Mol. Wt. | Obs. Mass $[M]^+$ |
|---|---|---|---|
| 333 | 4-phenyl-benzyl | 455 | 456 |
| 334 | 2-chloro-4,5-(OCH$_2$CH$_2$O)-benzyl | 457 | 458 |
| 335 | 3-nitro-benzyl | 424 | 425 |
| 336 | 4-phenoxy-butyl | 437 | 438 |
| 337 | 3-phenyl-propyl | 407 | 408 |
| 338 | 3-(4-methoxy)phenyl-propyl | 437 | 438 |
| 339 | 2-methoxyphenacetyl | 437 | 438 |
| 340 | 2-(2,5-dimethoxy-phenyl)-2-oxoethyl | 467 | 468 |
| 341 | 4-CO$_2$CH$_3$-benzyl | 437 | 438 |
| 342 | 2-(anthraquinonyl)-methyl | 509 | 510 |
| 343 | perfluorobenzoyl | 483 | 484 |
| 344 | 2-(3-indolyl)ethyl | 432 | 433 |
| 345 | 3-pyridinylmethyl | 380 | 381 |
| 346 | (5-chloro-2-thienyl)-methyl | 419 | 420 |
| 347 | 4-methoxy-benzyl | 409 | 410 |
| 348 | 3-methoxy-benzyl | 409 | 410 |
| 349 | 4-pyridinylmethyl | 380 | 381 |
| 350 | 3,5-dimethoxy-benzyl | 439 | 440 |
| 351 | 3-(phenyl)propenoyl | 419 | 420 |
| 352 | 3-phenyl-2,3-propenyl | 405 | 406 |
| 353 | 3,5-dimethoxy-benzoyl | 453 | 454 |
| 354 | 2,4,5-trimethoxy-benzyl | 469 | 470 |
| 355 | 2,5-dimethoxy-benzyl | 439 | 440 |
| 356 | 3-CO$_2$H-benzyl | 423 | 424 |
| 357 | 3-OH-benzyl | 395 | 396 |
| 358 | 2,5-dihydroxy-benzyl | 411 | 412 |
| 359 | 3,4,5-trihydroxy-benzyl | 427 | 428 |
| 360 | 3,5,-dihydroxy-benzyl | 411 | 412 |
| 361 | 2-(phenoxy)phenacetyl | 499 | 500 |
| 362 | 2-quinolinylmethyl | 430 | 431 |
| 363 | 2-pyridinylmethyl | 380 | 381 |
| 364 | 2-benzimidazolyl-methyl | 419 | 420 |
| 365 | 1-benzyl-2-imidazolyl-methyl | 459 | 460 |
| 366 | (2,6-dichloro-4-pyridinyl)methyl | 449 | 450 |

EXAMPLE 367

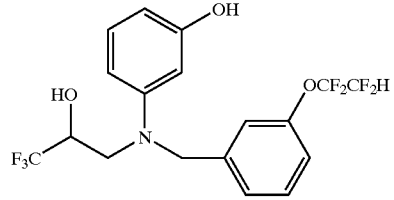

N'-(4-butoxyphenyl)-N-(3,3,3-trifluoro-2-hydroxypropyl)-N-[3-(trifluoromethoxy)phenyl]urea The silylated aminopropanol (0.150 g, 0.372 mmol) from EX-321B was dissolved in chloroform (0.5 mL). Then 4-n-butoxyphenyl isocyanate (78.25 mg, 0.409 mmol) was added, and the resulting solution was stirred at 23° C. in a sealed vial for 16 h followed by heating to 65° C. for 24 h. The reaction was cooled to 23° C., and a solution of tetrabutylammonium fluoride (1.0 M, THF, 0.5 mL, 0.50 mmol) was added to the reaction, which was then stirred at 23° C. for 2 h. The solution was diluted with ethyl acetate and washed with water and brine. The residue was purified by silica gel chromatography eluting with 0–50% ethyl acetate in hexane to afford 73.6 mg (38%) of the desired urea product as a pale yellow glass. FABMS m/z=481 [M+H]$^+$. $^1$H NMR (CDCl$_3$), δ0.99 (t, 3H), 1.484 (m, 2H), 1.740 (m, 2H), 3.25–3.35 (m, 1H), 3.55 (dd, 1H), 3.94 (m, 2H), 4.207 (m, 1H), 6.17 (s, 1H), 6.48 (s, 1H), 6.50–6.65 (m, 2H), 6.83 (d, 2H), 7.15 (d, 2H), 7.58 (t, 1H), $^{19}$F NMR (CDCl$_3$) δ−78.87 (s, 3F), −58.29 (s, 3F).

Additional examples of N'-(aryl and sulfonylaryl)-N-(3,3,3-trifluoro-2-hydroxypropyl)-N-[3-(trifluoromethoxy)phenyl]ureas are prepared by one skilled in the art using similar methods, as shown in Example Table 16.

EXAMPLE TABLE 16

N'-(aryl and sulfonylaryl)-N-(3,3,3-trifluoro-2-hydroxy-propyl)-N-[3-(trifluoromethoxy)phenyl]ureas.

| Ex. No. | $R_{SUB}$ | Calculated Mol. Wt. | Observed Mass $[M]^+$ |
|---|---|---|---|
| 368 | 2-CH$_3$S-phenyl | 454 | 455 |
| 369 | 4-biphenyl | 484 | 485 |
| 370 | 4-CH$_3$-phenyl-SO$_2$— | 486 | 487 |

EXAMPLE 371

3-[[[3-(1,1,2,2-tetrafluoroethoxy)phenyl]methyl](3,3,3-trifluoro-2-hydroxypropyl)amino]phenol EX-371A) To a solution of 3-aminophenol (4.91 g, 45.0 mmol) and 3-(1,1,2,2-tetrafluoroethoxy)benzaldehyde (10.0 g, 45.0 mmol) dissolved in 100 mL of 1,2-dichloroethane was added sodium triacetoxyborohydride (14.28 g 67.5 mmol) and glacial acetic acid (2.7 mL, 47.3 mmol). The reaction mixture was stirred for 6 h, water was added, and the mixture was extracted with dichloromethane. The organics were washed with saturated aqueous sodium bicarbonate then dried over MgSO$_4$. The dried organic layer was evaporated to give 11.00 g (78%) of the desired 3-[[[3-(1,1,2,2-tetrafluoroethoxy)phenyl]methyl]amino]phenol product as a dark orange oil. $^1$H NMR (CDCl$_3$) δ4.32 (s, 2H), 5.88 (tt, 1H), 6.08 (t, 1H), 6.17–6.22 (m, 2H), 7.00 (t, 1H), 7.11 (dd, 1H), 7.24–7.27 (m, 2H), 7.33 (t, 1H).

A solution of 3-[[[3-(1,1,2,2-tetafluoroethoxy)phenyl]methyl]amino]phenol (11.0 g, 34.9 mmol), 3,3,3-trifluoro-1,2-epoxypropane (4.5 mL, 52.4 mmol) and ytterbium trifluoromethanesulfonate (2.2 g, 10 mol %) in 20 mL of acetonitrile was heated at 50° C. in a sealed glass tube for 16 h. The reaction mixture was cooled, water was added, and the reaction mixture was extracted with ether.

The ether layer was washed with saturated aqueous sodium bicarbonate and brine and dried over MgSO$_4$ The dried organic layer was evaporated to give 8.07 g (89%) of the desired 3-[[[3-(1,1,2,2-tetrafluoroethoxy)phenyl]methyl](3,3,3-trifluoro-2hydroxypropyl)amino]phenol product as a yellow oil. HRMS calcd. for C$_{18}$H$_{17}$F$_7$NO$_3$: 428.1097 [M+H]$^+$, found: 428.1104. $^1$H NMR (CDCl$_3$), δ3.58 (dd, 1H), 3.88 (dd, 1H), 4.39 (m, 1H), 4.68 (s, 2H), 5.91 (tt, 1H), 6.25–6.37 (m, 3H), 7.07–7.14 (m, 4H), 7.35 (t, 1H).

EXAMPLE 372

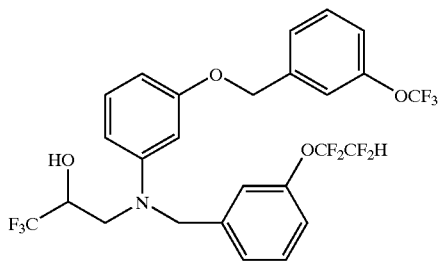

3-[[[3-(1,1,2,2-tetrafluoroethoxy)phenyl]methyl][3-[[3-(trifluoromethoxy)phenyl]-methoxy]phenyl]amino]-1,1,1-trifluoro-2-propanol To a solution of 3-[[[3-(1,1,2,2-tetrafluoroethoxy)phenyl]methyl](3,3,3-trifluoro-2-hydroxypropyl)amino]phenol (100 mg, 0.23 mmol), 3-trifluoromethoxybenzyl bromide (70.0 mg, 0.27 mmol) in 2.5 mL of acetone and cesium carbonate (100 mg, 0.31 mmol) were added. The reaction mixture was heated to 60° C. for 18 h then cooled. The reaction mixture was filtered through celite, and the solvent was evaporated. The residue was purified by reverse phase HPLC eluting with 50% to 90% acetonitrile in water to afford 63.3 mg (45%) of the desired benzyl ether product as an orange oil. HRMS calcd. for C$_{26}$H$_{22}$F$_{10}$NO$_4$: 602.1389 [M+H]$^+$, found: 602.1380. $^1$H NMR (CDCl$_3$) δ3.61 (dd, 1H), 3.83 (dd, 1H), 4.32–4.39 (m, 1H), 4.62 (s, 2H), 4.98 (s, 2H), 5.84 (tt, 1H), 6.43–6.55 (m, 3H), 7.04–7.42 (m, 9H).

Additional examples of 3-[[[3-(1,1,2,2-tetrafluoroethoxy)phenyl]methyl][3-[(substituted)methoxy]phenyl]amino]-1,1,1-trifluoro-2-propanols are prepared by one skilled in the art using similar methods as shown in Example Tables 17 and 18.

EXAMPLE TABLE 17

3-[[[3-(1,1,2,2-tetrafluoroethoxy)phenyl]methyl][3-[(substituted-phenyl)methoxy]phenyl]amino]-1,1,1-trifluoro-2-propanols.

| Ex. No. | R$_{SUB}$ | Calculated Mass [M + H]$^+$ | Observed Mass [M + H]$^+$ |
|---|---|---|---|
| 373 | H | 518.1566 | 518.1578 |
| 374 | 4-trifluoromethoxy | 602.1389 | 602.1383 |

EXAMPLE TABLE 17-continued

3-[[[3-(1,1,2,2-tetrafluoroethoxy)phenyl]methyl][3-[(substituted-phenyl)methoxy]phenyl]amino]-1,1,1-trifluoro-2-propanols.

| Ex. No. | R$_{SUB}$ | Calculated Mass [M + H]$^+$ | Observed Mass [M + H]$^+$ |
|---|---|---|---|
| 375 | 4-nitro | 563.1417 | 563.1457 |
| 376 | 2,3,4,5,6-pentafluoro | 608.1095 | 608.1092 |
| 377 | 3,5-di(trifluoromethyl) | 654.1314 | 654.1308 |
| 378 | 3,5-difluoro | 554.1378 | 554.1390 |
| 379 | 3-trifluoromethyl | 586.1440 | 586.1419 |
| 380 | 2,3,5,6-tetrafluoro-4-trifluoromethyl | 658.1063 | 658.1003 |
| 381 | 4-fluoro-2-trifluoromethyl | 604.1346 | 604.1321 |
| 382 | 3-nitro | 563.1417 | 563.1416 |
| 383 | 3-cyano | 543.1519 | 543.1523 |
| 384 | 4-cyano | 543.1519 | 543.1517 |
| 385 | 4-methyl | 532.1723 | 532.1729 |
| 386 | 2,3,5,6-tetrafluoro-4-methoxy | 620.1295 | 620.1261 |
| 387 | 3-methoxycarbonyl | 576.1621 | 576.1613 |
| 388 | 4-methoxycarbonyl | 576.1621 | 576.1614 |
| 389 | 4-difluoromethoxy | 584.1483 | 584.1480 |
| 390 | 2-fluoro | 536.1472 | 536.1465 |
| 391 | 4-fluoro | 536.1472 | 536.1454 |
| 392 | 2,4,6-trifluoro | 572.1284 | 572.1267 |
| 393 | 3-chloro-2-fluoro | 570.1082 | 570.1069 |
| 394 | 2-6-difluoro | 554.1378 | 554.1385 |
| 395 | 2,4-difluoro | 554.1378 | 554.1346 |
| 396 | 2,4-di(trifluoromethyl) | 654.1314 | 654.1321 |
| 397 | 2,5-difluoro | 554.1378 | 554.1350 |
| 398 | 3,4-difluoro | 554.1378 | 554.1381 |
| 399 | 2,3-difluoro | 554.1378 | 554.1364 |
| 400 | 2-fluoro-3-trifluoromethyl | 604.1346 | 604.1329 |
| 401 | 3-bromo | 596.0671 | 596.0641 |
| 402 | 3-methyl | 532.1723 | 532.1692 |
| 403 | 2-bromo | 596.0671 | 596.0666 |
| 404 | 2-chloro | 552.1176 | 552.1175 |
| 405 | 3-iodo | 644.0533 | 644.0517 |
| 406 | 3-fluoro | 536.1472 | 536.1475 |
| 407 | 3-methoxy | 548.1672 | 548.1676 |
| 408 | 2,3,5-trifluoro | 572.1284 | 572.1276 |
| 409 | 4-trifluoromethylthio | 618.1161 | 618.1165 |
| 410 | 3-trifluoromethylthio | 618.1161 | 618.1151 |
| 411 | 3-fluoro-5-trifluoromethyl | 604.1346 | 604.1309 |
| 412 | 4-fluoro-3-trifluoromethyl | 604.1346 | 604.1336 |
| 413 | 4-(phenylmethoxy) | 624.1985 | 624.1956 |
| 414 | 4-phenyl | 594.1879 | 594.1845 |
| 415 | 4-ethyl | 546.1879 | 546.1862 |
| 416 | 4-trifluoromethyl | 586.1440 | 586.1400 |
| 417 | 2-methyl-3-nitro | 577.1573 | 577.1576 |
| 418 | 4-tert-butyl | 574.2192 | 574.2163 |
| 419 | 3,4-dimethyl | 546.1879 | 546.1881 |
| 420 | 3-chloro | 552.1176 | 552.1157 |
| 421 | 4-bromo | 596.0671 | 596.0669 |
| 422 | 3,5-dichloro | 586.1787 | 586.1378 |
| 423 | 3,5-dimethyl | 546.1879 | 546.1890 |
| 424 | 4-chloro | 552.1176 | 552.1188 |
| 425 | 2-fluoro-3-methyl | 550.1628 | 550.1625 |
| 426 | 3-phenoxy | 610.1828 | 610.1819 |
| 427 | 4-isopropyl | 560.2036 | 560.2020 |

EXAMPLE TABLE 18

3-[[[3-(1,1,2,2-tetrafluoroethoxy)phenyl]methyl][3-[(substituted)-methoxy]phenyl]amino]-1,1,1-trifluoro-2-propanols.

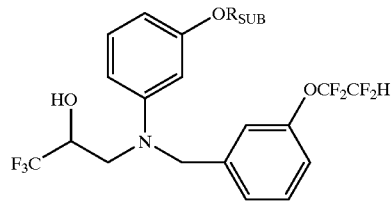

| Ex. No. | $R_{SUB}$ | Calculated Mass $[M + H]^+$ | Observed Mass $[M + H]^+$ |
|---|---|---|---|
| 428 | 3-pyridylmethyl | 519.1519 | 519.1483 |
| 429 | 1-phenylethyl | 532.1723 | 532.1711 |
| 430 | 1-benzylimidazol-2-ylmethyl | 598.1941 | 598.1946 |
| 431 | 5-chlorobenzo[b]thien-3-ylmethyl | 608.0897 | 608.0884 |
| 432 | 2-pyridylmethyl | 519.1519 | 519.1522 |
| 433 | 4-pyridylmethyl | 519.1519 | 519.1515 |

EXAMPLE 434

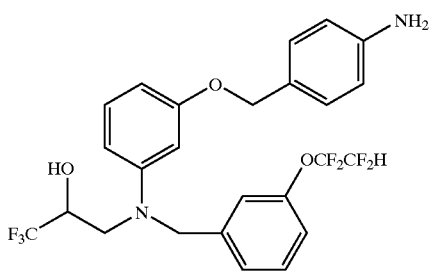

3-[[3-[(4-aminophenyl)methoxy]phenyl][[3-(1,1,2,2-tetrafluoroethoxy)phenyl]methyl]amino]1,1,1-trifluoro-2-propanol EX-434A) A solution of 3-[[[3-(1,1,2,2-tetrafluoroethoxy)phenyl]methyl][3-[(3-nitrophenyl)methoxy]phenyl]amino]-1,1,1-trifluoro-2-propanol (42.0 mg, 0.07 mmol) and zinc dust (37 mg, 0.57 mmol) in acetic acid (0.5 mL) was stirred for 4 d. The reaction mixture was filtered, and the solvent was evaporated. The residue was purified by reverse phase HPLC eluting with 50% to 90% acetonitrile in water to afford 15.4 mg (39%) of the desired reduced amine product as a brown oil. HRMS calcd. for $C_{25}H_{24}F_7N_2O_3$: 533.1675 [M+H]$^+$, found: 533.1656. $^1$H NMR (acetone-d$_6$) δ3.60 (dd, 1H), 3.85 (m, 1H), 3.90 (s, 2H), 4.45 (m, 1H), 4.73 (s, 2H), 6.22–6.64 (m, 4H), 6.94 (dd, 1H), 7.12–7.45 (m, 9H).

EX-434B) 3-[[3-[(3-aminophenyl)methoxy]phenyl][[3-(1,1,2,2-tetrafluoroethoxy)-phenyl]methyl]amino]-1,1,1-trifluoro-2-propanol is prepared by one skilled in the art using similar methods. HRMS calcd. for $C_{25}H_{24}F_7N_2O_3$: 533.1675 [M+H]$^+$, found: 533.1654.

EXAMPLE 435

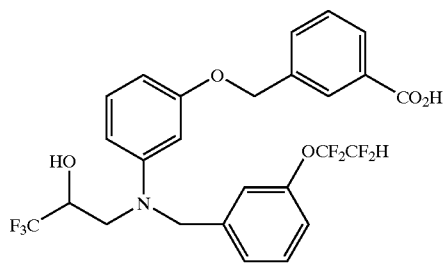

3-[[3-[[[3-(1,1,2,2-tetrafluoroethoxy)phenyl]methyl](3,3,3-trifluoro-2-hydroxypropyl)amino]phenoxy]methyl]benzoic acid EX-435A) A solution of ethyl 3-[[3-[[[3-(1,1,2,2-tetrafluoroethoxy)phenyl]methyl]-(3,3,3-trifluoro-2-hydroxypropyl)amino]phenoxy]methyl]benzoate (22.1 mg, 0.04 mmol) and lithium hydroxide (5 mg, 0.12 mmol) in water (1 mL) and tetrahydrofuran (0.5 mL) was heated at 80° C. for 16 h. The reaction mixture was added to 6 N hydrochloric acid and extracted with ethyl acetate. The organic layer was dried over magnesium sulfate, and the solvent was evaporated. The residue was purified by reverse phase HPLC eluting with 10% to 90% acetonitrile in water to afford 5.6 mg (19%) of the desired benzoic acid product as a brown oil. HRMS calcd. for $C_{26}H_{23}F_7NO_5$: 562.1464 [M+H]$^+$, found: 562.1418. $^1$H NMR (acetone-d$_6$) δ3.64 (dd, 1H), 3.95 (m, 1H), 4.45–4.50 (m, 1H), 4.80 (s, 2H), 5.12 (s, 2H), 6.27–6.63 (m, 4H), 7.06–7.27 (m, 4H), 7.41 (t, 1H), 7.50 (t, 1H), 7.66 (d, 1H), 7.99 (d, 1H), 8.10 (s, 1H).

EX-435B) 4-[[3-[[[3-(1,1,2,2-tetrafluoroethoxy)phenyl]methyl](3,3,3-trifluoro-2-hydroxypropyl)amino]phenoxy]methyl]benzoic acid is prepared by one skilled in the art using similar methods. HRMS calcd. for $C_{26}H_{23}F_7NO_5$: 562.1464 [M+H]$^+$, found: 562.1445.

EXAMPLE 436

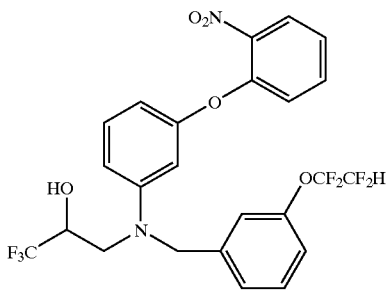

3-[[3-(2-nitrophenoxy)phenyl][[3-(1,1,2,2-tetrafluoroethoxy)phenyl]-methyl]amino]-1,1,1-trifluoro-2-propanol A solution of 3-[[[3-(1,1,2,2-tetrafluoroethoxy)phenyl]methyl](3,3,3-trifluoro-2-hydroxypropyl)amino]phenol (100 mg, 0.23 mmol), 1-bromo-2-nitrobenzene (52.4 mg, 0.26 mmol), copper(I) trifluoromethanesulfonate benzene complex (3 mg, 2.5 mol %) and cesium carbonate (100 mg, 0.31 mmol) in toluene (1 mL) and ethyl acetate (1 mL) was heated at 95° C. in a sealed vial for 4 d. The reaction mixture was filtered through celite, and the solvent was evaporated. The residue was purified by reverse phase HPLC eluting with 50% to 90% acetonitrile in water to afford 14.1 mg (11%) of the desired 2-nitrophenyl ether product as an orange oil. HRMS calcd. for $C_{24}H_{20}F_7N_2O_5$: 549.1260 [M+H]$^+$, found: 549.1235. $^1$H NMR (CDCl$_3$) δ3.63 (dd, 1H), 3.84 (dd, 1H), 4.35–4.42 (m, 1H), 4.64 (s, 2H), 5.90 (tt, 1H), 6.47–6.67 (m, 3H), 6.98–7.50 (m, 8H), 7.97 (d, 1H).

Additional examples of 3-[[3-aryloxyphenyl][[3-(1,1,2,2-tetrafluoroethoxy)-phenyl]methyl]amino]-1,1,1-trifluoro-2-propanols are prepared by one skilled in the art using similar methods, as shown in Example Table 19.

EXAMPLE TABLE 19

3-[[3-aryloxyphenyl][[3-(1,1,2,2-tetrafluoroethoxy)phenyl]methyl]amino]-1,1,1-trifluoro-2-propanols.

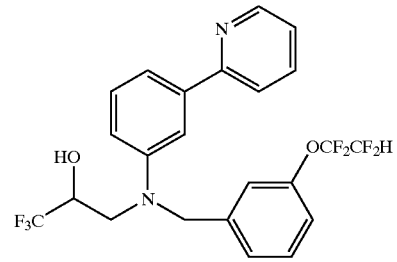

| Ex. No. | R$_{SUB}$ | Calculated Mass [M + H]$^+$ | Observed Mass [M + H]$^+$ |
|---|---|---|---|
| 437 | 4-tert-butylphenyl | 560.2036 | 560.2050 |
| 438 | 4-nitrophenyl | 549.1260 | 549.1306 |
| 439 | 4-bromo-2-nitrophenyl | 627.0366 | 627.0375 |
| 440 | 3-fluoro-2-nitrophenyl | 567.1166 | 567.1135 |
| 441 | 2-cyano-3-pyridyl | 530.1315 | 530.1300 |
| 442 | 5-carboxy-3-pyridyl | 549.1260 | 549.1269 |
| 443 | 4-fluoro-2-pyridyl | 523.1268 | 523.1243 |
| 444 | 3-trifluoromethyl-2-pyridyl | 573.1236 | 573.1205 |
| 445 | 5-trifluoromethyl-2-pyridyl | 573.1236 | 573.1197 |
| 446 | 5-bromo-2-pyridyl | 583.0667 | 583.0405 |
| 447 | 2-methyl-5-nitrophenyl | 563.1417 | 563.1416 |
| 448 | thiazol-2-yl | 511.0926 | 511.0911 |
| 449 | 5-pyrimidinyl | 506.1315 | 506.1315 |

EXAMPLE 450

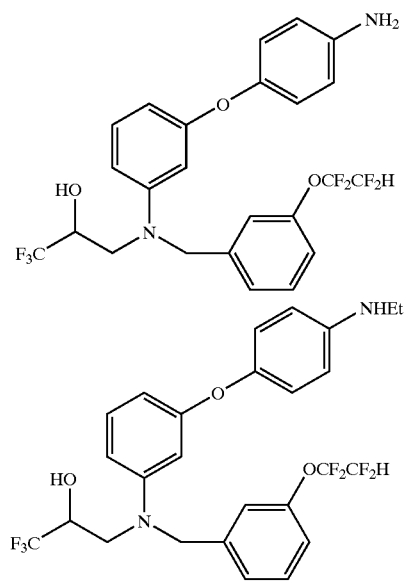

3-[[3-(4-aminophenoxy)phenyl][[3-(1,1,2,2-tetrafluoroethoxy)phenyl]-methyl]amino]-1,1,1-trifluoro-2-propanol and 3-[[3-[4-(ethylamino)phenoxy]phenyl][[3-(1,1,2,2-tetrafluoroethoxy)phenyl]-methyl]amino]-1,1,1-trifluoro-2-propanol A solution of 3-[[3-(4-nitrophenoxy)phenyl][[3-(1,1,2,2-tetrafluoroethoxy)phenyl]-methyl]amino]-1,1,1-trifluoro-2-propanol (33.8 mg, 0.06 mmol) in ethanol and 5% palladium on carbon (4 mL) was placed under 40 psi hydrogen gas for 7 h. The mixture was filtered through celite, the solvent was evaporated, and the residue was purified by silica gel chromatography eluting with 25% ethyl acetate in hexane to give 13.4 mg (42%) of (EX-450A) as 3-[[3-(4-aminophenoxy)phenyl][[3-(1,1,2,2-tetrafluoroethoxy)phenyl]methyl]amino]-1,1,1-trifluoro-2-propanol and 13.9 mg (41%) of (EX-450B) as 3-[[3-[4-(ethylamino)phenoxy]phenyl][[3-(1,1,2,2-tetrafluoroethoxy)phenyl]methyl]amino]-1,1,1-trifluoro-2-propanol both as orange oils. 3-[[3-(4 aminophenoxy)phenyl][[3-(1,1,2,2-tetrafluoroethoxy)phenyl]methyl]-amino]-1,1,1-trifluoro-2-propanol: HRMS calcd. for $C_{24}H_{22}F_7N_2O_3$: 519.1519 [M+H]$^+$, found: 519.1529. $^1$H NMR (acetone-d$_6$) δ3.63 (dd, 1H), 3.96 (dd, 1H), 4.42–4.58 (m, 1H), 4.80 (s, 2H), 5.88 (m, 1H), 6.20 (m, 1H), 6.32–6.77 (m, 6H), 6.92 (d, 1H), 7.06–7.26 (m, 3H), 7.43 (m, 1H). 3-[[3-[4 (ethylamino)phenoxy]phenyl][[3-(1,1,2,2-tetrafluoroethoxy) phenyl]-methyl]amino]-1,1,1-trifluoro-2-propanol: HRMS calcd. for $C_{26}H_{26}F_7N_2O_3$: 547.1832 [M+H]$^+$, found: 547.1819. $^1$H NMR (acetone-d$_6$) δ1.23 (t, 3H), 3.17 (q, 2H), 3.63 (dd, 1H), 3.96 (dd, 1H), 4.42–4.58 (m, 1H), 4.79 (s, 2H), 5.85 (d, 1H), 6.20 (m, 1H), 6.33 (m, 1H), 6.47 (m, 1H), 6.50 (tt, 1J), 6.61 (d, 2H), 6.78 (d, 2H), 7.09 (t, 1H), 7.20 (m, 1H), 7.23 (d, 1H), 7.42 (m, 1H).

EXAMPLE 451

3-[[3-(2-pyridinyl)phenyl][[3-(1,1,2,2-tetrafluoroethoxy)phenyl]methyl]amino]-1,1,1-trifluoro-2-propanol A solution of 3-[(3-bromophenyl)[[3-(1,1,2,2-tetrafluoroethoxy)phenyl]methyl]amino]-1,1,1-trifluoro-2-propanol (100 mg, 0.22 mmol), 2-tributylstannyl pyridine (96 mg, 0.26 mmol), dichlorobis(triphenylphospine) palladium(II) (6 mg, 6.7 mol %) and lithium chloride (46 mg, 1.09 mmol) in toluene (4 mL) was heated at 105° C. for 16 h. The reaction mixture was filtered through celite, and the solvent was evaporated. The residue was purified by silica gel column chromatography eluting with 25% ethyl acetate in hexane to afford 47.7 mg (45%) of the desired pyridyl product as an orange oil. HRMS calcd. for $C_{23}H_{20}F_7N_2O_2$: 489.1377 [M+H]$^+$, found: 489.1413. $^1$H NMR (acetone-d$_6$) δ3.78 (dd, 1H), 4.06 (dd, 1H), 4.52–4.61 (m, 1H), 4.94 (s, 2H), 5.89 (d, 1H), 6.43 (tt, 1H), 6.94 (m, 1H), 7.18 (m, 1H), 7.22–7.42 (m, 5H), 7.60 (s, 1H), 7.80 (m, 2H), 8.61 (m, 1H).

Additional examples of 3-[[3-(heteroaryl)phenyl][[3-(1,1,2,2-tetrafluoroethoxy)phenyl]methyl]amino]-1,1,1-trifluoro-2-propanols are prepared by one skilled in the art using similar methods, as shown in Example Table 20.

EXAMPLE TABLE 20

3-[[3-(heteroaryl)phenyl][[3-(1,1,2,2-tetrafluoroethoxy)phenyl]methyl]amino]-1,1,1-trifluoro-2-propanols.

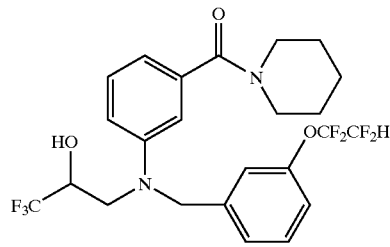

| Ex. No. | $R_{SUB}$ | Calculated Mass $[M + H]^+$ | Observed Mass $[M + H]^+$ |
|---|---|---|---|
| 452 | 2-thienyl | 494.1024 | 494.0987 |
| 453 | 2-furyl | 478.1025 | 478.1025 |
| 454 | 3-pyridyl | 489.1413 | 489.1391 |
| 455 | 3-methyl-2-pyridyl | 503.1570 | 503.1531 |

EXAMPLE 456

1-[3-[[[3-(1,1,2,2-tetrafluoroethoxy)phenyl]methyl](3,3,3-trifluoro-2-hydroxypropyl)benzoyl]piperidine EX-456A) Ethyl 3-aminobenzoate (6.75 mL, 0.045 mol) and 3-(1,1,2,2-tetrafluoroethoxy)benzaldehyde (10 g, 45 mmol) were dissolved in 100 mL of dichloroethane and acetic acid (2.7 mL, 47 mmol), then solid NaBH(OAc)$_3$ (14.3 g, 67 mmol) was added. The mixture was stirred at room temperature for 3 hours, then quenched with aqueous sodium bicarbonate and extracted with dichloromethane. The organic layer was washed with brine, then dried over MgSO$_4$, and evaporated to give 16.7 g (98%) of the desired ethyl 3-[[[3-(1,1,2,2-tetrafluoroethoxy)phenyl]methyl]amino]benzoate product as a yellow oil. $^1$H NMR (CDCl$_3$) δ1.3 (t, 3H), 4.3 (q, 2H), 4.5 (s, 2H), 6.5 (tt, 1H), 6.9 (d, 1H), 7.1–7.4 (m, 7H).

EX-456B) A solution of EX-456A (16.7 g, 45 mmol) and 1,1,1-trifluoro-2,3-epoxypropane (4.26 mL, 49.5 mmol) were dissolved in 30 mL of acetonitrile. Ytterbium (III) trifluoromethanesulfonate (2.79 g, 4.5 mmol) was added, and the stirred solution was warmed to 50° C. for 18 hours. The reaction was quenched with water and extracted with ether. The ether layer was washed with brine, then dried over MgSO$_4$. The crude product was purified by flash column chromatography on silica gel eluting with dichloromethane to give 12 g (55%) of the desired ethyl 3-[[[3-(1,1,2,2-tetrafluoroethoxy)phenyl]methyl](3,3,3-trifluoro-2-hydroxypropyl)amino]-benzoate product as a colorless oil, which was greater than 98% pure by reverse phase HPLC analysis. HRMS calcd. for C$_{21}$H$_{21}$F$_7$NO$_4$: 484.1359 [M+H]$^+$, found: 484.1342. $^1$H NMR (CDCl$_3$) δ1.4 (t, 3H), 3.6 (dd, 1H), 3.9 (dd, 1H), 4.3 (m, 3H), 4.7 (dd, 2H 5.9 (tt, 1H), 6.9 (d, 1H), 7.1–7.2 (m, 3H), 7.2–7.4 (m, 2H), 7.5 (m, 1H To a solution of piperidine (102 μL, 1.03 mmol) in toluene (620 μL) was added 2 M trimethylaluminum in toluene (620 μL), and the solution was stirred for 2 h. To the reaction mixture was added a solution of ethyl 3-[(1,1,1-trifluoro-2-hydroxypropyl)[[3-(1,1,2,2-tetrafluoroethoxy)phenyl]methyl]amino]benzoate (100 mg, 0.21 mmol) in toluene (1 mL). The reaction mixture was heated at 40° C. for 20 h and 60° C. for 5 h, then cooled. To the reaction mixture was added water dropwise followed by 2 M hydrochloric acid and ethyl acetate. The solution was placed on a celite plug for 5 min, then eluted with dichloromethane, and the solvent was evaporated. The residue was purified by reverse phase HPLC eluting with 50% to 90% acetonitrile in water to afford 42.6 mg (38%) of the desired 1-[3-[[[3-(1,1,2,2-tetrafluoroethoxy)phenyl]-methyl]-(3,3,3-trifluoro-2-hydroxypropyl)benzoyl]piperidine product as an orange oil. HRMS calcd. for C$_{24}$H$_{26}$F$_7$N$_2$O$_3$: 523.1832 [M+H]$^+$, found: 523.1815. $^1$H NMR (acetone-d$_6$) δ1.22–1.63 (m, 6H), 3.16–3.62 (m, 4H), 3.74 (dd, 1H), 4.00 (dd, 1H), 4.44–4.55 (m, 1H), 4.83 (s, 2H), 6.46 (tt, 1H), 6.64–6.69 (m, 2H), 6.83 (dd, 1H), 7.14–7.28 (m, 4H), 7.41 (t, 1H).

Additional examples of N,N-disubstituted-3-[(3,3,3-trifluoro-2-hydroxypropyl)-[[3-(1,1,2,2-tetrafluoroethoxy)phenyl]methyl]amino]benzamide are prepared by one skilled in the art using similar methods, as shown in Example Table 21.

EXAMPLE TABLE 21

N,N-disubstituted-3-[(3,3,3-trifluoro-2-hydroxypropyl)[[3-(1,1,2,2-tetrafluoroethoxy)phenyl]methyl]amino]benzamide

| Ex. No. | $R_{SUB}$ | $R'_{SUB}$ | Calculated Mass $[M + H]^+$ | Observed Mass $[M + H]^+$ |
|---|---|---|---|---|
| 457 | H | isopropyl | 497.1675 | 497.1697 |
| 458 | H | n-butyl | 511.1832 | 511.1809 |
| 459 | H | cyclohexyl | 537.1988 | 537.1969 |
| 460 | H | tert-butyl | 511.1832 | 511.1845 |
| 461 | H | cyclopentyl | 523.1832 | 523.1854 |
| 462 | H | neo-pentyl | 525.1988 | 525.2028 |
| 463 | H | 2,2,2-trifluoroethyl | 537.1236 | 537.1250 |
| 464 | H | 2,2,3,3,4,4,4-heptafluorobutyl | 637.1172 | 637.1177 |
| 465 | H | phenylmethyl | 545.1675 | 545.1705 |
| 466 | H | (3-trifluoromethoxy)-phenylmethyl | 629.1498 | 629.1510 |
| 467 | H | 4-(fluorophenyl)methyl | 563.1581 | 563.1611 |
| 468 | methyl | phenyl | 545.1675 | 545.1631 |
| 469 | methyl | phenylmethyl | 559.1832 | 559.1853 |

EXAMPLE TABLE 21-continued

N,N-disubstituted-3-[(3,3,3-trifluoro-2-hydroxypropyl)[[3-(1,1,2,2-tetra-fluoroethoxy)phenyl]methyl]amino]benzamide

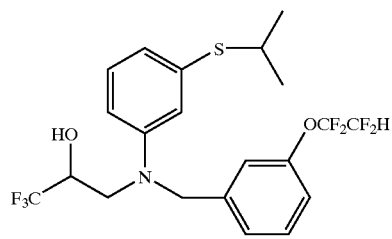

| Ex. No. | $R_{SUB}$ | $R'_{SUB}$ | Calculated Mass $[M + H]^+$ | Observed Mass $[M + H]^+$ |
|---|---|---|---|---|
| 470 | —CH$_2$CH$_2$N(CH$_3$)CH$_2$CH$_2$— | | 538.1941 | 538.1969 |
| 471 | —CH$_2$CH$_2$OCH$_2$CH$_2$— | | 525.1624 | 525.1615 |
| 472 | —CH$_2$CH$_2$CH$_2$CH$_2$— | | 509.1675 | 509.1675 |

EXAMPLE 473

3-[[3-[(1-methylethyl)thio]phenyl][[3-(1,1,2,2-tetrafluoroethoxy)phenyl]-methyl]amino]-1,1,1-trifluoro-2-propanol EX-473A) 3-Aminobenzenethiol (2.4 mL, 22.5 mmol) and 3-(1,1,2,2-tetrafluoroethoxy)benzaldehyde (5 g, 22.5 mmol) were dissolved in 40 mL of dichloroethane and acetic acid (1.35 mL, 23.7 mmol), then solid NaBH(OAc)$_3$ (6.2 g, 29.3 mmol) was added. The mixture was stirred at room temperature for 18 hours, then quenched with water and diluted with dichloromethane. The organic layer was washed with aqueous saturated sodium bicarbonate, then dried over MgSO$_4$, and concentrated in vacuo. The crude product was purified by flash column chromatography on silica gel eluting with ethyl acetate-:hexane 1:10 to give 5.36 g (72%) of the desired 3-[[[3-(1,1,2,2-tetrafluoroethoxy)phenyl]methyl]amino] benzenethiol product as a brown oil. $^1$H NMR (CDCl$_3$) δ3.4 (s, 1H), 4.4 (s, 2H), 5.9 (tt, 1H), 6.4 (dd, 1H), 6.55 (m, 1H), 6.65 (d, 1H), 7.05 (t, 1H), 7.2–7.4 (m, 4H).

EX-473B) The EX-473A benzenethiol amine (5.36 g, 16.2 mmol) and 1,1,1-trifluoro-2,3-epoxypropane (1 g, 1.6 mmol) were dissolved in 20 mL of acetonitrile. Ytterbium (III) trifluoromethanesulfonate (1 g, 1.6 mmol) was added, and the stirred solution was warmed to 50° C. for 48 hours, at which time HPLC analysis indicated that no secondary amine starting material remained. The reaction was quenched with water and extracted with ether. The ether layer was washed with brine, then dried over MgSO$_4$, and concentrated in vacuo. The crude product was purified by flash column chromatography on silica gel eluting with ethyl acetate:hexane 1:10 to give 4.5 g (63%) of the desired 3-[[[3-(1,1,2,2-tetrafluoroethoxy)phenyl]methyl](3,3,3-trifluoro-2-hydroxypropyl)amino] benzenethiol product as a yellow oil. $^1$H NMR (CDCl$_3$) δ3.0 (s, 1H), 3.6 (dd, 1H), 3.9 (dd, 1H), 4.2 (m, 1H), 4.7 (m, 2H), 5.9 (tt, 1H), 6.5 (dd, 1H), 6.7 (m, 2H), 7.1 (m, 4H), 7.4 (t, 1H). HRMS calcd. for C$_{36}$H$_{31}$F$_{14}$N$_2$O$_4$S$_2$: 885.1502 [2(M−1)+H]$^+$, found: 885.1471.

The EX-473B thiol product (150 mg, 0.34 mmol) and 2-iodopropane (37 μL, 0.37 mmol) were dissolved in 2 mL of acetonitrile. Cesium carbonate (144 mg, 0.44 mmol) was added, and the stirred solution was warmed to 55° C. for 18 hours, at which time HPLC analysis indicated that no thiol/disulfide starting material remained. The reaction was quenched with water and filtered through pre-wetted celite eluting with ethyl acetate. The solvent was evaporated, and the residue was purified by reverse phase HPLC eluting with 10% to 90% acetonitrile in water to afford 69 mg (42%) of the desired 3-[[3-[(1-methylethyl)thio]phenyl][[3-(1,1,2,2-tetrafluoroethoxy)phenyl]-methyl]amino]-1,1,1-trifluoro-2-propanol product as a yellow oil, which was greater than 98% pure by reverse phase HPLC analysis. HRMS calcd. for C$_{21}$H$_{23}$F$_7$NO$_2$S: 486.1338 [M+H]$^+$, found: 486.1351. $^1$H NMR (CDCl$_3$) δ1.2 (t, 3H), 3.3 (q, 1H), 3.6 (dd, 1H), 3.9 (dd, 1H), 4.3 (m, 1H), 4.7 (m, 3H), 5.9 (tt, 1H), 6.7 (dd, 1H), 6.9 (m, 2H), 7.0–7.2 (m, 4H), 7.3 (t, 1H).

Additional examples of 3-[[3-(alkanoyl-, aryl-, heteroaryl-, and aralkylthio)phenyl][[3-(1,1,2,2-tetrafluoroethoxy)phenyl]methyl]amino]-1,1,1-trifluoro-2-propanols are prepared by one skilled in the art using similar methods, as shown in Example Table 22.

EXAMPLE TABLE 22

3-[[3-(alkanoyl-, aryl-, heteroaryl-, and aralkylthio)phenyl][[3-(1,1,2,2-tetrafluoro-ethoxy)phenyl]methyl]amino]-1,1,1-trifluoro-2-propanols.

| Ex. No. | $R_{SUB}$ | Calculated Mass $[M + H]^+$ | Observed Mass $[M + H]^+$ |
|---|---|---|---|
| 474 | 4-pyridyl | 521.1134 | 521.1115 |
| 475 | 4-nitrophenyl | 565.1032 | 565.1034 |
| 476 | 4-piperidyl | 527.1603 | 527.1597 |
| 477 | 2-pyridylmethyl | 535.1290 | 535.1291 |
| 478 | 4-acetylphenyl | 562.1287 | 562.1261 |
| 479 | 4-(methylsulfonyl)phenyl | 598.0957 | 598.0946 |
| 480 | (4-chloro-thien-2-yl)methyl | 574.0512 | 574.0523 |
| 481 | acetyl | 486.0974 | 486.0936 |

EXAMPLE 482

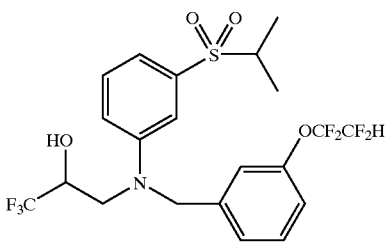

3-[[3-[(1-methylethyl)sulfonyl]phenyl][[3-(1,1,2,2-tetrafluoroethoxy)-phenyl]methyl]amino]-1,1,1-trifluoro-2-propanol To a solution of 3-[[3-[(1-methylethyl)thio]phenyl][[3-(1,1,2,2-tetrafluoroethoxy)-phenyl]methyl]amino]-1,1,1-trifluoro-2-propanol (58 mg, 0.12 mmol) in 2 mL of trifluoroacetic acid, was added 30% aqueous $H_2O_2$ (28 µL, 0.25 mmol). The mixture was stirred at room temperature for 18 hours, then quenched with 5% aqueous sodium hydroxide and extracted with ether. The organic layer was concentrated in vacuo. The crude product was purified by reverse phase HPLC eluting with 10% to 90% acetonitrile in water to give 29.5 mg (48%) of the desired sulfone product as a brown oil, which was greater than 98% pure by reverse phase HPLC analysis. HRMS calcd. for $C_{21}H_{23}F_7NO_4S$: 518.1236 [M+H]$^+$, found: 518.1226. $^1$H NMR (CDCl$_3$) δ1.1 (d, 6H), 3 (q, 1H), 3.7 (dd, 1H), 3.9 (dd, 1H), 4.3 (m, 1H), 4.7 (s, 1H), 5.9 (tt, 1H), 7 (m, 2H), 7.1–7.2 (m, 4H), 7.3 (m, 2H).

Additional examples of 3-[(3-(aryl-, heteroaralkyl-, and heterocyclylsulfonyl)phenyl][[3-(1,1,2,2-tetrafluoroethoxy)phenyl]methyl]amino]-1,1,1-trifluoro-2-propanols are prepared by one skilled in the art using similar methods, as shown in Example Table 23.

EXAMPLE TABLE 23

3-[(3-(aryl-, heteroaralkyl-, and heterocyclyl-sulfonyl)phenyl][[3-(1,1,2,2-tetrafluoroethoxy)phenyl]methyl]amino]-1,1,1-trifluoro-2-propanols.

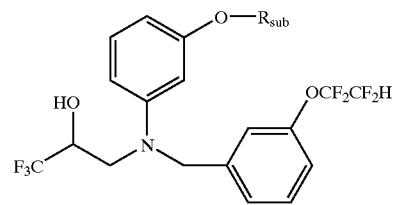

| Ex. No. | R$_{SUB}$ | Calculated Mass [M + H]$^+$ | Observed Mass [M + H]$^+$ |
|---|---|---|---|
| 483 | 4-nitrophenyl | 597.0930 | 597.0925 |
| 484 | 4-piperidyl | 559.1502 | 559.1526 |
| 485 | 3-(pyridyl-N-oxide)methyl | 583.1138 | 583.1137 |
| 486 | 4-acetylphenyl | 594.1185 | 594.1181 |
| 487 | 4-(methylsulfonyl)phenyl | 630.0855 | 630.0826 |

EXAMPLE 488

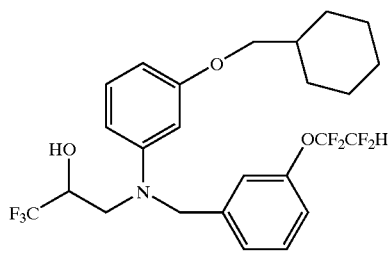

3-[[3-(cyclohexylmethoxy)phenyl][[(3-(1,1,2,2-tetrafluoroethoxy)phenyl]-methyl]amino]-1,1,1-trifluoro-2-propanol 3-[[[3-(1,1,2,2-tetrafluoroethoxy)phenyl]methyl](1,1,1-trifluoro-2-hydroxypropyl)-amino]phenol (100 mg, 0.23 mmol) and bromomethylcyclohexane (42 µL, 0.30 mmol) were dissolved in 2 mL of acetonitrile. Cesium carbonate (144 mg, 0.44 mmol) was added, and the stirred solution was warmed to 50° C. for 48 hours, at which time HPLC analysis indicated that no phenolic starting material remained. The reaction was quenched with water and filtered through pre-wetted celite eluting with ethyl acetate. The solvent was evaporated and the residue was purified by reverse phase HPLC eluting with 10% to 90% acetonitrile in water to afford 55 mg (35%) of the desired ether product as a brown oil, which was greater than 99% pure by reverse phase HPLC analysis. HRMS calcd. for $C_{25}H_{29}F_7NO_3$: 524.2036 [M+H]$^+$, found: 524.2028. $^1$H NMR (CDCl$_3$) δ0.9–1.4 (m, 5H), 1.7–1.9 (m, 6H), 3.6 (m, 3H), 3.9 (dd, 1H), 4.3 (m, 1H), 4.7 (m, 2H), 5.1 (s, 1H), 5.9 (tt, 1H), 6.5 (m, 3H), 7.0–7.4 (m, 5H).

Additional examples of 3-[(3-alkoxy- and cycloalkoxyphenyl)[[3-(1,1,2,2-tetrafluoroethoxy)phenyl]methyl]amino]-1,1,1-trifluoro-2-propanols are prepared by one skilled in the art using similar methods, as shown in Example Table 24.

EXAMPLE TABLE 24

3-[(3-alkoxy- and cycloalkoxy-phenyl)[[3-(1,1,2,2-tetrafluoroethoxy)phenyl]methyl]amino]-1,1,1-trifluoro-2-propanols.

| Ex. No. | R$_{SUB}$ | Calculated Mass [M + H]$^+$ | Observed Mass [M + H]$^+$ |
|---|---|---|---|
| 489 | isopropyl | 470.1488 | 470.1565 |
| 490 | (methoxycarbonyl)methyl | 500.1308 | 500.1297 |
| 491 | cyanomethyl | 467.1206 | 467.1228 |
| 492 | 2-methylpropyl | 484.1723 | 484.1718 |
| 493 | 2-oxobutyl | 498.1515 | 498.1529 |
| 494 | cyclohexyl | 510.1880 | 510.1910 |
| 495 | 5-oxohexyl | 526.1828 | 526.1827 |
| 496 | 4-(methoxycarbonyl)butyl | 542.1777 | 542.1827 |
| 497 | 2-(phenylsulphonyl)ethyl | 596.1342 | 596.1349 |
| 498 | 2-pyrrolidinylethyl | 525.1988 | 525.2008 |
| 499 | 3-(methoxycarbonyl)-2-propenyl | 526.1464 | 526.1482 |

EXAMPLE TABLE 24-continued

3-[(3-alkoxy- and cycloalkoxy-phenyl)[[3-(1,1,2,2-tetrafluoroethoxy)phenyl]methyl]amino]-1,1,1-trifluoro-2-propanols.

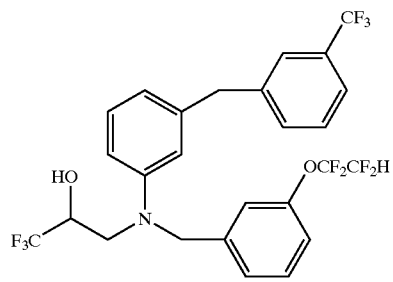

| Ex. No. | $R_{SUB}$ | Calculated Mass $[M + H]^+$ | Observed Mass $[M + H]^+$ |
|---|---|---|---|
| 500 | carbamoylmethyl | 485.1311 | 485.1304 |
| 501 | 3-cyanopropyl | 495.1519 | 495.1541 |
| 502 | 1-(N-phenylcarbamoyl)ethyl | 575.1780 | 575.1778 |
| 503 | 2-oxo-2-phenylethyl | 546.1515 | 546.1543 |
| 504 | 3-hydroxypropyl | 486.1515 | 484.1481 |
| 505 | 2-methoxyethyl | 486.1515 | 486.1537 |
| 506 | neo-pentyl | 498.1879 | 498.1845 |
| 507 | 4-tetrahydropyranyl | 512.1672 | 512.1631 |
| 508 | 1-ethoxycarbonylbutyl | 556.1934 | 556.1948 |
| 509 | cyclopentyl | 496.1723 | 496.1719 |
| 510 | 3-methyl-2-butenyl | 496.1722 | 496.1675 |
| 511 | 2-(N,N-dimethylamino)ethyl | 499.1831 | 499.1826 |
| 512 | 3-hydroxy-2,2-dimethylpropyl | 514.1828 | 514.1814 |
| 513 | 3,3-dimethyl-2-oxobutyl | 526.1828 | 526.1806 |

EXAMPLE 514

3-[[[3-(1,1,2,2-tetrafluoroethoxy)phenyl]methyl][3-[[(3-trifluoromethyl)-phenyl]methyl]phenyl]amino]-1,1,1-trifluoro-2-propanol EX-514A) To a solution of (3-nitrobenzene)methanol (10 g, 65.3 mmol) in 50 mL of 5% aqueous sodium hydroxide, was added dimethylsulfate (20 g, 156 mmol). The mixture was stirred at 70° C. for 18 hours, then diluted with water and ethyl acetate. The organic layer was washed with water, then dried over $MgSO_4$, and concentrated in vacuo. The crude product was purified by flash column chromatography on silica gel eluting with ethyl acetate:hexane 1:5 to give 4.73 g (43%) of the desired 3-(methoxymethyl)nitrobenzene product as a yellow oil. $^1$H NMR ($CDCl_3$) δ3.5 (s, 3H), 4.5 (s, 2H), 6.5 (t, 1H), 7.7 (d, 1H), 8.1 (d, 1H), 8.2 (s, 1H).

EX-514B) The 3-(methoxymethyl)nitrobenzene (4.18 g, 25 mmol) from EX-514A was dissolved in 160 mL of acetic acid. Zinc dust (5 g, 76.5 mmol) was added, and the solution was stirred at room temperature for 18 hours, at which time HPLC analysis indicated that no 3-(methoxymethyl)nitrobenzene starting material remained. The reaction mixture was filtered through celite and concentrated in vacuo. The residue was dissolved in ethyl acetate and washed with aqueous saturated sodium bicarbonate. The organic layer was washed with water, then dried over $MgSO_4$, and concentrated in vacuo to give 3.4 g (99%) of the desired 3-(methoxymethyl)aniline as a brown oil. The crude product was used without further purification. HRMS calcd. for $C_8H_{12}NO$: 138.0919 $[M+H]^+$, found: 138.0929. $^1$H NMR ($CDCl_3$) δ3.4 (s, 3H), 3.7 (s, 2H), 4.4 (s, 2H), 6.6 (d, 1H), 6.7 (m, 2H), 7.2 (t, 1H).

EX-514C) The 3-(methoxymethyl)aniline (1.85 g, 13.51 mmol) product from EX-514B and 3-(1,1,2,2-tetrafluoroethoxy)benzaldehyde (3 g, 13.5 mmol) were dissolved in 25 mL of dichloroethane and acetic acid (0.85 mL, 14.8 mmol), then solid $NaBH(OAc)_3$ (3.73 g, 17.6 mmol) was added. The mixture was stirred at room temperature for 48 hours, then quenched with aqueous saturated sodium bicarbonate and diluted with ethyl acetate. The organic layer was washed with brine, then dried over $MgSO_4$, and concentrated in vacuo to give 4.27 g (12.4 mmol) of crude product. The crude product and 1,1,1-trifluoro-2,3-epoxypropane (1.2 mL, 13.7 mmol) were dissolved in 20 mL of acetonitrile. Ytterbium (III) trifluoromethanesulfonate (0.77 g, 1.24 mmol) was added, and the stirred solution was warmed to 50° C. for 18 hours. The reaction was quenched with water and extracted with ethyl acetate. The organic layer was washed with brine, then dried over $MgSO_4$, and concentrated in vacuo to give 5.96 g (97%) of the desired 3-[[3-(methoxymethyl)phenyl][[3-(1,1,2,2-tetrafluoroethoxy)-phenyl]methyl]amino]-1,1,1-trifluoro-2-propanol product as a brown oil. The crude product was greater than 95% pure by reverse phase HPLC analysis and was used without further purification. HRMS calcd. for $C_{20}H_{21}F_7NO_3$: 456.1410 $[M+H]^+$, found: 456.1409. $^1$H NMR (CDCl3) δ3.3 (s, 3H), 3.6 (dd, 1H), 3.9 (dd, 1H), 4.3 (m, 1H), 4.4 (s, 2H), 4.7 (m, 2H), 5.9 (tt, 1H), 6.6–6.8 (m, 3H), 7.1–7.2 (m, 4H), 7.3 (t, 1H).

EX-51 4D) The 3-[[3-(methoxymethyl)phenyl][[3-(1,1,2,2-tetrafluoroethoxy)phenyl]-methyl]amino]-1,1,1-trifluoro-2-propanol from EX-514C (1 g, 2.2 mmol) was dissolved in 10 mL of dichloromethane. The solution was cooled to −50° C. and a 1 M solution of $BBr_3$ in dichloromethane (2.3 mL, 2.3 mmol) was added. The solution was stirred at −50° C. for 1 hour and warmed to room temperature over 1 hour, at which time HPLC analysis indicated that no methyl ether starting material remained. The reaction mixture was quenched with aqueous saturated sodium bicarbonate and diluted in dichloromethane. The organic layer was washed with brine, then dried over $MgSO_4$, and concentrated in vacuo. The crude product was purified by flash column chromatography on silica gel eluting with ethyl acetate:hexane 1:7 to give 0.65 g (59%) of the desired 3-[[3-(bromomethyl)phenyl][[3-(1,1,2,2-tetrafluoroethoxy)-phenyl]methyl]amino]-1,1,1-trifluoro-2-propanol product as a brown oil. HRMS calcd. for $C_{19}H_{18}BrF_7NO_2$: 504.0409 $[M+H]^+$, found: 504.0361. $^1$H NMR ($CDCl_3$) δ3.3 (s, 1H), 3.6 (dd, 1H), 3.9 (dd, 1H), 4.3 (m, 1H), 4.4 (s, 2H), 4.8 (m, 2H), 5.9 (tt, 1H), 6.7 (d, 1H), 6.8–6.9 (m, 2H), 7.1–7.3 (m, 4H), 7.4 (t, 1H).

The 3-[[3-(bromomethyl)phenyl][[3-(1,1,2,2-tetrafluoroethoxy)phenyl]methyl]amino]-1,1,1-trifluoro-2-propanol from EX-514D (0.1 g, 0.19 mmol) and 3-trifluoromethyl-benzeneboronic acid (47.5 mg, 0.25 mmol) were dissolved in 2 mL of toluene and 0.2 mL of 2 M aqueous sodium carbonate. $Pd(PPh_3)_4$ was added, and the solution was stirred at 105° C. for 2.5 hours, at which time HPLC analysis indicated that no bromomethyl starting material remained. The reaction mixture was filtered through celite and concentrated in vacuo. The residue was quenched with water and filtered through pre-wetted celite eluting with ethyl acetate. The solvent was evaporated, and the residue was purified by reverse phase HPLC eluting with 10% to 90% acetonitrile in water to afford 16.7 mg (15%) of the desired 3-[[[3-(1,1,2,2-tetrafluoroethoxy)phenyl]methyl]-[3-[(3-trifluoromethyl)phenyl]methyl]phenyl]-amino]-1,1,1-trifluoro-2-propanol product as a brown oil. HRMS calcd. for $C_{26}H_{22}F_{10}NO_2$: 570.1413 [M+H]$^+$, found: 570.1480. $^1$H NMR (CDCl$_3$) δ3.8 (m, 2H), 4.0 (s, 2H), 4.3 (m, 1H), 4.5 (d, 1H), 4.8 (d, 1H), 5.9 (tt, 1H), 6.6–6.8 (m, 4H), 6.9–7.1 (m, 3H), 7.2–7.5 (m, 5H).

Additional examples of 3-[[[3-(1,1,2,2-tetrafluoroethoxy)phenyl]methyl][3-(aryl)methyl]phenylamino]-1,1,1-trifluoro-2-propanols are prepared by one skilled in the art using similar methods, as shown in Example Table 25.

EXAMPLE TABLE 25

3-[[[3-(1,1,2,2-tetrafluoroethoxy)phenyl]methyl]-[3-(aryl)methyl]phenylamino]-1,1,1-trifluoro-2-propanols.

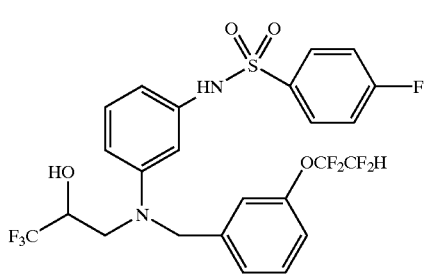

| Example Number | $R_{SUB}$ | Calculated Mass [M + H]$^+$ | Observed Mass [M + H]$^+$ |
| --- | --- | --- | --- |
| 515 | H | 502.1617 | 502.1609 |
| 516 | 3-nitro | 547.1468 | 547.1449 |
| 517 | 4-methyl | 516.1774 | 516.1769 |
| 518 | 3,5-dichloro | 570.0838 | 570.0801 |
| 519 | 4-fluoro | 520.1523 | 520.1505 |
| 520 | 4-tert-butyl | 558.2243 | 558.2236 |
| 521 | 3-methyl-4-fluoro | 534.1679 | 534.1688 |
| 522 | 3-methyl-4-chloro | 550.1384 | 550.1380 |
| 523 | 3,4-dimethyl | 530.1930 | 530.1887 |
| 524 | 3-chloro, 4-fluoro | 554.1133 | 554.1108 |
| 525 | 3-chloro | 536.1227 | 536.1218 |
| 526 | 4-methylthio | 548.1494 | 548.1503 |
| 527 | 3-methoxy | 532.1723 | 532.1705 |

EXAMPLE 528

4-fluoro-N-[3-[[[3-(1,1,2,2-tetrafluoroethoxy)phenyl]methyl](3,3,3-trifluoro-2-hydroxypropyl)amino]phenyl]benzenesulfonamide EX-528A) 3-nitroaniline (1.87 g, 13.51 mmol) and 3-(1,1,2,2-tetrafluoroethoxy)-benzaldehyde (3 g, 13.5 mmol) were dissolved in 25 mL of dichloroethane and acetic acid (0.85 mL, 14.9 mmol), then solid NaBH(OAc)$_3$ (3.73 g, 17.6 mmol) was added. The mixture was stirred at room temperature for 48 hours, then quenched with aqueous saturated sodium bicarbonate and diluted with ethyl acetate. The organic layer was dried over MgSO$_4$, and concentrated in vacuo. The crude product was purified by flash column chromatography on silica gel eluting with ethyl acetate:hexane 1:7 to give 3.25 g (70%) of the desired N-(3-nitrophenyl)-3-(1,1,2,2-tetrafluoroethoxy)benzenemethan-amine product as a brown oil. HRMS calcd. for $C_{15}H_{13}F_4N_2O_3$: 345.0862 [M+H]$^+$, found: 345.0864. $^1$H NMR (CDCl$_3$) δ4.4 (s, 2H), 4.5 (s, 1H), 5.9 (tt, 1H), 6.9 (d, 1H), 7.1 (d, 1H), 7.2–7.3 (m, 3H), 7.4 (m, 2H), 7.5 (d, 1H).

EX-528B) N-(3-nitrophenyl)-3-(1,1,2,2-tetrafluoroethoxy)benzenemethanamine (3.25 g, 9.44 mmol) from EX-528A and 1,1,1-trifluoro-2,3-epoxypropane (0.895 mL, 10.4 mmol) were dissolved in 15 mL of acetonitrile. Ytterbium (III) trifluoromethanesulfonate (0.77 g, 1.24 mmol) was added, and the stirred solution was warmed to 55° C. for 48 hours. The reaction was quenched with water and extracted with ethyl acetate. The organic layer was dried over MgSO$_4$, and concentrated in vacuo. The crude product was purified by flash column chromatography on silica gel eluting with ethyl acetate:hexane 1:10 to give 1.93 g (45%) of the desired 3-[(3-nitrophenyl)[[3-(1,1,2,2-tetrafluoroethoxy)phenyl]methyl]amino]-,1,1,1-trifluoro-2-propanol product as a brown oil. HRMS calcd. for $C_{18}H_{16}F_7N_2O_4$: 457.0998 [M+H]$^+$, found: 457.1008. $^1$H NMR (CDCl$_3$) δ3.7 (dd, 1H), 3.9 (dd, 1H), 4.4 (m, 1H), 4.8 (m, 2H), 5.9 (tt, 1H), 7.0–7.2 (m, 4H), 7.3–7.4 (m, 2H), 7.6 (m, 2H).

EX-528C) The 3-[(3-nitrophenyl)[[3-(1,1,2,2-tetrafluoroethoxy)phenyl]methyl]amino]-1,1,1-trifluoro-2-propanol (1.93 g, 4.2 mmol) from EX-528B was dissolved in 60 mL of acetic acid. Zinc dust (2.1 g, 31.5 mmol) was added, and the solution was stirred at room temperature for 18 hours, at which time HPLC analysis indicated that no nitro starting material remained. The reaction mixture was filtered through celite and concentrated in vacuo. The residue was dissolved in ethyl acetate and washed with aqueous saturated sodium bicarbonate. The organic layer was washed with brine, then dried over MgSO$_4$, and concentrated in vacuo to give 1.4 g (78%) of the desired 3-[(3-aminophenyl)[[3-(1,1,2,2-tetrafluoroethoxy)phenyl]methyl]amino]-1,1,1-trifluoro-2-propanol product as a red oil. The crude product was used without further purification. HRMS calcd. for $C_{18}H_{18}F_7N_2O_2$: 427.1256 [M+H]$^+$, found: 427.1251. $^1$H NMR (CDCl$_3$) δ3.4–3.7 (m, 4H), 3.8 (dd, 1H), 4.3 (m, 1H), 4.8 (m, 2H), 5.9 (tt, 1H), 6.1 (s, 1H), 6.2 (m, 2H), 7.0–7.2 (m, 4H) 7.3 (t, 1H).

The 3-[(3-aminophenyl)[[3-(1,1,2,2-tetrafluoroethoxy)phenyl]methyl]amino]-1,1,1-trifluoro-2-propanol from EX-528C (50 mg, 0.12 mmol) was dissolved in 1 mL of dichloromethane. Triethylamine (25 μL, 0.18 numol) followed by 4 fluorobenzenesulfonyl chloride were added. The solution was stirred at room temperature for 5 hours, at which time HPLC analysis indicated that no free amine starting material remained. The reaction was quenched with water and filtered through pre-wetted celite eluting with ethyl acetate. The solvent was evaporated, and the residue was purified by reverse phase HPLC eluting with 10% to 90% acetonitrile in water to afford 20.1 mg (29%) of the desired 4-fluoro-N-[3-[[[3-(1,1,2,2-tetrafluoroethoxy)phenyl]methyl]-(3,3,3-trifluoro-2- hydroxypropyl)amino]phenyl]benzenesulfonamide product as a yellow oil, which was greater than 98% pure by reverse phase HPLC analysis. HRMS calcd. for $C_{24}H_{21}F_8N_2O_4S$: 585.1094 [M+H]$^+$, found: 585.1083. $^1$H NMR (CDCl$_3$) δ3.6 (m, 2H), 3.8 (dd, 1H), 4.3 (m, 1H), 4.6 (s, 2H), 5.9 (tt, 1H), 6.4 (d, 1H), 6.5–6.6 (m, 3H), 6.9–7.4 (m, 7H), 7.6 (m, 1H).

Additional examples of N-[3-[[[3-(1,1,2,2-tetrafluoroethoxy)phenyl]methyl]-(3,3,-trifluoro-2-hydroxypropyl)amino]phenyl]aryl or alkylsulfonamide are prepared by one skilled in the art using similar methods, as shown in Example Table 26.

EXAMPLE TABLE 26

N-[3-[[[3-(1,1,2,2-tetrafluoroethoxy)phenyl]methyl]-(3,3,3-trifluoro-2-hydroxypropyl)amino]phenyl]aryl or alkylsulfonamides.

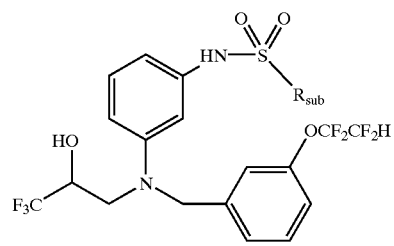

| Example Number | R$_{SUB}$ | Calculated Mass [M + H]$^+$ | Observed Mass [M + H]$^+$ |
|---|---|---|---|
| 529 | phenyl | 567.1189 | 567.1198 |
| 530 | 3-methylphenyl | 581.1345 | 581.1327 |
| 531 | 3-trifluoromethylphenyl | 635.1062 | 635.1066 |
| 532 | 3-nitrophenyl | 612.1039 | 612.1011 |
| 533 | 3-chloro-4-fluorophenyl | 619.0705 | 619.0711 |
| 534 | isopropyl | 533.1345 | 533.1359 |

EXAMPLE 535

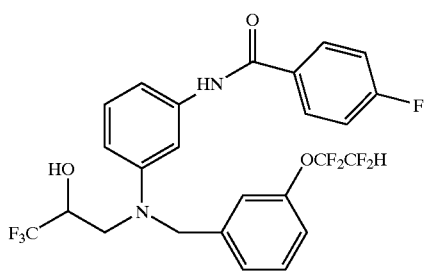

4-fluoro-N-[3-[[[3-(1,1,2,2-tetrafluoroethoxy) phenyl]methyl](3,3,3-trifluoro-2-hydroxypropyl) amino]phenyl]benzamide 3-[(3-aminophenyl)[[3-(1,1,2,2-tetrafluoroethoxy)phenyl] methyl]amino]-1,1,1-trifluoro -2-propanol (50 mg, 0.12 mmol) was dissolved in 1 mL of dichloromethane. Triethylamine (25 μL, 0.18 mmol) followed by 4-fluorobenzoyl chloride were added. The solution was stirred at room temperature for 5 hours, at which time HPLC analysis indicated that no starting material remained. The reaction was quenched with water and filtered through pre-wetted celite eluting with ethyl acetate. The solvent was evaporated, and the residue was purified by reverse phase HPLC eluting with 10% to 90% acetonitrile in water to afford 15 mg (23%) of the desired 4-fluoro-N-[3-[[[3-(1,1,2,2-tetrafluoroethoxy)phenyl] methyl](3,3,3-trifluoro-2-hydroxypropyl)amino]phenyl] benzamide product as a yellow oil, which was greater than 98% pure by reverse phase HPLC analysis. HRMS calcd. for $C_{25}H_{21}F_8N_2O_3$: 549.1424 [M+H]$^+$, found: 549.1436. $^1$H NMR (CDCl$_3$) δ3.6 (dd, 1H), 3.8 (dd, 1H), 4.4 (m, 1H), 4.6 (s, 2H), 5.9 (tt, 1H), 6.6 (d, 1H), 6.8 (d, 1H), 7.0–7.4 (m, 7H), 7.8 (m, 3H).

Additional examples of N-[3-[[[3-(1,1,2,2-tetrafluoroethoxy)phenyl]methyl]-(3,3,3-trifluoro-2-hydroxypropyl)amino]phenyl]carboxamides are prepared by one skilled in the art using similar methods, as shown in Example Table 27.

EXAMPLE TABLE 27

N-[3-[[[3-(1,1,2,2-tetrafluoroethoxy)phenyl]methyl]-(3,3,3-trifluoro-2-hydroxypropyl)amino]phenyl]carboxamides.

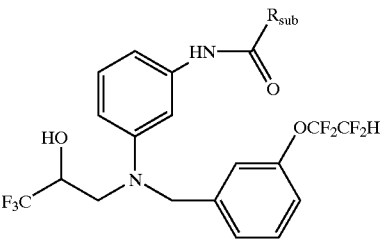

| Example Number | R$_{SUB}$ | Calculated Mass [M + H]$^+$ | Observed Mass [M + H]$^+$ |
|---|---|---|---|
| 536 | phenyl | 531.1589 | 531.1538 |
| 537 | 3-methoxylphenyl | 561.1624 | 561.1625 |
| 538 | isobutoxy | 527.1781 | 527.1768 |
| 539 | 3-pyridyl | 532.1471 | 532.1458 |
| 540 | isopropyl | 497.1675 | 497.1701 |

EXAMPLE 541

3-[[3-[(2-methylpropyl)amino]phenyl][[3-(1,1,2,2-tetrafluoroethoxy)phenyl]-methyl]amino]-1,1,1-trifluoro-2-propanol The 3-[(3-aminophenyl)[[3-(1,1,2,2-tetrafluoroethoxy) phenyl]methyl]amino]-1,1,1-trifluoro-2-propanol (50 mg, 0.12 mmol) was dissolved in 1 mL of dichloroethane. Acetic acid (8 μL, 0.14 mmol) followed by isobutyraldehyde (11.7 μL, 0.13 mmol) and solid NaBH(OAc)$_3$ (37.3 mg, 0.18 mmol) were added. The solution was stirred at room temperature for 18 hours. The reaction was filtered through pre-wetted celite eluting with ethyl acetate. The solvent was evaporated, and the residue was purified by reverse phase HPLC eluting with 10% to 90% acetonitrile in water to afford 16.1 mg (29%) of the desired 3-[[3-[(2-methylpropyl)amino]phenyl][[3-(1,1,2,2-tetrafluoroethoxy) phenyl]methyl]amino]-1,1,1-trifluoro-2-propanol product as a yellow oil, which was greater than 98% pure by reverse phase HPLC analysis. HRMS calcd. for $C_{22}H_{26}F_7N_2O_2$: 483.1883 $[M+H]^+$, found: 483.1932. $^1$H NMR (CDCl$_3$) δ1.0 (m, 6H), 2.0 (m, 1H), 3.0 (m, 2H), 3.6 (dd, 1H), 3.8 (dd, 1H), 4.3 (m, 1H), 4.6 (m, 2H), 5.9 (tt, 1H), 6.6 (d, 1H), 6.7 (d, 1H), 6.9–7.4 (m, 6H).

Additional examples of 3-[[3-(aralkylamino)phenyl][[3-(1,1,2,2-tetrafluoroethoxy)phenyl]methyl]amino]-1,1,1-trifluoro-2-propanols are prepared by one skilled in the art using similar methods, as shown in Example Table 28.

EXAMPLE TABLE 28

1,1,1-trifluoro-3-[[3-(aralkylamino)phenyl]-[[3-(1,1,2,2-tetrafluoroethoxy)phenyl]methyl]amino]-2-propanols.

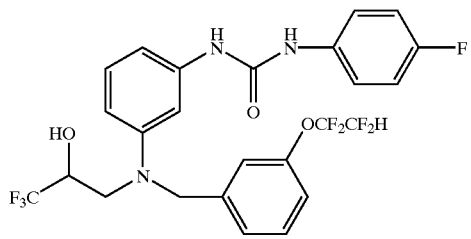

| Example Number | $R_{SUB}$ | Calculated Mass $[M + H]^+$ | Observed Mass $[M + H]^+$ |
|---|---|---|---|
| 542 | phenyl | 517.1726 | 517.1750 |
| 543 | 4-fluorophenyl | 535.1632 | 535.1627 |
| 544 | 3-(OCF$_2$CF$_2$H)-phenyl | 633.1611 | 633.1653 |

EXAMPLE 545

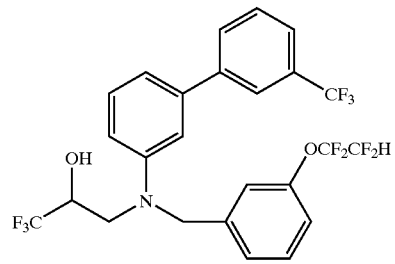

N-(4-fluorophenyl)-N'-[3-[[[3-(1,1,2,2-tetrafluoroethoxy)phenyl]methyl]-(3,3,3-trifluoro-2-hydroxypropyl)amino]phenyl]urea The 3-[(3-aminophenyl)[[3-(1,1,2,2-tetrafluoroethoxy)phenyl]methyl]amino]-1,1,1-trifluoro-2-propanol (50 mg, 0.12 mmol) was dissolved in 1 mL of dichloromethane. Triethylamine (20 μL, 0.14 mmol) followed by 4-fluorophenyl isocyanate (14.6 μL, 0.13 mmol) were added. The solution was stirred at room temperature for 18 hours. The reaction was filtered through pre-wetted celite eluting with ethyl acetate. The solvent was evaporated, and the residue was purified by reverse phase HPLC eluting with 10% to 90% acetonitrile in water to afford 26 mg (40%) of the desired N-(-fluorophenyl)-N'-[3-[[[3-(1,1,2,2-tetrafluoroethoxy)phenyl]methyl](3,3,3-trifluoro-2-hydroxypropyl)amino]phenyl]urea product as a yellow oil, which was greater than 95% pure by reverse phase HPLC analysis. HRMS calcd. for $C_{25}H_{22}F_8N_3O_3$: 564.1533 $[M+H]^+$, found: 564.1566. $^1$H NMR (CDCl$_3$) δ3.7 (m, 2H), 4.1 (m, 1H), 4.7 (m, 2H), 5.9 (tt, 1H), 6.6 (d, 1H), 6.9–7.4 (m, 11H), 7.5 (s, 1H), 7.8 (s, 1H).

Additional examples of N-substituted-N'-[3-[[[3-(1,1,2,2-tetrafluoroethoxy)-phenyl]methyl](3,3,3-trifluoro-2-hydroxypropyl)amino]phenyl]ureas are prepared by one skilled in the art using similar methods, as shown in Example Table 29.

EXAMPLE TABLE 29

N-substituted-N'-[3-[[[3-(1,1,2,2-tetrafluoroethoxy)phenyl]-methyl](3,3,3-trifluoro-2-hydroxypropyl))amino]phenyl]ureas.

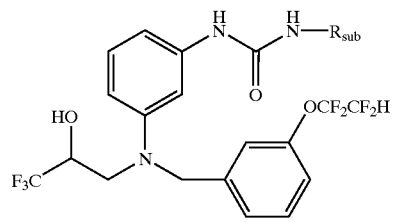

| Example Number | $R_{SUB}$ | Calculated Mass $[M + H]^+$ | Observed Mass $[M + H]^+$ |
|---|---|---|---|
| 546 | phenyl | 546.1628 | 546.1655 |
| 547 | 3-methoxyphenyl | 576.1733 | 576.1773 |
| 548 | 3-trifluoromethylphenyl | 614.1501 | 614.1518 |
| 549 | isopropyl | 512.1784 | 512.1801 |

EXAMPLE 550

1,1,1-trifluoro-3-[[[3-(1,1,2,2-tetrafluoroethoxy)phenyl]methyl][[3'-(trifluoromethyl)1,1'-biphenyl]-3-yl]amino]-2-propanol 3-Trifluoromethylbenzene boronic acid (35.4 mg, 0.233 mmol) was dissolved in 640 mL of 2 M Na$_2$CO$_3$, and 630 mL of ethanol then 1.5 mL of a stock solution of 3-[(3-bromophenyl)[[3-(1,1,2,2-tetrafluoroethoxy)phenyl]methyl]amino]-1,1,1-trifluoro-2-propanol (0.105 M) and 10.9 mg/mL of Pd(PPh$_3$)$_4$ in toluene was added. After stirring at 105° C. for 5 hours, HPLC analysis indicated that the reaction had gone to completion. The reaction mixture was filtered through celite, evaporated, and the crude material purified by reverse phase HPLC eluting with 40% to 90% acetonitrile in water to afford 40.5 mg (44.7%) of the desired biphenyl aminopropanol product as an orange oil. HRMS calcd. for $C_{25}H_{19}F_{10}NO_2$: 556.1334 $[M+H]^+$, found: 556.1339. $^1$H NMR (CDCl$_3$) δ3.60–3.73 (m, 1H), 3.95 (dd, 1H), 4.36–4.44 (m, 1H), 4.76 (s, 2H), 5.87 (tt, 1H), 6.81 (dd, 1H), 6.95 (s, 1H), 7.03 (d, 1H), 7.05–7.20 (m, 3H), 7.26–7.40 (m, 2H), 7.46–7.73 (m, 4H).

Additional examples of 3-[[[3-(1,1,2,2-tetrafluoroethoxy)phenyl]methyl][[3-aryl]phenyl]amino]-1,1,1-trifluoro-2-propanols are prepared by one skilled in the art using similar methods, as shown in Example Table 30.

EXAMPLE TABLE 30

3-[[[3-(1,1,2,2-tetrafluoroethoxy)phenyl]methyl][[3-aryl]phenyl]amino]-1,1,1-trifluoro-2-propanols.

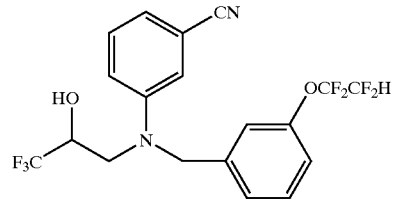

| Example Number | $R_{SUB}$ | Calculated Mass $[M + H]^+$ | Observed Mass $[M + H]^+$ |
|---|---|---|---|
| 551 | 3,5-di(trifluoromethyl) | 624.1208 | 624.1216 |
| 552 | 4-trifluoromethyl | 556.1334 | 556.1355 |
| 553 | 4-methylthio | 534.1337 | 534.1366 |
| 554 | 3-chloro-4-fluoro | 540.0976 | 540.0957 |
| 555 | 3,5-dichloro-4-methoxy | 586.0786 | 586.0818 |
| 556 | 3-nitro | 533.1311 | 533.1262 |
| 557 | 3,5-dichloro | 556.0681 | 556.0612 |
| 558 | 4-methoxy | 518.1566 | 518.1533 |
| 559 | 3,4-difluoro | 524.1272 | 524.1249 |
| 560 | 2,3,4-trifluoro | 542.1177 | 542.1152 |
| 561 | 3,4-dichloro | 556.0681 | 556.0698 |
| 562 | 3-methyl4-methoxy | 532.1722 | 532.1676 |
| 563 | 3,5-dimethyl-4-(N,N-dimethylamino) | 559.2195 | 559.2182 |
| 564 | H | 488.1460 | 488.1457 |
| 565 | 4-chloro | 522.1071 | 522.1049 |
| 566 | 4-methyl | 502.1617 | 502.1613 |
| 567 | 2,4-dichloro | 556.0681 | 556.0651 |
| 568 | 4-fluoro | 506.1366 | 506.1336 |
| 569 | 4-fluoro-3-methyl | 520.1523 | 520.1494 |
| 570 | 2-trifluoromethyl | 556.1334 | 556.1286 |
| 571 | 3-methoxy | 518.1566 | 518.1544 |
| 572 | 3-amino | 503.1569 | 503.1593 |
| 573 | 4-carboxy | 532.1358 | 532.1329 |
| 574 | 4-tert-butyl | 544.2087 | 544.2090 |

EXAMPLE 575

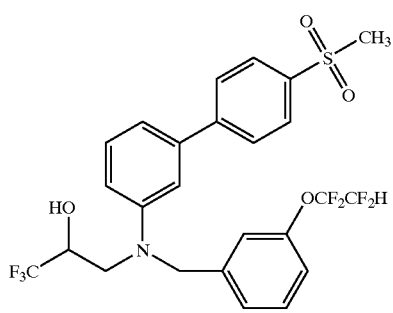

3-[[[4'-(methylsulfonyl)1,1'-biphenyl]-3-yl][[3-(1,1,2,2-tetrafluoroethoxy)phenyl]-methyl]amino]-1,1,1-trifluoro-2-propanol To a solution of 3-[[[3-(1,1,2,2-tetrafluoroethoxy)phenyl]methyl][[4-methylthio)-phenyl]phenyl]amino]-1,1,1-trifluoro-2-propanol in 2 mL of trifluoroacetic acid was added 11 mL of 30% $H_2O_2$ (0.097 mmol). After stirring at room temperature overnight, an additional 11 mL of 30% $H_2O_2$ (0.097 mmol) was added. After 5 hours, TLC analysis indicated that the reaction had gone to completion. The solvent was removed, and the residue was filtered through silica gel eluting with 30% ethyl acetate in hexane. The material was evaporated to give 36.6 mg (100%) of the desired sulfone product as an oil which was 100% pure by reverse phase HPLC analysis. HRMS calcd. for $C_{25}H_{22}F_7NO_4S$: 566.1236 [M+H], found: 566.1193. $^1$H NMR (CDCl$_3$) δ3.04 (s, 3H), 3.66–3.79 (m, 1H), 3.97 (d, 1H), 4.35–4.43 (m, 1H), 4.69–4.81 (m, 2H), 5.86 (dt, 1H), 6.90 (d, 1H), 7.01(s, 1H), 7.05–7.18 (m, 4H), 7.31–7.40 (m, 2H), 7.60 (d, 2H), 7.93 (d, 2H).

EXAMPLE 576

3-[[[3-(1,1,2,2-tetrafluoroethoxy)phenyl]methyl](3,3,3-trifluoro-2-hydroxypropyl)amino]benzonitrile EX-576A) A solution of 3-aminobenzonitrile (1.06 g, 9.1 mmol) and 3-(1,1,2,2-tetrafluoroethoxy)benzaldehyde (2.00 g, 9.01 mmol) was dissolved in 25 mL of dichloroethane and acetic acid (536 mL, 9.37 mmol), then solid NaBH(OAc)$_3$ (2.48 g, 11.7 mmol) was added. The mixture was stirred at room temperature for 3 hours, then quenched with water and extracted with dichloromethane. The organic layer was washed with saturated NaHCO$_3$, then dried over MgSO$_4$, and evaporated. The crude product was purified by MPLC on silica gel eluting with 20% to 30% ethyl acetate in hexane to give 1.58 g (54%) of the desired 3-[[[3-(1,1,2,2-tetrafluoroethoxy)phenyl]methyl]amino]benzonitrile product as a clear oil. $^1$H NMR (CDCl$_3$) δ4.38 (s, 3H), 5.89 (dt, 1H), 6.79 (t, 1H), 6.98 (d, 2H), 7.12–7.28 (m, 4H), 7.40 (t, 1H).

The benzonitrile (1.58 g, 4.88 mmol) from EX-576A and 1,1,1-trifluoro-2,3-epoxypropane (546 mL, 6.34 mmol) were dissolved in 4 mL of acetonitrile. Ytterbium (III) trifluoromethanesulfonate (304 mg, 0.49 mmol) was added, and the stirred solution was warmed to 50° C. overnight. The reaction was quenched with water and extracted with ether. The ether layer was washed with brine, dried over MgSO$_4$ and evaporated. The crude product was purified by MPLC on silica gel eluting with dichloromethane to give 1.61 g (76%) of the desired 3-[[[3-(1,1,2,2-tetrafluoroethoxy)phenyl]methyl]-(3,3,3-trifluoro-2-hydroxypropyl)amino]benzonitrile product as a clear oil, greater than 98% by reverse phase HPLC. HRMS calcd. for $C_{19}H_{15}F_7N_2O_2$: 437.1100 [M+H]$^+$, found: 437.1097. $^1$H NMR (CDCl3) δ3.60–3.69 (m, 1H), 3.86 (d, 1H), 4.32 (bs, 1H), 4.69 (q, 2H), 5.86 (dt, 1H), 6.85–6.95 (m, 2H), 6.97–7.01 (m, 2H), 7.04–7.12 (m, 2H), 7.23–7.37 (m, 2H).

EXAMPLE 577

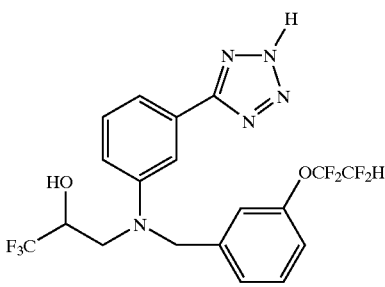

3-[[[3-(1,1,2,2-tetrafluoroethoxy)phenyl]methyl][3-(1H-tetrazol-5-yl)phenyl]amino]-1,1,1-trifluoro-2-propanol To a solution of 3-[[[3-(1,1,2,2-tetrafluoroethoxy)phenyl]methyl](3,3,3-trifluoro-2-hydroxypropyl)amino]benzonitrile (76 mg, 0.17 mmol) in 2 mL of toluene was added trimethyltin azide (41 mg, 0.20 mmol). The reaction mixture was heated to 105° C. and stirred overnight. TLC showed starting material to still be present so additional trimethyltin azide (41 mg, 0.20 mmol) was added. The reaction mixture was stirred overnight at 105° C., cooled to room temperature, then THF (800 μL) and concentrated HCl (500 μL) were added. HPLC analysis showed 2 peaks after 5 hours, so additional concentrated HCl (200 μL) was added. After stirring overnight, HPLC analysis showed the reaction to be complete. The mixture was filtered through a celite plug and evaporated in vacuo. The residue was purified by reverse phase HPLC eluting with 10% to 90% acetonitrile in water to give 27.2 mg (33%) of the desired tetrazole product as an oil. HRMS calcd. for $C_{19}H_{16}F_7N_5O_2$: 480.1270 $[M+H]^+$, found: 480.1252. $^1$H NMR (CDCl$_3$) δ3.66–3.99 (m, 2H), 4.45–4.75 (m, 3H), 5.80 (dt, 1H), 6.49–6.70 (m, 1H), 6.95 (s, 1H), 6.97–7.06 (m, 3H), 7.18–7.28 (m, 3H), 7.34 (s, 1H).

EXAMPLE 578

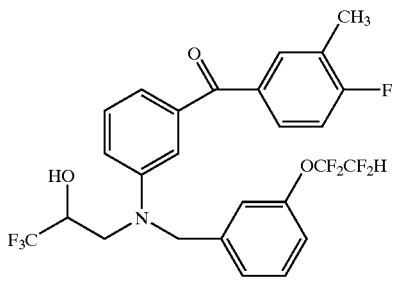

(4-Fluoro-3-methylphenyl)[3-[[[(1,1,2,2-tetrafluoroethoxy)phenyl]methyl](3,3,3-trifluoro-2-hydroxypropyl)amino]phenyl]methanone To a solution of 3-[[[3-(1,1,2,2-tetrafluoroethoxy)phenyl]methyl](3,3,3-trifluoro-2-hydroxypropyl)amino]benzonitrile (100 mg, 0.23 mmol) in 1 mL of anhydrous THF under nitrogen was added 4-fluoro-3-methylphenylmagnesium bromide (0.81 mL of 1.0 M solution, 0.81 mmol), and the mixture was stirred at room temperature overnight. HPLC analysis of the reaction mixture showed the presence of starting material so additional 4-fluoro-3-methylphenylmagnesium bromide (0.46 mL, 0.41 mmol) was added. HPLC analysis 24 hours later showed the reaction to be complete. The reaction was quenched and acidified with 1 N HCl. After hydrolysis of imine was complete by HPLC analysis, the mixture was filtered through celite and evaporated. The crude product was purified by reverse phase HPLC eluting with 10% to 90% acetonitrile in water to give 28.0 mg (22%) of the desired ketone product as an oil. HRMS calcd. for $C_{26}H_{21}F_8NO_3$: 548.1410 $[M+H]^+$, found: 548.1441. $^1$H NMR (CDCl$_3$) δ2.26 (s, 3H), 3.60–3.70 (m, 1H), 3.92 (d, 1H), 4.26–4.40 (m, 1H), 4.68 (t, 2H), 5.87 (dt, 1H), 6.91–7.03 (m, 3H), 7.05–7.12 (m, 4H), 7.26–7.35 (m, 2H), 7.43–7.52 (m, 1H), 7.63 (d, 1H).

Additional examples of (aryl-, alkyl- or cycloalkyl-)[3-[[[(1,1,2,2-tetrafluoroethoxy)phenyl]methyl](3,3,3-trifluoro-2-hydroxypropyl)amino]phenyl]methanones are prepared by one skilled in the are using similar methods, as shown in Example Table 31.

EXAMPLE TABLE 31

(Aryl-, alkyl- or cycloalkyl-)[3-[[[(1,1,2,2-tetrafluoroethoxy)-phenyl]methyl](3,3,3-trifluoro-2-hydroxypropyl)amino]phenyl]methanones.

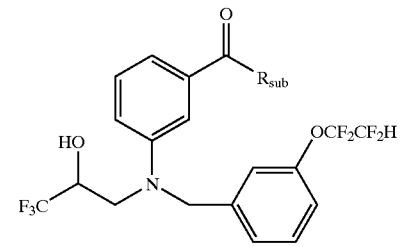

| Example Number | $R_{SUB}$ | Calculated Mass $[M + H]^+$ | Observed Mass $[M + H]^+$ |
|---|---|---|---|
| 579 | phenyl | 516.1410 | 516.1383 |
| 580 | 4-fluorophenyl | 534.1315 | 534.1273 |
| 581 | cyclopentyl | 508.1723 | 508.1675 |
| 582 | isopropyl | 482.1566 | 482.1576 |

EXAMPLE 583

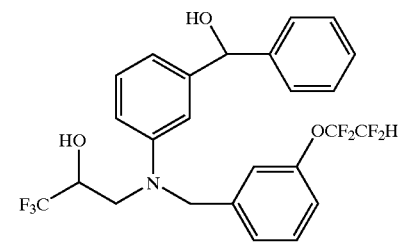

α-Phenyl-3-[[[3-(1,1,2,2-tetrafluoroethoxy)phenyl]methyl]](3,3,3-trifluoro-2-hydroxypropyl)benzenemethanol To a solution of phenyl[3-[[[(1,1,2,2-tetrafluoroethoxy)phenyl]methyl](3,3,3-trifluoro-2-hydroxypropyl)amino]phenyl]methanone (155.8 mg, 0.302 mmol) in 2.3 mL of methanol cooled to 5° C. was added solid NaBH$_4$ (34.5 mg, 0.912 mmol). HPLC analysis after 1 hour showed no ketone starting material. The reaction was evaporated to dryness and purified by reverse phase HPLC eluting with 50% to 90% acetonitrile in water to give 35.6 mg (24%) of the desired alcohol product as an oil. HRMS calcd. for $C_{25}H_{22}F_7NO_3$: 518.1566 [M+H]$^+$, found: 518.1563. $^1$H NMR (acetone-d$_6$) δ3.56–3.73 (m, 1H), 3.92–4.06 (m, 1H), 4.40–4.55 (m, 1H), 4.82 (s, 2H), 5.71 (s, 1H), 6.28–6.69 (m, 2H), 6.71–6.82 (m, 1H), 6.93 (s, 1H), 7.07–7.51 (m, 10H).

Additional examples of α-alkyl-3-[[[3-(1,1,2,2-tetrafluoroethoxy)phenyl]methyl][(3,3,3-trifluoro-2-hydroxypropyl)benzenemethanols are prepared by one skilled in the art using similar methods, as shown in Example Table 32.

EXAMPLE TABLE 32

α-alkyl-3-[[[3-(1,1,2,2,-tetrafluoroethoxy)phenyl]methyl]-[(3,3,3-trifluoro-2-hydroxypropyl)benzenemethanols

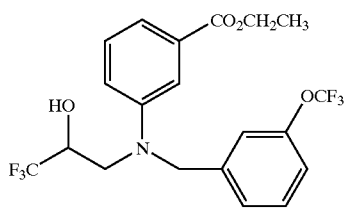

| Example Number | $R_{SUB}$ | Calculated Mass [M + H]$^+$ | Observed Mass [M + H]$^+$ |
|---|---|---|---|
| 584 | isopropyl | 484.1723 | 484.1725 |

EXAMPLE 585

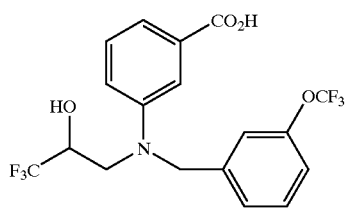

Ethyl 3-[(3,3,3-trifluoro-2-hydroxypropyl)[[(3-trifluoromethoxy)phenyl]methyl]amino]benzoate EX-585A) Ethyl 3-aminobenzoate (3.9 mL, 26 mmol) and 3-trifluoromethoxybenzaldehyde (4.91 g, 25.8 mmol) were dissolved in 65 mL of dichloroethane and acetic acid (1.6 mL, 28 mmol), then solid NaBH(OAc)$_3$ (7.5 g, 34.2 mmol) was added. The mixture was stirred at room temperature overnight, then quenched with water and extracted with dichloromethane. The organic layer was washed with brine, then dried over MgSO$_4$, and evaporated to give 9.76 g (>100%) of the desired ethyl 3-[[[(3-trifluoromethyl)phenyl]methyl]amino]benzoate product as a yellow oil, which was greater than 95% pure by reverse phase HPLC analysis. $^1$H NMR (CDCl$_3$) δ1.35 (t, 3H), 4.26–4.41 (m, 5H), 6.73 (d, 1H), 7.12 (d, 1H), 7.15–7.25 (m, 2H), 7.25–7.43 (m, 4H).

The ethyl 3-[[[(3-trifluoromethyl)phenyl]methyl]amino]benzoate (9.76 g, 25.8 mmol) product from EX-585A and 1,1,1-trifluoro-2,3-epoxypropane (2.9 mL, 33.5 mmol) were dissolved in 25 mL of acetonitrile. Ytterbium (III) trifluoromethanesulfonate (1.6 g, 2.6 mmol) was added, and the stirred solution was warmed to 50° C. for 20 hours. The reaction was quenched with water and extracted with dichloromethane. The organic layer was washed with water and brine, then dried over MgSO$_4$. The crude product was purified by column chromatography on silica gel eluting with dichloromethane to give 10.7 g (92%) of the desired ethyl 3-[(3,3,3-trifluoro-2-hydroxypropyl)[[(3-trifluoromethyl)phenyl]methyl]amino]benzoate product as a yellow oil. HRMS calcd. for $C_{20}H_{19}NO_4F_6$: 452.1297 [M+H]$^+$, found: 452.1256. $^1$H NMR (CDCl$_3$) δ1.32 (t, 3H), 2.94–3.02 (m, 1H), 3.54–3.64 (m, 1H), 3.91 (d, 1H), 4.24–4.40 (m, 3H), 4.69 (t, 2H), 6.86 (d, 1H), 7.05 (s, 1H), 7.07–7.14 (m, 2H), 7.20–7.34 (m, 2H), 7.39–7.47 (m, 2H).

EXAMPLE 586

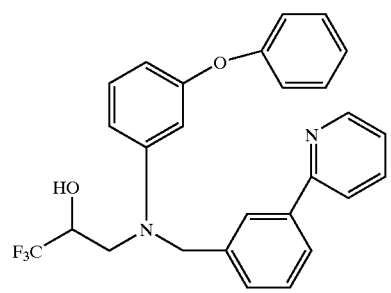

3-[(3,3,3-trifluoro-2-hydroxypropyl)[[(3-trifluoromethyl)phenyl]methyl]amino]benzoic Acid Ethyl 3-[(3,3,3-trifluoro-2-hydroxypropyl)[[(3-trifluoromethyl)phenyl]methyl]amino]-benzoate was dissolved in 70 mL of THF and 35 mL of water. Lithium hydroxide monohydrate (2.93 g, 69.8 mmol) was added, and the mixture was heated to 45° C. under nitrogen overnight, at which time HPLC analysis indicated that the reaction had gone to completion. The mixture was acidified with 1 N HCl to a pH of 3–4, then extracted with ethyl acetate several times, and the combined organic layers were dried over MgSO$_4$. The dried organic layer was evaporated to give 11.2 g (100%) of the desired benzoic acid product as a pale orange oil, which was greater than 98% pure by reverse phase HPLC analysis. HRMS calcd. for $C_{18}H_{15}NO_4F_6$: 424.0984 [M+H]$^+$, found: 424.0991. $^1$H NMR (acetone-d$_6$) δ3.68–3.81 (m, 1H), 3.99–4.09 (m, 1H), 4.43–4.58 (m, 1H), 4.87 (s, 2H), 7.02 (d, 1H), 7.19 (d, 1H), 7.22–7.40 (m, 4H), 7.40–7.49 (m, 2H).

EXAMPLE 587

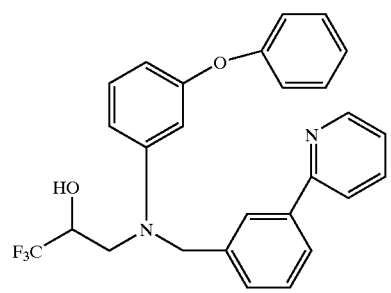

3-[(3-phenoxyphenyl)[[3-(2-pyridinyl)phenyl]methyl]amino]-1,1,1-trifluoro-2-propanol EX-587A) To a THF solution (8 mL) of 2-bromopyridine (1.30 g, 8.23 mmol) at −78° C. was added 1.6 M n-BuLi in hexanes (5.3 mL, 8.48 mmol). The resulting dark red solution was stirred at −78° C. for 10 min, and a solution of 0.5 M ZnCl$_2$ in THF (18 mL, 9.0 mmol) was added giving a light brown slurry. After warming to room temperature, 3-bromobenzaldehyde (0.816 mL, 7.0 mmol) and Pd(PPh$_3$)$_4$ (0.242 g, 0.21 mmol) were added, and the mixture was stirred for 18 h at room temperature under argon. The reaction mixture was poured into 1 N HCl (30 mL) and washed with diethyl ether. The aqueous layer was neutralized with NaHCO$_3$ and extracted with diethyl ether. The solvent was removed in vacuo to give the crude product as an oil. Purification by flash chromatography on silica gel eluting with 20% ethyl acetate in hexane gave 0.49 g (38%) of the desired 3-(2-pyridinyl)benzaldehyde product as a colorless oil. GCMS: m/z=183 [M$^+$].

EX-587B) To a 1,2-dichloroethane (5 mL) solution of aldehyde (0.37 g, 2.0 mmol) from EX-587A was added 3-phenoxyaniline (0.37 g, 2.0 mmol), NaB(OAc)$_3$H (0.55 g, 2.6 mmol) and acetic acid (0.12 mL, 2.0 mmol). The cloudy solution was stirred at room temperature for 2 h. The reaction mixture was poured into water and extracted with dichloromethane. The organic layer was washed with saturated NaHCO$_3$ and brine, dried (MgSO$_4$) and evaporated to yield 0.70 g (100%) of the desired N-3-(phenoxyphenyl)-[[3-(2-pyridinyl)phenyl]methyl]amine product as a yellow oil. HRMS: calcd. for C$_{24}$H$_{21}$N$_2$O: 353.1654 [M+H]$^+$, found: 353.1660.

A THF (1 mL) solution of amine (0.47 g, 1.3 mmol) from EX-587B and 1,1,1-trifluoro-2,3-epoxypropane (0.35 mL, 4.1 mmol) was placed in a sealed vial and heated to 90° C. for 18 h with stirring. The solvent was removed in vacuo to give the crude product as an oil. Purification by flash chromatography on silica gel eluting with 20% ethyl acetate in hexane gave 0.026 g (4.2%) of the desired 3-[(3-phenoxyphenyl)[[3-(2-pyridinyl)phenyl]methyl]amino]-1,1,1-trifluoro-2-propanol product as a yellow oil. HRMS calcd. for C$_{27}$H$_{24}$N$_2$O$_2$F$_3$: 465.1790 [M+H]$^+$, found: 465.1798. $^1$H NMR (CDCl$_3$) δ3.63 (dd, 1H), 3.73 (br s, 1H), 3.82 (dd, 1H), 4.30 (m, 1H), 4.67 (d, 2H), 6.34 (dd, 1H), 6.44 (t, 1H), 6.52 (dd, 1H), 6.92 (d, 2H), 7.02 (t, 1H), 7.12 (t, 1H), 7.2 (m, 4H), 7.38 (t, 1H), 7.65 (d, 1H), 7.72 (d, 1H), 7.74 (d 1H), 7.84 (s, 1H), 8.62 (d, 1H).

EXAMPLE 588

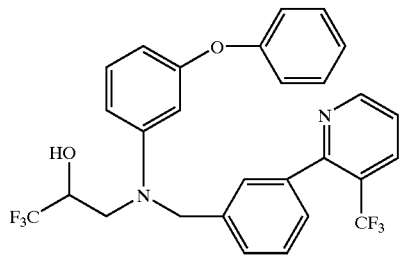

3-[(3-phenoxyphenyl)[[3-[(3-trifluoromethyl)-2-pyridinyl]phenyl]methyl]amino]-1,1,1-trifluoro-2-propanol EX-588A) To a toluene (10 mL) solution of 2-bromo-3-trifluoromethylpyridine (1.10 g, 4.87 mmol) was added 3-formylphenylboronic acid (0.90 g, 6.0 mmol) and DMF (4 mL). To the resulting solution was added K$_2$CO$_3$ (1.67 g, 12.1 mmol) and Pd(PPh$_3$)$_4$ (0.35 g, 0.30 mmol). The slurry was heated to reflux under argon for 18 h. The cooled mixture was poured into water and extracted with ethyl acetate. The organic layer was washed with brine, dried (MgSO$_4$) and evaporated to an oil. Purification by flash chromatography on silica gel eluting with 20% ethyl acetate in hexane gave 0.55 g (45%) of the desired 3-[(3-trifluoromethyl)-2-pyridinyl]benzaldehyde product as a color-less oil which solidified upon standing. HRMS: calcd. for C$_{13}$H$_9$NOF$_3$: 252.0636 [M+H]$^+$, found: 252.0639.

EX-588B)A mixture of solid 3-phenoxyaniline (2.96 g, 16 mmol) and 1,1,1-trifluoro-2,3-epoxypropane (1.30 mL, 15.0 mmol) was placed in a sealed tube and heated to 100° C. giving a dark solution. The stirred solution was heated 18 h and cooled to give a dark oil. Purification by flash chromatography on silica gel eluting with dichloromethane gave 3.15 g (71%) of the desired 3-[(N-3-phenoxyphenyl)amino]-1,1,1-trifluoro-2-propanol product as a colorless oil. Anal. calcd. for C$_{15}$H$_{14}$NO$_2$F$_3$·0.05 CH$_2$Cl$_2$: C, 59.92; H, 4.71; N, 4.64. Found: C, 59.92; H, 4.53; N, 4.73. HRMS calcd. 298.1055 [M+H]$^+$, found: 298.1056.

To a 1,2-dichloroethane (8 mL) solution of aldehyde (0.55 g, 2.2 mmol) from EX-588A was added the amine (0.66 g, 2.2 mmol) from EX-588B, NaB(OAc)$_3$H (0.61 g, 2.9 mmol) and acetic acid (0.15 mL, 2.6 mmol). The cloudy solution was stirred at room temperature for 4 h. The reaction mixture was poured into water and extracted with dichloromethane. The organic layer was washed with saturated NaHCO$_3$ and brine, dried (MgSO$_4$) and evaporated to give an oil. Purification by flash chromatography on silica gel eluting with 20% ethyl acetate in hexane gave 0.33 g (29%) of the desired 3-[(3-phenoxyphenyl)[[3-[(3-trifluoromethyl)-2-pyridinyl]phenyl]methyl]amino]-1,1,1-trifluoro-2-propanol product as a white foam, >97% pure by HPLC analysis. Anal. calcd. for C$_{28}$H$_{22}$N$_2$O$_2$F$_6$: C, 63.16; H, 4.16; N, 5.26. Found: C, 62.87; H, 4.02; N, 5.33. HRMS: calcd. 533.1664 [M+H]$^+$, found: 533.1658. $^1$H NMR (C$_6$D$_6$) δ2.97 (d, 1H), 3.26 (dd, 1H), 3.46 (dd, 1H), 3.77 (m, 1H), 4.22 (dd, 2H), 6.31 (dd, 1H), 6.35 (dd, 1H), 6.40 (dd, 1H), 6.54 (t, 1H), 6.80 (t, 1H), 6.9–7.0 (m, 7H), 7.26 (d, 1H), 7.33 (d, 1H), 7.40 (s, 1H), 8.17 (d, 1H).

Additional examples of 3-[(3-phenoxyphenyl)[[3-(heteroaryl)phenyl]methyl]-amino]-1,1,1-trifluoro-2-propanols are prepared by one skilled in the art using similar methods, as shown in Example Table 33.

EXAMPLE TABLE 33

3-[(3-phenoxyphenyl)[[3-(heteroaryl)phenyl]methyl]amino]-1,1,1-trifluoro-2-propanols.

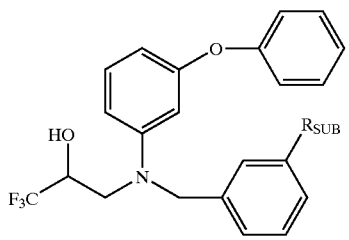

| Ex. No. | R$_{SUB}$ | Calculated Mass [M + H]$^+$ | Observed Mass [M + H]$^+$ |
|---|---|---|---|
| 589 | 3-methyl-pyridin-2-yl | 479.1949 | 479.1946 |
| 590 | pyridin-3-yl | 465.1790 | 465.1778 |
| 591 | pyridin-4-yl | 465.1790 | 465.1821 |

EXAMPLE 592

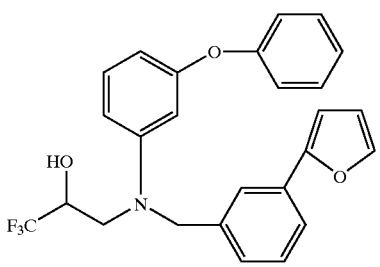

3-[(3-phenoxyphenyl)[[3-(2-furanyl)phenyl]methyl]amino]-1,1,1-trifluoro-2-propanol EX-592A) To a dioxane (20 mL) solution of 3-bromobenzaldehyde (0.63 mL, 5.4 mmol) was added 2-(tributylstannyl)furan (1.89 mL, 6.00 mL) and Pd(PPh$_3$)$_2$Cl$_2$ (0.21 g, 0.30 mmol). The mixture was heated to reflux under argon for 1.5 h. The cooled mixture was poured into a mixture of saturated KF and ethyl acetate and stirred 18 h. The slurry was filtered through celite. The organic layer was separated, washed with brine, dried (MgSO$_4$) and evaporated to an oil. Purification by flash chromatography on silica gel eluting with 5% ethyl acetate in hexane gave 0.80 g (86%) of the desired 3-(2-furanyl)benzaldehyde product as an yellow oil which solidified upon standing. MS: m/z=173.1 [M+H]$^+$.

EX-592B) To a 1,2-dichloroethane (7 mL) solution of aldehyde (0.40 g, 2.3 mmol) from EX-592A was added 3-phenoxyaniline (0.43 g, 2.3 mmol), NaB(OAc)$_3$H (0.64 g, 3.0 mmol) and acetic acid (0.15 mL, 2.6 mmol). The cloudy solution was stirred at room temperature for 2 h. The reaction mixture was poured into water and extracted with dichloromethane. The organic layer was washed with saturated NaHCO$_3$ and brine, dried (MgSO$_4$) and evaporated to yield 0.74 g (94%) of the desired N-(3-phenoxyphenyl)[[3-(2-furanyl)phenyl]methyl]amine product as an yellow oil which was used without further purification. MS: m/z=342.3 [M+H]$^+$.

To a dichloromethane (3 mL) solution of amine (0.74 g, 2.2 mmol) from EX-592B was added 1,1,1-trifluoro-2,3-epoxypropane (0.28 mL, 3.3 mmol) and Yb(OTf)$_3$ (0.136 g, 0.20 mmol). The cloudy solution was stirred at room temperature for 4 days, then diluted with diethyl ether, and washed with water and brine. The organic layer was dried (MgSO$_4$) and evaporated to an oil. Purification by flash chromatography on silica gel eluting with 10% ethyl acetate in hexane gave an oil which was dissolved in EtOH, stripped and dried in vacuo to give 0.49 g (49%) of the desired 3-[(3-phenoxyphenyl)[[3-(2-furanyl)phenyl]methyl]amino]-1,1,1-trifluoro-2-propanol product as a colorless oil, >98% pure by HPLC analysis. Anal. calcd. for C$_{26}$H$_{22}$NO$_3$F$_3$·0.5 EtOH·0.3H$_2$O: C, 67.30; H, 5.35; N, 2.91. Found: C, 67.12; H, 5.12; N, 2.89. HRMS calcd. 454.1630 [M+H]$^+$, found: 454.1635. $^1$H NMR (C$_6$D$_6$) δ2.15 (d, 1H), 3.21 (dd, 1H), 3.50 (dd, 1H), 3.81 (m, 1H), 4.24 (s, 2H), 6.09 (dd, 1H), 6.33 (d, 1H), 6.35 (d, 1H), 6.44 (dd, 1H), 6.52 (t, 1H), 6.79 (m, 1H), 6.81 (s, 1H), 6.9–7.0 (m, 7H), 7.44 (d, 1H), 7.47 (s, 1H).

Additional examples of 3-[(3-phenoxyphenyl)[[4substituted-3-(2-furanyl)-phenyl]methyl]amino]-1,1,1-trifluoro-2-propanols are prepared by one skilled in the art using similar methods, as shown in Example Table 34.

EXAMPLE TABLE 34

3-[(3-phenoxyphenyl)[[4-substituted-3-(2-furanyl)-phenyl]methyl]amino]-1,1,1-trifluoro-2-propanols.

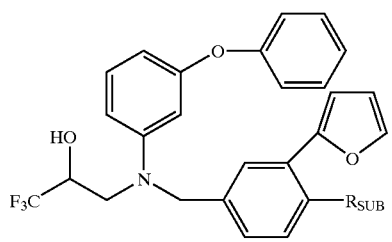

| Ex. No. | R$_{SUB}$ | Calculated Mass [M + H]$^+$ | Observed Mass [M + H]$^+$ |
|---|---|---|---|
| 593 | F | 472.1536 | 472.1530 |
| 594 | Me | 468.1787 | 468.1783 |

EXAMPLE 595

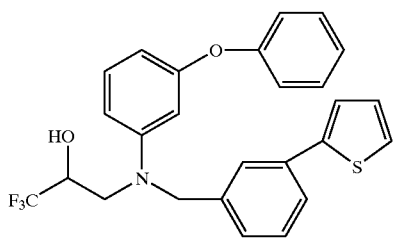

3-[(3-phenoxyphenyl)[[3-(2-thienyl)phenyl]methyl]amino]-1,1,1-trifluoro-2-propanol EX-595A) To a 1,2-dichloroethane (90 mL) solution of 3-bromobenzaldehyde (5.60 g, 30.3 mmol) was added 3-phenoxyaniline (5.60 g, 30.2 mmol), NaB(OAc)$_3$H (8.26 g, 39.0 mmol) and acetic acid (1.8 mL, 31. mmol). The cloudy solution was stirred at room temperature for 1.5 h. The reaction mixture was poured into water and extracted with dichloromethane. The organic layer was washed with saturated NaHCO$_3$ and brine, dried (MgSO$_4$) and evaporated to yield 10.49 g (98%) of the desired N-(3-phenoxyphenyl)[(3-bromophenyl)methyl]amine product as a light brown oil. $^1$H NMR (CDCl$_3$) δ4.26 (s, 2H), 6.27 (s, 1H), 6.38 (d, 2H), 7.00 (d, 2H), 7.13 (m, 2H), 7.19 (t, 1H), 7.26 (d, 1H), 7.30 (m, 2H), 7.38 (d, 1H), 7.96 (s, 1H). The formation of the desired product was monitored by the disappearance of the aldehyde peak (δ~10) and the formation of the benzyl peak (δ4.26) in the $^1$H NMR spectrum.

EX-595B) To a dichloromethane (15 mL) solution of amine from EX-595A (6.01 g, 17.0 mmol) was added 1,1,1-trifluoro-2,3-epoxypropane (1.75 mL, 20.3 mmol) and Yb(OTf)$_3$ (1.05 g, 1.69 mmol). The cloudy solution was stirred at room temperature for 24 h, diluted with diethyl ether, and washed with water and brine. The organic layer was dried (MgSO$_4$) and evaporated to an oil. Purification by flash chromatography on silica gel eluting with 3–8% ethyl acetate in hexane gave an oil which was dissolved in EtOH, stripped and dried in vacuo to give 4.71 g (60%) of the desired 3-[(3-phenoxyphenyl)[[3-bromophenyl]methyl]amino]-1,1,1-trifluoro-2-propanol product as a colorless oil. Anal. calcd. for C$_{22}$H$_{19}$NO$_2$F$_3$Br·0.41 EtOH: C, 56.49; H, 4.46; N, 2.89. Found: C, 56.15; H, 4.22; N, 2.92. HRMS calcd. 466.0629 [M+H]$^+$, found: 466.0598.

To a dioxane (5 mL) solution of aminopropanol from EX-595B (0.38 g, 0.82 mmol) was added 2-(tributylstannyl)thiophene (0.29 mL, 0.90 mmol) and Pd(PPh$_3$)$_2$Cl$_2$ (0.040 g, 0.057 mmol). The mixture was heated to reflux under argon for 18 h. The cooled mixture was poured into a mixture of 10% aq. KF and ethyl acetate and stirred 1 h. The slurry was filtered through celite. The organic layer was separated, washed with brine, dried (MgSO$_4$) and evaporated to an oil. Purification by flash chromatography on silica gel eluting with 5–15% ethyl acetate in hexane gave an oil which was dissolved in EtOH, stripped and dried in vacuo to give 0.17 g (45%) of the desired 3-[(3-phenoxyphenyl)[[3-(2-thienyl)phenyl]methyl]amino]-1,1,1-trifluoro-2-propanol product as a colorless oil. Anal. calcd. for C$_{26}$H$_{22}$NO$_2$F$_3$S·0.62 EtOH: C, 65.69; H, 5.20; N, 2.81. Found: C, 65.36; H, 4.84; N, 2.81. HRMS calcd. 470.1402 [M+H]$^+$, found: 470.1392. $^1$H NMR (CDCl$_3$) δ2.60 (br s, 1H), 3.64 (dd, 1H), 3.89 (dd, 1H), 4.37 (m, 1H), 4.68 (s, 2H), 6.42 (dd, 1H), 6.45 (t, 1H), 6.55 (dd, 1H), 6.98 (dd, 2H), 7.1 (m, 3H), 7.20 (t, 1H), 7.2–7.3 (m, 5H), 7.43 (s, 1H), 7.52 (d, 1H).

EXAMPLE 596

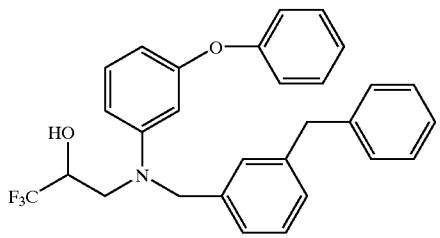

3-[(3-phenoxyphenyl)[[3-(phenylmethyl)phenyl]methyl]amino]-1,1,1-trifluoro-2-propanol To a THF (4 mL) solution of 3-[(3-phenoxyphenyl)[[3-bromophenyl]methyl]amino]-1,1,1-trifluoro-2-propanol (0.60 g, 1.3 mmol) from EX-595B was added benzylmagnesium bromide in THF (2.0 mL, 2.0 M, 4.0 mmol) and Pd(PPh$_3$)$_4$. The resulting yellow solution was refluxed under N$_2$ for 18 h. The cooled solution was poured into saturated aq. NH$_4$Cl, extracted with ethyl acetate, dried (MgSO$_4$) and evaporated to an oil. Purification by flash chromatography on silica gel eluting with 15% ethyl acetate in hexane gave an oil which was dissolved in EtOH, stripped and dried in vacuo to give 0.39 g (62%) of the desired 3-[(3-phenoxyphenyl)[[3-(phenylmethyl)phenyl]methyl]amino]-1,1,1-trifluoro-2-propanol product as a colorless oil. Anal. calcd. for C$_{29}$H$_{26}$NO$_2$F$_3$·0.4 EtOH: C, 72.17; H, 5.77; N, 2.82. Found: C, 72.17; H, 5.42; N, 2.83. HRMS calcd. 478.1994 ([M+H]$^+$, found: 478.1984. $^1$H NMR (C$_6$D$_6$) δ1.58 (d, 1H), 3.22 (dd, 1H), 3.46 (dd, 1H), 3.69 (s, 2H), 3.73 (m, 1H), 4.18 (s, 2H), 6.34 (dd, 1H), 6.47 (dd, 1H), 6.53 (t, 1H), 6.8–7.1 (m 15H).

Additional examples of 3-[(3-phenoxyphenyl)[[3-(alkyl- or cycloalkyl-)phenyl]methyl]amino]-1,1,1-trifluoro-2-propanols are prepared by one skilled in the art using similar methods, as shown in Example Table 35.

EXAMPLE TABLE 35

3-[(3-phenoxyphenyl)[[3-(alkyl- or cycloalkyl-)phenyl]methyl]amino]-1,1,1-trifluoro-2-propanols.

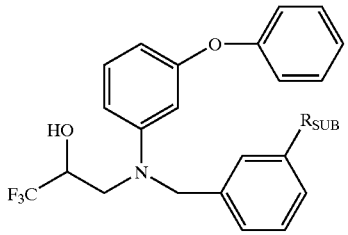

| Ex. No. | R$_{SUB}$ | Calculated Mass [M + H]$^+$ | Observed Mass [M + H]$^+$ |
|---|---|---|---|
| 597 | 3-methylbutyl | 458.2307 | 458.2295 |
| 598 | 2-methylpropyl | 444.2150 | 444.2157 |
| 599 | cyclopropyl | 428.1837 | 428.1806 |

EXAMPLE 600

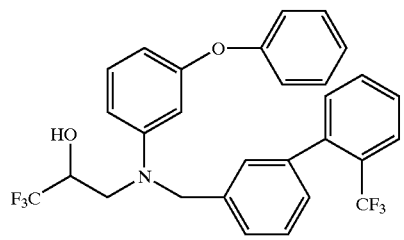

3-[(3-phenoxyphenyl)[[2'-(trifluoromethyl)[1,1'-biphenyl]-3-yl]methyl]amino]-1,1,1-trifluoro-2-propanol To a toluene (8 mL) solution of 3-[(3-phenoxyphenyl)[[3-bromophenyl]methyl]-amino]-1,1,1-trifluoro-2-propanol (0.51 g, 1.1 mmol) from EX-595B was added 2-(trifluoromethyl)phenylboronic acid (0.33 g, 1.7 mmol) and DMF (3 mL). To the resulting solution was added K$_2$CO$_3$ (0.31 g, 2.2 mmol) and Pd(PPh$_3$)$_4$ (0.060 g, 0.05 mmol). The slurry was heated to reflux under argon for 18 h. The cooled mixture was poured into water and extracted with ethyl acetate. The organic layer was washed with brine, dried (MgSO$_4$) and evaporated to an oil. Purification by flash chromatography on silica gel eluting with 20% ethyl acetate in hexane gave an oil which was dissolved in EtOH, stripped and dried in vacuo to give 0.32 g (55%) of the desired 3-[(3-phenoxyphenyl)[[(2'-(trifluoromethyl)[1,1'-biphenyl]-3-yl]methyl]amino]-1,1,1-trifluoro-2-propanol product as a colorless oil. Anal. calcd. for C$_{29}$H$_{23}$NO$_2$F$_6$·0.8 EtOH: C, 64.67; H, 4.93; N, 2.46. Found: C, 64.53; H, 4.69; N, 2.49. HRMS calcd. 532.1711 [M+H]$^+$, found: 532.1708. $^1$H NMR (C$_6$D$_6$) δ1.72 (d, 1H), 3.17 (dd, 1H), 3.46 (dd, 1H), 3.72 (m, 1H), 4.23 (s, 2H), 6.33 (dd, 1H), 6.43 (dd, 1H), 6.52 (t, 1H), 6.82 (m, 2H), 6.9–7.1 (m, 11H), 7.43 (d, 1H).

EXAMPLE 601

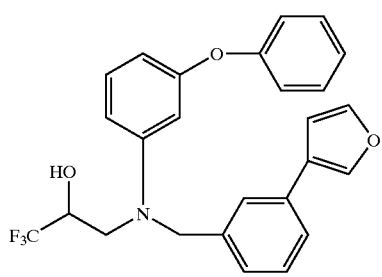

3-[(3-phenoxyphenyl)[[3-(3-furanyl)phenyl]methyl]amino]-1,1,1-trifluoro-2-propanol EX-601A) To a toluene (10 mL) solution of 3-bromofuran (0.54 mL, 6.0 mmol) was added 3-formylphenylboronic acid (1.00 g, 6.7 mmol) and DMF (4 mL). To the resulting solution was added $K_2CO_3$ (1.85 g, 13.4 mmol) and $Pd(PPh_3)_4$ (0.40 g, 0.35 mmol). The slurry was heated to reflux under argon for 2 h. The cooled mixture was poured into water and extracted with ethyl acetate. The organic layer was washed with brine, dried ($MgSO_4$) and evaporated to an oil. Purification by flash chromatography on silica gel eluting with 5% ethyl acetate in hexane gave 0.10 g (10%) of the desired 3-(3-furanyl)benzaldehyde product as a yellow oil. MS: m/z=173.0 $[M+H]^+$.

EX-601B) To a 1,2-dichloroethane (3 mL) solution of the aldehyde (0.10 g, 0.58 mmol) from EX-601A was added 3-phenoxyaniline (0.11 g, 0.59 mmol), $NaB(OAc)_3H$ (0.16 g, 0.75 mmol) and acetic acid (0.040 mL, 0.70 mmol). The cloudy solution was stirred at room temperature for 2 h. The reaction mixture was poured into water and extracted with dichloromethane. The organic layer was washed with saturated $NaHCO_3$ and brine, dried ($MgSO_4$) and evaporated to yield 0.20 g (100%) of the desired N-3-phenoxyphenyl)-[[3-(3-furanyl)phenyl]methyl]amine product as a yellow oil which was used without further purification. $^1H$ NMR ($CDCl_3$) δ4.1 (br s, 1H), 4.30 (s, 2H), 6.29 (d, 1H), 6.32 (dd, 1H), 6.39 (dd, 1H), 6.66 (s, 1H), 6.95–7.05 (m, 4H), 7.2–7.5 (m, 7H), 7.70 (s, 1H). The formation of the desired product was monitored by the disappearance of the aldehyde peak (δ~10) and the formation of the benzyl peak (δ4.30) in the $^1H$ NMR spectrum.

To a $CH_3CN$ (2 mL) solution of amine (0.20 g, 0.58 mmol) from EX-601B was added 1,1,1-trifluoro-2,3-epoxypropane (0.10 mL, 1.2 nmmol) and $Yb(OTf)_3$ (0.035 g, 0.056 mmol). The cloudy solution was stirred in a sealed flask at 40° C. After 18 h, additional 1,1,1-trifluoro-2,3-epoxypropane (0.20 mL, 2.4 mmol) and $Yb(OTf)_3$ (0.035 g, 0.056 mmol) were added, and the mixture was heated an additional 4 h, diluted with diethyl ether and washed with water and brine. The organic layer was dried ($MgSO_4$) and evaporated to an oil. Purification by flash chromatography on silica gel eluting with 10% ethyl acetate in hexane gave an oil which was dissolved in EtOH, stripped and dried in vacuo to give 0.14 g (53%) of the desired 3-[(3-phenoxyphenyl)[[3-(3-furanyl)phenyl]methyl]amino]-1,1,1-trifluoro-2-propanol product as a colorless oil, >99% pure by HPLC analysis. Anal. calcd. for $C_{26}H_{22}NO_3F_3·0.3$ EtOH: C, 68.37; H, 5.13; N, 3.00. Found: C, 68.29; H, 5.09; N, 2.99. HRMS calcd. 454.1630 $[M+H]^+$, found: 454.1635. $^1H$ NMR ($C_6D_6$) δ1.62 (d, 1H), 3.18 (dd, 1H), 3.48 (dd, 1H), 3.74 (m, 1H), 4.22 (s, 2H), 6.32 (dd, 1H), 6.35 (m, 1H), 6.44 (dd, 1H), 6.52 (t, 1H), 6.78 (m, 1H), 6.82 (d, 1H), 6.9–7.1 (m, 9H), 7.37 (s, 1H).

EXAMPLE 602

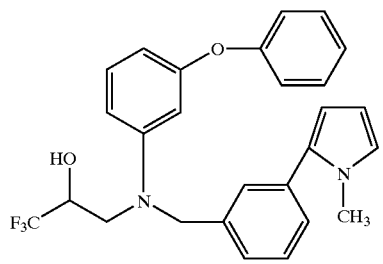

3-[(3-phenoxyphenyl)[[3-(1-methyl-1-pyrrol-2-yl)phenyl]methyl]amino]-1,1,1-trifluoro-2-propanol EX-602A) To solution of N-methylpyrrole (0.97 mL, 11 mmol) in $Et_2O$ (20 mL) was added neat TMEDA (1.5 mL, 10 mmol) and 1.6 M n-BuLi in hexanes (6.3 mL, 10 mmol). The solution was heated to reflux under $N_2$ for 1 h and then cooled to −78° C. A 1.0 M solution of $Me_3SnCl$ in THF was added over 15 min, and the resulting solution stirred for 30 min at −78° C. After warming to room temperature, 3-bromo-benzaldehyde (0.70 mL, 6.0 mmol), $Pd(PPh_3)_2Cl_2$ (0.25 g, 0.35 mmol) and dioxane (10 mL) were added. The slurry was heated to reflux for 18 h. The cooled mixture was poured into a mixture of saturated KF and ethyl acetate and stirred 15 min. The slurry was filtered through celite. The organic layer was separated, washed with brine, dried ($MgSO_4$) and evaporated to an oil. Purification by flash chromatography on silica gel eluting with 5% ethyl acetate in hexane gave 0.45 g (24%) of the desired 3-(1-methyl-1H-pyrrol-2-yl)benzaldehyde product as a yellow oil. MS: m/z=186.2 $[M+H]^+$.

EX-602B) To a 1,2-dichloroethane (10 mL) solution of aldehyde (0.45 g, 2.4 mmol) from EX-602A was added 3-phenoxyaniline (0.45 g, 2.4 mmol), $NaB(OAc)_3H$ (0.67 g, 3.2 mmol) and acetic acid (0.15 mL, 2.4 mmol). The cloudy solution was stirred at room temperature for 2 h. The reaction mixture was poured into water and extracted with dichloromethane. The organic layer was washed with saturated $NaHCO_3$ and brine, dried ($MgSO_4$) and evaporated to yield 0.67 g (79%) of the desired N-(3-phenoxyphenyl)[[3-(1-methyl-1H-pyrrol-2-yl)phenyl]methyl]amine product as a yellow oil which was used without further purification. $^1H$ NMR ($CDCl_3$) δ3.60 (s, 3H), 4.15 (br s, 1H), 4.35 (s, 2H), 6.2–6.4 (m, 5H), 6.67 (s, 1H), 7.00–7.05 (m, 4H), 7.1–7.2 (m, 6H). The formation of the desired product was monitored by the disappearance of the aldehyde peak (δ~10) and the formation of the benzyl peak (δ4.35) in the $^1H$ NMR spectrum.

To a $CH_3CN$ (2 mL) solution of amine (0.67 g, 1.9 mmol) from EX-602B was added 1,1,1-trifluoro-2,3-epoxypropane (0.33 mL, 3.8 mmol) and $Yb(OTf)_3$ (0.120 g, 0.19 mmol). The cloudy solution as stirred in a sealed flask at 40° C. for 18 h. The cooled reaction mixture was diluted with diethyl ether and washed with water and brine. The organic layer was dried ($MgSO_4$) and evaporated to an oil. Purification by flash chromatography on silica gel eluting with 10% ethyl acetate in hexane gave an oil which was dissolved in EtOH, stripped and dried in vacuo to give 0.57 g (66%) of the desired 3-[(3- phenoxyphenyl)[[3-(1-methyl-1H-pyrrol-2-yl)phenyl]
methyl]amino]-1,1,1-trifluoro-2-propanol product as a
colorless oil, >99% pure by HPLC analysis. Anal. calcd.
for $C_{27}H_{25}N_2O_2F_3 \cdot 0.9$ EtOH: C, 68.10; H, 6.03; N, 5.51.
Found: C, 68.36; H, 5.94; N, 5.65. HRMS calcd. 467.1946
[M+H]$^+$, found: 467.1950. $^1$H NMR ($C_6D_6$) δ2.01(d, 1H),
2.97 (s, 3H), 3.21 (dd, 1H), 3.49 (dd, 1H), 3.78 (m, 1H),
4.28 (s, 2H), 6.3–6.4 (m, 4H), 6.45 (dd, 1H), 6.53 (t 1H),
6.8–7.1 (m, 10H).

EXAMPLE 603

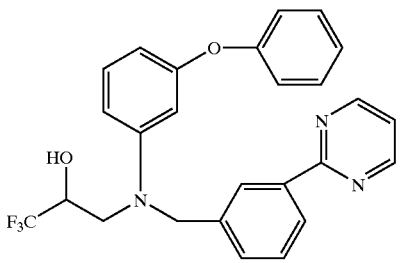

3-[(3-phenoxyphenyl)[[3-(2-pyrimidinyl)phenyl]
methyl]amino]1,1,1-trifluoro-2-propanol EX-603A) To a toluene (15 mL) solution of
2-chloropyrimidine (1.00 g, 8.7 mmol) was added
3-formylphenylboronic acid (1.42 g, 9.5 mmol) and DMF
(8 mL). To the resulting solution was added $K_2CO_3$ (2.63
g, 19.0 mmol) and Pd(PPh$_3$)$_4$ (0.52 g, 0.45 mmol). The
slurry was heated to reflux under argon for 18 h. The
cooled mixture was poured into water and extracted with
ethyl acetate. The organic layer was washed with brine,
dried (MgSO$_4$) and evaporated to an oil. Purification by
flash chromatography on silica gel eluting with 20% ethyl
acetate in hexane gave 0.63 g (39%) of the desired
3-(2-pyrimidinyl)benzaldehyde product as a brown oil
which solidified upon standing. MS: m/z=185.1 [M+H]$^+$.

EX-603B) To a 1,2-dichloroethane (10 mL) solution of
aldehyde (0.62 g, 3.4 mmol) from EX-603A was added
3-phenoxyaniline (0.62 g, 3.4 mmol), NaB(OAc)$_3$H (0.93
g, 4.4 mmol) and acetic acid (0.20 mL, 3.4 mmol). The
cloudy solution was stirred at room temperature for 2 h.
The reaction mixture was poured into water and extracted
with dichloromethane. The organic layer was washed with
saturated NaHCO$_3$ and brine, dried (MgSO$_4$) and evaporated to yield 1.19 g (99%) of the desired N-(3-phenoxyphenyl)-[[3-(2-pyrimidinyl)phenyl]methyl]
amine product as a brown oil which was used without
further purification. MS: m/z=354.2 [M+H]$^+$.

To a $CH_3CN$ (4 mL) solution of amine (1.19 g, 3.4 minol)
from EX-603B was added 1,1,1-trifluoro-2,3-epoxypropane (0.585 mL, 6.8 mmol) and Yb(OTf)$_3$
(0.112 g, 0.18 mmol). The cloudy solution was stirred in
a sealed flask at 40° C. After 18 h, more 1,1,1-trifluoro-2,3-epoxypropane (0.585 mL, 6.8 mmol) and Yb(OTf)$_3$
(0.112 g, 0.18 mmol) were added, and the slurry was
heated an additional 4 h. The cooled reaction mixture was
diluted with diethyl ether and washed with water and
brine. The organic layer was dried (MgSO$_4$) and evaporated to an oil. Purification by silica gel flash chromatography eluting with 25% ethyl acetate in hexane gave an oil
which was dissolved in EtOH, concentrated and dried in
vacuo to give 0.33 g (21%) of the desired 3-[(3-phenoxyphenyl)[[3-(2-pyrimidinyl)phenyl]methyl]
amino]-1,1,1-trifluoro-2-propanol product as a pale yellow oil, >99% pure by HPLC analysis. Anal. calcd. for
$C_{26}H_{22}N_3O_2F_3 \cdot 0.5$ EtOH: C, 66.39; H, 5.16; N, 8.60.
Found: C, 66.26; H, 4.85; N, 8.60. HRMS calcd. 466.1742
[M+H]$^+$, found: 466.1724. $^1$H NMR ($C_6D_6$) δ2.28 (br s,
1H), 3.27 (dd, 1H), 3.50 (dd, 1H), 3.78 (m, 1H), 4.26 (m,
2H), 6.08 (t, 1H), 6.39 (dd, 1H), 6.52 (t, 1H), 6.75 (m,
1H), 6.9–7.0 (m, 6H), 7.18 (t, 1H), 8.12 (d, 2H), 8.58 (s,
1H), 8.66 (d, 1H).

EXAMPLE 604

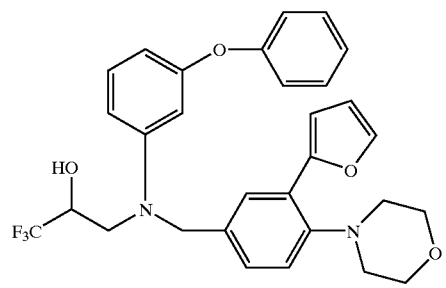

3-[(3-phenoxyphenyl)[[3-(2-furanyl)-4-(4-morpholinyl)phenyl]methyl]amino]-1,1,1-trifluoro-
2-propanol EX-604A) To a pyridine (15 mL) solution of 3-bromo-4-fluorobenzaldehyde (1.0 g, 4.9 mmol) was added morpholine (0.5 mL, 5.7 mmol) and $K_2CO_3$ (0.69 g, 5.0
mmol), and the slurry was refluxed for 18 h. The solvent
was removed, and the residue was partitioned between
ethyl acetate and water. The organic layer was separated,
dried (MgSO$_4$) and evaporated to a yellow oil. Purification by flash chromatography on silica gel eluting with
15% ethyl acetate in hexane gave 0.77 g (58%) of the
desired 3-bromo-4-(4-morpholinyl)benzaldehyde product
as an white solid. $^1$H NMR (CDCl$_3$) δ3.18 (m, 4H), 3.90
(m, 4H), 7.10 (d, 1H), 7.78 (d, 1H), 8.07 (s, 1H), 9.83 (s,
1H).

EX-604B) To a dioxane (8 mL) solution of the aldehyde
from EX-604A (0.77 g, 2.8 mmol) was added
2-(tributylstannyl)furan (1.07 mL, 3.42 mmol) and
Pd(PPh$_3$)$_2$Cl$_2$ (0.12 g, 0.17 mmol). The mixture was
heated to reflux under argon for 18 h. The cooled mixture
was poured into a mixture of saturated aq. KF and ethyl
acetate and stirred 3 h. The slurry was filtered through
celite. The organic layer was separated, washed with
brine, dried (MgSO$_4$) and evaporated to a yellow oil.
Purification by silica gel flash chromatography eluting
with 20% ethyl acetate in hexane gave 0.61 g (84%) of the
desired 3-(2-furanyl)-4-(4-morpholinyl)benzaldehyde
product as a yellow oil. MS: m/z=258.1 [M+H]$^+$.

To a 1,2-dichloroethane (6 mL) solution of aldehyde (0.59 g,
2.0 mmol) from EX-604B was added N-(3-phenoxyphenyl)-3-amino-1,1,1-trifluoro-2-propanol
(0.50 g, 1.9 mmol), NaB(OAc)$_3$H (0.52 g, 2.5 mmol) and
acetic acid (0.12 mL, 2.1 mmol). The cloudy solution was
stirred at room temperature for 18 h. The reaction mixture
was poured into water and extracted with dichloromethane. The organic layer was washed with saturated
NaHCO$_3$ and brine, dried (MgSO$_4$) and evaporated to
give an oil. Purification by flash chromatography on silica
gel eluting with 15% ethyl acetate in hexane gave 0.25 g
(25%) of the desired 3-[(3-phenoxyphenyl)[[3-(2-furanyl)-4-(4-morpholinyl)phenyl]methyl]amino]-1,1,1-trifluoro-2-propanol product as a white foam, >99% pure by HPLC analysis. Anal. calcd. for $C_{30}H_{29}N_2O_4F_3$: C, 66.91; H, 5.43; N, 5.20. Found: C, 66.54; H, 5.67; N, 5.02. HRMS: calcd. 539.2187 [M+H]+, found: 539.2158. $^1$H NMR ($C_6D_6$) δ 1.73 (d, 1H), 2.55 (m, 4H), 3.23 (dd, 1H), 3.50 (dd, 1H), 3.52 (m, 4H), 3.75 (m, 1H), 4.25 (s, 2H), 6.21 (dd, 1H), 6.36 (dd, 1H), 6.34 (dd, 1H), 6.56 (t, 1H), 6.69 (d, 1H), 6.8 (m, 2H), 6.9–7.0 (m, 5H), 7.09 (t, 1H), 7.22 (d, 1H), 7.34 (d, 1H).

EXAMPLE 605

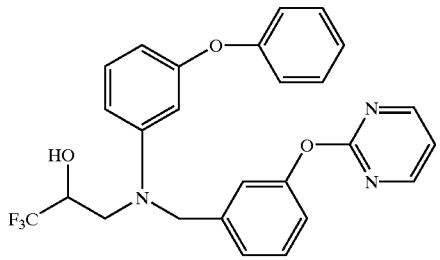

3-[(3-phenoxyphenyl)[[3-(2-pyrimidinyloxy)phenyl]methyl]amino]-1,1,1-trifluoro-2-propanol EX-605A) A slurry of 3-hydroxybenzaldehyde (1.22 g, 10 mmol), 2-chloropyrimidine (1.14 g, 10 mmol) and $K_2CO_3$ (1.65 g, 12 mmol) in DMSO (20 mL) was heated to 100° C. for 1 h. The cooled mixture was poured into water and extracted with $Et_2O$. The organic layer was washed with 2.5 N NaOH, 1 N HCl, saturated $NaHCO_3$ and brine, dried ($MgSO_4$) and evaporated to yield 1.42 g (71%) of the desired 3-(2-pyrimidinyl-oxy)benzaldehyde product as a white solid which was used without further purification. $^1$H NMR ($C_6D_6$) δ 7.12 (t, 1H), 7.54 (m, 1H), 7.66 (t, 1H), 7.78 (m, 1H), 7.83 (m, 1H), 8.64 (d, 2H), 10.05 (s, 1H).

To a 1,2-dichloroethane (10 mL) solution of aldehyde (0.56 g, 2.8 mmol) from EX-605A was added N-(3-phenoxyphenyl)-3-amino-1,1,1-trifluoro-2-propanol (0.83 g, 2.8 mmol), NaB(OAc)$_3$H (0.77 g, 3.6 mmol) and acetic acid (0.84 mL, 15 mmol). The cloudy solution was stirred at room temperature for 18 h. The reaction mixture was poured into water and extracted with dichloromethane. The organic layer was washed with saturated $NaHCO_3$ and brine, dried ($MgSO_4$) and evaporated to give an oil. Purification by flash chromatography on silica gel eluting with 2% methanol in $CH_2Cl_2$ gave an oil which was dissolved in EtOH, stripped and dried in vacuo to give 0.28 g (21%) of the desired 3-[(3-phenoxyphenyl)[[3-(2-pyrimidinyloxy)phenyl]-methyl]amino]-,1,1,1-trifluoro-2-propanol product as a colorless oil, >99% pure by HPLC analysis. Anal. calcd. for $C_{26}H_{22}N_3O_3F_3$·0.4 EtOH: C, 64.39; H, 4.92; N, 8.41. Found: C, 64.22; H, 4.87; N, 8.53. HRMS calcd. 482.1692 [M+H]+, found: 482.1698. $^1$H NMR ($C_6D_6$) δ 3.12 (d, 1H), 3.16 (dd, 1H), 3.49 (d, 1H), 3.79 (m, 1H), 4.12 (dd, 1H), 5.88 (t, 1H), 6.31 (dd, 1H), 6.41 (dd, 1H), 6.51 (t, 1H), 6.65 (t, 1H), 6.80 (t, 1H), 6.85–7.05 (m, 8H), 7.82 (d 2H).

EXAMPLE 606

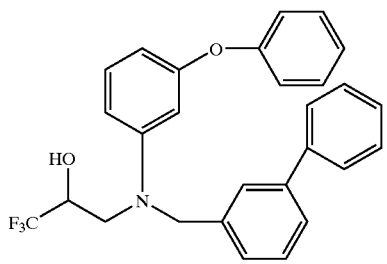

3-[(3-phenoxyphenyl)[([1,1'-biphenyl]-3-ylmethyl)amino]-1,1,1-trifluoro-2-propanol EX-606A) To an ethylene glycol dimethyl ether (10 mL) solution of 3-bromo-benzaldehyde (0.63 mL, 5.4 mmol) was added phenylboronic acid (0.73 g, 6.0 mmol), 2 M $Na_2CO_3$ (10 mL) and Pd(PPh$_3$)$_4$ (0.35 g, 0.30 mmol). The slurry was heated to reflux under argon for 18 h. The cooled mixture was poured into water and extracted with ethyl acetate. The organic layer was washed with brine, dried ($MgSO_4$) and evaporated to an oil. Purification by flash chromatography on silica gel eluting with 15% ethyl acetate in hexane gave 0.77 g (98%) of the desired [(1,1'-biphenyl)-3-carboxaldehyde product as a colorless oil which solidified upon standing. $^1$H NMR ($C_6D_6$) δ 7.45 (m, 3H), 7.65 (m, 3H), 7.70 (dd, 2H), 8.15 (m, 1H), 10.13 (s, 1H).

EX-606B) To a 1,2-dichloroethane (12 mL) solution of aldehyde (0.77 g, 4.2 mmol) from EX-606A was added 3-phenoxyaniline (0.78 g, 4.2 mmol), NaB(OAc)$_3$H (1.16 g, 5.5 mmol) and acetic acid (0.25 mL, 4.2 mmol). The cloudy solution was stirred at room temperature for 2 h. The reaction mixture was poured into water and extracted with dichloromethane. The organic layer was washed with saturated $NaHCO_3$ and brine, dried ($MgSO_4$) and evaporated to yield 1.49 g (100%) of the desired N-(3-phenoxyphenyl)([1,1'-biphenyl]-3-ylmethyl)amine product as a colorless oil which was used without further purification. $^1$H NMR (CDCl$_3$) δ 4.35 (s, 2H), 6.35 (m, 2H), 6.44 (d, 1H), 6.97 (d, 2H), 7.05 (t, 1H), 7.12 (t, 1H), 7.3–7.4 (m, 7H), 7.49 (d, 1H), 7.56 (m, 3H). The formation of the desired product was monitored by the disappearance of the aldehyde peak (δ~10) and the formation of the benzyl peak (δ 4.35) in the $^1$H NMR spectrum.

To a CH$_3$CN (4 mL) solution of amine (1.48 g, 4.2 mmol) from EX-606B was added 1,1,1-trifluoro-2,3-epoxypropane (0.475 mL, 5.5 mmol) and Yb(OTf)$_3$ (0.26 g, 0.42 mmol). The cloudy solution was stirred in a sealed flask at 40° C. for 18 h. The cooled reaction mixture was diluted with diethyl ether and washed with water and brine. The organic layer was dried (MgSO$_4$) and evaporated to an oil. Purification by flash chromatography on silica gel eluting with 10% ethyl acetate in hexane gave an oil which was dissolved in EtOH, stripped and dried in vacuo to give 0.65 g (34%) of the desired 3-[(3-phenoxyphenyl)[([1,1'-biphenyl]-3-ylmethyl)amino]-1,1,1-trifluoro-2-propanol product as a colorless oil which solidified upon standing, >99% pure by HPLC analysis. Anal. calcd. for $C_{28}H_{24}NO_2F_3$·0.05 CH$_2$Cl$_2$: C, 72.03; H, 5.19; N, 2.99. Found: C, 71.67; H, 5.10; N, 2.94. HRMS calcd. 464.1837 [M+H]+, found: 464.1834. $^1$H NMR ($C_6D_6$) δ 1.43 (d, 1H), 3.17 (dd, 1H), 3.46 (dd, 1H) 3.70 (m, 1H), 4.26 (s, 2H), 6.32 (dd, 1H), 6.44 (dd, 1H), 6.52 (t, 1H), 6.77 (m, 1H), 6.85–6.95 (m, 5H), 7.1 (m, 3H), 7.16 (t, 2H), 7.26 (s, 1H), 7.27 (d, 1H), 7.40 (dd, 2H).

EXAMPLE 607

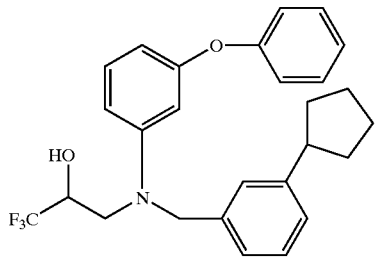

3-[(3-phenoxyphenyl)[[3-cyclopentylphenyl]methyl]amino]-1,1,1-trifluoro-2-propanol EX-607A) To a 1,2-dichloroethane (12 mL) solution of 3-cyclopentylbenzaldehyde (0.69 g, 4.0 mmol; P. L. Ornstein et al., *J. Med. Chem.* 1998, 41, 358–378) was added 3-phenoxyaniline (0.73 g, 4.0 mmol), NaB(OAc)$_3$H (1.08 g, 5.1 mmol) and acetic acid (0.24 mL, 4.2 mmol). The cloudy solution was stirred at room temperature for 2 h. The reaction mixture was poured into water and extracted with dichloromethane. The organic layer was washed with saturated NaHCO$_3$ and brine, dried (MgSO$_4$) and evaporated to an oil. Purification by flash chromatography on silica gel eluting with 10% ethyl acetate in hexane gave 0.30 g (22%) of the desired N-(3-phenoxyphenyl)-[[3-cyclopentylphenyl]methyl]amine product as a colorless oil. $^1$H NMR (CDCl$_3$) δ 1.55 (m, 2H), 1.63 (m, 2H), 1.78 (m, 2H), 2.02 (m, 2H), 2.94 (m, 1H), 4.10 (m, 1H), 4.22 (m, 2H), 6.35 (m, 3H), 7.0–7.2 (m, 10H). The formation of the desired product was monitored by the disappearance of the aldehyde peak (δ~10) and the formation of the benzyl peak (δ 4.22) in the $^1$H NMR spectrum.

To a CH$_3$CN (0.9 mL) solution of amine (0.30 g, 0.87 mmol) from EX-607A was added 1,1,1-trifluoro-2,3-epoxypropane (0.15 mL, 1.7 mmol) and Yb(OTf)$_3$ (0.080 g, 0.13 mmol). The cloudy solution was stirred in a sealed flask at 50° C. for 18 h. The cooled reaction mixture was diluted with diethyl ether and washed with water and brine. The organic layer was dried (MgSO$_4$) and evaporated to an oil. Purification by flash chromatography on silica gel eluting with 10% ethyl acetate in hexane gave an oil which was dissolved in EtOH, stripped and dried in vacuo to give 0.19 g (48%) of the desired 3-[(3-phenoxyphenyl)[[3-cyclopentylphenyl]methyl]amino]-1,1,1-trifluoro-2-propanol product as a colorless oil which solidified upon standing, >99% pure by HPLC analysis. Anal. calcd. for C$_{27}$H$_{28}$NO$_2$F$_3$·0.4 EtOH: C, 70.45; H, 6.47; N, 2.96. Found: C, 70.21; H, 6.39; N, 2.94. HRMS calcd. 456.2150 [M+H]$^+$, found: 456.2143. $^1$H NMR (C$_6$D$_6$) δ 1.43 (m, 4H), 1.58 (m, 2H), 1.62 (d, 2H), 1.85 (m, 2H), 2.71 (m, 1H), 3.22 (dd, 1H), 3.49 (dd, 1H), 3.73 (m, 1H), 4.26 (s, 2H), 6.35 (dd, 1H), 6.43 (dd, 1H), 6.55 (t, 1H), 6.8 (m, 2H), 6.95–7.05 (m, 8H).

EXAMPLE 608

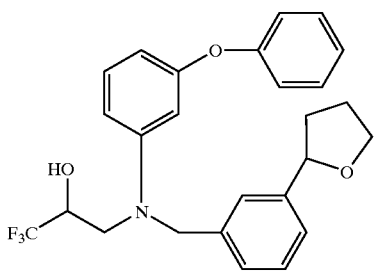

3-[(3-phenoxyphenyl)[[3-(tetrahydro-2-furanyl)phenyl]methyl]amino]-1,1,1-trifluoro-2-propanol EX-608A) Trifluoromethanesulfonic anhydride (2.0 mL, 11.9 mmol) was added dropwise over 5 minutes to a slurry of 3-hydroxybenzaldehyde (1.11 g, 9.09 mmol) in dichloromethane (40 mL) at −78° C. To this slurry was added neat N,N-di-isopropyl-ethylamine (2.4 mL, 13.8 mmol) dropwise over 5 min, and the resulting yellow solution was allowed to warm to room temperature. After 30 min at room temperature, the dark solution was diluted with dichloromethane and washed with 2.5 N NaOH, 1 N HCl, saturated NaHCO$_3$ and brine. The organic layer was dried (MgSO$_4$) and evaporated to give a red oil. Purification by flash chromatography on silica gel eluting with 10% ethyl acetate in hexane gave 1.70 g (74%) of the desired triflate ester product as a pale yellow oil. MS: m/z=254 [M+H]$^+$.

EX-608B) To a mixture of Pd$_2$(dba)$_3$ (120 mg, 0.13 mmol) and P(o-tolyl)$_3$ (150 mg, 0.50 mmol) in toluene (15 mL) was added the triflate ester from EX-608A (1.70 g, 6.7 mmol), N,N-di-isopropylethylamine (3.50 mL, 20.1 mmol) and 2,3-dihydrofuran (2.53 mL, 33.5 mmol). The solution was heated to 70° C. in a sealed flask under argon for 18 h. The cooled solution was then diluted with ethyl acetate and washed with water, 1 N HCl, saturated NaHCO$_3$ and brine. The organic layer was dried (MgSO$_4$) and evaporated to give a red oil. The major product was isolated by flash chromatography on silica gel eluting with 10% ethyl acetate in hexane and gave 0.72 g (62%) of the desired 3-(dihydro-2-furanyl)benzaldehyde product as a cloudy yellow oil. MS: m/z=175.1 [M+H]$^+$.

EX-608C) A THF (15 mL) solution of the aldehyde from EX-608B (0.70 g, 4.0 mmol) and 2,6-lutidine (0.46 mL, 4.0 mmol) was stirred in a hydrogen atmosphere (50 psi) in the presence of 10% Pd/C (0.29 g) for 18 h at room temperature. The slurry was filtered through celite, and the solvent was removed. The residue was taken up in ethyl acetate and washed with 1 N HCl and brine. The organic layer was dried (MgSO$_4$) and evaporated to give 0.50 g (70%) of the desired 3-(tetrahydro-2-furanyl)phenylmethanol product as a yellow oil. The formation of the desired product was monitored by the disappearance of the aldehyde (δ~10) and olefin peaks in the $^1$H NMR spectrum.

EX-608D) A slurry of the phenylmethanol product from EX-608C (0.50 g, 2.8 mmol) and MnO$_2$ (2.10 g, 24.3 mmol) in dichloromethane (15 mL) was refluxed for 3 h. The slurry was filtered through celite, and the filtrate was evaporated to a yellow oil. Purification by flash chromatography on silica gel eluting with 10% ethyl acetate in hexane gave 0.19 g (45%) of the desired aldehyde product as a pale yellow oil. GCMS: m/z=177 [M+H]$^+$.

EX-608E) To a 1,2-dichloroethane (4 mL) solution of the aldehyde (0.19 g, 1.1 mmol) from EX-608D was added 3-phenoxyaniline (0.20 g, 1.1 mmol), NaB(OAc)$_3$H (0.30 g, 1.4 mmol) and acetic acid (0.065 mL, 1.1 mmol). The cloudy solution was stirred at room temperature for 3 h. The reaction mixture was poured into water and extracted with dichloromethane. The organic layer was washed with saturated NaHCO$_3$ and brine, dried (MgSO$_4$) and evaporated to yield 0.32 g (84%) of the desired N-(3-phenoxyphenyl)-[[3-(tetrahydro-2-furanyl)phenyl] methyl]amine product as a yellow oil which was used without further purification. The formation of the desired product was monitored by TLC.

To a CH$_3$CN (1 mL) solution of the amine (0.32 g, 0.93 mmol) from EX-608E was added 1,1,1-trifluoro-2,3-epoxypropane (0.24 mL, 2.8 mmol) and Yb(OTf)$_3$ (0.115 g, 0.18 mmol). The cloudy solution was stirred in a sealed flask at 40° C. for 18 h. The cooled reaction mixture was diluted with diethyl ether and washed with water and brine. The organic layer was dried (MgSO$_4$) and evaporated to an oil. Purification by flash chromatography on silica gel eluting with 15% ethyl acetate in hexane gave an oil which was dissolved in EtOH, stripped and dried in vacuo to give 0.13 g (30%) of the desired 3-[(3-phenoxyphenyl)[[3-(tetrahydro-2-furanyl)phenyl]methyl] amino]-1,1,1-trifluoro-2-propanol product as a colorless oil. Anal. calcd. for C$_{26}$H$_{26}$NO$_3$F$_3$·0.5 EtOH: C, 67.33; H, 6.04; N, 2.94. Found: C, 67.49; H, 6.08; N, 2.91. HRMS calcd. 458.1943 [M+H]$^+$, found: 458.1937. $^1$H NMR (C$_6$D$_6$) δ 0.45 (d, 1H), 1.43 (m, 3H), 1.79 (m, 1H), 1.99 (m, 1H), 3.24 (m, 1H), 3.43 (m, 1H), 3.76 (m, 2H), 4.24 (s, 2H), 4.60 (t, 1H), 6.35 (m, 1H), 6.43 (dd, 1H), 6.54 (dd, 1H), 6.8 (m, 2H), 6.9–7.0 (m, 7H), 7.15 (d, 1H).

EXAMPLE 609

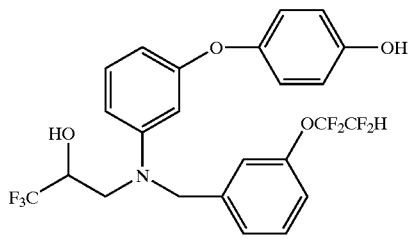

4-[3-[[[3-(1,1,2,2-tetrafluoroethoxy)phenyl]methyl] (3,3,3-trifluoro-2-hydroxypropyl)amino]phenoxy] phenol A 1,2-dichloroethane (4 mL) solution of N-[(4-methoxyphenoxy)phenyl]-3-[[3-(1,1,2,2-tetrafluoroethoxy)phenyl]methyl]amino]-1,1,1-trifluoro-2-propanol (0.33 g, 0.62 mmol) and boron tribromide-methyl sulfide complex (2.5 mL, 1.0 M in CH$_2$Cl$_2$, 2.5 mmol) was refluxed for 8 h under argon. The reaction was diluted with Et$_2$O and washed with water, 1 N NaOH and saturated aq. NH$_4$Cl. The organic layer was dried (MgSO$_4$) and evaporated to give a red oil. Purification by flash chromatography on silica gel eluting with 30% ethyl acetate in hexane gave an oil which was dissolved in EtOH, stripped and dried in vacuo to give 0.082 g (25%) of the desired 4-[3-[[[3-(1,1,2,2-tetrafluoroethoxy) phenyl]methyl](3,3,3-trifluoro-2-hydroxypropyl)amino] phenoxy]phenol product as a light red oil. Anal. calcd. for C$_{24}$H$_{20}$NO$_4$F$_7$·0.35 EtOH·0.65H$_2$O: C, 54.21; H, 4.31; N, 2.56. Found: C, 54.20; H, 4.30; N, 2.55. HRMS calcd. 520.1359 [M+H]$^+$, found: 520.1325.$^1$H NMR (C$_6$D$_6$) δ 1.96 (d, 1H), 3.09 (dd, 1H), 3.43 (dd, 1H), 3.74 (m, 1H), 4.10 (s, 2H), 4.52 (s, 1H), 5.09 (tt, 1H), 6.17 (dd, 1H), 6.4 (m, 4H), 6.66 (d, 1H), 6.8–6.9 (m, 6H).

EXAMPLE 610

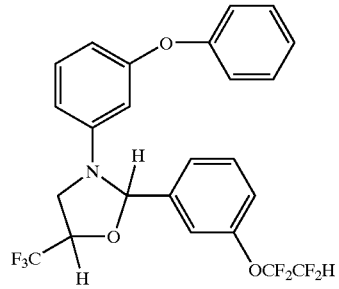

3-(3-phenoxyphenyl)-2-[3-(1,1,2,2-tetrafluoroethoxy)phenyl]-5-(trifluoromethyl) oxazolidine A toluene solution (5 mL) of 3-(1,1,2,2-tetrafluoroethoxy) benzaldehyde (0.45 g, 2.0 mol) and N-(3-phenoxyphenyl)-3-amino-1,1,1-trifluoro-2-propanol (0.60 g, 2.0 mmol) was refluxed in the presence of molecular sieves and ZnI$_2$ (~5 mg) for 18 h under N$_2$. The reaction mixture was filtered to remove the sieves, and the filtrate was diluted with ethyl acetate. The organic layer was washed with brine, dried (MgSO$_4$) and evaporated to give 0.92 g (92%) of the desired 3-(3-phenoxyphenyl)-2-[3-(1,1,2,2-tetrafluoro-ethoxy)phenyl]-5-(trifluoromethyl) oxazolidine product as a colorless oil. The formation of the desired product was monitored by the disappearance of the aldehyde peak (δ~10) in the $^1$H NMR spectrum. HRMS calcd. 502.1253 [M+H]$^+$, found: 502.1220.

EXAMPLE 611

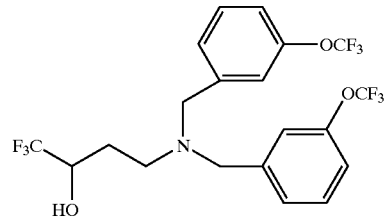

4-[bis-[[3-(trifluoromethoxy)phenyl]methyl]amino]-1,1,1-trifluoro-2-butanol

EX-611A) The 2-hydroxy-1,1,1-trifluorobutyronitrile (5.0 g, 36 mmol; H. C. Brown et al. *J. Org. Chem.* 60, 41–46, 1995) was added slowly to a stirred suspension of LiAlH$_4$ (1.7 g, 43.7 mmol) in 8 mL of dry diethyl ether at 0–5° C. The mixture was stirred at this temperature for 30 min, heated for 45 min, then stirred at room temperature for 2 h. The reaction mixture was quenched with 5.5 mL of aq. sat. Na$_2$SO$_4$ and stirred for 1 h. The mixture was filtered through a celite pad, and the pad was washed with ether. The filtrate and ether washings were collected and evaporated to give 4.2 g (82%) of crude 4-amino-2-hydroxy-1,1,1-trifluorobutane product as a brownish solid. HRMS calcd. for C$_4$H$_8$NOF$_3$: 144.0636 [M+H]$^+$, found 144.0622.

The 4amino-2-hydroxy-1,1,1-trifluorobutane (0.57 g, 4 mmol) from EX-611A and 3-(trifluoromethoxy)benzyl bromide (2.04 g, 8.0 mmol) were dissolved in 10 mL of anhydrous ethanol. Potassium carbonate (1.10 g, 8 mmol) was added, and the mixture was heated to reflux for 3 days, at which time HPLC analysis indicated the formation of product, as confirmed by MS. The reaction mixture was quenched with water and extracted with ether. The ether layer was washed with water and brine, then dried over MgSO$_4$, and evaporated to give crude product, which was purified by flash column chromatography on silica gel eluting with 1:10:0.01 to 1:7:0.01 of ethyl acetate::hexane:ammonium hydroxide to give 0.53 (27%) of the desired 4-[bis-[[3-(tri-fluoromethoxy)phenyl]methyl]amino]-1,1,1-trifluoro-2-butanol product as a yellow oil. $^1$H NMR (CDCl$_3$) δ 7.37 (t, 2H), 7.23 (d, 2H), 7.14 (d, 4H), 5.68 (bs, 1H), 3.98 (m, 1H), 3.76 (d, 2H), 3.45 (d, 2H), 2.78 (dd, 2H), 1.90 (m, 1H), 1.83 (m, 1H). $^1$F NMR (CDCl$_3$) δ −58.27 (s, 6F), −80.54 (d, 3F). HRMS calcd. for C$_{20}$H$_{18}$NO$_3$F$_9$: 492.1221 [M+H]$^+$, found: 492.1184.

EXAMPLE 612

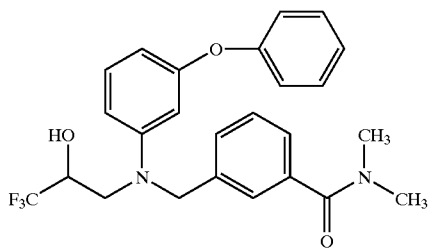

N,N-dimethyl-3-[[(3-phenoxyphenyl)(3,3,3-trifluoro-2-hydroxypropyl)amino]methyl]benzamide EX-612A) Methyl 3-(bromomethyl)benzoate (7.2 g, 0.031 mol) was added dropwise to a solution of 3-phenoxyaniline (20.5 g, 0.11 mol) in 160 mL of cyclohexane. The reaction mixture was refluxed overnight then cooled to room temperature and diluted with water and methylene chloride. The layers were separated, and the aqueous layer was extracted with methylene chloride. The combined organic layers were washed with brine, dried over Na$_2$SO$_4$, and concentrated in vacuo to give a dark oil. The crude product was purified by reverse phase HPLC eluting with 20% to 90% acetonitrile in water to afford 6.2 g (59%) of the desired methyl 3-[[(3-phenoxyphenyl)amino]methyl] benzoate product as a yellow oil. ESMS m/z=334 [M+H]$^+$.

EX-612B) To a mixture of methyl 3-[[(3-phenoxyphenyl)amino]methyl]benzoate (6.2 g, 0.019 mol) from EX-612A and 1,1,1-trifluoro-2,3-epoxypropane (8.58 g, 0.077 mol) in 12 mL of acetonitrile was added ytterbium (III) trifluoromethanesulfonate (1.2 g, 0.0019 mol). The resulting mixture was heated at 50° C. in a sealed glass tube for 18 h. The reaction mixture was cooled to room temperature, then diluted with water and methylene chloride. The aqueous layer was extracted with methylene chloride. The organic layers were combined, dried over MgSO$_4$, and concentrated in vacuo. The crude product was purified by column chromatography on silica gel eluting with 1:9 ethyl acetate in hexane to afford 8.0 g (96%) of the desired methyl 3-[[(3-phenoxy-phenyl)(3,3,3-trifluoro-2-hydroxypropyl)amino]methyl]benzoate product as a yellow oil. Anal. calcd. for C$_{24}$H$_{22}$F$_3$NO$_4$·1.4H$_2$O: C, 61.25; H, 5.31; N, 2.98. found: C, 61.52; H, 5.06; N, 2.89. HRMS calcd.: 446.1579 [M+H]$^+$, found: 446.1596. $^1$H NMR (CDCl3) δ 7.28 (m, 4H), 7.14 (t, 1H), 7.07, (m, 3H), 7.00 (s, 1H), 6.94 (d, 2H), 6.46 (dd, 1H), 6.38 (dd, 1H), 6.35 (t, 1H), 5.84 (t, 1H), 4.60 (t, 2H), 4.36 (m, 1H), 3.82 (d, 1H), 3.48 (m, 1H). $^{19}$F NMR (CDCl$_3$) δ −79.0 (d, 3F).

To a solution of N,N-dimethylamine hydrochloride (525 mg, 0.0064 mol) in 3.0 mL of toluene at −40° C. was added dropwise a 2.0 M solution of trimethylaluminum in toluene (3.2 mL, 0.0064 mol) over 15 min. The reaction mixture was warmed to room temperature and stirred for 2 h. To a solution of methyl 3-[[(3-phenoxyphenyl)(3,3,3-trifluoro-2-hydroxypropyl)amino]methyl] benzoate (209 mg, 0.00047 mol) from EX-612B in 2.5 mL of toluene at −10° C. was slowly added the (N,N-dimethylamino)-chloromethylaluminum reagent (850 μL, 0.00085 mol). The reaction mixture was warmed to room temperature then heated at 40° C. overnight. The reaction mixture was cooled to room temperature, then diluted with ethyl acetate and quenched with 10% aqueous potassium hydrogen phosphate. The organic layer was dried over MgSO$_4$ and concentrated in vacuo. The crude product was purified by column chromatography on silica gel eluting with 2:3 ethyl acetate in hexane to afford 195 mg (91%) of the desired N,N-dimethyl-3-[[(3-phenoxyphenyl)(3,3,3-trifluoro-2-hydroxypropyl) amino] methyl]-benzamide product as a pale yellow solid. Anal. calcd. for C$_{25}$H$_{25}$F$_3$N$_2$O$_3$·0.5H$_2$O: C, 64.23; H, 5.61; N, 5.99. Found: C, 64.49; H, 5.77; N, 5.85. HRMS calcd. 459.1896 [M+H]$^+$, found: 458.1887. $^1$H NMR (C$_6$D$_6$) δ 7.01–6.95 (m, 3H), 6.92–6.87 (m, 5H), 6.79 (t, 1H), 6.46 (s, 1H), 6.37 (t, 2H), 4.91 (bs, 1H), 4.26 (s, 2H), 4.10 (bq, 1H), 3.84 (dd, 1H), 3.38 (dd, 1H), 2.53 (bs, 3H), 2.14 (bs, 3H). $^{19}$F NMR (C$_6$D$_6$) δ −78.69 (d, 3F).

Additional examples of N,N-dialkyl- and N,N-cycloalkyl-3-[[(3-phenoxy-phenyl)-(3,3,3-trifluoro-2-hydroxypropyl) amino]methyl]benzamides can be prepared by one skilled in the art using similar methods, as shown in Example Table 36.

EXAMPLE TABLE 36

N,N-dialkyl- and N,N-cycloalkyl-3-[[3-phenoxyphenyl)-(3,3,3-trifluoro-2-hydroxypropyl)amino]methyl]benzamides.

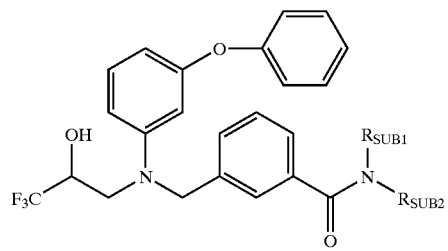

| Ex. No. | R$_{SUB1}$ | R$_{SUB2}$ | Calculated Mass [M + H]$^+$ | Observed Mass [M + H]$^+$ |
|---|---|---|---|---|
| 613 | methyl | ethyl | 473.2052 | 473.2055 |
| 614 | methyl | propyl | 487.2209 | 487.2193 |
| 615 | methyl | butyl | 501.2365 | 501.2357 |
| 616 | —(CH$_2$CH$_2$CH$_2$CH$_2$)— | | 485.2052 | 485.2057 |

EXAMPLE 617

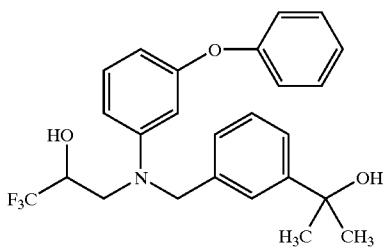

α,α-dimethyl-3-[[(3-phenoxyphenyl)(3,3,3-trifluoro-2-hydroxypropyl)amino]methyl]benzenemethanol To a solution of methyl 3-[[(3-phenoxyphenyl)(3,3,3-trifluoro-2-hydroxypropyl)amino]methyl]benzoate (218 mg, 0.00049 mol) in 0.7 mL of tetrahydrofuran at 0° C. was slowly added a 3.0 M solution of methylmagnesium chloride in THF (650 μL, 0.0020 mol). The reaction mixture was warmed to room temperature, stirred for 2 h, then diluted with diethyl ether and quenched with saturated aqueous ammonium chloride. The aqueous layer was extracted with dichloromethane, and the combined organic layers were dried over MgSO$_4$ and concentrated in vacuo. The crude product was purified by column chromatography on silica gel eluting with 1:4 ethyl acetate:hexane to afford 174 mg (80%) of the desired α,α-dimethyl-3-[[3-phenoxy-phenyl)(3,3,3-trifluoro-2-hydroxypropyl) amino]methyl]benzenemethanol product as a slightly yellow oil. Anal. calcd. for C$_{25}$H$_{26}$F$_3$NO$_3$·0.5H$_2$O: C, 66.07; H, 5.99; N, 3.08. found: C, 66.12; H, 6.34; N, 2.92. HRMS calcd. 466.1943 [M+H]$^+$, found: 446.1938. $^1$H NMR (CDCl$_3$) δ 7.34 (s, 1H), 7.32–7.21 (m, 4H), 7.13 (t, 1H), 7.09–7.01 (m, 2H), 6.94 (d, 2H), 6.50 (d, 1H), 6.41 (s, 1H), 6.37 (d, 1H), 4.61 (s, 2H), 4.27 (bt, 1H), 3.81 (appd, 1H), 3.53 (dd, 1H), 3.33 (bs, 1H), 1.96 (bs, 1H), 1.51 (s, 6H). $^{19}$F NMR (CDCl$_3$) δ −78.88 (d, 3F).

EXAMPLE 618

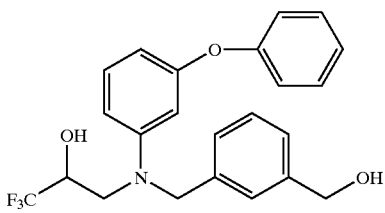

3-[[(3-phenoxyphenyl)(3,3,3-trifluoro-2-hydroxypropyl) amino]methyl]benzenemethanol To a solution of methyl 3-[[(3-phenoxyphenyl)(3,3,3-trifluoro-2-hydroxypropyl)amino]methyl]benzoate (197 mg, 0.00044 mol) in 2.0 mL of dichloromethane at −40° C. was slowly added a 1.0 M solution of lithium aluminum hydride in THF (1.1 mL, 0.0011 mol). The reaction mixture was stirred at −40° C. for 1 h, then diluted with ethyl acetate and quenched with water. The organic layer was dried over MgSO$_4$ and concentrated in vacuo. The crude material was determined to contain a significant amount of unreacted starting material by HPLC at this stage. The crude material was resubjected to the reaction conditions using 2 mL of anhydrous tetrahydrofuran and 1.0 M lithium aluminum hydride (1.3 mL, 0.0013 mol) at −40° C. for 1 h, then diluted with ethyl acetate and quenched with water. The aqueous layer was extracted with ethyl acetate, and the combined organic layers were dried over MgSO$_4$ and concentrated in vacuo. The crude product was purified by column chromatography on silica gel eluting with 2:3 ethyl acetate:hexane to afford 99 mg (54%) of the desired 3-[[(3-phenoxyphenyl)-(3,3,3-trifluoro-2-hydroxypropyl)amino]methyl] benzenemethanol product as a white solid. Anal. calcd. for C$_{23}$H$_{22}$F$_3$NO$_3$: C, 66.18; H, 5.31; N, 3.36. Found: C, 65.98; H, 5.39; N, 3.22. HRMS calcd. 418.1630 [M+H]$^+$, found: 418.1636. $^1$H NMR (C$_6$D$_6$) δ 7.08–6.92 (m, 8H), 6.89–6.80 (m, 2H), 6.56 (s, 1H), 6.46 (d, 1H). 6.38 (d, 1H), 4.26 (s, 2H), 4.21 (d, 2H), 3.77 (appq, 1H), 3.52 (d, 1H), 1.92 (bs, 1H), 0.96 (bs, 1H). $^{19}$F NMR (C$_6$D$_6$) δ −78.91 (d, 3F).

EXAMPLE 619

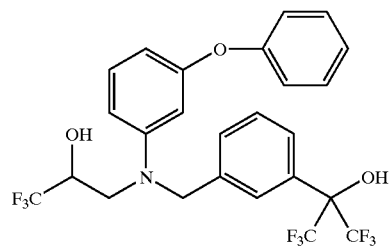

α,α-bis(trifluoromethyl)-3-[[(3-phenoxyphenyl)(3,3,3-trifluoro-2-hydroxypropyl)amino]methyl] benzenemethanol To a solution of methyl 3-[[(3-phenoxyphenyl)(3,3,3-trifluoro-2-hydroxypropyl)-amino]methyl]benzoate (331 mg, 0.00074 mol) and trimethyl(trifluoromethyl)silane (423 mg, 0.0030 mol) in 3.0 mL of toluene at room temperature was added a 1.0 M solution of tetrabutylammonium fluoride in THF (150 μL, 0.00015 mol) which had been dried over molecular sieves. The reaction mixture was heated at 40° C. for 18 h. HPLC analysis indicated incomplete reaction therefore additional trimethyl(trifluoromethyl)silane (440 μL, 0.0030 mol) and tetrabutylammonium fluoride (150 μL, 0.00015 mol) were added, and the reaction mixture was heated to 50° C. in a sealed glass vial. After 2 h, HPLC analysis indicated no ester starting material remained. The reaction mixture was quenched with water and extracted with dichloromethane. The organic layer was dried over MgSO$_4$ and concentrated in vacuo. The crude product was purified by column chromatography on silica gel eluting with 1:9 ethyl acetate:hexane to afford 26 mg (6%) of the desired α,α-bis(trifluoromethyl)-3-[[(3-phenoxyphenyl)(3,3,3-trifluoro-2-hydroxypropyl) amino]methyl] benzenemethanol product as a yellow-brown oil. HRMS calcd. for C$_{25}$H$_{20}$F$_9$NO$_3$: 554.1378 [M+H]$^+$, found: 554.1385. $^1$H NMR (CDCl$_3$) δ 7.69 (dd, 1H), 7.57 (apps, 1H), 7.52 (dd, 1H), 7.37 (t, 1H), 7.29–7.23 (m, 2H), 7.14 (t, 1H), 7.05 (t, 1H), 6.92 (d, 2H), 6.47 (d, 1H), 6.38 (d, 1H), 6.37 (s, 1H), 4.66 (s, 2H), 4.29 (m, 1H), 3.82 (d, 1H), 3.54 (dd, 1H). $^{19}$F NMR (CDCl$_3$) δ −75.81 (dq, 6F), −79.18 (d, 3F).

EXAMPLE 620

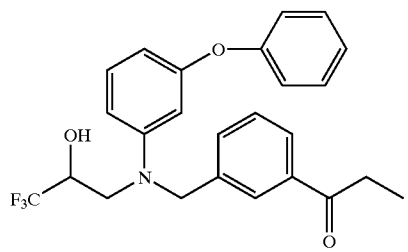

1-[3-[[3-phenoxyphenyl)(3,3,3-trifluoro-2-hydroxypropyl)-amino]methyl]phenyl]-1-propanone EX-620A) To a slurry of methyl 3-[[(3-phenoxyphenyl)(3,3,3-trifluoro-2-hydroxypropyl)amino]methyl]benzoate (1.03 g, 0.0023 mol) and N, O-dimethyl-hydroxylamine hydrochloride (386 mg, 0.0040 mol) in 4.6 mL of tetrahydrofuran at −15° C. was added a 2.0 M solution of isopropylmagnesium chloride in THF (4.6 mL, 0.0092 mol) over 15 min. The reaction was stirred for 1 h at −15° C., then quenched with 20% aqueous ammonium chloride and extracted with ethyl acetate. The organic layers were dried over $Na_2SO_4$ and concentrated in vacuo. The crude product was purified by column chromatography on silica gel eluting with 1:1 ethyl acetate:hexane to afford 0.72 g (66%) of the desired N-methoxy-N-methyl-3-[[(3-phenoxyphenyl)-(3,3,3-trifluoro-2-hydroxypropyl)amino]methyl]benzamide product as an off-white solid. HRMS calcd. for $C_{25}H_{25}N_2O_4F_3$: 475.1845 $[M+H]^+$, found: 475.1840.

To a solution of N-methoxy-N-methylbenzamide (208 mg, 0.00044 mol) from EX-620A in 2.2 mL of tetrahydrofuran at −15° C. was added a 1.0 M solution of ethylmagnesium bromide in THF (950 μL, 0.0095 mol). The reaction mixture was slowly warmed to room temperature then left stirring overnight. HPLC analysis indicated unreacted starting material was still present so additional ethylmagnesium bromide (440 μL, 0.0044 mol) was added. After 3 h at room temperature, the reaction mixture was diluted with diethyl ether and quenched with 1 N HCl. The aqueous layer was extracted with diethyl ether and the combined organic layers were dried over $MgSO_4$ and concentrated in vacuo. The crude product was purified by column chromatography on silica gel eluting with 1:4 ethyl acetate in hexane to afford 121 mg (62%) of the desired 1-[3-[[(3-phenoxyphenyl)(3,3,3-trifluoro-2-hydroxypropyl)-amino]methyl]phenyl]-1-propanone product as a pale yellow oil. HRMS calcd. for $C_{25}H_{24}F_3NO_3$: 444.1787 $[M+H]^+$, found: 444.1786. $^1H$ NMR ($CDCl_3$) δ 7.83 (d, 1H), 7.78 (s, 1H), 7.38 (appq, 2H), 7.27 (appq, 2H), 7.15 (t, 1H), 7.06 (t, 1H), 6.94 (d, 2H), 6.48 (d, 1H), 6.39 (d, 1H), 6.37 (s, 1H), 4.68 (s, 2H), 4.35 (m, 1H), 3.88 (dd, 1H), 3.56 (dd, 1H), 2.95 (q, 2H), 1.20 (t, 3H). $^{19}F$ NMR ($CDCl_3$) δ −79.17 (d, 3F).

Additional examples of 1-[3-[[(3-phenoxyphenyl)(3,3,3-trifluoro-2-hydroxypropyl)amino]methyl]-phenyl]-1-alkanones can be prepared by one skilled in the art using similar methods, as shown in Example Table 37.

EXAMPLE TABLE 37

1-[3-[[(3-phenoxyphenyl)(3,3,3-trifluoro-2-hydroxypropyl)amino]methyl]-phenyl]-1-alkanones.

| Ex. No. | $R_{SUB}$ | Calculated Mass $[M + H]^+$ | Observed Mass $[M + H]^+$ |
|---|---|---|---|
| 621 | isobutyl | 472.2130 | 472.2100 |

EXAMPLE 622

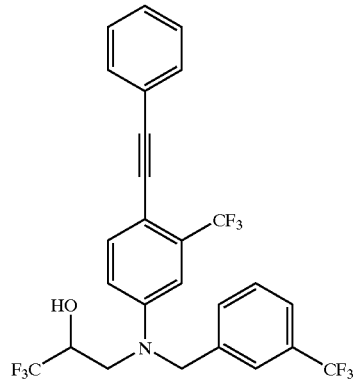

3-([4-(phenylethynyl)-(3-(trifluoromethyl)phenyl]
[[3-(trifluoromethyl)phenyl]methyl]amino]-1,1,1-trifluoro-2-propanol The 3-[(3-(trifluoromethyl)-4-bromophenyl)][[3-(1,1,1-trifluoromethyl)phenyl]methyl]amino]-1,1,1-trifluoro-2-propanol (0.33 g, 0.648 mmol) and tributylstannylphenylacetylene (0.278 g, 0.712 mmol) were added to degassed 1,2-dichloroethane. The resulting mixture was stirred at room temperature for 10 min, then $Pd(PPh_3)_2Cl_2$ (0.032 g. 0.045 mmol) was added. The mixture was stirred 18 h at room temperature. More tributyl-stannylphenylacetylene (0.278 g, 0.712 mmol) and $Pd(PPh_3)_2Cl_2$ (0.032 g, 0.045 mmol) were added. The solution was refluxed for 72 h. The reaction mixture was diluted with diethyl ether and stirred in 10% aq. KF for 18 h. The organic layer was collected, dried over $MgSO_4$ and concentrated. The crude product was purified by flash column chromatography on silica gel eluting with 1:4 ethyl acetate in hexane to give 0.102 g (30%) of the desired 3-[[+(phenylethynyl)-(3-(trifluoromethyl)phenyl]-[[3-(trifluoromethyl)phenyl]methyl]amino]-1,1,1-trifluoro2-propanol product as a pure yellow oil. Anal calcd. For $C_{26}H_{18}NOF_9$: C, 58.76; H, 3.41; N, 2.64. Found: C, 58.72; H, 3.67; N, 2.47. HRMS calcd. 532.1322 $[M+H]^+$, found: 532.1304. $^1H$ NMR ($CDCl_3$) δ 7.52 (m, 4H), 7.38 (dd, 2H), 7.32 (dd, 2H), 7.24 (dd, 1H), 7.00 (s, 1H), 6.78 (dd, 1H), 4.80 (s, 2H), 4.36 (m, 1H), 3.92 (d, 1H), 3.65 (m, 1H), 2.60 (d, 1H). $^{19}F$ NMR ($CDCl_3$) δ −63.5 (s, 6F), −79.38 (d, 3F).

Additional examples of 3-[[4-(heteroaryl)-(3-(trifluoromethyl)phenyl][[3-(trifluoromethyl)phenyl]methyl]amino]-1,1,1-trifluoro-2-propanols can be prepared by one skilled in the art using similar methods, as shown in Example Table 38.

EXAMPLE TABLE 38

3-[[4-(heteroaryl)-(3-(trifluoromethyl)phenyl]-[[3-(trifluoromethyl)phenyl]methyl]amino]-1,1,1-trifluoro-2-propanols.

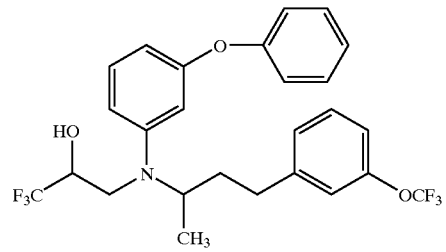

| Ex. No. | R$_{SUB}$ | Calculated Mass [M + H]$^+$ | Observed Mass [M + H]$^+$ |
|---|---|---|---|
| 623 | 2-thienyl | 514.0887 | 514.0912 |
| 624 | 2-furanyl | 498.1037 | 498.1116 |

EXAMPLE 625

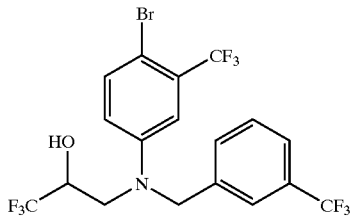

3-[4-bromo-3-(trifluoromethyl)phenyl[[3-(trifluoromethyl)-phenyl]methyl]amino]-1,1,1-trifluoro-2-propanol EX-625A) The α,α,α-trifluoro-m-tolualdehyde (3.63 g, 0.021 mol) was added neat to 4-bromo-3-trifluoromethylaniline (5.0 g, 0.021 mol). Dichloroethane (50 mL) was added followed by sodium triacetoxyborohydride (4.85 g, 0.023 mol) and acetic acid (1.42 g, 0.024 mol). The resulting mixture was stirred at room temperature for 18 h, then diluted with methylene chloride, quenched with sodium bicarbonate and extracted with methylene chloride. The organic layers were combined and dried over MgSO$_4$ and concentrated to give 6.97 g of the desired 3-(4-bromo-3-(trifluoromethyl)-phenyl[[3-(trifluoromethyl) phenyl]methyl]amine product as a yellow oil, which was carried forward without purification. ESMS m/z=397 [M+H]$^+$.

The amine product (6.97 g, 0.018 mol) from EX-625A was mixed with 1,1,1-trifluoro-2,3-epoxypropane (3.92 g, 0.035 mol) in a pressurized vial. A suspension of ytterbium triflate (1.08 g, 0.002 mol) in 2.0 mL of acetonitrile was added. The resulting mixture was stirred at room temperature for 18 h, then quenched with water and extracted with ethyl acetate. The crude product was purified by flash column chromatography on silica gel eluting with 1:4 ethyl acetate in hexane to give 1.04 g (11%) of the desired 3-[4-bromo-3-(trifluoromethyl) phenyl[[3-(trifluoromethyl)-phenyl]methyl]amino]-1,1,1-trifluoro-2-propanol product as a pure yellow oil. Anal calcd. for C$_{18}$H$_{13}$NOF$_9$Br: C, 42.38; H, 2.57; N, 2.75. Found: C, 42.16; H, 2.71; N, 2.71. HRMS calcd. 510.0115 [M+H]$^+$, found: 510.0139. $^1$H NMR (C$_6$D$_6$) δ 7.40 (d, 2H), 7.20 (d, 1H), 7.10 (m, 2H), 6.98 (d, 1H), 6.18 (dd, 1H), 4.00 (s, 2H), 3.63 (m, 1H), 3.40 (d, 1H), 3.02 (m, 1H), 1.80 (d, 1H). $^{19}$F NMR (C$_6$D$_6$) δ −62.35 (s, 3F), −65.00 (s, 3F), −78.58 (d,3F).

EXAMPLE 626

3-[[1-methyl-3-[3-(trifluoromethoxy)phenyl]propyl](3-phenoxyphenyl)amino]-1,1,1-trifluoro-2-propanol EX-626A) Tetrabutylammonium iodide (0.4 g, 0.05 mol) was added to a well-stirred biphasic mixture of 12 mL of 50% NaOH and 20 mL of methylene chloride under a nitrogen atmosphere. A solution of 3-trifluoromethoxybenzaldehyde (4.0 g, 0.021 mol) and diethyl (2-oxopropyl)phosphonate (4.08 g, 0.021 mol) in 4.0 mL of methylene chloride was added dropwise to the stirred solution. The resulting mixture was stirred at room temperature for 15 min, then quenched with water and extracted with hexane. The hexane layer was dried over MgSO$_4$. The crude product was purified by flash column chromatography on silica gel eluting with 1:10 ethyl acetate in hexane to give 2.6 g (54%) of the desired 4-[3-(trifluoromethoxy)phenyl]-3-buten-2-one product as a yellow oil. $^1$H NMR (CDCl$_3$) δ 7.43 (m, 4H), 7.20 (d, 1H), 6.65 (d, 2H), 2.29 (s, 3H). $^{19}$F NMR (CDCl$_3$) δ −62.05 (s, 3F).

EX-626B) The product (1.0 g, 0.0004 mol) from EX-626A was dissolved in 25 mL of ethanol and the reaction vessel was charged with nitrogen. Palladium (10% on carbon) (0.30 g, 30%) was added to the solution. The mixture was hydrogenated for 3 h at room temperature. The palladium was filtered off through a celite pad. The filtrate was concentrated to give 0.79 g (85%) of the desired 4[3-(trifluoromethoxy)phenyl]-butan-2-one as a yellow oil. ESMS m/z=232 [M+H]$^+$.

EX-626C) In a flask equipped with a stir bar and molecular sieves, a solution of 3-phenoxyaniline (1.1 g, 0.0059 mol) in 15 mL of cyclohexane was prepared under nitrogen. A solution of the ketone (1.3 g, 0.006 mol) product from EX-626B dissolved in 5 mL of cyclohexane was added. The mixture was refluxed for 18 h, filtered and concentrated to give the desired imine product as a dark yellow oil. ESMS m/z=400 [M+H]$^+$.

EX-626D) The imine product (1.3 g, 0.003 mol) from EX-626C was stirred with 5 mL of methanol at 0° C. Sodium borohydride (0.23 g, 0.005 mol) was added to the mixture, and the mixture was stirred at room temperature for 18 h. The mixture was acidified with 4 mL of 3% HCl and extracted with diethyl ether. The ether layers were combined, dried over MgSO$_4$ and concentrated to give 1.07 g (81%) of the desired 3-[1-methyl-3-[3-

(trifluoromethoxy)phenyl]propyl](3-phenoxyphenyl) amine product as an orange oil. ESMS m/z=402 [M+H]+.

The 3-[1-methyl-3-p3-(trifluoromethoxy)phenyl]propyl](3-phenoxyphenyl)amine (1.0 g, 0.002 mol) product from EX-626D and 1,1,1-trifluoro-2,3-epoxypropane (0.56 g, 0.005 mol) were heated at 90° C. for 18 h. Excess epoxide was evaporated. The crude product was purified by flash column chromatography on silica gel eluting with 1:13 ethyl acetate in hexane to give 0.16 g (13%) of the desired 3-[[1-methyl-3-[3-(trifluoromethoxy)phenyl]propyl](3-phenoxyphenyl) amino]-1,1,1-trifluoro-2-propanol product as a yellow oil. Anal calcd. for $C_{26}H_{25}NO_3F_6$: C, 60.82; H, 4.91; N, 2.72. Found: C, 60.63; H, 4.89; N, 2.70. HRMS calcd. 514.1816 [M+H]+, found: 514.1789. $^1H$ NMR ($C_6D_6$) δ 7.28 (m, 4H), 7.14 (t, 1H), 7.07, (m, 3H), 7.00 (s, 1H), 6.94 (d, 2H), 6.46(dd, 1H), 6.38 (dd, 1H), 6.35 (t, 1H), 4.18 (m, 1H), 3.78 (m, 1H), 3.52 (dd, 1H), 3.28 (m, 1H), 2.76 (s, 1H), 2.53 (m, 2H), 1.92 (m, 1H), 1.63 (m, 1H), 1.24 (m, 3H). $^{19}F$ NMR (CDCl$_3$) δ −56.84 (s, 3F), −79.0 (s, 3F).

EXAMPLE 627

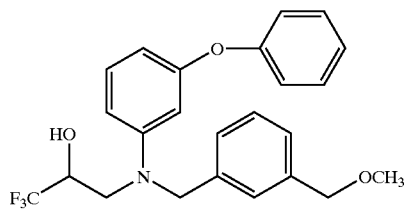

3-[[(3-phenoxyphenyl) (3,3,3-trifluoro-2-hydroxypropyl) amino]methyl] methoxymethylbenzene EX-627A) A suspension of N-bromosuccinimide (17.6 g, 0.099 mol) in carbon tetra-chloride was added to a stirring solution of m-xylene in carbon tetrachloride. Then 2,2'-azobisisobutyronitrile catalyst (0.71 g, 0.004 mol) was added. The resulting mixture was refluxed for 2 h, then quenched with 50 mL of water. The organic layer was collected, washed with water followed by brine, dried over MgSO$_4$ and concentrated to give 2.0 g (16%) of the desired crude 1,3-dibromoxylene product. ESMS m/z=264 [M+H]+.

EX-627B) The 1,3-dibromoxylene (2.0 g, 0.0076 mol) from EX-627A and sodium methoxide (2.45 g, 0.045 mol) were mixed in 25 mL of MeOH. The resulting mixture was stirred at room temperature for 18 h, concentrated, dissolved in methylene chloride and washed with water. The organic layer was further washed with brine and dried over MgSO$_4$ and concentrated to give 0.912 g (72%) of the desired 1,3-di-(methoxy-methyl)benzene product as a yellow oil. ESMS m/z=166 [M+H]+.

EX-627C) The diether product (0.90 g, 0.0054 mol) from EX-627B was stirred in a mixture of 10:1 methylene chloride:water. To this was added 2,3-dichloro-5,6-dicyano-benzoquinone (1.84 g, 0.0081 mol). The resulting biphasic mixture was stirred at room temperature for 72 h. The mixture was then washed with saturated sodium bicarbonate followed by brine, dried over MgSO$_4$ and concentrated. The crude product was purified by flash column chromatography on silica eluting with 1:4 ethyl acetate:hexane to give 0.430 g (53%) of the desired 3-(methoxymethyl)benzaldehyde product as a pink oil. $^1H$ NMR (CDCl$_3$) δ 10.00 (s, 1H), 7.89 (s, 1H), 7.83 (d, 1H), 7.63 (d, 1H), 7.51 (t, 1H), 4.58 (s, 2H), 3.40 (s, 3H).

EX-627D) The 3-(methoxymethyl)benzaldehyde (0.430 g, 2.87 mmol) from EX-627C was added to a stirring solution of 3-phenoxyaniline (0.530 g, 2.87 mmol) in 5 mL of dichloromethane. Then sodium triacetoxyborohydride (0.670 g, 3.16 mmol) was added followed by acetic acid (0.196 g, 3.27 mmol). The resulting mixture was stirred at room temperature 18 h, then diluted in methylene chloride and quenched with sodium bicarbonate. The organic layer was washed with brine, dried over MgSO$_4$ and concentrated to give 0.870 g (95%) of the desired N-3-(phenoxyphenyl)-[[3-(methoxymethyl)phenyl]methyl]amine product as a pink oil. ESMS m/z=320 [M+H]+.

The N-3-(phenoxyphenyl)-[[3-(methoxymethyl)phenyl]methyl]amine product (0.87 g, 0.003 mol) from EX-627D was mixed with 1,1,1-trifluoro-2,3-epoxypropane (0.61 g, 0.005 mol), in a pressurized vial. A suspension of ytterbium triflate (0.16 g, 0.272 mmol) in 0.5 mL of acetonitrile was added. The resulting mixture was stirred at room temperature for 18 h, then quenched with water and extracted with ethyl acetate. The crude product was purified by flash column chromatography on silica gel eluting with 1:4 ethyl acetate:hexane to give 0.35 g (30%) of the desired 3-[[(3-phenoxyphenyl)-(3,3,3-trifluoro-2-hydroxypropyl)amino]methyl]methoxymethylbenzene product as a pure yellow oil. Anal calcd. for $C_{24}H_{24}NO_3F_3 \cdot 0.5H_2O$: C, 65.18; H, 5.61; N, 3.17. Found: C, 65.19; H, 5.36; N, 3.13. HRMS calcd. 432.1786 [M+H]+, found: 432.1803. $^1H$ NMR ($C_6D_6$) δ 6.82 (m, 7H), 6.60 (dd, 1H), 6.42 (dd, 1H), 6.38 (s, 1H), 6.18 (dd, 1H), 4.00 (s, 2H), 3.63 (m, 1H), 3.40 (d, 1H), 3.02 (m, 1H), 1.80 (d, 1H). $^{19}F$ NMR ($C_6D_6$) δ −78.55 (s, 3F).

EXAMPLE 628

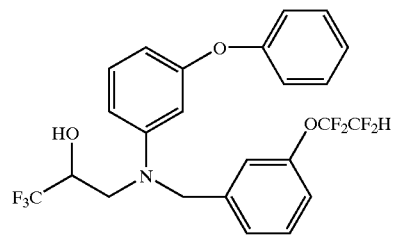

3-[(3-phenoxyphenyl)[[3-(1,1,2,2-tetrafluoroethoxy)phenyl]methyl]amino]-1,1,1-trifluoro-2-propanol EX-628A) To a solution of 3-(1,1,2,2-tetrafluoroethoxy) toluene (50 g, 0.24 mol) and N-bromosuccinimide (42.75 g, 0.24 mol) in 100 mL of carbon tetrachloride under nitrogen was added 2,2'-azobisisobutyronitrile (0.71 g, 0.004 mol). The resultant mixture was refluxed for 2 h then cooled to room temperature and quenched with 300 mL of water. The organic layer was collected, washed with water and brine, dried over MgSO$_4$, and concentrated in vacuo to give 66.0 g (96%) of the desired crude 3-(1,1,2,2-tetrafluoroethoxy)bromomethylbenzene product as a yellow oil. $^1H$ NMR indicates that this oil is a mixture of products: 7% dibrominated, 67% monobrominated, and 20% starting material. The crude product was used without further purification. ESMS m/z=287 [M+H]+.

EX-628B) The crude product (56 g, 0.14 mol) from EX-628A in 200 mL of cyclohexane was added dropwise under nitrogen to a solution of 3-phenoxyaniline (89 g, 0.480 mol) in 500 mL of cyclohexane. The reaction mixture was refluxed overnight, then cooled to room temperature and diluted with water and diethyl ether. The layers were separated, and the aqueous layer was extracted with diethyl ether. The combined organic layers were dried over MgSO$_4$ and concentrated in vacuo to give a dark oil. The crude product was purified by column chromatography on silica gel eluting with 1:4 ethyl acetate in hexane to afford 44.96 g (83%) of the desired N-3-(phenoxyphenyl)-[[3-(1,1,2,2-tetrafluoroethoxy)phenyl]methyl]amine product as a yellow oil. ESMS m/z=392 [M+H]$^+$. To a mixture of the amine product (15.0 g, 0.038 mol) from EX-628B and 1,1,1-tri-fluoro-2,3-epoxypropane (8.58 g, 0.077 mol) was added a suspension of ytterbium (III) trifluoromethanesulfonate (2.37 g, 0.0031 mol) in 15 mL of acetonitrile. The resulting mixture was heated at 50° C. in a sealed glass vial for 1.5 h. The reaction mixture was cooled to room temperature then diluted with water and ethyl acetate and extracted. The organic layers were combined, dried over MgSO$_4$, and concentrated in vacuo. The crude product was purified by column chromatography on silica gel eluting with 1:4 ethyl acetate in hexane to afford 12.03 g (62%) of the desired 3-[(3-phenoxyphenyl)-[[3-(1,1,2,2-tetrafluoroethoxy)phenyl]methyl]amino]-1,1,1-trifluoro-2-propanol product as a yellow oil. Anal. calcd. for C$_{24}$H$_{20}$F$_7$NO$_3$: C, 57.26; H, 4.00; N, 2.78. Found: C, 56.96; H, 4.35; N, 2.69. HRMS calcd. 504.1410 [M+H]$^+$, found: 504.1431. $^1$H NMR (CDCl$_3$) δ 7.28 (m, 4H), 7.14 (t, 1H), 7.07, (m, 3H), 7.00 (s, 1H), 6.94 (d, 2H), 6.46 (dd, 1H), 6.38 (dd, 1H), 6.35 (t, 1H), 5.84 (t, 1H), 4.60 (t, 2H), 4.36 (m, 1H), 3.82 (d, 1H), 3.48 (m, 1H), 2.51 (s, 1H). $^{19}$F NMR (CDC$_3$) δ −79.0 (s, 3F), −88.21 (d, 2F), −137.05 (dd, 2F).

EXAMPLE 629

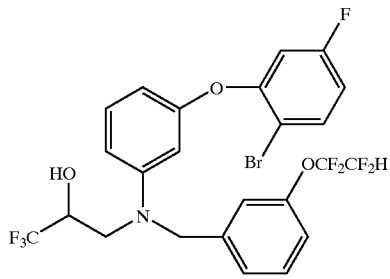

3-[[3-(2-bromo-5-fluorophenoxy)phenyl][[3-(1,1,2,2-tetrafluoroethoxy)phenyl]methyl]amino]-1,1,1-trifluoro-2-propanol EX-629A) 3-Aminophenol (5 g, 46 mmol), 1-bromo-2,4-difluorobenzene (10 g, 50 mmol) and Cs$_2$CO$_3$ (16 g, 50 mmol) were mixed in 25 mL of dimethylformamide. Solid (CuOTf)$_2$C$_6$H$_6$ (100 mg) was added, and the mixture was stirred under nitrogen at 85° C. for 22 h, at which time HPLC analysis indicated that the reaction had gone to completion and formed two products. The DMF was removed under reduced pressure. The residue was diluted with ether and filtered through a celite pad. The pad was washed with ether and a small amount of water. The mixture was extracted with ether several times. The combined ether layers were washed with water and brine, then dried over MgSO$_4$. The dried organic layer was evaporated to give 10.2 g (80%) of the desired product, which consisted of a 11:1 ratio of 3-(2-bromo-5-fluorophenoxy)-aniline and 3-(4-bromo-3-fluorophenoxy)aniline. The crude product was purified by flash column chromatography on silica gel eluting with 1:7:0.01 of ethyl acetate:hexane:ammonium hydroxide to give 8.8 g (68%) of the desired product as a yellow oil, which was a 25:1 ratio of 3-(2-bromo-5-fluorophenoxy)aniline and 3-(4-bromo-3-fluorophenoxy)aniline. HRMS calcd. for C$_{12}$H$_9$NOFBr: 281.9930 [M+H]$^+$, found: 281.9950.

EX-629B) The crude 3-(2-bromo-5-fluorophenoxy)aniline (1.39 g, 4.95 mmol) product from EX-629A and 3-(1,1,2,2-tetrafluoroethoxy)benzaldehyde (1.0 g, 4.5 mmol) were dissolved in 15 mL of dichloroethane and acetic acid (0.30 mL, 5.4 mmol), then solid NaBH(OAc)$_3$ (1.26 g, 5.9 mmol) was added. The mixture was stirred at room temperature for 1 h, then quenched with water and extracted with ether. The ether layer was washed with water and brine, then dried over MgSO$_4$, and evaporated to give 2.1 g (97%) of crude product, which was purified by flash column chromatography on silica gel eluting with 1:7:0.01 of ethyl acetate:hexane:ammonium hydroxide to give 2.0 g (91%) of the desired 3-[3-(2-bromo-5-fluorophenoxy)phenyl][[3-(1,1,2,2-tetrafluoroethoxy)phenyl]methyl]amine product, as a light yellow oil, >90% pure by HPLC analysis. HRMS calcd. for C$_{21}$H$_{15}$NO$_2$BrF$_5$: 488.0285 [M+H]$^+$, found: 488.0269.

The 3-[3-(2-bromo-5-fluorophenoxy)phenyl][[3-(1,1,2,2-tetrafluoroethoxy) phenyl]-methyl]amine (0.97 g, 2.0 mmol) product from EX-629B and 1,1,1-trifluoro-2,3-epoxypropane (0.45 g, 4.0 mmol) were dissolved in 1.0 mL of acetonitrile. Ytterbium (III) trifluoromethanesulfonate (0.12 g, 0.2 mmol) was added, and the stirred solution was warmed to 40° C. for 1 h, at which time HPLC analysis indicated that no secondary amine starting material remained. The reaction was quenched with water and extracted with ether. The ether layer was washed with water and brine, then dried over MgSO$_4$. The crude product was purified by flash column chromatography on silica gel eluting with 1:7:0.01 of ethyl acetate:hexane:ammonium hydroxide to give 0.83 g (69%) of the desired 3-[[3-(2-bromo-5-fluorophenoxy)phenyl][[3-(1,1,2,2-tetrafluoroethoxy) phenyl]-methyl]amino]-1,1,1-trifluoro-2-propanol product as a clear colorless oil, >95% pure by HPLC analysis. $^1$H NMR (CDCl$_3$) δ 7.50 (dd, 1H), 7.30 (t, 1H), 7.18 (t, 1H), 7.07 (t, 2H), 6.99 (s, 1H), 6.70 (dt, 1H), 6.56 (dd, 1H), 6.52 (dd, 1H), 6.38 (dd, 1H), 6.32 (m, 1H), 5.87 (tt, 1H), 4.65 (d, 2H), 4.33 (m, 1H), 3.85 (dd, 1H), 3.56 (dd, 1H), 2.48 (bs, 1H). NOE difference spectra confirmed that the isolated material was the indicated N-[3-(2-bromo-5-fluorophenoxy)phenyl]-3-aminopropanol product. $^{19}$F NMR (CDCl$_3$) δ −79.24 (d, 3F), −88.57 (m, 2F), −112.04 (q, 1H), −137.16 (dt, 2F). Anal. calcd. for C$_{24}$H$_{18}$NO$_3$BrF$_8$: C, 48.02; H, 3.02; N, 2.33. Found: C, 48.48; H, 3.18; N, 2.33. HRMS calcd. 600.0420 [M+H]$^+$, found: 600.0415.

EXAMPLE 630

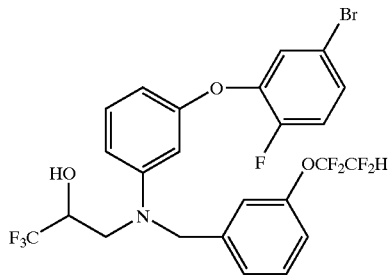

3-[[3-(-5-bromo-2-fluorophenoxy)phenyl]][3-(1,1,2,
2-tetrafluoro-ethoxy)phenyl]methyl]amino]-1,1,1-
trifluoro-2-propanol EX-630A) 3-Aminophenol (5 g, 46 mmol), 1-bromo-3,4-difluorobenzene (10 g, 50 mmol) and $Cs_2CO_3$ (16 g, 50 mmol were mixed in 25 mL of DMF. Solid (CuOTf)$_2C_6H_6$ (100 mg) was added, and the mixture was stirred under nitrogen at 85° C. for 22 h, at which time HPLC analysis indicated that the reaction had gone to completion and formed two products. The DMF was removed under reduced pressure. The residue was diluted with ether and filtered through a celite pad. The pad was washed with ether and a small amount of water. The mixture was extracted with ether several times. The combined ether layers were washed with water and brine, then dried over $MgSO_4$. The dried organic layer was evaporated to give 7.5 g (58%) of the desired products, which comprised a 10:1 ratio of 3-(5-bromo-2-fluorophenoxy)aniline and 3-(4-bromo-2-fluorophenoxy) aniline. The crude product was purified by flash column chromatography on silica gel eluting with 1:7:0.01 of ethyl acetate:hexane:ammonium hydroxide to give 4.5 g (35%) of the desired products as a yellow oil, which were a 20:1 ratio of 3-(5-bromo-2-fluorophenoxy)aniline and 3-(4-bromo-2-fluorophenoxy)-aniline. HRMS calcd. for $C_{12}H_9NOFBr$: 281.9930 [M+H]$^+$, found 281.9951.

EX-630B) The crude 3-(5-bromo-2-fluorophenoxy)aniline (1.39 g, 4.95 mmol) product from EX-630A and 3-(1,1,2,2-tetrafluoroethoxy)benzaldehyde (1.0 g, 4.5 mmol) were dissolved in 15 mL of dichloroethane and acetic acid (0.30 mL, 5.4 mmol), then solid $NaBH(OAc)_3$ (1.26 g, 5.9 mmol) was added. The mixture was stirred at room temperature for 1 h, then quenched with water and extracted with ether. The ether layer was washed with water and brine, then dried over $MgSO_4$, and evaporated to give 2.1 g (97%) of crude product, which was purified by flash column chromatography on silica gel eluting with 1:7 ethyl acetate:hexane to give 2.0 g (91%) of the desired 3-[3-(5-bromo-2-fluorophenoxy)phenyl][[3-(1,1,2,2-tetrafluoroethoxy)phenyl]methyl]amine product, as a yellow oil, >95% pure by HPLC analysis. Anal. calcd. for $C_{21}H_{15}NO_2BrF_2$: C, 51.66; H, 3.10; N, 2.87. Found: C, 51.90; H, 3.08; N, 2.86. HRMS calcd. 488.0284 [M+H]$^+$, found 488.0281.

The amine (1.1 g, 2.26 mmol) product from EX-630B and 1,1,1-trifluoro-2,3-epoxypropane (0.38 g, 3.39 mmol) were dissolved in 1 mL of acetonitrile. Ytterbium (III) trifluoromethanesulfonate (0.14 g, 0.23 mmol) was added, and the stirred solution was warmed to 40° C. for 1 h, at which time HPLC analysis indicated that no secondary amine starting material remained. The reaction was quenched with water and extracted with ether. The ether layer was washed with water and brine, then dried over $MgSO_4$. The crude product was purified by flash column chromatography on silica gel eluting with 1:7 ethyl acetate:hexane to give 0.5 g (37%) of the desired 3-[[3-(5-bromo-2-fluorophenoxy)phenyl][[3-(1,1,2,2-tetrafluoroethoxy)phenyl]methyl]amino]-1,1,1-tri-fluoro-2-propanol product as a yellow oil, >95% pure by HPLC analysis. $^1$H NMR (CDCl$_3$) δ 7.50 (t, 1H), 7.20 (dd, 1H), 7.17 (dd, 1H), 7.17 (dd, 1H), 7.09 (t, 2H), 7.00 (dd, 2H), 6.52 (dd, 1H), 6.38 (dd, 1H), 6.37 (s, 1H), 5.87 (tt, 1H), 4.64 (s, 2H), 4.33 (m, 1H), 3.85 (dd, 1H), 3.56 (dd, 1H). $^{19}$F NMR (CDCl$_3$) δ -79.20 (d, 3F), -88.55 (m, 2F), -113.04 (m, 1H), -137.05 (dt, 2F). NOE difference and pcosy spectra confirmed that the isolated material was the indicated N-[3-(5-bromo-2-fluorophenoxy)phenyl]-3-aminopropanol product. Anal. calcd. for $C_{24}H_{18}NO_3BrF_8$: C, 48.02; H, 3.02; N, 2.33. Found: C, 48.07; H, 3.14; N, 2.31. HRMS calcd. 600.0420 [M+H]$^+$, found: 600.0404.

EXAMPLE 631

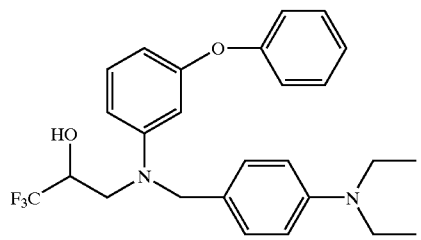

3-[(3-phenoxyphenyl)[[4-(N,N-diethylamino)
phenyl]methyl]amino]-1,1,1-trifluoro-2-propanol EX-631A) The 3-phenoxyaniline aniline (0.74 g, 4.0 mmol) and 4-(N,N-diethylamino) benzaldehyde (0.59 g, 3.3 mmol) were dissolved in 10 mL of dichloroethane and acetic acid (0.22 mL, 4.0 mmol). Then solid $NaBH(OAc)_3$ (0.94 g, 4.4 mmol) was added. The mixture was stirred at room temperature for 1 h, then quenched with water and extracted with ether. The ether layer was washed with water and brine, then dried over $MgSO_4$, and evaporated to give 1.3 g of crude product, which was purified by flash column chromatography on silica gel eluting with 1:7 ethyl acetate:hexane to give 1.0 g (87%) of the desired 3-[(3-phenoxyphenyl)[4-(N,N-diethylamino)phenyl] methyl]-amine product. HRMS calcd. for $C_{23}H_{26}N_2O$: 347.2123 [M+H]$^+$, found 347.2124.

The 3-[(3-phenoxyphenyl)[4-(N,N-diethylamino)phenyl] methyl]amine (0.69 g, 2.0 mmol) product from EX-631A and 1,1,1-trifluoro-2,3-epoxypropane (0.45 g, 4 mmol) were dissolved in 1 mL of acetonitrile. Ytterbium (III) trifluoromethanesulfonate (0.12 g, 0.1 mmol) was added, and the stirred solution was warmed to 40° C. for 4 h, at which time HPLC analysis indicated that no secondary amine starting material remained. The reaction was quenched with water and extracted with ether. The ether layer was washed with water and brine, then dried over $MgSO_4$. The crude product was purified by flash column chromatography on silica gel eluting with 1:7:0.01 ethyl acetate:hexane:ammonium hydroxide followed by reverse phase preparative HPLC eluting with 10% to 90% acetonitrile in water to give 160 mg (17%) of the desired 3-[(3-phenoxyphenyl)-[[4(N,N-diethylamino)phenyl] methyl]amino]-1,1,1-trifluoro-2-propanol product as a yellow oil, >95% pure by HPLC analysis. $^1$H NMR (CD$_3$OD) δ 7.39 (d, 2H), 7.31 (d, 2H), 7.22 (m, 3H), 7.13 (d, 1H), 6.98 (t, 1H), 6.75 (dd, 2H), 6.47 (dd, 1H), 6.20 (d, 1H), 4.03 (m, 1H), 3.90 (s, 2H), 3.58 (m, 4H), 3.36 (dd, 1H), 3.12 (dd, 1H), 1.05 (t, 6H). $^{19}$F NMR (CD$_3$OD) δ −80.51 (d, 3F). HRMS calcd. 459.2259 [M+H]$^+$, found: 459.2250.

EXAMPLE 632

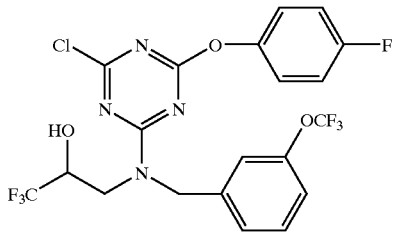

N-[2-chloro-6-(p-fluorophenoxy)-1,3,5-triazin-4-yl]-3-[[[3-(trifluoromethoxy)phenyl]methyl]amino]-1,1,1-trifluoro-2-propanol EX-632A) 3-Trifluoromethoxybenzenemethanamine (1.15 g, 6 mmol) and 1,1,1-trifluoro-2,3-epoxypropane (0.67 g, 6 mmol) were combined and stirred at 80° C. for 1.5 h. The mixture was cooled to room temperature, and the resulting solid was recrystallized from hot hexanes. The white solid was isolated by vacuum filtration and washed with cold hexanes to give 0.67 g (37%) of pure 3-[[[3-(trifluoromethoxy)-phenyl]methyl]amino]-1,1,1-trifluoro-2-propanol. $^1$H NMR (CDCl$_3$) δ 7.37 (t, 1H), 7.24 (d, 1H), 7.15 (m, 2H), 3.99 (m, 1H), 3.85 (d, 2H), 2.98 (dd, 1H), 2.88 (dd, 1H), 2.79 (s, 1H). $^{19}$F NMR (CDCl$_3$) δ −58.19 (s, 3F), −78.88 (s, 3F). HRMS calcd. for C$_{11}$H$_{11}$F$_6$NO$_2$: 304.0772 [M+H]$^+$, found: 304.0794.

EX-632B) To a solution of 4-fluorophenol 1.00 g (8.92 mmol) in 30 mL of tetrahydrofuran at 0° C. was added a 60% dispersion of sodium hydride in mineral oil (0.36 g, 8.92 mmol). After 30 min, cyanuric chloride (1.64 g, 8.92 mmol) was added as a heterogeneous mixture in tetrahydrofuran at 0° C. The reaction mixture was allowed to slowly warm to room temperature. After 14 h, the mixture was cooled to 0° C., and a saturated aq. NH$_4$Cl solution was added. The aqueous solution was extracted with diethyl ether (3×50 mL). The combined ether extracts were washed with brine, dried (MgSO$_4$), and concentrated in vacuo to afford 1.34 g (58%) of the desired 2,4-dichloro-6-(4-fluorophenoxy)-1,3,5-triazine product as an off white solid which was taken on to the next step without purification. MS m/z=260 [M+H]$^+$.

To a stirred solution of aminopropanol from EX-632A (0.100 g, 0.330 mmol) in N,N-dimethylformiamide at 0° C. was added the 2,4-dichloro-(4-fluorophenoxy)-1,3,5-triazine ether product from EX-632B (0.086 g, 0.330 mmol) as a solution in N,N-di-methylformamide. The reaction mixture was allowed to slowly warm to room temperature. After 14 h, the reaction mixture was cooled to 0° C., and a saturated aq. NaHCO$_3$ solution was added. After stirring the reaction mixture for 30 min at room temperature, the aqueous layer was extracted with ether (3×30 mL). The combined ether extracts were washed with brine, dried (MgSO$_4$), and concentrated in vacuo to give a yellow oil. The crude residue was purified by column chromatography on silica gel eluting with 20% ethyl acetate in hexanes to give 0.075 g (43%) of the desired N-[2-chloro 6-(p-fluorophenoxy)-1,3,5-triazin-4-yl]-3-[[[3-(trifluoromethoxy)phenyl]-methyl]amino]-1,1,1-trifluoro-2-propanol product as a pale yellow oil. HRMS calcd. for C$_{20}$H$_{14}$ClF$_7$N$_4$O$_3$: 526.0643 [M]$^+$, found: 526.0632. $^1$H NMR (C$_6$D$_6$) δ 6.95 (s, 1H), 6.63 (m, 14H), 4.74 (d, 1H), 4.37 (d, 1H), 4.16 (d, 1H), 4.00 (d, 2H), 3.73 (m, 1H), 3.48 (m, 2H), 3.26 (m, 2H), 3.12 (m, 2H).

EXAMPLE 633

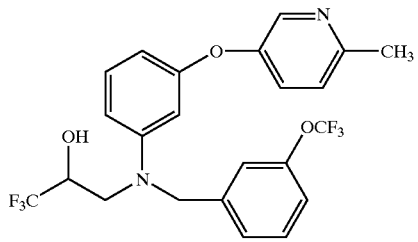

3-[[3-(2-methyl-5-pyridyloxy)phenyl][[3-(trifluoromethoxy) phenyl]methyl]-amino]-1,1,1-trifluoro-2-propanol EX-633A) 3-Bromoaniline (2.15 g, 12.5 mmol) and 1,1,1-trifluoro-2,3-epoxypropane (1.0 g, 8.9 mmol) were placed in a sealed vial, heated to 70° C. and stirred for 1 h under an atmosphere of nitrogen. The crude product was purified by flash column chromatography on silica gel eluting with CH$_2$CH$_2$:hexane (2:1) to give 2.11 g (84%) of the desired 3-[(3-bromophenyl)amino]-1,1,1-trifluoro-2-propanol product as a light amber oil, 98% pure by HPLC analysis. MS m/z=284/286 [M+H]$^+$.

EX-633B) The 3-[(3-bromophenyl)amino]-1,1,1-trifluoro-2-propanol (1.14 g, 4 mmol) from EX-633A and 3-(trifluoromethoxy)benzaldehyde (0.78 g, 4.1 mmol) were dissolved in dichloroethane (18 mL). Acetic acid (0.253 mL, 4.2 mmol) and solid NaBH(OAc)$_3$ (1.07 g, 5.05 mmol) were added. The mixture was stirred at room temperature for 3 h, then acidified with 1 N HCl solution. After neutralizing to pH 7.5 with 2.5 N sodium hydroxide, the mixture was extracted with methylene chloride. The organic layer was washed with brine and water, then dried over anhydrous MgSO$_4$, and evaporated to give 1.12 g (62%) of the desired N-3-bromophenyl-[[3-(trifluoromethoxy)phenyl]methyl]amino]-1,1,1-trifluoro-2-propanol product as a brown oil, which was greater than 80% pure by reverse phase HPLC analysis. HRMS calcd. for C$_{17}$H$_{14}$NO$_2$F$_6$Br: 458.0190 [M+H]$^+$, found: 458.0199.

The 3-[(3-bromophenyl)[[3-(trifluoromethoxy)phenyl]methyl]amino]-1,1,1-trifluoro-2-propanol (500 mg, 1.1 mmol) product from EX-633B and 5-hydroxy-2-methylpyridine (262 mg, 2.4 mmol) were dissolved in dimethylacetamide (6 mL). Cs$_2$CO$_3$ (1.0 g, 3.1 mmol) and (CuCF$_3$SO$_3$)$_2$C$_6$H$_6$ (150 mg) were added, and the mixture was heated to 105° C. for 96 h under an atmosphere of nitrogen, at which time HPLC analysis indicated that most of the starting materials had been consumed. After adding water, the reaction mixture was extracted with ether, and the ether extracts were washed with brine and dried over anhydrous MgSO$_4$. The crude product was purified by flash column chromatography on silica gel eluting with ethyl acetate:hexane (1:12) to give 326 mg (61%) of the desired 3-[[3-(2-methyl-5-pyridyloxy) phenyl][[3-(trifluoromethoxy)phenyl]methyl]amino]-1,1,1-trifluoro-2-propanol product as a light amber oil, 99% pure by HPLC analysis. $^1$H NMR (CDCl$_3$) δ 8.00 (s, 1H), 7.29 (t 1H), 6.99 (s, 1H), 7.02–7.15 (m, 5H), 6.46 (dd, 1H), 6.29 (t, 1H), 6.25 (dd, 1H), 4.88 (br s, 1H), 4.67 (ABq, 2H), 4.36 (m, 1H), 3.88 (dd, 1H), 3.56(dd, 1H), 2.49 (s, 3H). $^{19}$F NMR (CDCl$_3$) δ −58.2, (s, 3F), −79.1 (d, 3F). HRMS calcd. for $C_{23}H_{20}N_2O_3F_6$: 487.1456 [M+H]$^+$, found: 487.1425.

EXAMPLE 634

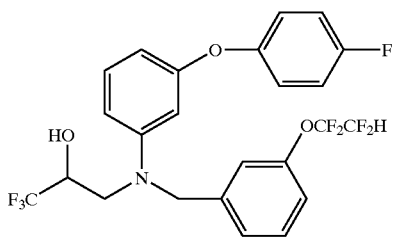

3-[[3-(4-fluorophenoxy)phenyl][[3-(1,1,2,2-tetrafluoroethoxy)-phenyl]methyl]amino]-1,1,1-trifluoro-2-propanol EX-634A) Dinitrobenzene (1.68 g, 10 mmol) and 4-fluorophenol (1.13 g, 10 mmol) were dissolved in anhydrous dimethylsulfoxide (25 mL), and powdered cesium carbonate (8 g, 24.8 mmol) was added. The mixture was stirred and heated to 100° C. using a reflux condenser under a nitrogen atmosphere. After 16 h, the mixture was diluted with water (120 mL), and the aqueous layer was extracted with diethyl ether (4×60 mL). The combined ether layers were washed with 3% HCl, 5% sodium hydroxide, and water, then dried over anhydrous MgSO$_4$. The ether was removed in vacuo, and the recovered oil was purified by flash column chromatography on silica gel eluting with ethyl acetate in hexane (1:25) to give 1.68 g (69%) of the desired 3-(4 -fluorophenoxy) nitrobenzene product as orange crystals, 97% pure by HPLC analysis. MS m/z=234 [M+H$^+$].

EX-634B) 3-(4Fluorophenoxy)nitrobenzene (1.15 g, 4.93 mmol) from EX-634A was dissolved in ethanol (45 mL), and the solution was hydrogenated for 4 h in the presence of 5% palladium on charcoal. After the mixture was filtered through celite, the ethanol was removed in vacuo. The product was purified by flash column chromatography on silica gel eluting with ethyl acetate in hexane (1:10) to give 0.92 g (90%) of 3-(4-fluorophenoxy)aniline as a yellow oil, 99% pure by HPLC analysis. HRMS calcd. for $C_{12}H_{11}FNO$: 204.0824 [M+H]$^+$, found: 204.0837.

EX-634C) The 3-(4-fluorophenoxy)aniline (812 mg, 4 mmol) from EX-634B and 3-(1,1,2,2-tetrafluoroethoxy) benzaldehyde (888 mg, 2 mmol) were dissolved in dichloroethane (15 mL) and acetic acid (0.25 mL, 4.2 mmol), then solid NaBH(OAc)$_3$ (1.01 g, 5 mmol) was added. The mixture was stirred at room temperature for 3 h, then acidified with 1 N HCl. After neutralizing to pH 7.5 with 2.5 N sodium hydroxide, the mixture was extracted with methylene chloride. The organic layer was washed with brine and water, then dried over anhydrous MgSO$_4$, and evaporated to give 1.32 g (78%) of the desired N-[3-(4-fluorophenoxy)phenyl][[3-(1,1,2,2-tetrafluoroethoxy) phenyl]methyl]amine product as a brown oil, which was greater than 90% pure by reverse phase HPLC analysis. MS m/z=410 [M+H]$^+$.

The N-[3-(4-fluorophenoxy)phenyl][[3-(1,1,2,2-tetrafluoroethoxy)phenyl]methyl]amine (612 mg, 1.5 mmol) product from EX-634C and 1,1,1-trifluoro-2,3-epoxypropane (268 mg, 2.4 mmol) were dissolved in 1.0 mL of acetonitrile. Ytterbium (III) trifluoromethanesulfonate (43 mg, 0.07 mmol) was added, and the stirred solution was warmed to 40° C. for 2.5 h under an atmosphere of nitrogen, at which time HPLC analysis indicated that no secondary amine starting material remained. The reaction was quenched with water and extracted with ether. The ether layer was washed with brine and water, then dried over anhydrous MgSO$_4$. The ether was removed in vacuo, and the crude product was purified by flash column chromatography on silica gel eluting with ethyl acetate in hexane (1:11) to give 633 mg (81%) of the desired 3-[[3-(4-fluorophenoxy)phenyl][[3-(1,1,2,2-tetrafluoro-ethoxy)phenyl]methyl] amino]-1,1,1-trifluoro-2-propanol product as a yellow oil, 99% pure by HPLC analysis. $^1$H NMR (CDCl$_3$) δ 7.35 (t, 1H), 7.15 (m, 3H), 6.98 (m, 5H), 6.49 (dd, 1H), 6.38 (dd, 1H), 6.33 (m, 1H), 5.92 (tt, 1H), 4.67 (ABq, 2H), 4.37 (m, 1H), 3.91 (dd, 1H), 3.59 (dd, 1H), 2.48 (d, 1H). $^{19}$F NMR (CDCl$_3$) δ −79.2 (d, 3F), −88.5 (m, 2F), −120.33 (m, 1F), −137.2 (dt, 2F). HRMS calcd. for $C_{24}H_{19}F_8NO_3$: 522.1315 [M+H]$^+$, found: 522.1297.

Additional examples 3-[(aryloxyphenyl)[[phenyl]methyl] amino]-1,1,1-trifluoro-2-propanols are prepared by one skilled in the art using similar methods, as shown in Example Tables 39 and 40.

EXAMPLE TABLE 39

3-[(aryloxyphenyl)[[phenyl]methyl]amino]-1,1,1-trifluoro-2-propanols.

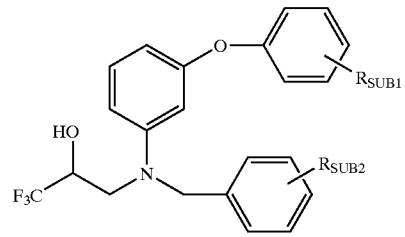

| Ex. No. | $R_{SUB1}$ | $R_{SUB2}$ | Calculated Mass [M + H]$^+$ | Observed Mass [M + H]$^+$ |
|---|---|---|---|---|
| 635 | 4-F | 3-OH | 422.1379 | 422.1396 |
| 636 | 4-F | 3-SCF$_3$ | 505.0946 | 505.0927 |
| 637 | 4-CH$_3$ | 3-SCF$_3$ | 502.1275 | 502.1261 |
| 638 | 3,4-F$_2$ | 3-OCF$_2$CF$_2$H | 540.1221 | 540.1248 |
| 639 | 2,4-F$_2$ | 3-OCF$_2$CF$_2$H | 540.1221 | 540.1194 |
| 640 | 4-F | 4-CF$_3$ | 474.1304 | 474.1300 |

EXAMPLE TABLE 40

3-[[(3-aryloxy)-5-(trifluoromethyl)phenyl][phenyl]methyl]amino]-1,1,1-trifluoro-2-propanols.

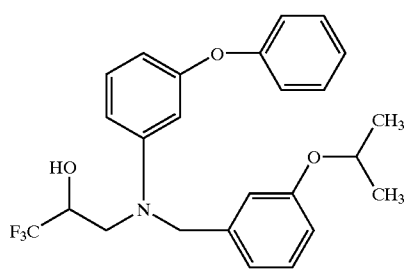

| Ex. No. | $R_{SUB1}$ | $R_{SUB2}$ | Calculated Mass $[M + H]^+$ | Observed Mass $[M + H]^+$ |
|---|---|---|---|---|
| 641 | 4-F | 3-CF$_3$ | 542.1178 | 542.1205 |
| 642 | 4-F | 3-SCF$_3$ | 574.0898 | 574.0899 |
| 643 | 4-F | 3-OCF$_3$ | 558.1127 | 558.1137 |
| 644 | 4-F | 3-OCF$_2$CF$_2$H | 590.1189 | 590.1212 |

EXAMPLE 645

3-[(3-phenoxyphenyl)[[3-(isopropoxy)phenyl]methyl]amino]-1,1,1-trifluoro-2-propanol EX-645A) 3-Hydroxybenzaldehyde (5.60 g, 45.9 mmol) and 2-iodopropane (7.86 g, 46.2 mmol) were dissolved in 50 mL of isopropanol. Potassium carbonate (20 g, 145 mmol) was added, and the mixture was heated to reflux for 8 h, at which time TLC analysis indicated that the reaction had gone to completion. Water was added to dissolve all solids, and the mixture was extracted with ether (3×). The combined ether layer was washed with water, 2 M NaOH, again with water until clear (4×), and finally with brine. The solution was dried over MgSO$_4$, filtered, and evaporated to give 5.03 g (67%) of the desired 3-isopropoxybenzaldehyde product as a pale oil. $^1$H NMR (C$_6$D$_6$) δ 9.62 (s, 1H), 7.29 (s, 1H), 7.03 (m, 1H), 6.91 (t, 1H), 6.84 (m, 1H), 4.03 (septet, 1H), 0.96 (d, 6H).

EX-645B) The 3-isoproxybenzaldehyde (0.780 g, 4.75 mmol) product from EX-645A and 3-phenoxyaniline (0.881 g, 4.76 mmol) were combined in 20 mL of methanol, then solid NaCNBH$_3$ (0.238 g, 3.79 mmol) was added, and the mixture was stirred until uniform. Acetic acid (2 ml) was added, and the mixture was stirred at room temperature overnight, then quenched with water, made basic with potassium carbonate, and extracted with ether (3×). The combined ether layers were washed with water and brine, dried over MgSO$_4$, filtered, and evaporated to give 1.32 g (84%) of the desired N-(3-phenoxyphenyl)-[[3-isopropoxyphenyl]methyl]amine product as an amber oil. $^1$H NMR (C$_6$D$_6$) δ 6.6–7.1 (m, 10H), 6.44 (m, 1H), 6.25–6.00 (dd, 1H), 6.15 (m, 1H), 4.25 (s, 1H), 4.19 (m, 1H), 3.80 (s, 1H), 2.65 (s, 1H), 1.07 (m, 6H). MS m/z=333 [M$^+$].

The N-(3-phenoxyphenyl)-[[3-isopropoxyphenyl]methyl]amine (0.528 g, 1.59 mmol) product from EX-645B and 1,1,1-trifluoro-2,3-epoxypropane (0.506 g, 4.51 mmol) were heated to 90° C. in a sealed container for 2 d under an argon atmosphere. The resulting mixture was eluted from silica gel with an ethyl acetate in hexane gradient (0–10% ethyl acetate) and fractions were pooled after TLC analysis to give 197 mg (28%) of the desired 3-[(3-phenoxyphenyl)[[3-(isopro-poxy)phenyl]methyl]amino]-1,1,1-trifluoro-2-propanol product as clear, colorless oil. HRMS calcd. for C$_{25}$H$_{26}$F$_3$NO$_3$: 446.1943 [M+H]$^+$, found: 446.1936. $^1$H NMR (C$_6$D$_6$) δ 6.9–7.1 (m, 6H), 6.84 (tt, 1H), 6.74 (s, 1H), 6.66 (dd, 1H), 6.61 (d, 1H), 6.56 (t, 1H), 6.41 (td, 2H), 4.33 (s, 2H), 4.17 (septet, 1H), 3.91 (br s, 1H), 3.56 (dd, 1H), 3.31 (m, 1H,), 2.8 (br s, 1H). 1.06 (s, 6H). $^{19}$F NMR (C$_6$D$_6$) δ −78.85 (d, 3F).

Additional examples of 3-[aryloxyphenyl[[3-aryl]methyl]amino]-1,1,1-trifluoro-2-propanols are prepared by one skilled in the art using similar methods, as shown in Example Table 41.

EXAMPLE TABLE 41

3-[aryloxyphenyl[[3-aryl]methyl]amino]-1,1,1-trifluoro-2-propanols.

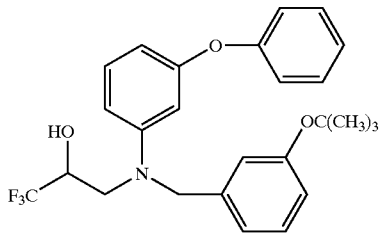

| Ex. No. | $R_{SUB1}$ | $R_{SUB2}$ | Calculated Mass $[M + H]^+$ | Observed Mass $[M + H]^+$ |
|---|---|---|---|---|
| 646 | F | ethyl | 450.1692 | 450.1682 |
| 647 | F | isopropyl | 464.1849 | 464.1867 |
| 648 | F | n-propyl | 464.1849 | 464.1820 |
| 649 | F | n-butyl | 478.2005 | 478.2015 |
| 650 | F | sec-butyl | 478.2005 | 478.1880 |
| 651 | F | —CH$_2$-cyclopropyl | 476.1849 | 476.1857 |
| 652 | F | isobutyl | 478.2005 | 478.1970 |
| 653 | F | cyclopentyl | 490.2005 | 490.1998 |

EXAMPLE 654

3-[(3-phenoxyphenyl) [[3-(1,1-dimethylethoxy)phenyl]methyl]amino]-1,1,1-trifluoro-2-propanol EX-654A) 3-Hydroxybenzaldehyde (4.08 g, 33.4 mmol) was slurried in 50 mL of anhydrous CH$_2$Cl$_2$ and added to t-butyl-2,2,2-trichloroacetimidate (25.0 g, 114 mmol) in 200 mL of anhydrous cyclohexane with an additional 50 mL of CH$_2$Cl$_2$ used in transfer. The mixture was stirred under nitrogen until uniform, then boron trifluoride diethyl etherate (0.50 mL, 4 mmol) was added via syringe and stirring was continued for 1 h. Powdered sodium bicarbonate (50 g, 0.6 mol) was added, and the solution was filtered through a silica gel plug, washing the plug with hexane. The solvent was evaporated to give crude product 3.54 g (59%) as an amber oil (85% pure by GC analysis). Chromatography on silica gel eluting with 0–10% ethyl acetate in hexane gave 1.88 g (32%) of pure 3-t-butoxybenzaldehyde product as a colorless oil. $^1$H NMR (C$_6$D$_6$) δ 9.59 (s, 1H), 7.44 (br s, 1H), 7.20 (d t, 1H), 6.92 (m, 2H), 1.07 (s, 9H).

EX-654B) The 3-t-butoxybenzaldehyde (0.585 g, 3.27 mmol) product from EX-654A and 3-phenoxyaniline (0.595 g, 3.21 mmol) were combined in 50 mL of THF, then solid NaBH(OAc)$_3$ (0.860 g, 4.06 mmol) was added, and the mixture was stirred until uniform. Acetic acid (0.2 g, 3.33 mmol) was added, and the mixture was stirred at room temperature for 4 h, then quenched with 5% aq. NaHCO$_3$. The aqueous layer was separated and extracted twice with ether. The combined ether layers were washed with water and brine, dried over MgSO$_4$, filtered, and evaporated to give 1.29 g (115%) of crude product as a brown oil. Chromatography on silica gel eluting with 0–10% ethyl acetate in hexane gave 464 mg (40%) of the desired N-(3-phenoxyphenyl)[[3-(1,1-dimethylethoxy) phenyl]methylamine product as a colorless oil, pure by TLC. MS m/z=347 [M$^+$].

The N-(3-phenoxyphenyl)[[3-(1,1-dimethylethoxy)phenyl] methyl]amine (0.270 g, 0.78 mmol) product from EX-654B was dissolved in 2 mL of acetonitrile. Ytterbium triflate (16 mg, 0.026 mmol) was added in 0.5 mL of acetonitrile, and the mixture was stirred under nitrogen. 1,1,1-Trifluoro-2,3-epoxypropane (0.105 g, 0.94 mmol) was added, the vial was sealed and heated to 45° C. After 24 h, TLC analysis showed 50% conversion, so additional 1,1,1-trifluoro-2,3-epoxypropane (88.6 mg, 0.79 mmol) was added and heating continued for an additional 24 h. The resulting mixture was eluted from silica gel with an ethyl acetate in hexane gradient (1.5–7% ethyl acetate). Fractions were pooled based on TLC analysis to give 150 mg (42%) of the desired 3-[(3-phenoxy-phenyl)[[3-(1,1-dimethylethoxy)phenyl]methyl]amino]-1,1,1-trifluoro-2-propanol product as a clear, colorless oil, and an additional 60 mg (17%) was obtained as an amber oil. HRMS calcd. for C$_{26}$H$_{28}$F$_3$NO$_3$: 460.2100 [M+H]$^+$, found: 460.2103. $^1$H NMR (C$_6$D$_6$) δ 6.78–7.08 (m, 9H), 6.68 (d, 1H), 6.55 (t, 1H), 6.43 (dd 1H), 6.34 (dd, 1H), 4.23 (s, 2H), 3.81 (m, 1H), 3.48 (dd, 1H), 3.24 (m, 1H), 2.25 (br s, 1H), 1.07 (s, 9H). $^{19}$F NMR (C$_6$D$_6$) δ −78.92 (d, 3F).

EXAMPLE 655

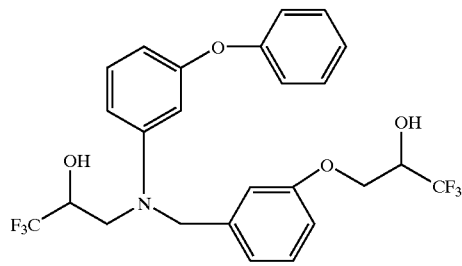

3-[(3-phenoxyphenyl)[[3-(2-hydroxy-3,3,3-trifluoro-n-propoxy)phenyl]methyl]amino]-1,1,1-trifluoro-2-propanol EX-655A) The 3-(phenoxy)aniline (555 mg, 3 mmol) and 3-hydroxybenzaldehyde (366 mg, 3 mmol) were dissolved in 7 mL of 1,2-dichloroethane. Acetic acid (0.189 mL, 3.15 mmol) and solid NaBH(OAc)$_3$ (1.01 g, 5 mmol) were added. The mixture was stirred at room temperature for 3 h, then acidified with 1 N HCl solution. After neutralizing to pH 7.5 with 2.5 N sodium hydroxide, the mixture was extracted with methylene chloride. The organic layer was washed with brine and water, then dried over anhydrous MgSO$_4$, and evaporated to give 609 mg (69%) of the desired N-(3-phenoxyphenyl)[[3-hydroxyphenyl]methyl]amine product as a brown oil, which was greater than 90% pure by reverse phase HPLC analysis. MS m/z=291.

The N-(3-phenoxyphenyl)[[3-hydroxyphenyl]methyl]amine (400 mg, 1.35 mmol) product from EX-655A and 1,1,1-trifluoro-2,3-epoxypropane (348 mg, 3 mmol) were placed in a sealed vial, then stirred and heated to 95° C. for 15 h under an atmosphere of nitrogen. The vial was cooled, and more 1,1,1-trifluoro-2,3-epoxypropane (112 mg, 1 mmol) was added. The vial was sealed, then stirred and heated to 95° C. for a further 20 h under an atmosphere of nitrogen. The crude product was purified by flash column chromatography on silica gel eluting with ethyl acetate in hexane (1:6) to give 518 mg (77%) of the desired 3-[(3-phenoxyphenyl)[[3-(2-hydroxy-3,3,3-trifluoro-n-propoxy)-phenyl]methyl]amino]-1,1,1-trifluoro-2-propanol product as a light amber oil, 98% pure by HPLC analysis. $^1$H NMR (CDCl$_3$) δ 7.20–7.32 (m, 3H), 7.14 (t, 1H), 7.07 (t, 1H), 6.95 (d, 2H), 6.80 (m, 2H), 6.74 (s, 1H), 6.48 (dd, 1H), 6.38 (m, 2H), 4.59 (ABq, 2H), 4.31 (m, 1H), 4.18 (dd, 1H), 4.10 (dd, 1H), 3.83 (dd, 1H), 3.54 (dd, 1H), 2.92 (d, 1H), 2.61 (d, 1H). $^{19}$F NMR (CDCl$_3$) δ −78.0 (d, 3F), −79.2 (d, 3F). HRMS calcd. for C$_{25}$H$_{23}$F$_6$NO$_4$: 516.1611 [M+H]$^+$, found: 516.1618.

EX-655B) Another example, 3-[3-(4-fluorophenoxy)phenyl [[3-(2-hydroxy-3,3,3-trifluoro-n-propoxy)phenyl]methyl] amino]-1,1,1-trifluoro-2-propanol, was prepared by a similar method using 3-(4-fluorophenoxy)aniline as the staring material. HRMS calcd. for C$_{25}$H$_{22}$F$_7$NO$_4$: 534.1515 [M+H]$^+$, found: 534.1505.

EXAMPLE 656

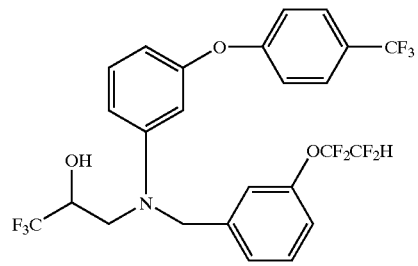

3-[[3-(4-trifluoromethylphenoxy)phenyl][[3-(1,1,2,2-tetrafluoroethoxy)-phenyl]methyl]amino]-1,1,1-trifluoro-2-propanol EX-656A) 3-Aminophenol (5.0 g, 45.8 mmol) and 4-bromo-α,α,α-trifluorotoluene (14.0 g, 62.2 mmol) were dissolved in anhydrous dimethylacetamide (20 mL), then anhydrous cesium carbonate (30 g, 92.3 mmol) and copper triflate benzene complex (200 mg) were added. The mixture was stirred and heated to 85° C. using a reflux condenser under an argon atmosphere. After 16 h, the mixture was diluted with water (120 mL), and the aqueous layer was extracted with diethyl ether (4×60 mL). The combined ether layers were washed with 3% HCl, 5% NaOH and water, then dried over anhydrous MgSO$_4$. The ether was removed in vacuo, and the recovered oil purified by flash column chromatography on silica gel eluting with ethyl acetate in hexane (1:8) to give 6.8 g (59%) of the desired 3-(4-trifluoromethylphenoxy)aniline product as a yellow oil, which solidified to a yellow powder, 98% pure by HPLC analysis. HRMS calcd. for C$_{13}$H$_{10}$F$_3$NO: 254.0792 [M+H]$^+$, found: 254.0798.

EX-656B) The 3-(4-trifluoromethylphenoxy)aniline (632 mg, 2.5 mmol) from EX-656A and 3-(1,1,2,2-tetrafluoroethoxy)benzaldehyde (555 mg, 2.5 mmol) were dissolved in 6 mL of dichloroethane and glacial acetic acid (0.15 mL, 2.8 mmol), and solid NaBH(OAc)$_3$ (1.01 g, 5 mmol) was added. The mixture was stirred at room temperature for 3 h, then acidified with 1 N HCl. After neutralizing to pH 7.5 with 2.5 N sodium hydroxide, the mixture was extracted with $CH_2Cl_2$ (3×20 mL). The organic layer was washed with brine and water, then dried over anhydrous $MgSO_4$, and evaporated to give 861 mg (75%) of the desired N-3-(4-trifluoromethylphenoxy)-phenyl[[3-(1,1,2,2-tetrafluoroethoxy) phenyl]methyl] amine product as a brown oil, which was greater than 90% pure by reverse phase HPLC analysis. MS m/z=460 [M+H]$^+$.

The N-3-(4-trifluoromethylphenoxy)-phenyl[[3-(1,1,2,2-tetrafluoroethoxy) phenyl]-methyl]amine (689 mg, 1.5 mmol) product from EX-656B and 1,1,1-trifluoro-2,3-epoxypropane (252 mg, 2.25 mmol) were dissolved in 1.0 mL of acetonitrile. Ytterbium (III) trifluoromethanesulfonate (43 mg, 0.07 mmol) was added, and the stirred solution was warmed to 50° C. for 2.5 h under an atmosphere of nitrogen, at which time HPLC analysis indicated that no secondary amine starting material remained. The reaction was quenched with water and extracted with ether. The ether layer was washed with brine and water, then dried over anhydrous $MgSO_4$. The crude product was purified by flash column chromatography on silica gel eluting with ethyl acetate in hexane (1:12) to give 520 mg (61%) of the desired 3-[[3-(4-trifluoromethylphenoxy)phenyl][[3-(1,1,2,2-tetrafluoroethoxy)phenyl]methyl]amino]-1,1,1-trifluoro-2-propanol product as a yellow oil, 99% pure by HPLC analysis. $^1$H NMR (CDCl$_3$) δ 7.49 (d, 2H), 7.30 (t, 1H), 7.20 (t, 1H), 7.07 (m, 2H), 7.00 (s, 1H), 6.95 (d, 2H), 6.55 (dd, 1H), 6.43 (dd, 1H), 6.34 (t, 1H), 5.87 (tt, 1H), 4.64 (ABq, 2H), 4.33 (m, 1H), 3.88 (dd, 1H), 3.58 (dd, 1H), 2.43 (bs, 1H). $^{19}$F NMR (CDCl$_3$) δ −62.2 (s, 3F), −79.2 (d, 3F), −88.6 (m, 2F), −137.2 (dt, 2F). HRMS calcd. for $C_{25}H_{19}F_{10}NO_3$: 572.1282 [M+H]$^+$, found: 572.1268.

Additional examples of 3-[aryloxyphenyl[[phenyl]methyl]amino]-1,1,1-tri-fluoro-2-propanols are prepared by one skilled in the art using similar methods, as shown in Example Table 42.

EXAMPLE TABLE 42

3-[Aryloxyphenyl[[phenyl]methyl]amino]-1,1,1-trifluoro-2-propanols

| Ex. No. | $R_{SUB1}$ | Calculated Mass [M + H]$^+$ | Observed Mass [M + H]$^+$ |
|---|---|---|---|
| 657 | CN | 529.1362 | 529.1364 |
| 658 | OCF$_3$ | 588.1233 | 588.1241 |

EXAMPLE 659

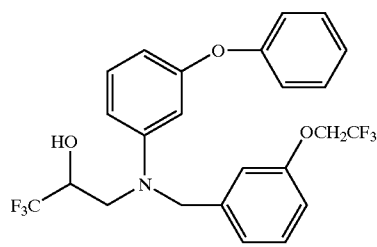

3-[(3-phenoxyphenyl)[[3-(2,2,2-trifluoroethoxy)phenyl]methyl]amino]-1,1,1-trifluoro-2-propanol EX-659A) 3-Hydroxybenzaldehyde (12.22 g, 0.10 mol) and 100 mL of anhydrous methanol were combined in a 250 mL round-bottom flask. Sodium methoxide was slowly added as a 25 wt. % solution in methanol (21.61 g, 0.10 mol), and the methanol was removed under vacuum. Then 2,2,2-trifluoroethyl-p-toluenesulfonate (25.42 g, 0.10 mol) was added, the flask was purged with nitrogen, and 100 mL of N-methyl pyrrolidine was added. The solution was stirred for 24 h at 90° C., quenched with water, and extracted with ether (3×). The combined ether layers were washed with 1 M NaOH (2×), water, and brine, dried over MgSO$_4$, filtered, and evaporated to give 11.72 g of crude product. Chromatography over silica gel eluting with 0–10% ethyl acetate in hexane followed by a second chromatography with toluene gave 5.24 g (26%) of the desired 3-(2,2,2-trifluoroethoxy)benzaldehyde product as a pale oil. $^1$H NMR (C$_6$D$_6$) δ 9.61 (s, 1H), 7.14 (d, 1H), 7.06 (s, 1H), 6.97 (t, 1H), 6.75 (m, 1H), 3.75 (m, 2H). $^{19}$F NMR (C$_6$D$_6$) δ −74.45 (t, 3F).

EX-659B) The 3-(2,2,2-trifluoroethoxy)benzaldehyde (0.360 g, 1.76 mmol) product from EX-659A and 3-phenoxyaniline (0.326 g, 1.76 mmol) were combined in 50 mL of cyclohexane with 3 Å molecular sieves (1 g) and stirred overnight at 80° C. The mixture was cooled, filtered, and evaporated, then dissolved in 50 mL of methanol and cooled to 0° C. Solid sodium borohydride (0.030 g, 0.79 mmol) was added in portions, and the mixture was stirred overnight. The reaction was quenched with 5% aq. NaHCO$_3$ and extracted with ether (3×). The combined ether layers were washed with water and brine, dried over MgSO$_4$, filtered, and evaporated to give 0.50 g (76%) of the desired N-(3-phenoxyphenyl)[[3-(2,2,2-trifluoroethoxy)phenyl]methyl]amine product as an amber oil, >95% pure by normal phase HPLC analysis. MS m/z=373 [M$^+$].

The N-(3-phenoxyphenyl)[[3-(2,2,2-trifluoroethoxy)phenyl]methyl]amine (0.50 g, 1.35 mmol) product from EX-659B and 1,1,1-trifluoro-2,3-epoxy-propane (1.0 ml, 11 mmol) were heated to 90° C. in a sealed container under argon for 2 d. The resulting mixture was eluted from silica gel with 4% ethyl acetate in hexane, and fractions were pooled based on TLC analysis to give 134 mg (21%) of the desired 3-[(3-phenoxyphenyl)[[3-(2,2,2-trifluoroethoxy)phenyl]methyl] amino]-1,1,1-trifluoro-2-propanol product as a clear, colorless oil. $^1$H NMR (C$_6$D$_6$) δ 6.80–7.08 (m, 7H), 6.64 (d, 1H), 6.53 (bt, 1H), 6.49 (t, 1H), 6.44 (dd, 1H), 6.34 (dt, 2H), 4.23 (s, 2H), 3.84 (m, 1H), 3.61 (m, 2H), 3.53 (dd, 1H), 3.20 (m, 1H), 2.03 (d, 1H). $^{19}$F NMR (C$_6$D$_6$) δ −74.20 (t, 3F), −78.95 (d, 3F). HRMS calcd. for $C_{24}H_{21}F_6NO_3$: 486.1504 [M+H]$^+$, found: 486.1498.

EXAMPLE 660

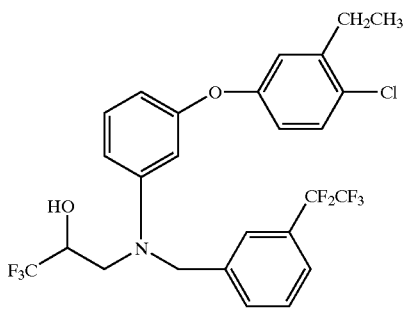

3-[(4-chloro-3-ethylphenoxy)phenyl[[3-(pentafluoroethyl)phenyl]methyl]-amino]-1,1,1-trifluoro-2-propanol.

EX-660A) Sodium pentafluoroethyl propionate (8.4 g, 50 mmol) and 3-iodotoluene (5.5 g, 25 mmol) were dissolved in anhydrous DMF (300 mL). CuI (9.5 g, 50 mmol) was added, and the mixture was heated to 160° C. under nitrogen for 4 h, at which time a 15 mL fraction of a mixture of DMF and 3-pentafluoroethyl toluene was collected. The distillate was diluted with Et$_2$O and was washed with brine. The ether layer was dried over MgSO$_4$, filtered and concentrated in vacuo to give 5.25 g (55%) of the desired 3-pentafluoroethyl-toluene product as a colorless oil. $^1$H NMR (CDCl$_3$) δ 7.36 (m, 4H), 2.40 (s, 3H). $^{19}$F NMR (CDCl$_3$) δ −85.2 (s, 3F), −115.2 (s, 2F).

EX-660B) The 3-pentafluoroethyl-toluene (2.9 g, 13.8 mmol) product from EX-660A and N-bromosuccinimide (2.5 g, 13.8 mmol) were dissolved in CCl$_4$ (25 mL). AIBN (50 mg) was added, and the mixture was refluxed for 3.5 h under N$_2$. The reaction mixture was cooled to room temperature and diluted with water. The layers were separated, and the organic layer was washed with brine, dried with anhydrous MgSO$_4$, filtered, and concentrated in vacuo to give 3.4 g (87%) of a colorless oil. The $^1$H NMR spectrum indicated that the crude product contained 3-pentafluoroethyl-benzylbromide (70%), the benzyl dibromide (10%) and 3-pentafluoroethyl toluene (20%). $^1$H NMR (CDCl$_3$) δ 7.60 (m, 2H), 7.50 (m, 2H), 4.50 (s, 2H). $^{19}$F NMR (CDCl$_3$) δ −85.1 (s, 3F), −115.4 (s, 2F).

EX-66° C.) A solution of 3-(4chloro-3-ethylphenoxy)aniline (1.7 g, 6.9 mmol) was prepared in cyclohexane (13 mL). A solution of crude 3-pentafluoroethyl benzylbromide (1 g, 3.5 mmol) product from EX-660B in cyclohexane (10 mL) was added dropwise over 3 min. The reaction mixture was refluxed under N$_2$ for 24 h and then was cooled to room temperature. The mixture was diluted with Et$_2$O and saturated aqueous NaHCO$_3$. The layers were separated, and the aqueous layer was extracted with Et20. The organic layer was washed with brine, dried with anhydrous MgSO$_4$, filtered and concentrated in vacuo. The residue was purified by chromatography on silica gel eluting with hexanes in ethyl acetate (95:5) which gave 0.56 g (35%) of the desired N-[3-(4-chloro-3-ethylphenoxy)phenyl][[3-(pentafluoroethyl)phenyl] methyl]amine product as an amber oil. $^1$H NMR (CDCl$_3$) δ 7.53 (m, 4H), 7.27 (d, 1H), 7.15 (t, 1H), 6.93 (d, 1H), 6.77 (dd, 1H), 6.41 (tt, 2H), 6.30 (t, 1H), 4.41 (s, 2H), 2.73 (q, 2H), 1.23 (t, 3H). $^{13}$C NMR (CDCl$_3$) δ 158.6, 156.1, 143.4, 141.3, 140.2, 131.3, 130.7, 130.4, 129.4, 128.1, 120.4, 117.8, 108.8. 103.9, 48.5, 27.5, 14.1. $^{19}$F NMR (CDCl$_3$) δ −85.1 (s, 3F), −115.2 (s, 2F). HRMS calcd. for C$_{23}$H$_{19}$ClF$_5$NO: 456.1154 [M+H]$^+$, found: 456.1164.

The N-[3-(4-chloro-3-ethylphenoxy)phenyl][[3-(pentafluoroethyl)phenyl] methyl]-amine (0.05 g, 0.11 mmol) product of EX-660C was dissolved in anhydrous acetonitrile (0.2 mL). 1,1,1-trifluoro-2,3-epoxypropane (0.1 g, 0.89 mmol) and Yb(OTf)$_3$ (7 mg, 0.001 mmol) were added, and the reaction mixture was stirred under N$_2$ at 45° C. After 3 h, the reaction mixture was cooled to room temperature and diluted with Et$_2$O and saturated aqueous NaHCO$_3$. The layers were separated and the aqueous layer was extracted with Et$_2$O. The ether layers were combined, washed with brine, dried with anhydrous Na$_2$SO$_4$, filtered, and concentrated in vacuo. The viscous oil was adsorbed onto silica gel and eluted with hexanes in ethyl acetate (95:5) which gave 20 mg (32%) of the desired 3-[(4-chloro-3-ethylphenoxy)phenyl[[3-(pentafluoroethyl)phenyl]-methyl]amino]-1,1,1-trifluoro-2-propanol product as a viscous, colorless oil. $^1$H NMR (CDCl$_3$) δ 7.47 (m, 4H), 7.23 (m, 3H), 6.90 (d, 1H), 6.72 (dd, 1H), 6.52 (d, 1H), 6.42 (m, 2H), 4.73 (s, 2H), 4.39 (m, 1H), 3.91 (dd, 1H), 3.58 (m, 2H), 2.73 (q, 2H), 2.57 (s, 1H), 1.22 (t, 3H). $^{19}$F NMR (CDCl$_3$) δ −79.2 (s, 3F), −84.9(s, 3F), −115.2 (s, 2F). HRMS calcd. for C$_{26}$H$_{22}$ClF$_8$NO$_2$: 568.1290 [M+H]$^+$, found: 568.1314.

EXAMPLE 661

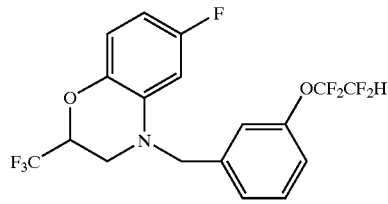

6-fluoro-3,4-dihydro-4-[[3-(1,1,2,2-tetrafluoroethoxy)phenyl]methyl]-2-(trifluoromethyl)-2H-1,4-benzoxazine EX-661A) A mixture of 2,5-difluoroaniline (2.58 g, 20 mmol) and 3-(1,1,2,2-tetrafluoroethoxy)benzaldehyde (4.44 g, 20 mmol) in cyclohexane (50 mL) was heated under reflux for 5 h using a Dean-Stark trap to remove water. The solvent was removed in vacuo, and the residue was dissolved in methanol (30 mL). The solution was stirred and cooled to 0° C., then sodium borohydride was added (1.32 g, 35 mmol). The mixture was allowed to warm to room temperature and stirred for 2 h, then acidified with 1 N HCl. After neutralizing to pH 7.5 with 2.5 N sodium hydroxide, the mixture was extracted with diethyl ether (3×20 mL). The organic layer was washed with brine and water, then dried over anhydrous MgSO$_4$, and evaporated to give 5.7 g (86%) of the desired N-(2,5-difluorophenyl)[[3-(1,1,2,2-tetrafluoroethoxy)phenyl]-methyl]amine product as a brown oil, which was greater than 90% pure by reverse phase HPLC analysis. MS m/z=336 [M$^+$].

EX-661B) The N-(2,5-difluorophenyl)[[3-(1,1,2,2-tetrafluoroethoxy)phenyl]methyl]-amine (2.22 g, 6.67 mmol) product from EX-661A and 1,1,1-trifluoro-2,3-epoxypropane (1.12 g, 10 mmol) were dissolved in 1.5 mL of acetonitrile. Ytterbium (III) trifluoromethanesulfonate (0.21 g, 0.33 mmol) was added, and the stirred solution was warmed to 50° C. for 2 h under an atmosphere of nitrogen, at which time HPLC analysis indicated that no secondary amine starting material remained. The reaction was quenched with water and extracted with ether. The ether layer was washed with water and brine, then dried over anhydrous MgSO$_4$. The crude product was purified by flash column chromatography on silica gel eluting with ethyl acetate in hexane (1:10) to give 2.49 g (84%) of the desired 3-[(2,5-difluorophenyl)[[3-(1,1,2,2-tetrafluoro-ethoxy)phenyl]methyl]amino]-1,1,1-trifluoro-2-propanol product as a yellow oil, 99% pure by HPLC analysis. HRMS calcd. for C$_{18}$H$_{14}$F$_9$NO$_2$: 448.0959 [M+H]$^+$, found: 448.0940.

The 3-[(2,5-difluorophenyl)[13-(1,1,2,2-tetrafluoroethoxy)phenyl]methyl]amino]-1,1,1-trifluoro-2-propanol (200 mg, 0.45 mmol) product from EX-661B was dissolved in anhydrous dimethylformamide (20 mL), and powdered K$_2$CO$_3$ (180 mg) was added. The mixture was stirred and heated to 145° C. for 15 h. The mixture was diluted with water (60 mL) and extracted into ether (2×40 mL), which was washed with brine and water. The ether solution was dried over anhydrous MgSO$_4$, and the ether was removed in vacuo. The crude product was purified by flash column chromatography on silica gel eluting with ethyl acetate in hexane (1:15) to give 86.9 mg (48%) of the desired 6-fluoro-3,4 dihydro-4-[[3-(1,1,2,2-tetrafluoroethoxy)phenyl]methyl]-2-(tri-fluoromethyl)-2H-1,4-benzoxazine product as a yellow oil, 98% pure by HPLC analysis. $^1$H NMR (CDCl$_3$) δ 7.39 (t, 1H), 7.17 (m, 3H), 6.88 (m, 1H), 6.41 (m, 2H), 5.92 (tt, 1H), 4.54 (m, 1H), 4.45 (s, 2H), 3.44 (m, 2H). $^{19}$F NMR (CDCl3) δ −77.7 (d, 3F), −88.6 (m, 2F), −120.28 (m, 1F), −137.2 (dt, 2F). HRMS calcd. for C$_{18}$H$_{13}$F$_8$NO$_2$: 428.0899 [M+H]$^+$, found: 428.0910.

EXAMPLE 662

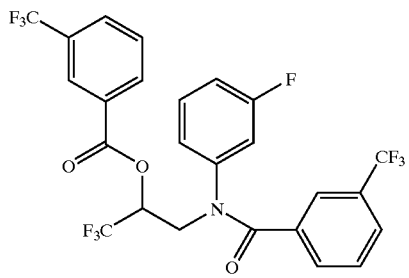

2,2,2-trifluoro-1-[[(3-fluorophenyl) [3-(trifluoromethyl) benzoyl]amino]-methyl]ethyl 3-trifluoromethylbenzoate EX-662A) 3-[(3-fluorophenyl)[phenylmethyl]amino]-1,1,1-trifluoro-2-propanol (2.56 g, 8.2 mmol) was dissolved in methanol (30 mL) and hydrogenated over 5% palladium on charcoal for 3 h. The mixture was filtered through celite, and the solvent was removed in vacuo to give 1.8 g (98%) of the desired 3-[(3-fluorophenyl)amino]-1,1,1-trifluoro-2-propanol product as an oil, 99% pure by HPLC analysis. MS m/z=224 [M+H]$^+$.

The 3-[(3-fluorophenyl)amino]-1,1,1-trifluoro-2-propanol (446 mg, 2.0 mmol) from EX-662A and triethylamine (544 mg) were dissolved in anhydrous CHCl$_3$ (30 mL) and cooled to 0° C. Then a solution of 3-trifluoromethylbenzoyl chloride (1.04 g, 5.0 mmol) in anhydrous CHCl$_3$ (6 mL) was added over a period of 15 min. The solution was stirred at room temperature. After 14 h, the solution was washed with 5% NaHCO$_3$ (2×20 mL) and brine (2×10 mL), and then dried over anhydrous MgSO$_4$. Removal of the solvent in vacuo gave 832 mg (73%) of the desired 2,2,2-trifluoro-1-[[(3-fluorophenyl) [3-(trifluoromethyl)benzoyl]amino]methyl]ethyl 3-trifluoromethyl-benzoate product as an amber oil, which was greater than 95% pure by reverse phase HPLC analysis. $^1$H NMR (CDCl$_3$) δ 7.25–8.39 (m, 9H), 7.02 (q, 1H), 6.71 (m, 2H), 6.11 (m, 1H), 4.58 (dd, 1H), 4.35 (dd, 1H). $^{19}$F NMR (CDCl$_3$) δ −64.4 (m, 6F), −77.4 (s, 3F), −111.3 (m, 1F). HRMS calcd. for C$_{25}$H$_{15}$F$_{10}$NO$_3$: 568.0970 [M+H]$^+$, found: 568.0968.

EXAMPLE 663

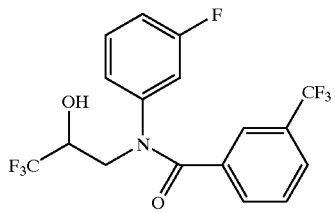

N-(3-fluorophenyl)-N-(3,3,3-trifluoro-2-hydroxypropyl)-3-(trifluoromethyl)benzamide A solution of 2,2,2-trifluoro-1-[[(3-fluorophenyl)[3-(trifluoromethyl)benzoyl]amino]-methyl]ethyl 3-trifluoromethyl-benzoate (600 mg, 1.06 mmol) from EX-662 in methanol was treated with 28% ammonia solution (122 µL). The solution was stirred at room temperature for 10 h. The reaction was quenched with water and extracted with ether. The ether layer was washed with brine and water, then dried over anhydrous MgSO$_4$. The crude product was purified by flash column chromatography on silica gel eluting with ethyl acetate in hexane (1:8) to give 255 mg (61%) of the desired N-(3-fluorophenyl)-N-(3,3,3-trifluoro-2-hydroxypropyl)-3-(trifluoromethyl)benzamide product as a white powder, 97% pure by HPLC analysis. $^1$H NMR (CDCl$_3$) δ 7.56 (m, 3H), 7.32 (m 2H), 6.98 (m, 1H), 6.90 (m, 2H), 4.49 (dd, 1H), 4.34 (d, 1H), 4.26 (m, 1H), 4.01 (dd, 1H). $^{19}$F NMR (CDCl$_3$) δ −64.7 (s, 3F), −80.3 (s, 3F), −111.0 (m, 1F). HRMS calcd. for C$_{17}$H$_{12}$F$_7$NO$_2$: 396.0854 [M+H]$^+$, found: 396.0821.

EXAMPLE 664

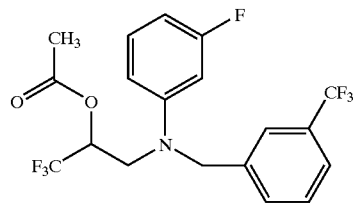

2,2,2-trifluoro-1-[[[(3-fluorophenyl)[3-(trifluoromethyl) phenyl]-methyl]amino]methyl] ethyl Acetate A solution of 3-[(3-fluorophenyl)[[3-(3-trifluoromethyl)phenyl]methyl]amino]-1,1,1-tri-fluoro-2-propanol (200 mg, 0.52 mmol) from EX-1 in triethylamine (0.6 mL) and acetic anhydride (0.5 mL) was stirred and heated to 80° C. for 1 h. The mixture was cooled and diluted with water (20 mL) and extracted into ether (2×40 mL), which was washed with 0.1 N NaOH and water. The ether solution was dried over anhydrous MgSO$_4$. The ether was removed in vacuo giving the desired 2,2,2-trifluoro-1-[[[(3-fluorophenyl) [3-(trifluoromethyl) phenyl]methyl] amino] methyl]ethyl acetate product as an amber oil, 98% pure by HPLC analysis. $^1$H NMR (CDCl$_3$) δ 7.42–7.59 (m, 3H), 7.38 (d 1H), 7.18 (q, 1H), 6.42–6.56 (m, 3H), 5.69 (m, 1H), 4.64 (ABq, 2H), 3.89 (d, 1H), 3.87(s, 1H), 1.98 (s, 3H). $^{19}$F NMR (CDCl$_3$) δ 64.0 (s, 3F), −77.2 (s, 3F), −112.9 (s, 1F). HRMS calcd. for C$_{19}$H$_{16}$F$_7$NO$_2$: 424.1148 [M+H]$^+$, found: 424.1159.

EXAMPLE 665

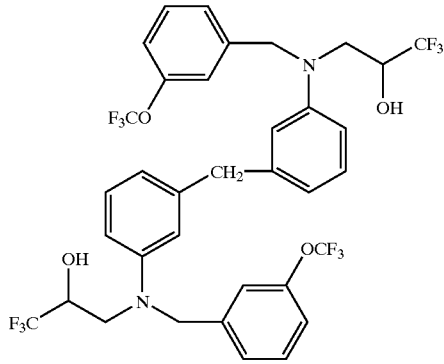

1,1'-[methylenebis[3,1-phenylene[[[3-(trifluoromethoxy)phenyl]methyl]imino]]]bis[3,3,3-trifluoro-2-propanol]

EX-665A) A solution of 3,3'-diaminophenylmethane (1.48 g, 7.5 mmol) and 3-trifluoromethoxy-benzaldehyde (2.85 g, 15 mmol) in cyclohexane (50 mL) was heated under reflux for 5 h using a Dean-Stark trap to remove water. The solvent was removed in vacuo, and the residue was dissolved in methanol (30 mL). The solution was stirred and cooled to 0° C., and solid sodium borohydride was added (0.87 g, 23 mmol). The mixture was allowed to warm to room temperature and stirred for 2 h, then acidified with 1 N HCl. After neutralizing to pH 7.5 with 2.5 N sodium hydroxide, the mixture was extracted with diethyl ether (3×30 mL). The organic layer was washed with brine and water, then dried over anhydrous MgSO$_4$, and evaporated to give 3.19 g (78%) of the desired 3,3'-N,N'-bis(trifluoromethoxyphenyl) diaminophenylmethane product as a brown oil, which was greater than 90% pure by reverse phase HPLC analysis. MS m/z=546 [M$^+$].

The amine (2.18 g, 4 mmol) product from EX-665A and 1,1,1-trifluoro-2,3-epoxy-propane (0.67 g, 6 mmol) were combined in a sealed vial and heated to 95° C. for 2 days, at which time HPLC analysis indicated that little secondary amine starting material remained. The excess oxirane was removed under nitrogen, and the crude product was purified by flash column chromatography on silica gel eluting with ethyl acetate in hexane (1:12) to give 2.0 g (67%) of the desired 1,1'-[methylenebis[3,1-phenylene [[[3-(trifluoromethoxy)phenyl]methyl]imino]]]bis-[3,3,3-trifluoro-2-propanol] product as a light amber oil, 99% pure by HPLC analysis. $^1$H NMR (CDCl$_3$) δ 7.30 (t, 2H), 7.10 (m, 6H), 7.02 (s, 2H), 6.58 (m, 4H), 6.52 (s, 2H), 4.60 (s, 4H), 4.22 (m, 2H), 3.80 (s, 2H), 3.79 (dd, 2H), 3.48 (dd, 2H), 2.60 (br s, 2H). $^{19}$F NMR (CDCl$_3$) δ −66.2 (s, 6F), −79.2 (d, 6F). HRMS calcd. for C$_{35}$H$_{30}$F$_{12}$N$_2$O$_4$: 771.2092 [M+H]$^+$, found: 771.2072.

Example EX-666

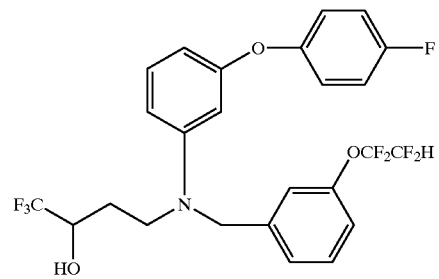

4-[[(4-fluorophenoxy)phenyl][[3-(1,1,2,2-tetrafluoroethoxy) phenyl]-methyl]amino]-1,1,1-trifluoro-2-butanol EX-666A) The 4-amino-2-hydroxy-1,1,1-trifluorobutane (1.0 g, 7.0 mmol) from EX-611A and 3-(1,1,2,2-tetrafluoroethoxy)benzaldehyde (1.5 g, 7.0 mmol) were dissolved in 20 mL of dichloroethane and acetic acid (0.40 mL, 7.7 mmol), then solid NaBH(OAc)$_3$ (1.8 g, 8.4 mmol) was added. The mixture was stirred at room temperature for 3 d, then quenched with water and extracted with ether. The ether layer was washed with water and brine, then dried over MgSO$_4$, and evaporated to give 1.6 g of crude product, which was purified by reverse phase HPLC to give 0.90 g (37%) of the desired 4-[[[3-(1,1,2,2-tetrafluoroethoxy)phenyl]methyl]amino]-1,1,1-trifluoro-2-butanol product as a yellow oil. HRMS calcd. for C$_{13}$H$_{14}$F$_7$NO$_2$: 350.0991 [M+H]$^+$, found: 350.0971.

The 1,1,1-trifluoro[[3-(1,1,2,2-tetrafluoroethoxy)phenyl] methyl]amino]-2-butanol (0.35 g, 1 mmol) from EX-666A, 3-(4-fluorophenoxy)bromobenzene (0.32 g, 1.2 mmol), Pd$_2$(dba)$_2$ (18 mg, 0.02 mmol), (R,+) BINAP (49 mg, 0.08 mmol), and Cs$_2$CO$_3$ (0.46 g, 1.4 mmol) were mixed in 9 mL of toluene and heated to 100° C. for over 2 weeks, at which time FABMS (m/z=536.3 [M+H]$^+$) indicated that the desired 4-[[(4-fluorophenoxy)phenyl]-[[3-(1,1,2,2-tetrafluoroethoxy)phenyl]methyl]amino]-1, 1,1-tri-fluoro-2-butanol product had formed.

Based on the preceding procedures, other substituted 3-[(N-aryl)-[[aryl]methyl]amino]-halo-2-propanols can be prepared by one skilled in the art using similar methods, as shown in Example Tables 43, 46, and 47. Substituted 3-[(N-aralkyl)-[[aralkyl]amino]-halo-2-propanols can also be prepared by one skilled in the art using similar methods, as shown in Example Tables 44 and 45. Substituted 3-[(N-aryl)-[[aryl]methyl]amino]-haloalkoxy-2-propanols can be prepared by one skilled in the art using similar methods, as shown in Example Table 48.

EXAMPLE TABLE 43

3-[(N-aryl)-[(aryl)methyl]amino]-1,1,1-trifluoro-2-propanols.

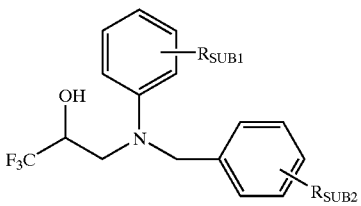

| Ex. No. | $R_{SUB1}$ | $R_{SUB2}$ | Calculated Mass [M + H]⁺ | Observed Mass [M + H]⁺ |
|---|---|---|---|---|
| 667 | 2-OCH₃ | 4-CH₃ | 340.1524 | 340.1492 |
| 668 | 2-OCH₃ | 3-CH₃ | 340.1524 | 340.1527 |
| 669 | 2-OCH₃ | 3-CF₃ | 394.1242 | 394.1239 |
| 670 | 3-F | 2-CF₃ | 382.1042 | 382.1029 |
| 671 | 3-F | 2-CH₃ | 328.1325 | 328.1319 |
| 672 | 4-CF₃ | 4-CH₃ | 378.1293 | 378.1273 |
| 673 | 2-CF₃ | 4-CH₃ | 378.1293 | 378.1284 |
| 674 | 3-F | 3-(3-CF₃-phenoxy) | 474.1304 | 474.1276 |
| 675 | 3-F | 3-(4-OCH₃-phenoxy) | 436.1536 | 436.1532 |
| 676 | 3-F | 3-(4-Cl-phenoxy) | 440.1040 | 440.1048 |
| 677 | 3-F | 3,5-(CF₃)2 | 450.0916 | 450.0923 |
| 678 | 2,3-difluoro | 3-CH₃ | 346.1230 | 346.1209 |
| 679 | 2-F, 3-CF₃ | 4-CH₃ | 396.1198 | 396.1200 |
| 680 | 2-F, 3-CF₃ | 3-CH₃ | 396.1198 | 396.1180 |
| 681 | 2,3-difluoro | 4-CH₃ | 346.1230 | 346.1228 |
| 682 | 2-OCH₃ | 4-CF₃ | 394.1242 | 394.1246 |
| 683 | 3-OCF₃ | 4-benzyloxy | 486.1504 | 486.1538 |
| 684 | 3-phenoxy | 2-NO₂, 4-Cl | 467.9 | 467.9 |
| 685 | 3-phenoxy | 4-(3,4-Cl₂-phenoxy) | 548 | 548 |
| 686 | 3-phenoxy | 4-OCH₃ | 418 | 418 |
| 687 | 3-phenoxy | 3,4-(OCF₂CF₂O) | 518.1202 | 518.1286 |
| 688 | 3-OCF₃ | 3-CF₃ | 448 | 448 |
| 689 | 4-phenyl | 3-CF₃ | 440.1449 | 440.1430 |
| 690 | 3,5-(CF₃)₂ | 3-phenoxy | 524 | 524 |
| 691 | 2,5-(CF₃)₂ | 3-CF₃ | 500 | 500 |
| 692 | 3-OH | 3-OCF₃ | 396.1034 | 396.1053 |
| 693 | 3-[4-(propanoyl)phenoxy] | 3-OCF₂CF₂H | 560.1672 | 560.1694 |

EXAMPLE TABLE 44

3-[N-[(aryl)methyl]-[(aryl)methyl]amino]-1,1,1-trifluoro-2-propanols.

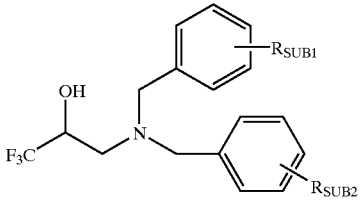

| Ex. No. | $R_{SUB1}$ | $R_{SUB2}$ | Calculated Mass [M + H] | Observed Mass [M + H] |
|---|---|---|---|---|
| 694 | 3-Cl | 3-OCF₃ | 428.0852 | 428.0817 |
| 695 | 3-Br | 3-OCH₃ | 472.0347 | 472.0312 |
| 696 | 2-F | 2-CF₃ | 396.1198 | 396.1193 |

EXAMPLE TABLE 45

3-[N-[(aryl)methyl]-[(aryl)methyl]amino]-1,1,1-trifluoro-2-propanols.

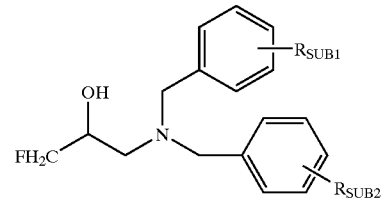

| Ex. No. | $R_{SUB1}$ | $R_{SUB2}$ | Calculated Mass [M + H] | Observed Mass [M + H] |
|---|---|---|---|---|
| 697 | 3-OCF₃ | 3-OCF₃ | 442.1253 | 442.1232 |

EXAMPLE TABLE 46

3-[N-(aryl)-N-(aralkyl)amino]-1,1,1-trifluoro-2-propanols.

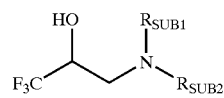

| Ex. No. | $R_{SUB1}$ | $R_{SUB2}$ | Calculated Mass [M + H] | Observed Mass [M + H] |
|---|---|---|---|---|
| 698 | 3-OCF₃-benzyl | 2-methoxy-dibenzofuran-3-yl | 500.1297 | 500.1295 |
| 699 | 3-OCF₃-benzyl | 2-fluorenyl | 468.1398 | 468.1374 |

EXAMPLE TABLE 47

3-[N-(aryl)-[(aryl)methyl]amino]-1,1,1-trifluoro-2-propanols.

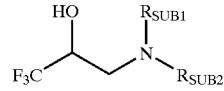

| Ex. No. | $R_{SUB1}$-N-$R_{SUB2}$ | Calculated Mass [M + H] | Observed Mass [M + H] |
|---|---|---|---|
| 700 | 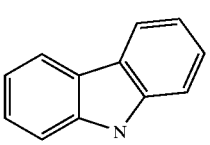 | 280.0949 | 280.0938 |

EXAMPLE TABLE 48

3-[N-(aryl)-N-(aralkyl)amino]-1-haloalkoxy-2-propanols.

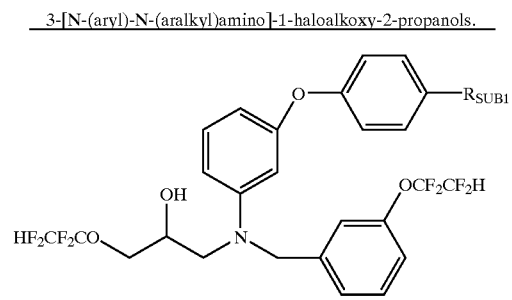

| Ex. No. | $R_{SUB1}$ | Calculated Mass [M + H] | Observed Mass [M + H] |
|---|---|---|---|
| 701 | F | 584.1483 | 584.1473 |
| 702 | $CF_3$ | 634.1451 | 634.1432 |

Based on the preceding procedures, additional substituted 3-[(N-aryl)-[[aryl]methyl]amino]-halo-2-propanols are prepared by one skilled in the art using similar methods, as shown in the multiple sections of Example Table 49. Substituted 4-[N-(aryl)-[(aryl)methyl]amino]-1,1,1,2,2-pentafluoro-3-butanols are prepared by one skilled in the art using similar methods, as shown in Example Table 50. Substituted 3-[N-(aryl)-[(aryl)oxy]amino]-1,1,1-trifluoro-2-propanols are prepared by one skilled in the art using similar methods, as shown in Example Table 51. Substituted 3-[N-(aryl)-L(aryl)methyl]amino]-1,1,1-trifluoro-2-butanols are prepared by one skilled in the art using similar methods, as shown in Example Table 52.

Substituted 3-[N,N'-(diaryl)amino]-1,1,1-trifluoro-2-propanols are prepared by one skilled in the art using similar methods, as shown in Example Table 53. Substituted 2-[N-(aryl)-[(aryl)methyl]amino]-1-trifluoromethylcyclopentanols are prepared by one skilled in the art using similar methods, as shown in Example Table 54.

EXAMPLE TABLE 49

Substituted 3-[N-(aryl)-[(aryl)methyl]amino]-1,1,1-trifluoro-2-propanols.

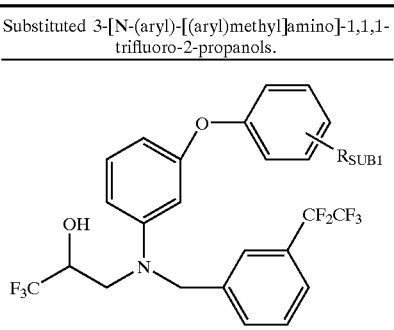

| Ex. No. | $R_{SUB1}$ |
|---|---|
| 703 | 3-isopropyl |
| 704 | 2-Cl, 3-Cl |
| 705 | 3-$CF_3$O |
| 706 | 4-F |
| 707 | 4-$CH_3$ |
| 708 | 2-F, 5-Br |
| 709 | 3-$CHF_2$O |
| 710 | 3-$CH_3CH_2$ |
| 711 | 3-$CH_3$, 5-$CH_3$ |
| 712 | 3-$(CH_3)_3$C |
| 713 | 4-F, 3-$CH_3$ |

EXAMPLE TABLE 49-continued

| | |
|---|---|
| 714 | 3-Cl, 4-Cl |
| 715 | 3,4-$(CH_2)_4$ |
| 716 | 3-$HCF_2CF_2$O |
| 717 | H |
| 718 | 3-$(CH_3)_2$N |
| 719 | 3-cyclopropyl |
| 720 | 3-(2-furyl) |
| 721 | 3-$CF_3CF_2$ |
| 722 | 4-$NH_2$ |
| 723 | 3-$CH_3$, 4-$CH_3$, 5-$CH_3$ |
| 724 | 4-$CH_3CH_2CH_2$O |
| 725 | 2-$NO_2$ |

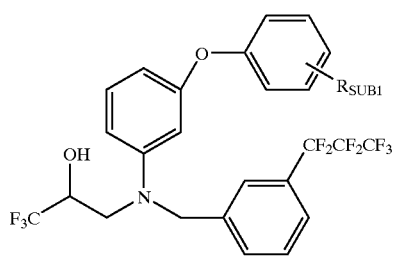

| Ex. No. | $R_{SUB1}$ |
|---|---|
| 726 | 3-isopropyl |
| 727 | 2-Cl, 3-Cl |
| 728 | 3-$CF_3$O |
| 729 | 4-F |
| 730 | 4-$CH_3$ |
| 731 | 2-F, 5-Br |
| 732 | 2-Br, 5-F |
| 733 | 3-$CH_3CH_2$ |
| 734 | 3-$CH_3$, 5-$CH_3$ |
| 735 | 3-$(CH_3)_3$C |
| 736 | 4-F, 3-$CH_3$ |
| 737 | 3-Cl, 4-Cl |
| 738 | 3,4-$(CH_2)_4$ |
| 739 | 3-$HCF_2CF_2$O |
| 740 | 3-$CHF_2$O |
| 741 | 3-$(CH_3)_2$N |
| 742 | 3-cyclopropyl |
| 743 | 3-(2-furyl) |
| 744 | 3-$CF_3CF_2$ |
| 745 | 4-$NH_2$ |
| 746 | 3-$CH_3$, 4-$CH_3$, 5-$CH_3$ |
| 747 | 4-$CH_3CH_2CH_2$O |
| 748 | 2-$NO_2$ |

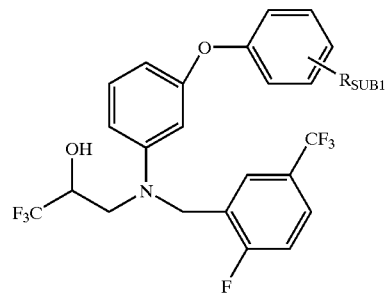

| Ex. No. | $R_{SUB1}$ |
|---|---|
| 749 | 3-isopropyl |
| 750 | 2-Cl, 3-Cl |
| 751 | 3-$CF_3$O |
| 752 | 4-F |
| 753 | 4-$CH_3$ |
| 754 | 2-F, 5-Br |
| 755 | 4-Cl, 3-$CH_3CH_2$ |
| 756 | 3-$CH_3CH_2$ |
| 757 | 3-$CH_3$, 5-$CH_3$ |
| 758 | 3-$(CH_3)_3$C |

EXAMPLE TABLE 49-continued

| 759 | 4-F, 3-CH$_3$ |
| 760 | 3-Cl, 4-Cl |
| 761 | 3,4-(CH$_2$)$_4$ |
| 762 | 3-HCF$_2$CF$_2$O |
| 763 | 3-CHF$_2$O |
| 764 | 3-(CH$_3$)$_2$N |
| 765 | 3-cyclopropyl |
| 766 | 3-(2-furyl) |
| 767 | 3-CF$_3$CF$_2$ |
| 768 | 4-NH$_2$ |
| 769 | 3-CH$_3$, 4-CH$_3$, 5-CH$_3$ |
| 770 | 4-CH$_3$CH$_2$CH$_2$O |
| 771 | 2-NO$_2$ |

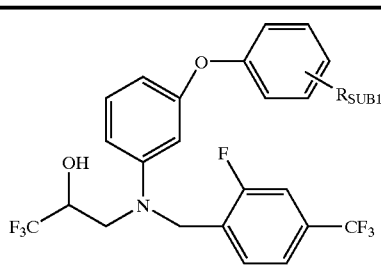

| Ex. No. | R$_{SUB1}$ |
|---|---|
| 772 | 3-isopropyl |
| 773 | 2-Cl, 3-Cl |
| 774 | 3-CF$_3$O |
| 775 | 4-F |
| 776 | 4-CH$_3$ |
| 777 | 2-F, 5-Br |
| 778 | 4-Cl, 3-CH$_3$CH$_2$ |
| 779 | 3-CH$_3$CH$_2$ |
| 780 | 3-CH$_3$, 5-CH$_3$ |
| 781 | 3-(CH$_3$)$_3$C |
| 782 | 4-F, 3-CH$_3$ |
| 783 | 3-Cl, 4-Cl |
| 784 | 3,4-(CH$_2$)$_4$ |
| 785 | 3-HCF$_2$CF$_2$O |
| 786 | 3-CHF$_2$O |
| 787 | 3-(CH$_3$)$_2$N |
| 788 | 3-cyclopropyl |
| 789 | 3-(2-furyl) |
| 790 | 3-CF$_3$CF$_2$ |
| 791 | 4-NH$_2$ |
| 792 | 3-CH$_3$, 4-CH$_3$, 5-CH$_3$ |
| 793 | 4-CH$_3$CH$_2$CH$_2$O |
| 794 | 2-NO$_2$ |

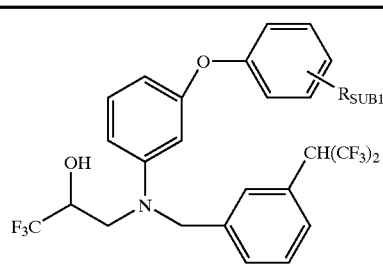

| Ex. No. | R$_{SUB1}$ |
|---|---|
| 795 | 3-isopropyl |
| 796 | 2-Cl, 3-Cl |
| 797 | 3-CF$_3$O |
| 798 | 4-F |
| 799 | 4-CH$_3$ |
| 800 | 2-F, 5-Br |
| 801 | 4-Cl, 3-CH$_3$CH$_2$ |
| 802 | 3-CH$_3$CH$_2$ |
| 803 | 3-CH$_3$, 5-CH$_3$ |
| 804 | 3-(CH$_3$)$_3$C |
| 805 | 4-F, 3-CH$_3$ |

EXAMPLE TABLE 49-continued

| 806 | 3-Cl, 4-Cl |
| 807 | 3,4-(CH$_2$)$_4$ |
| 808 | 3-HCF$_2$CF$_2$O |
| 809 | 3-CHF$_2$O |
| 810 | 3-(CH$_3$)$_2$N |
| 811 | 3-cyclopropyl |
| 812 | 3-(2-furyl) |
| 813 | 3-CF$_3$CF$_2$ |
| 814 | 4-NH$_2$ |
| 815 | 3-CH$_3$, 4-CH$_3$, 5-CH$_3$ |
| 816 | 4-CH$_3$CH$_2$CH$_2$O |
| 817 | 2-NO$_2$ |

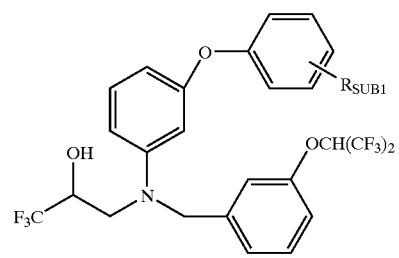

| Ex. No. | R$_{SUB1}$ |
|---|---|
| 818 | 3-isopropyl |
| 819 | 2-Cl, 3-Cl |
| 820 | 3-CF$_3$O |
| 821 | 4-F |
| 822 | 4-CH$_3$ |
| 823 | 2-F, 5-Br |
| 824 | 4-Cl, 3-CH$_3$CH$_2$ |
| 825 | 3-CH$_3$CH$_2$ |
| 826 | 3-CH$_3$, 5-CH$_3$ |
| 827 | 3-(CH$_3$)$_3$C |
| 828 | 4-F, 3-CH$_3$ |
| 829 | 3-Cl, 4-Cl |
| 830 | 3,4-(CH$_2$)$_4$ |
| 831 | 3-HCF$_2$CF$_2$O |
| 832 | 3-CHF$_2$O |
| 833 | 3-(CH$_3$)$_2$N |
| 834 | 3-cyclopropyl |
| 835 | 3-(2-furyl) |
| 836 | 3-CF$_3$CF$_2$ |
| 837 | 4-NH$_2$ |
| 838 | 3-CH$_3$, 4-CH$_3$, 5-CH$_3$ |
| 839 | 4-CH$_3$CH$_2$CH$_2$O |
| 840 | 2-NO$_2$ |

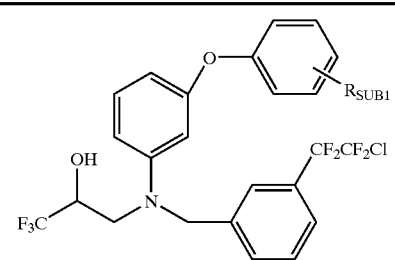

| Ex. No. | R$_{SUB1}$ |
|---|---|
| 841 | 3-isopropyl |
| 842 | 2-Cl, 3-Cl |
| 843 | 3-CF$_3$O |
| 844 | 4-F |
| 845 | 4-CH$_3$ |
| 846 | 2-F, 5-Br |
| 847 | 4-Cl, 3-CH$_3$CH$_2$ |
| 848 | 3-CH$_3$CH$_2$ |
| 849 | 3-CH$_3$, 5-CH$_3$ |
| 850 | 3-(CH$_3$)$_3$C |
| 851 | 4-F, 3-CH$_3$ |
| 852 | 3-Cl, 4-Cl |

EXAMPLE TABLE 49-continued

| Ex. No. | R$_{SUB1}$ |
|---|---|
| 853 | 3,4-(CH$_2$)$_4$ |
| 854 | 3-HCF$_2$CF$_2$O |
| 855 | 3-CHF$_2$O |
| 856 | 3-(CH$_3$)$_2$N |
| 857 | 3-cyclopropyl |
| 858 | 3-(2-furyl) |
| 859 | 3-CF$_3$CF$_2$ |
| 860 | 4-NH$_2$ |
| 861 | 3-CH$_3$, 4-CH$_3$, 5-CH$_3$ |
| 862 | 4-CH$_3$CH$_2$CH$_2$O |
| 863 | 2-NO$_2$ |

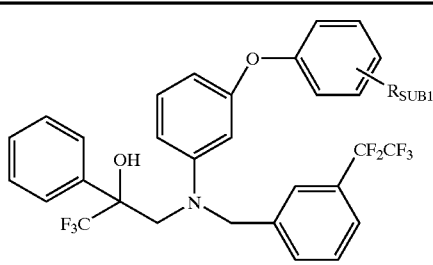

| Ex. No. | R$_{SUB1}$ |
|---|---|
| 864 | 3-isopropyl |
| 865 | 2-Cl, 3-Cl |
| 866 | 3-CF$_3$O |
| 867 | 4-F |
| 868 | 4-CH$_3$ |
| 869 | 2-F, 5-Br |
| 870 | 4-Cl, 3-CH$_3$CH$_2$ |
| 871 | 3-CH$_3$CH$_2$ |
| 872 | 3-CH$_3$, 5-CH$_3$ |
| 873 | 3-(CH$_3$)$_3$C |
| 874 | 4-F, 3-CH$_3$ |
| 875 | 3-Cl, 4-Cl |
| 876 | 3,4-(CH$_2$)$_4$ |
| 877 | 3-HCF$_2$CF$_2$O |
| 878 | 3-CHF$_2$O |
| 879 | 3-(CH$_3$)$_2$N |
| 880 | 3-cyclopropyl |
| 881 | 3-(2-furyl) |
| 882 | 3-CF$_3$CF$_2$ |
| 883 | 4-NH$_2$ |
| 884 | 3-CH$_3$, 4-CH$_3$, 5-CH$_3$ |
| 885 | 4-CH$_3$CH$_2$CH$_2$O |
| 886 | 2-NO$_2$ |

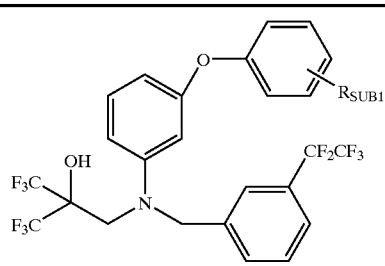

| Ex. No. | R$_{SUB1}$ |
|---|---|
| 887 | 3-isopropyl |
| 888 | 2-Cl, 3-Cl |
| 889 | 3-CF$_3$O |
| 890 | 4-F |
| 891 | 4-CH$_3$ |
| 892 | 2-F, 5-Br |
| 893 | 4-Cl, 3-CH$_3$CH$_2$ |
| 894 | 3-CH$_3$CH$_2$ |
| 895 | 3-CH$_3$, 5-CH$_3$ |
| 896 | 3-(CH$_3$)$_3$C |
| 897 | 4-F, 3-CH$_3$ |
| 898 | 3-Cl, 4-Cl |
| 899 | 3,4-(CH$_2$)$_4$ |

EXAMPLE TABLE 49-continued

| Ex. No. | R$_{SUB1}$ |
|---|---|
| 900 | 3-HCF$_2$CF$_2$O |
| 901 | 3-CHF$_2$O |
| 902 | 3-(CH$_3$)$_2$N |
| 903 | 3-cyclopropyl |
| 904 | 3-(2-furyl) |
| 905 | 3-CF$_3$CF$_2$ |
| 906 | 4-NH$_2$ |
| 907 | 3-CH$_3$, 4-CH$_3$, 5-CH$_3$ |
| 908 | 4-CH$_3$CH$_2$CH$_2$O |
| 909 | 2-NO$_2$ |

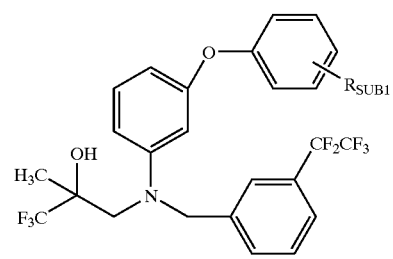

| Ex. No. | R$_{SUB1}$ |
|---|---|
| 910 | 3-isopropyl |
| 911 | 2-Cl, 3-Cl |
| 912 | 3-CF$_3$O |
| 913 | 4-F |
| 914 | 4-CH$_3$ |
| 915 | 2-F, 5-Br |
| 916 | 4-Cl, 3-CH$_3$CH$_2$ |
| 917 | 3-CH$_3$CH$_2$ |
| 918 | 3-CH$_3$, 5-CH$_3$ |
| 919 | 3-(CH$_3$)$_3$C |
| 920 | 4-F, 3-CH$_3$ |
| 921 | 3-Cl, 4-Cl |
| 922 | 3,4-(CH$_2$)$_4$ |
| 923 | 3-HCF$_2$CF$_2$O |
| 924 | 3-CHF$_2$O |
| 925 | 3-(CH$_3$)$_2$N |
| 926 | 3-cyclopropyl |
| 927 | 3-(2-furyl) |
| 928 | 3-CF$_3$CF$_2$ |
| 929 | 4-NH$_2$ |
| 930 | 3-CH$_3$, 4-CH$_3$, 5-CH$_3$ |
| 931 | 4-CH$_3$CH$_2$CH$_2$O |
| 932 | 2-NO$_2$ |

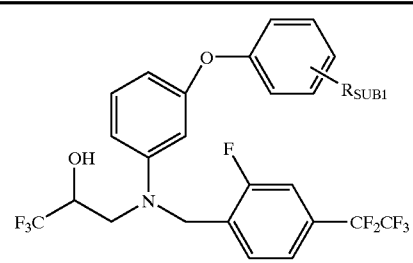

| Ex. No. | R$_{SUB1}$ |
|---|---|
| 933 | 3-isopropyl |
| 934 | 2-Cl, 3-Cl |
| 935 | 3-CF$_3$O |
| 936 | 4-F |
| 937 | 4-CH$_3$ |
| 938 | 2-F, 5-Br |
| 939 | 4-Cl, 3-CH$_3$CH$_2$ |
| 940 | 3-CH$_3$CH$_2$ |
| 941 | 3-CH$_3$, 5-CH$_3$ |
| 942 | 3-(CH$_3$)$_3$C |
| 943 | 4-F, 3-CH$_3$ |
| 944 | 3-Cl, 4-Cl |
| 945 | 3,4-(CH$_2$)$_4$ |
| 946 | 3-HCF$_2$CF$_2$O |

EXAMPLE TABLE 49-continued

| 947 | 3-CHF$_2$O |
| 948 | 3-(CH$_3$)$_2$N |
| 949 | 3-cyclopropyl |
| 950 | 3-(2-furyl) |
| 951 | 3-CF$_3$CF$_2$ |
| 952 | 4-NH$_2$ |
| 953 | 3-CH$_3$, 4-CH$_3$, 5-CH$_3$ |
| 954 | 4-CH$_3$CH$_2$CH$_2$O |
| 955 | 2-NO$_2$ |

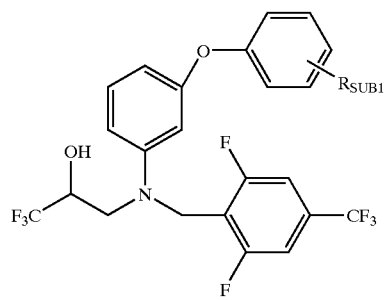

| Ex. No. | R$_{SUB1}$ |
| --- | --- |
| 956 | 3-isopropyl |
| 957 | 2-Cl, 3-Cl |
| 958 | 3-CF$_3$O |
| 959 | 4-F |
| 960 | 4-CH$_3$ |
| 961 | 2-F, 5-Br |
| 962 | 2-Br, 5-F |
| 963 | 3-CH$_3$CH$_2$ |
| 964 | 3-CH$_3$, 5-CH$_3$ |
| 965 | 3-(CH$_3$)$_3$C |
| 966 | 4-F, 3-CH$_3$ |
| 967 | 3-Cl, 4-Cl |
| 968 | 3,4-(CH$_2$)$_4$ |
| 969 | 3-HCF$_2$CF$_2$O |
| 970 | 3-CHF$_2$O |
| 971 | 3-(CH$_3$)$_2$N |
| 972 | 3-cyclopropyl |
| 973 | 3-(2-furyl) |
| 974 | 3-CF$_3$CF$_2$ |
| 975 | 4-NH$_2$ |
| 976 | 3-CH$_3$, 4-CH$_3$, 5-CH$_3$ |
| 977 | 4-CH$_3$CH$_2$CH$_2$O |
| 978 | 2-NO$_2$ |

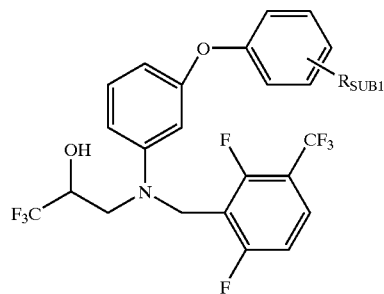

| Ex. No. | R$_{SUB1}$ |
| --- | --- |
| 979 | 3-isopropyl |
| 980 | 2-Cl, 3-Cl |
| 981 | 3-CF$_3$O |
| 982 | 4-F |
| 983 | 4-CH$_3$ |
| 984 | 2-F, 5-Br |
| 985 | 4-Cl, 3-CH$_3$CH$_2$ |
| 986 | 3-CH$_3$CH$_2$ |
| 987 | 3-CH$_3$, 5-CH$_3$ |
| 988 | 3-(CH$_3$)$_3$C |
| 989 | 4-F, 3-CH$_3$ |

EXAMPLE TABLE 49-continued

| 990 | 3-Cl, 4-Cl |
| 991 | 3,4-(CH$_2$)$_4$ |
| 992 | 3-HCF$_2$CF$_2$O |
| 993 | 3-CHF$_2$O |
| 994 | 3-(CH$_3$)$_2$N |
| 995 | 3-cyclopropyl |
| 996 | 3-(2-furyl) |
| 997 | 3-CF$_3$CF$_2$ |
| 998 | 4-NH$_2$ |
| 999 | 3-CH$_3$, 4-CH$_3$, 5-CH$_3$ |
| 1000 | 4-CH$_3$CH$_2$CH$_2$O |
| 1001 | 2-NO$_2$ |

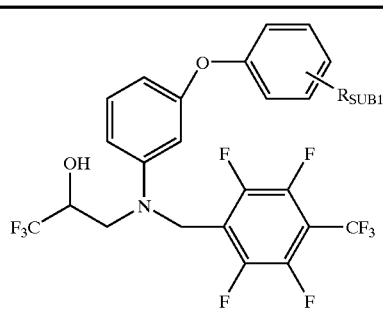

| Ex. No. | R$_{SUB1}$ |
| --- | --- |
| 1002 | 3-isopropyl |
| 1003 | 2-Cl, 3-Cl |
| 1004 | 3-CF$_3$O |
| 1005 | 4-F |
| 1006 | 4-CH$_3$ |
| 1007 | 2-F, 5-Br |
| 1008 | 4-Cl, 3-CH$_3$CH$_2$ |
| 1009 | 3-CH$_3$CH$_2$ |
| 1010 | 3-CH$_3$, 5-CH$_3$ |
| 1011 | 3-(CH$_3$)$_3$C |
| 1012 | 4-F, 3-CH$_3$ |
| 1013 | 3-Cl, 4-Cl |
| 1014 | 3,4-(CH$_2$)$_4$ |
| 1015 | 3-HCF$_2$CF$_2$O |
| 1016 | 3-CHF$_2$O |
| 1017 | 3-(CH$_3$)$_2$N |
| 1018 | 3-cyclopropyl |
| 1019 | 3-(2-furyl) |
| 1020 | 3-CF$_3$CF$_2$ |
| 1021 | 4-NH$_2$ |
| 1022 | 3-CH$_3$, 4-CH$_3$, 5-CH$_3$ |
| 1023 | 4-CH$_3$CH$_2$CH$_2$O |
| 1024 | 2-NO$_2$ |

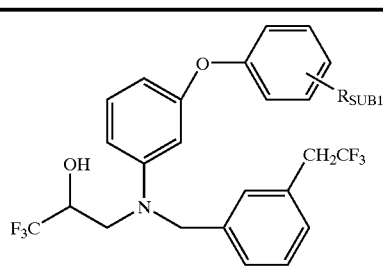

| Ex. No. | R$_{SUB1}$ |
| --- | --- |
| 1025 | 3-isopropyl |
| 1026 | 2-Cl, 3-Cl |
| 1027 | 3-CF$_3$O |
| 1028 | 4-F |
| 1029 | 4-CH$_3$ |
| 1030 | 2-F, 5-Br |
| 1031 | 4-Cl, 3-CH$_3$CH$_2$ |
| 1032 | 3-CH$_3$CH$_2$ |
| 1033 | 3-CH$_3$, 5-CH$_3$ |
| 1034 | 3-(CH$_3$)$_3$C |

EXAMPLE TABLE 49-continued

| Ex. No. | $R_{SUB2}$ |
|---|---|
| 1035 | 4-F, 3-CH$_3$ |
| 1036 | 3-Cl, 4-Cl |
| 1037 | 3,4-(CH$_2$)$_4$ |
| 1038 | 3-HCF$_2$CF$_2$O |
| 1039 | 3-CHF$_2$O |
| 1040 | 3-(CH$_3$)$_2$N |
| 1041 | 3-cyclopropyl |
| 1042 | 3-(2-furyl) |
| 1043 | 3-CF$_3$CF$_2$ |
| 1044 | 4-NH$_2$ |
| 1045 | 3-CH$_3$, 4-CH$_3$, 5-CH$_3$ |
| 1046 | 4-CH$_3$CH$_2$CH$_2$O |
| 1047 | 2-NO$_2$ |

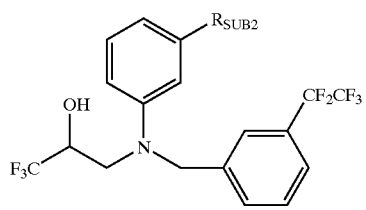

| Ex. No. | $R_{SUB2}$ |
|---|---|
| 1048 | 3-CF$_3$O-benzyloxy |
| 1049 | 3-CF$_3$-benzyloxy |
| 1050 | 3-F, 5-F-benzyloxy |
| 1051 | cyclohexylmethyleneoxy |
| 1052 | benzyloxy |
| 1053 | 3-CF$_3$, 5-CF$_3$-benzyloxy |
| 1054 | 4-CF$_3$O-benzyloxy |
| 1055 | 4-CH$_3$CH$_2$-benzyloxy |
| 1056 | isopropoxy |
| 1057 | 3-CF$_3$-benzyl |
| 1058 | isopropylthio |
| 1059 | cyclopentoxy |
| 1060 | 3-Cl-5-pyridinyloxy |
| 1061 | 3-CF$_3$S-benzyloxy |
| 1062 | 3-CH$_3$, 4-CH$_3$-benzyloxy |
| 1063 | 2-F, 3-CF$_3$-benzyloxy |
| 1064 | 3-F, 5-CF$_3$-benzyloxy |
| 1065 | 4-(CH$_3$)$_2$CH-benzyloxy |
| 1066 | 1-phenylethoxy |
| 1067 | 4-F, 3-CH$_3$-benzoyl |
| 1068 | 3-CF$_3$-phenyl- |
| 1069 | 4-CH$_3$O-phenylamino- |
| 1070 | 4-NO$_2$-phenylthio- |

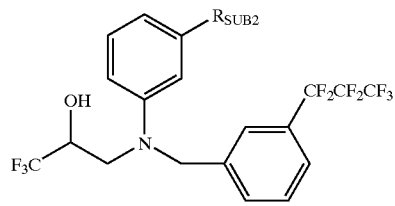

| Ex. No. | $R_{SUB2}$ |
|---|---|
| 1071 | 3-CF$_3$O-benzyloxy |
| 1072 | 3-CF$_3$-benzyloxy |
| 1073 | 3-F, 5-F-benzyloxy |
| 1074 | cyclohexylmethyleneoxy |
| 1075 | benzyloxy |
| 1076 | 3-CF$_3$, 5-CF$_3$-benzyloxy |
| 1077 | 4-CF$_3$O-benzyloxy |
| 1078 | 4-CH$_3$CH$_2$-benzyloxy |
| 1079 | isopropoxy |
| 1080 | 3-CF$_3$-benzyl |
| 1081 | isopropylthio |
| 1082 | cyclopentoxy |
| 1083 | 3-Cl-5-pyridinyloxy |
| 1084 | 3-CF$_3$S-benzyloxy |
| 1085 | 3-CH$_3$, 4-CH$_3$-benzyloxy |
| 1086 | 2-F, 3-CF$_3$-benzyloxy |
| 1087 | 3-F, 5-CF$_3$-benzyloxy |
| 1088 | 4-(CH$_3$)$_2$CH-benzyloxy |
| 1089 | 1-phenylethoxy |
| 1090 | 4-F, 3-CH$_3$-benzoyl |
| 1091 | 3-CF$_3$-phenyl- |
| 1092 | 4-CH$_3$O-phenylamino- |
| 1093 | 4-NO$_2$-phenylthio- |

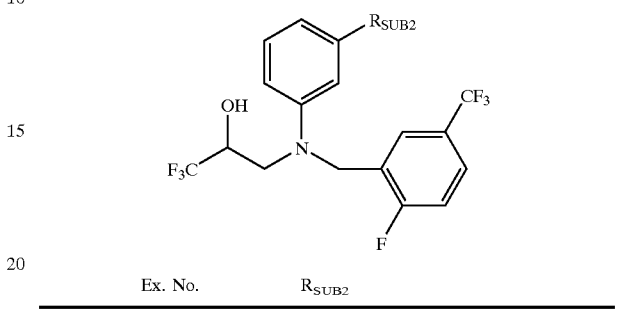

| Ex. No. | $R_{SUB2}$ |
|---|---|
| 1094 | 3-CF$_3$O-benzyloxy |
| 1095 | 3-CF$_3$-benzyloxy |
| 1096 | 3-F, 5-F-benzyloxy |
| 1097 | cyclohexylmethyleneoxy |
| 1098 | benzyloxy |
| 1099 | 3-CF$_3$, 5-CF$_3$-benzyloxy |
| 1100 | 4-CF$_3$O-benzyloxy |
| 1101 | 4-CH$_3$CH$_2$-benzyloxy |
| 1102 | isopropoxy |
| 1103 | 3-CF$_3$-benzyl |
| 1104 | isopropylthio |
| 1105 | cyclopentoxy |
| 1106 | 3-Cl-5-pyridinyloxy |
| 1107 | 3-CF$_3$S-benzyloxy |
| 1108 | 3-CH$_3$, 4-CH$_3$-benzyloxy |
| 1109 | 2-F, 3-CF$_3$-benzyloxy |
| 1110 | 3-F, 5-CF$_3$-benzyloxy |
| 1111 | 4-(CH$_3$)$_2$CH-benzyloxy |
| 1112 | 1-phenylethoxy |
| 1113 | 4-F, 3-CH$_3$-benzoyl |
| 1114 | 3-CF$_3$-phenyl- |
| 1115 | 4-CH$_3$O-phenylamino- |
| 1116 | 4-NO$_2$-phenylthio- |

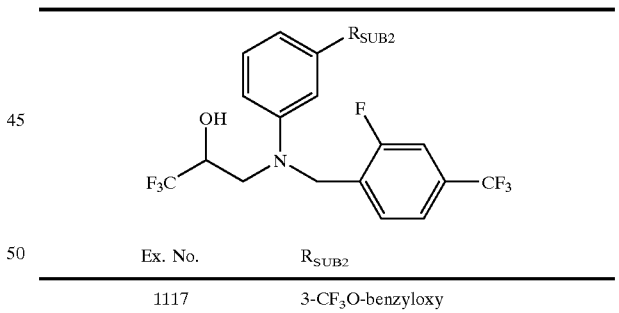

| Ex. No. | $R_{SUB2}$ |
|---|---|
| 1117 | 3-CF$_3$O-benzyloxy |
| 1118 | 3-CF$_3$-benzyloxy |
| 1119 | 3-F, 5-F-benzyloxy |
| 1120 | cyclohexylmethyleneoxy |
| 1121 | benzyloxy |
| 1122 | 3-CF$_3$, 5-CF$_3$-benzyloxy |
| 1123 | 4-CF$_3$O-benzyloxy |
| 1124 | 4-CH$_3$CH$_2$-benzyloxy |
| 1125 | isopropoxy |
| 1126 | 3-CF$_3$-benzyl |
| 1127 | isopropylthio |
| 1128 | cyclopentoxy |
| 1129 | 3-Cl-5-pyridinyloxy |
| 1130 | 3-CF$_3$S-benzyloxy |
| 1131 | 3-CH$_3$, 4-CH$_3$-benzyloxy |
| 1132 | 2-F, 3-CF$_3$-benzyloxy |
| 1133 | 3-F, 5-CF$_3$-benzyloxy |
| 1134 | 4-(CH$_3$)$_2$CH-benzyloxy |

EXAMPLE TABLE 49-continued

| 1135 | 1-phenylethoxy |
| 1136 | 4-F, 3-$CH_3$-benzoyl |
| 1137 | 3-$CF_3$-phenyl- |
| 1138 | 4-$CH_3$O-phenylamino- |
| 1139 | 4-$NO_2$-phenylthio- |

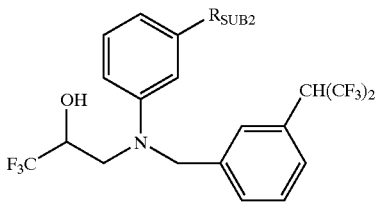

| Ex. No. | $R_{SUB2}$ |
|---|---|
| 1140 | 3-$CF_3$O-benzyloxy |
| 1141 | 3-$CF_3$-benzyloxy |
| 1142 | 3-F, 5-F-benzyloxy |
| 1143 | cyclohexylmethyleneoxy |
| 1144 | benzyloxy |
| 1145 | 3-$CF_3$, 5-$CF_3$-benzyloxy |
| 1146 | 4-$CF_3$O-benzyloxy |
| 1147 | 4-$CH_3CH_2$-benzyloxy |
| 1148 | isopropoxy |
| 1149 | 3-$CF_3$-benzyl |
| 1150 | isopropylthio |
| 1151 | cyclopentoxy |
| 1152 | 3-Cl-5-pyridinyloxy |
| 1153 | 3-$CF_3$S-benzyloxy |
| 1154 | 3-$CH_3$, 4-$CH_3$-benzyloxy |
| 1155 | 2-F, 3-$CF_3$-benzyloxy |
| 1156 | 3-F, 5-$CF_3$-benzyloxy |
| 1157 | 4-$(CH_3)_2$CH-benzyloxy |
| 1158 | 1-phenylethoxy |
| 1159 | 4-F, 3-$CH_3$-benzoyl |
| 1160 | 3-$CF_3$-phenyl- |
| 1161 | 4-$CH_3$O-phenylamino- |
| 1162 | 4-$NO_2$-phenylthio- |

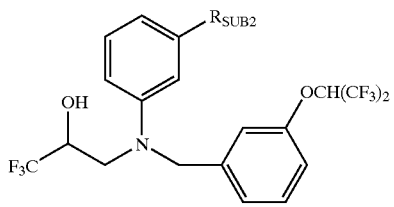

| Ex. No. | $R_{SUB2}$ |
|---|---|
| 1163 | 3-$CF_3$O-benzyloxy |
| 1164 | 3-$CF_3$-benzyloxy |
| 1165 | 3-F, 5-F-benzyloxy |
| 1166 | cyclohexylmethyleneoxy |
| 1167 | benzyloxy |
| 1168 | 3-$CF_3$, 5-$CF_3$-benzyloxy |
| 1169 | 4-$CF_3$O-benzyloxy |
| 1170 | 4-$CH_3CH_2$-benzyloxy |
| 1171 | isopropoxy |
| 1172 | 3-$CF_3$-benzyl |
| 1173 | isopropylthio |
| 1174 | cyclopentoxy |
| 1175 | 3-Cl-5-pyridinyloxy |
| 1176 | 3-$CF_3$S-benzyloxy |
| 1177 | 3-$CH_3$, 4-$CH_3$-benzyloxy |
| 1178 | 2-F, 3-$CF_3$-benzyloxy |
| 1179 | 3-F, 5-$CF_3$-benzyloxy |
| 1180 | 4-$(CH_3)_2$CH-benzyloxy |
| 1181 | 1-phenylethoxy |
| 1182 | 4-F, 3-$CH_3$-benzoyl |
| 1183 | 3-$CF_3$-phenyl- |

EXAMPLE TABLE 49-continued

| 1184 | 4-$CH_3$O-phenylamino- |
| 1185 | 4-$NO_2$-phenylthio- |

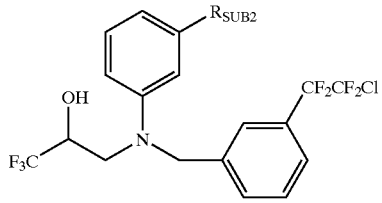

| Ex. No. | $R_{SUB2}$ |
|---|---|
| 1186 | 3-$CF_3$O-benzyloxy |
| 1187 | 3-$CF_3$-benzyloxy |
| 1188 | 3-F, 5-F-benzyloxy |
| 1189 | cyclohexylmethyleneoxy |
| 1190 | benzyloxy |
| 1191 | 3-$CF_3$, 5-$CF_3$-benzyloxy |
| 1192 | 4-$CF_3$O-benzyloxy |
| 1193 | 4-$CH_3CH_2$-benzyloxy |
| 1194 | isopropoxy |
| 1195 | 3-$CF_3$-benzyl |
| 1196 | isopropylthio |
| 1197 | cyclopentoxy |
| 1198 | 3-Cl-5-pyridinyloxy |
| 1199 | 3-$CF_3$S-benzyloxy |
| 1200 | 3-$CH_3$, 4-$CH_3$-benzyloxy |
| 1201 | 2-F, 3-$CF_3$-benzyloxy |
| 1202 | 3-F, 5-$CF_3$-benzyloxy |
| 1203 | 4-$(CH_3)_2$CH-benzyloxy |
| 1204 | 1-phenylethoxy |
| 1205 | 4-F, 3-$CH_3$-benzoyl |
| 1206 | 3-$CF_3$-phenyl- |
| 1207 | 4-$CH_3$O-phenylamino- |
| 1208 | 4-$NO_2$-phenylthio- |

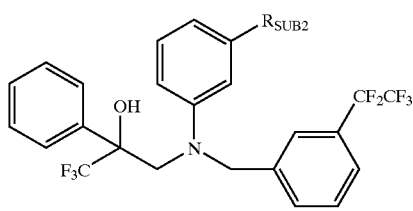

| Ex. No. | $R_{SUB2}$ |
|---|---|
| 1209 | 3-$CF_3$O-benzyloxy |
| 1210 | 3-$CF_3$-benzyloxy |
| 1211 | 3-F, 5-F-benzyloxy |
| 1212 | cyclohexylmethyleneoxy |
| 1213 | benzyloxy |
| 1214 | 3-$CF_3$, 5-$CF_3$-benzyloxy |
| 1215 | 4-$CF_3$O-benzyloxy |
| 1216 | 4-$CH_3CH_2$-benzyloxy |
| 1217 | isopropoxy |
| 1218 | 3-$CF_3$-benzyl |
| 1219 | isopropylthio |
| 1220 | cyclopentoxy |
| 1221 | 3-Cl-5-pyridinyloxy |
| 1222 | 3-$CF_3$S-benzyloxy |
| 1223 | 3-$CH_3$, 4-$CH_3$-benzyloxy |
| 1224 | 2-F, 3-$CF_3$-benzyloxy |
| 1225 | 3-F, 5-$CF_3$-benzyloxy |
| 1226 | 4-$(CH_3)_2$CH-benzyloxy |
| 1227 | 1-phenylethoxy |
| 1228 | 4-F, 3-$CH_3$-benzoyl |
| 1229 | 3-$CF_3$-phenyl |
| 1230 | 4-$CH_3$O-phenylamino- |
| 1231 | 4-$NO_2$-phenylthio- |

EXAMPLE TABLE 49-continued

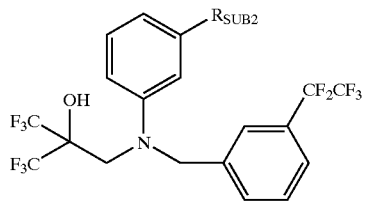

| Ex. No. | R<sub>SUB2</sub> |
|---|---|
| 1232 | 3-CF₃O-benzyloxy |
| 1233 | 3-CF₃-benzyloxy |
| 1234 | 3-F, 5-F-benzyloxy |
| 1235 | cyclohexylmethyleneoxy |
| 1236 | benzyloxy |
| 1237 | 3-CF₃, 5-CF₃-benzyloxy |
| 1238 | 4-CF₃O-benzyloxy |
| 1239 | 4-CH₃CH₂-benzyloxy |
| 1240 | isopropoxy |
| 1241 | 3-CF₃-benzyl |
| 1242 | isopropylthio |
| 1243 | cyclopentoxy |
| 1244 | 3-Cl-5-pyridinyloxy |
| 1245 | 3-CF₃S-benzyloxy |
| 1246 | 3-CH₃, 4-CH₃-benzyloxy |
| 1247 | 2-F, 3-CF₃-benzyloxy |
| 1248 | 3-F, 5-CF₃-benzyloxy |
| 1249 | 4-(CH₃)₂CH-benzyloxy |
| 1250 | 1-phenylethoxy |
| 1251 | 4-F, 3-CH₃-benzoyl |
| 1252 | 3-CF₃-phenyl- |
| 1253 | 4-CH₃O-phenylamino- |
| 1254 | 4-NO₂-phenylthio- |

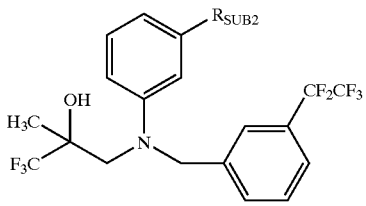

| Ex. No. | R<sub>SUB2</sub> |
|---|---|
| 1255 | 3-CF₃O-benzyloxy |
| 1256 | 3-CF₃-benzyloxy |
| 1257 | 3-F, 5-F-benzyloxy |
| 1258 | cyclohexylmethyleneoxy |
| 1259 | benzyloxy |
| 1260 | 3-CF₃, 5-CF₃-benzyloxy |
| 1261 | 4-CF₃O-benzyloxy |
| 1262 | 4-CH₃CH₂-benzyloxy |
| 1263 | isopropoxy |
| 1264 | 3-CF₃-benzyl |
| 1265 | isopropylthio |
| 1266 | cyclopentoxy |
| 1267 | 3-Cl-5-pyridinyloxy |
| 1268 | 3-CF₃S-benzyloxy |
| 1269 | 3-CH₃, 4-CH₃-benzyloxy |
| 1270 | 2-F, 3-CF₃-benzyloxy |
| 1271 | 3-F, 5-CF₃-benzyloxy |
| 1272 | 4-(CH₃)₂CH-benzyloxy |
| 1273 | 1-phenylethoxy |
| 1274 | 4-F, 3-CH₃-benzoyl |
| 1275 | 3-CF₃-phenyl- |
| 1276 | 4-CH₃O-phenylamino- |
| 1277 | 4-NO₂-phenylthio- |

EXAMPLE TABLE 49-continued

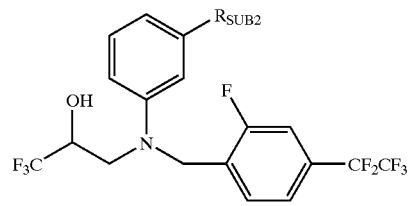

| Ex. No. | R<sub>SUB2</sub> |
|---|---|
| 1278 | 3-CF₃O-benzyloxy |
| 1279 | 3-CF₃-benzyloxy |
| 1280 | 3-F, 5-F-benzyloxy |
| 1281 | cyclohexylmethyleneoxy |
| 1282 | benzyloxy |
| 1283 | 3-CF₃, 5-CF₃-benzyloxy |
| 1284 | 4-CF₃O-benzyloxy |
| 1285 | 4-CH₃CH₂-benzyloxy |
| 1286 | isopropoxy |
| 1287 | 3-CF₃-benzyl |
| 1288 | isopropylthio |
| 1289 | cyclopentoxy |
| 1290 | 3-Cl-5-pyridinyloxy |
| 1291 | 3-CF₃S-benzyloxy |
| 1292 | 3-CH₃, 4-CH₃-benzyloxy |
| 1293 | 2-F, 3-CF₃-benzyloxy |
| 1294 | 3-F, 5-CF₃-benzyloxy |
| 1295 | 4-(CH₃)₂CH-benzyloxy |
| 1296 | 1-phenylethoxy |
| 1297 | 4-F, 3-CH₃-benzoyl |
| 1298 | 3-CF₃-phenyl- |
| 1299 | 4-CH₃O-phenylamino- |
| 1300 | 4-NO₂-phenylthio- |

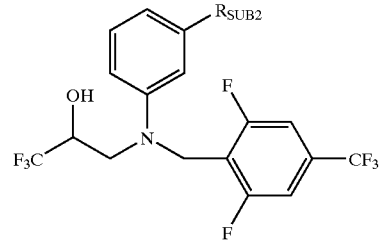

| Ex. No. | R<sub>SUB2</sub> |
|---|---|
| 1301 | 3-CF₃O-benzyloxy |
| 1302 | 3-CF₃-benzyloxy |
| 1303 | 3-F, 5-F-benzyloxy |
| 1304 | cyclohexylmethyleneoxy |
| 1305 | benzyloxy |
| 1306 | 3-CF₃, 5-CF₃-benzyloxy |
| 1307 | 4-CF₃O-benzyloxy |
| 1308 | 4-CH₃CH₂-benzyloxy |
| 1309 | isopropoxy |
| 1310 | 3-CF₃-benzyl |
| 1311 | isopropylthio |
| 1312 | cyclopentoxy |
| 1313 | 3-Cl-5-pyridinyloxy |
| 1314 | 3-CF₃S-benzyloxy |
| 1315 | 3-CH₃, 4-CH₃-benzyloxy |
| 1316 | 2-F, 3-CF₃-benzyloxy |
| 1317 | 3-F, 5-CF₃-benzyloxy |
| 1318 | 4-(CH₃)₂CH-benzyloxy |
| 1319 | 1-phenylethoxy |
| 1320 | 4-F, 3-CH₃-benzoyl |
| 1321 | 3-CF₃-phenyl- |
| 1322 | 4-CH₃O-phenylamino- |
| 1323 | 4-NO₂-phenylthio- |

EXAMPLE TABLE 49-continued

[Structure: 3-R_SUB2 phenyl connected to N with CH2-CH(OH)-CF3 group and CH2-(2-F,3-CF3,6-F-phenyl) group]

| Ex. No. | R<sub>SUB2</sub> |
|---|---|
| 1324 | 3-CF<sub>3</sub>O-benzyloxy |
| 1325 | 3-CF<sub>3</sub>-benzyloxy |
| 1326 | 3-F, 5-F-benzyloxy |
| 1327 | cyclohexylmethyleneoxy |
| 1328 | benzyloxy |
| 1329 | 3-CF<sub>3</sub>, 5-CF<sub>3</sub>-benzyloxy |
| 1330 | 4-CF<sub>3</sub>O-benzyloxy |
| 1331 | 4-CH<sub>3</sub>CH<sub>2</sub>-benzyloxy |
| 1332 | isopropoxy |
| 1333 | 3-CF<sub>3</sub>-benzyl |
| 1334 | isopropylthio |
| 1335 | cyclopentoxy |
| 1336 | 3-Cl-5-pyridinyloxy |
| 1337 | 3-CF<sub>3</sub>S-benzyloxy |
| 1338 | 3-CH<sub>3</sub>, 4-CH<sub>3</sub>-benzyloxy |
| 1339 | 2-F, 3-CF<sub>3</sub>-benzyloxy |
| 1340 | 3-F, 5-CF<sub>3</sub>-benzyloxy |
| 1341 | 4-(CH<sub>3</sub>)<sub>2</sub>CH-benzyloxy |
| 1342 | 1-phenylethoxy |
| 1343 | 4-F, 3-CH<sub>3</sub>-benzoyl |
| 1344 | 3-CF<sub>3</sub>-phenyl- |
| 1345 | 4-CH<sub>3</sub>O-phenylamino- |
| 1346 | 4-NO<sub>2</sub>-phenylthio- |

[Structure: 3-R_SUB2 phenyl connected to N with CH2-CH(OH)-CF3 group and CH2-(pentafluoro-4-CF3-phenyl) group]

| Ex. No. | R<sub>SUB2</sub> |
|---|---|
| 1347 | 3-CF<sub>3</sub>O-benzyloxy |
| 1348 | 3-CF<sub>3</sub>-benzyloxy |
| 1349 | 3-F, 5-F-benzyloxy |
| 1350 | cyclohexylmethyleneoxy |
| 1351 | benzyloxy |
| 1352 | 3-CF<sub>3</sub>, 5-CF<sub>3</sub>-benzyloxy |
| 1353 | 4-CF<sub>3</sub>O-benzyloxy |
| 1354 | 4-CH<sub>3</sub>CH<sub>2</sub>-benzyloxy |
| 1355 | isopropoxy |
| 1356 | 3-CF<sub>3</sub>-benzyl |
| 1357 | isopropylthio |
| 1358 | cyclopentoxy |
| 1359 | 3-Cl-5-pyridinyloxy |
| 1360 | 3-CF<sub>3</sub>S-benzyloxy |
| 1361 | 3-CH<sub>3</sub>, 4-CH<sub>3</sub>-benzyloxy |
| 1362 | 2-F, 3-CF<sub>3</sub>-benzyloxy |
| 1363 | 3-F, 5-CF<sub>3</sub>-benzyloxy |
| 1364 | 4-(CH<sub>3</sub>)<sub>2</sub>CH-benzyloxy |
| 1365 | 1-phenylethoxy |
| 1366 | 4-F, 3-CH<sub>3</sub>-benzoyl |
| 1367 | 3-CF<sub>3</sub>-phenyl- |
| 1368 | 4-CH<sub>3</sub>O-phenylamino- |
| 1369 | 4-NO<sub>2</sub>-phenylthio- |

EXAMPLE TABLE 49-continued

[Structure: 3-R_SUB2 phenyl connected to N with CH2-CH(OH)-CF3 group and CH2-(3-CH2CF3-phenyl) group]

| Ex. No. | R<sub>SUB2</sub> |
|---|---|
| 1370 | 3-CF<sub>3</sub>O-benzyloxy |
| 1371 | 3-CF<sub>3</sub>-benzyloxy |
| 1372 | 3-F, 5-F-benzyloxy |
| 1373 | cyclohexylmethyleneoxy |
| 1374 | benzyloxy |
| 1375 | 3-CF<sub>3</sub>, 5-CF<sub>3</sub>-benzyloxy |
| 1376 | 4-CF<sub>3</sub>O-benzyloxy |
| 1377 | 4-CH<sub>3</sub>CH<sub>2</sub>-benzyloxy |
| 1378 | isopropoxy |
| 1379 | 3-CF<sub>3</sub>-benzyl |
| 1380 | isopropylthio |
| 1381 | cyclopentoxy |
| 1382 | 3-Cl-5-pyridinyloxy |
| 1383 | 3-CF<sub>3</sub>S-benzyloxy |
| 1384 | 3-CH<sub>3</sub>, 4-CH<sub>3</sub>-benzyloxy |
| 1385 | 2-F, 3-CF<sub>3</sub>-benzyloxy |
| 1386 | 3-F, 5-CF<sub>3</sub>-benzyloxy |
| 1387 | 4-(CH<sub>3</sub>)<sub>2</sub>CH-benzyloxy |
| 1388 | 1-phenylethoxy |
| 1389 | 4-F, 3-CH<sub>3</sub>-benzoyl |
| 1390 | 3-CF<sub>3</sub>-phenyl- |
| 1391 | 4-CH<sub>3</sub>O-phenylamino- |
| 1392 | 4-NO<sub>2</sub>-phenylthio- |

EXAMPLE TABLE 50

Substituted 4-[N-(aryl)-[(aryl)methyl]amino]-1,1,1,2,2-pentafluoro-3-butanols.

[Structure: phenyl with R_SUB1-phenoxy group and N connected to CH2-CH(OH)-CF2CF3 and CH2-(3-CF2CF3-phenyl)]

| Ex. No. | R<sub>SUB1</sub> |
|---|---|
| 1393 | 3-isopropyl |
| 1394 | 2-Cl, 3-Cl |
| 1395 | 3-CF<sub>3</sub>O |
| 1396 | 4-F |
| 1397 | 4-CH<sub>3</sub> |
| 1398 | 2-F, 5-Br |
| 1399 | 4-Cl, 3-CH<sub>3</sub>CH<sub>2</sub> |
| 1400 | 3-CH<sub>3</sub>CH<sub>2</sub> |
| 1401 | 3-CH<sub>3</sub>, 5-CH<sub>3</sub> |
| 1402 | 3-(CH<sub>3</sub>)<sub>3</sub>C |
| 1403 | 4-F, 3-CH<sub>3</sub> |
| 1404 | 3-Cl, 4-Cl |
| 1405 | 3,4-(CH<sub>2</sub>)<sub>4</sub> |
| 1406 | 3-HCF<sub>2</sub>CF<sub>2</sub>O |
| 1407 | 3-CHF<sub>2</sub>O |
| 1408 | 3-(CH<sub>3</sub>)<sub>2</sub>N |
| 1409 | 3-cyclopropyl |
| 1410 | 3-(2-furyl) |
| 1411 | 3-CF<sub>3</sub>CF<sub>2</sub> |
| 1412 | 4-NH<sub>2</sub> |

EXAMPLE TABLE 50-continued

| Ex. No. | |
|---|---|
| 1413 | 3-$CH_3$, 4-$CH_3$, 5-$CH_3$ |
| 1414 | 4-$CH_3CH_2CH_2O$ |
| 1415 | 2-$NO_2$ |

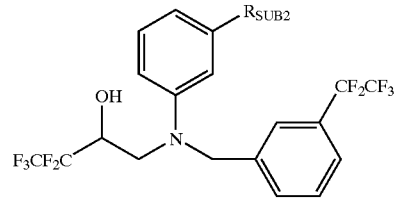

| Ex. No. | $R_{SUB2}$ |
|---|---|
| 1416 | 3-$CF_3$O-benzyloxy |
| 1417 | 3-$CF_3$-benzyloxy |
| 1418 | 3-F, 5-F-benzyloxy |
| 1419 | cyclohexylmethyleneoxy |
| 1420 | benzyloxy |
| 1421 | 3-$CF_3$, 5-$CF_3$-benzyloxy |
| 1422 | 4-$CF_3$O-benzyloxy |
| 1423 | 4-$CH_3CH_2$-benzyloxy |
| 1424 | isopropoxy |
| 1425 | 3-$CF_3$-benzyl |
| 1426 | isopropylthio |
| 1427 | cyclopentoxy |
| 1428 | 3-Cl-5-pyridinyloxy |
| 1429 | 3-$CF_3$S-benzyloxy |
| 1430 | 3-$CH_3$, 4-$CH_3$-benzyloxy |
| 1431 | 2-F, 3-$CF_3$-benzyloxy |
| 1432 | 3-F, 5-$CF_3$-benzyloxy |
| 1433 | 4-$(CH_3)_2$CH-benzyloxy |
| 1434 | 1-phenylethoxy |
| 1435 | 4-F, 3-$CH_3$-benzoyl |
| 1436 | 3-$CF_3$-phenyl- |
| 1437 | 4-$CH_3$O-phenylamino- |
| 1438 | 4-$NO_2$-phenylthio- |

EXAMPLE TABLE 51

Substituted 3-[N-(aryl)-[(aryl)oxy]amino]-1,1,1-trifluoro-2-propanols.

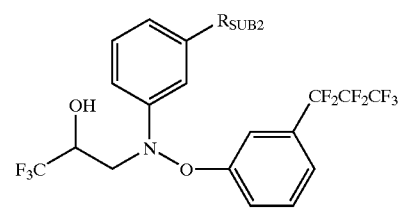

| Ex. No. | $R_{SUB1}$ |
|---|---|
| 1439 | 3-isopropyl |
| 1440 | 2-Cl, 3-Cl |
| 1441 | 3-$CF_3$O |
| 1442 | 4-F |
| 1443 | 4-$CH_3$ |
| 1444 | 2-F, 5-Br |
| 1445 | 4-Cl, 3-$CH_3CH_2$ |
| 1446 | 3-$CH_3CH_2$ |
| 1447 | 3-$CH_3$, 5-$CH_3$ |
| 1448 | 3-$(CH_3)_3$C |
| 1449 | 4-F, 3-$CH_3$ |
| 1450 | 3-Cl, 4-Cl |
| 1451 | 3,4-$(CH_2)_4$ |
| 1452 | 3-$HCF_2CF_2$O |
| 1453 | 3-$CHF_2$O |
| 1454 | 3-$(CH_3)_2$N |

EXAMPLE TABLE 51-continued

| Ex. No. | |
|---|---|
| 1455 | 3-cyclopropyl |
| 1456 | 3-(2-furyl) |
| 1457 | 3-$CF_3CF_2$ |
| 1458 | 4-$NH_2$ |
| 1459 | 3-$CH_3$, 4-$CH_3$, 5-$CH_3$ |
| 1460 | 4-$CH_3CH_2CH_2O$ |
| 1461 | 2-$NO_2$ |

| Ex. No. | $R_{SUB2}$ |
|---|---|
| 1462 | 3-$CF_3$O-benzyloxy |
| 1463 | 3-$CF_3$-benzyloxy |
| 1464 | 3-F, 5-F-benzyloxy |
| 1465 | cyclohexylmethyleneoxy |
| 1466 | benzyloxy |
| 1467 | 3-$CF_3$, 5-$CF_3$-benzyloxy |
| 1468 | 4-$CF_3$O-benzyloxy |
| 1469 | 4-$CH_3CH_2$-benzyloxy |
| 1470 | isopropoxy |
| 1471 | 3-$CF_3$-benzyl |
| 1472 | isopropylthio |
| 1473 | cyclopentoxy |
| 1474 | 3-Cl-5-pyridinyloxy |
| 1475 | 3-$CF_3$S-benzyloxy |
| 1476 | 3-$CH_3$, 4-$CH_3$-benzyloxy |
| 1477 | 2-F, 3-$CF_3$-benzyloxy |
| 1478 | 3-F, 5-$CF_3$-benzyloxy |
| 1479 | 4-$(CH_3)_2$CH-benzyloxy |
| 1480 | 1-phenylethoxy |
| 1481 | 4-F, 3-$CH_3$-benzoyl |
| 1482 | 3-$CF_3$-phenyl- |
| 1483 | 4-$CH_3$O-phenylamino- |
| 1484 | 4-$NO_2$-phenylthio- |

EXAMPLE TABLE 52

Substituted 3-[N-(aryl)-[(aryl)methyl]amino]-1,1,1-trifluoro-2-butanols.

| Ex. No. | $R_{SUB1}$ |
|---|---|
| 1485 | 3-isopropyl |
| 1486 | 2-Cl, 3-Cl |
| 1487 | 3-$CF_3$O |
| 1488 | 4-F |
| 1489 | 4-$CH_3$ |
| 1490 | 2-F, 5-Br |
| 1491 | 4-Cl, 3-$CH_3CH_2$ |
| 1492 | 3-$CH_3CH_2$ |
| 1493 | 3-$CH_3$, 5-$CH_3$ |

EXAMPLE TABLE 52-continued

| | |
|---|---|
| 1494 | 3-(CH$_3$)$_3$C |
| 1495 | 4-F, 3-CH$_3$ |
| 1496 | 3-Cl, 4-Cl |
| 1497 | 3,4-(CH$_2$)$_4$ |
| 1498 | 3-HCF$_2$CF$_2$O |
| 1499 | 3-CHF$_2$O |
| 1500 | 3-(CH$_3$)$_2$N |
| 1501 | 3-cyclopropyl |
| 1502 | 3-(2-furyl) |
| 1503 | 3-CF$_3$CF$_2$ |
| 1504 | 4-NH$_2$ |
| 1505 | 3-CH$_3$, 4-CH$_3$, 5-CH$_3$ |
| 1506 | 4-CH$_3$CH$_2$CH$_2$O |
| 1507 | 2-NO$_2$ |
| 1508 | 3-isopropyl |
| 1509 | 2-Cl, 3-Cl |
| 1510 | 3-CF$_3$O |
| 1511 | 4-F |
| 1512 | 4-CH$_3$ |
| 1513 | 2-F, 5-Br |
| 1514 | 4-Cl, 3-CH$_3$CH$_2$ |
| 1515 | 3-CH$_3$CH$_2$ |
| 1516 | 3-CH$_3$, 5-CH$_3$ |
| 1517 | 3-(CH$_3$)$_3$C |
| 1518 | 4-F, 3-CH$_3$ |
| 1519 | 3-Cl, 4-Cl |
| 1520 | 3,4-(CH$_2$)$_4$ |
| 1521 | 3-HCF$_2$CF$_2$O |
| 1522 | 3-CHF$_2$O |
| 1523 | 3-(CH$_3$)$_2$N |
| 1524 | 3-cyclopropyl |
| 1525 | 3-(2-furyl) |
| 1526 | 3-CF$_3$CF$_2$ |
| 1527 | 4-NH$_2$ |
| 1528 | 3-CH$_3$, 4-CH$_3$, 5-CH$_3$ |
| 1529 | 4-CH$_3$CH$_2$CH$_2$O |
| 1530 | 2-NO$_2$ |

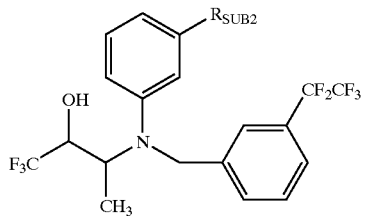

| Ex. No. | R$_{SUB2}$ |
|---|---|
| 1531 | 3-CF$_3$O-benzyloxy |
| 1532 | 3-CF$_3$-benzyloxy |
| 1533 | 3-F, 5-F-benzyloxy |
| 1534 | cyclohexylmethyleneoxy |
| 1535 | benzyloxy |
| 1536 | 3-CF$_3$, 5-CF$_3$-benzyloxy |
| 1537 | 4-CF$_3$O-benzyloxy |
| 1538 | 4-CH$_3$CH$_2$-benzyloxy |
| 1539 | isopropoxy |
| 1540 | 3-CF$_3$-benzyl |
| 1541 | isopropylthio |
| 1542 | cyclopentoxy |
| 1543 | 3-Cl-5-pyridinyloxy |
| 1544 | 3-CF$_3$S-benzyloxy |
| 1545 | 3-CH$_3$, 4-CH$_3$-benzyloxy |
| 1546 | 2-F, 3-CF$_3$-benzyloxy |
| 1547 | 3-F, 5-CF$_3$-benzyloxy |
| 1548 | 4-(CH$_3$)$_2$CH-benzyloxy |
| 1549 | 1-phenylethoxy |
| 1550 | 4-F, 3-CH$_3$-benzoyl |
| 1551 | 3-CF$_3$-phenyl- |
| 1552 | 4-CH$_3$O-phenylamino- |

EXAMPLE TABLE 52-continued

| | |
|---|---|
| 1553 | 4-NO$_2$-phenylthio- |
| 1554 | 3-CF$_3$O-benzyloxy |
| 1555 | 3-CF$_3$-benzyloxy |
| 1556 | 3-F, 5-F-benzyloxy |
| 1557 | cyclohexylmethyleneoxy |
| 1558 | benzyloxy |
| 1559 | 3-CF$_3$, 5-CF$_3$-benzyloxy |
| 1560 | 4-CF$_3$O-benzyloxy |
| 1561 | 4-CH$_3$CH$_2$-benzyloxy |
| 1562 | isopropoxy |
| 1563 | 3-CF$_3$-benzyl |
| 1564 | isopropylthio |
| 1565 | cyclopentoxy |
| 1566 | 3-Cl-5-pyridinyloxy |
| 1567 | 3-CF$_3$S-benzyloxy |
| 1568 | 3-CH$_3$, 4-CH$_3$-benzyloxy |
| 1569 | 2-F, 3-CF$_3$-benzyloxy |
| 1570 | 3-F, 5-CF$_3$-benzyloxy |
| 1571 | 4-(CH$_3$)$_2$CH-benzyloxy |
| 1572 | 1-phenylethoxy |
| 1573 | 4-F, 3-CH$_3$-benzoyl |
| 1574 | 3-CF$_3$-phenyl- |
| 1575 | 4-CH$_3$O-phenylamino- |
| 1576 | 4-NO$_2$-phenylthio- |

EXAMPLE TABLE 53

Substituted 3-[N,N'-(diaryl)amino]-1,1,1,2,2-pentafluoro-2-propanols.

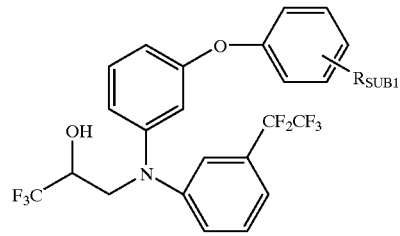

| Ex. No. | R$_{SUB1}$ |
|---|---|
| 1577 | 3-isopropyl |
| 1578 | 2-Cl, 3-Cl |
| 1579 | 3-CF$_3$O |
| 1580 | 4-F |
| 1581 | 4-CH$_3$ |
| 1582 | 2-F, 5-Br |
| 1583 | 4-Cl, 3-CH$_3$CH$_2$ |
| 1584 | 3-CH$_3$CH$_2$ |
| 1585 | 3-CH$_3$, 5-CH$_3$ |
| 1586 | 3-(CH$_3$)$_3$C |
| 1587 | 4-F, 3-CH$_3$ |
| 1588 | 3-Cl, 4-Cl |
| 1589 | 3,4-(CH$_2$)$_4$ |
| 1590 | 3-HCF$_2$CF$_2$O |
| 1591 | 3-CHF$_2$O |
| 1592 | 3-(CH$_3$)$_2$N |
| 1593 | 3-cyclopropyl |
| 1594 | 3-(2-furyl) |
| 1595 | 3-CF$_3$CF$_2$ |
| 1596 | 4-NH$_2$ |
| 1597 | 3-CH$_3$, 4-CH$_3$, 5-CH$_3$ |
| 1598 | 4-CH$_3$CH$_2$CH$_2$O |
| 1599 | 2-NO$_2$ |

EXAMPLE TABLE 53-continued (structure with $R_{SUB2}$ on phenyl, $CF_2CF_3$, OH, $F_3C$, N)

| Ex. No. | $R_{SUB2}$ |
|---|---|
| 1600 | 3-CF$_3$O-benzyloxy |
| 1601 | 3-CF$_3$-benzyloxy |
| 1602 | 3-F, 5-F-benzyloxy |
| 1603 | cyclohexylmethyleneoxy |
| 1604 | benzyloxy |
| 1605 | 3-CF$_3$, 5-CF$_3$-benzyloxy |
| 1606 | 4-CF$_3$O-benzyloxy |
| 1607 | 4-CH$_3$CH$_2$-benzyloxy |
| 1608 | isopropoxy |
| 1609 | 3-CF$_3$-benzyl |
| 1610 | isopropylthio |
| 1611 | cyclopentoxy |
| 1612 | 3-Cl-5-pyridinyloxy |
| 1613 | 3-CF$_3$S-benzyloxy |
| 1614 | 3-CH$_3$, 4-CH$_3$-benzyloxy |
| 1615 | 2-F, 3-CF$_3$-benzyloxy |
| 1616 | 3-F, 5-CF$_3$-benzyloxy |
| 1617 | 4-(CH$_3$)$_2$CH-benzyloxy |
| 1618 | 1-phenylethoxy |
| 1619 | 4-F, 3-CH$_3$-benzoyl |
| 1620 | 3-CF$_3$-phenyl |
| 1621 | 4-CH$_3$O-phenylamino |
| 1622 | 4-NO$_2$-phenylthio |

EXAMPLE TABLE 54

Substituted 2-[N-(aryl)-[(aryl)methyl]amino]-1-trifluoromethylcyclopentanols.

(structure with $R_{SUB1}$ on phenyl, $CF_2CF_3$, OH, $F_3C$, N, cyclopentane)

| Ex. No. | $R_{SUB1}$ |
|---|---|
| 1623 | 3-isopropyl |
| 1624 | 2-Cl, 3-Cl |
| 1625 | 3-CF$_3$O |
| 1626 | 4-F |
| 1627 | 4-CH$_3$ |
| 1628 | 2-F, 5-Br |
| 1629 | 4-Cl, 3-CH$_3$CH$_2$ |
| 1630 | 3-CH$_3$CH$_2$ |
| 1631 | 3-CH$_3$, 5-CH$_3$ |
| 1632 | 3-(CH$_3$)$_3$C |
| 1633 | 4-F, 3-CH$_3$ |
| 1634 | 3-Cl, 4-Cl |
| 1635 | 3,4-(CH$_2$)$_4$ |
| 1636 | 3-HCF$_2$CF$_2$O |
| 1637 | 3-CHF$_2$O |
| 1638 | 3-(CH$_3$)$_2$N |
| 1639 | 3-cyclopropyl |
| 1640 | 3-(2-furyl) |
| 1641 | 3-CF$_3$CF$_2$ |

EXAMPLE TABLE 54-continued

| 1642 | 4-NH$_2$ |
|---|---|
| 1643 | 3-CH$_3$, 4-CH$_3$, 5-CH$_3$ |
| 1644 | 4-CH$_3$CH$_2$CH$_2$O |
| 1645 | 2-NO$_2$ |

(structure with $R_{SUB2}$ on phenyl, $CF_2CF_3$, OH, $F_3C$, N, cyclopentane)

| Ex. No. | $R_{SUB2}$ |
|---|---|
| 1646 | 3-CF$_3$O-benzyloxy |
| 1647 | 3-CF$_3$-benzyloxy |
| 1648 | 3-F, 5-F-benzyloxy |
| 1649 | cyclohexylmethyleneoxy |
| 1650 | benzyloxy |
| 1651 | 3-CF$_3$, 5-CF$_3$-benzyloxy |
| 1652 | 4-CF$_3$O-benzyloxy |
| 1653 | 4-CH$_3$CH$_2$-benzyloxy |
| 1654 | isopropoxy |
| 1655 | 3-CF$_3$-benzyl |
| 1656 | isopropylthio |
| 1657 | cyclopentoxy |
| 1658 | 3-Cl-5-pyridinyloxy |
| 1659 | 3-CF$_3$S-benzyloxy |
| 1660 | 3-CH$_3$, 4-CH$_3$-benzyloxy |
| 1661 | 2-F, 3-CF$_3$-benzyloxy |
| 1662 | 3-F, 5-CF$_3$-benzyloxy |
| 1663 | 4-(CH$_3$)$_2$CH-benzyloxy |
| 1664 | 1-phenylethoxy |
| 1665 | 4-F, 3-CH$_3$-benzoyl |
| 1666 | 3-CF$_3$-phenyl- |
| 1667 | 4-CH$_3$O-phenylamino- |
| 1668 | 4-NO$_2$-phenylthio- |

EXAMPLE 1669

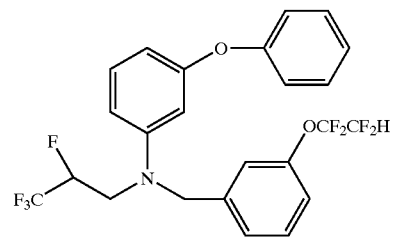

N-(3-phenoxyphenyl)-N-(3,3,3,2-tetrafluoropropyl)-3-(1,1,2,2-tetrafluoroethoxy)benzenemethanamine To a solution of 3-[(3-phenoxyphenyl)[[3-(1,1,2,2-tetrafluoroethoxy) phenyl]-methyl]amino]-1,1,1-trifluoro-2-propanol (474 mg, 0.00094 mol) in 4.5 mL of dichloromethane at 0° C. was added (diethylamino)sulfur trifluoride (378 mg, 0.0023 mol). The reaction mixture was warmed to room temperature and stirred for 2 h, then quenched with water and extracted with dichloromethane. The organic layers were combined, dried over MgSO4, and concentrated in vacuo. The crude product was purified by column chromatography on silica gel eluting with 1:9 ethyl acetate in hexane to afford 240 mg (50%) of the desired N-(3-phenoxyphenyl)-N-(3,3,3,2- tetrafluoropropyl)-3-(1,1,2,2-tetrafluoroethoxy) benzenemethanamine product as a yellow oil. HRMS calcd. for $C_{24}H_{19}F_8NO_2$: 506.1366 [M+H]$^+$, found: 506.1368. $^1$H NMR (CDCl$_3$) δ 7.26 (m, 3H), 7.20 (m, 5H), 6.87 (d, 2H), 6.62 (d, 1H), 6.50 (s, 1H), 6.49 (d 1H), 5.87 (t, 1H), 4.89 (d, 1H), 4.77–4.52 (m 1H), 4.73 (d, 1H), 4.60 (s, 2 H). $^{19}$F NMR (CDCl$_3$) δ −69.83 (t, 3F), −88.63 (s, 2F), −137.19 (dt, 2F), −228.82 (1F).

EXAMPLE 1670

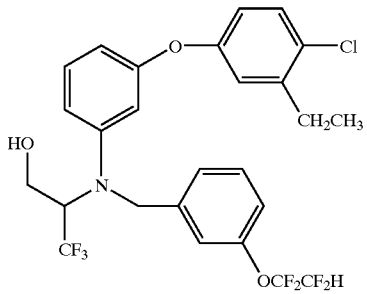

2-[[3-(4-chloro-3-ethylphenoxy)phenyl][[3-(1,1,2,2-tetrafluoroethoxy)phenyl]methyl]amino]-3,3,3-trifluoropropanol To a dichloromethane (2 mL) solution of N-[(4-chloro-3-ethylphenoxy)phenyl][[3-(1,1,2,2-tetrafluoroethoxy)phenyl]methyl]amine (0.25 g, 0.55 mmol) and 2-diazo-3,3,3-trifluoropropionic acid p-nitrophenyl ester (0.14 g, 0.51 mmol) was added solid Rh$_2$(OAc)$_4$ (0.015 g, 0.034 mmol). The resulting green slurry was stirred at room temperature under nitrogen for 24 h. The solvent was removed to give a green oil, and the crude intermediate was dissolved in THF (4 mL). This green solution was cooled to 0° C., and a 1.0 M solution of LiAlH$_4$ in THF (0.6 mL, 0.6 mmol) was added dropwise. The resulting dark solution was stirred for 30 min at 0° C. and quenched by the slow addition of water. The reaction mixture was extracted with Et$_2$O, dried (MgSO$_4$) and evaporated to give a brown oil. Purification by flash column chromatography on silica gel eluting with 20% ethyl acetate in hexane gave 0.032 g (11%) of the desired 2-[[3-(4-chloro-3-ethylphenoxy)phenyl][[3-(1,1,2,2-tetrafluoro-ethoxy)phenyl]methyl]amino]-3,3,3-trifluoropropanol product as a light brown oil. HRMS calcd. for $C_{26}H_{23}NO_3ClF_7$: 566.1333 [M+H]$^+$, found: 566.1335. $^1$H NMR (C$_6$D$_6$) δ 0.53 (t, 1H, exchangeable with D$_2$O), 0.93 (t, 31), 2.43 (t, 2H), 3.33 (m, 2H), 4.11 (s, 2H), 4.13 (m, 1H), 5.04 (tt, 1H), 6.4 (m, 3H), 6.55 (t, 1H), 6.7 –6.8 (m, 5H), 6.97 (d, 1H), 7.04 (s, 1H).

EXAMPLE 1671

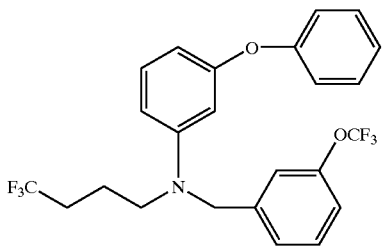

N-(3-phenoxyphenyl)-N-(4,4,4-trifluorobutyl)-3-(trifluoromethoxy) benzenemethanamine EX-1671A) To a solution of 3-phenoxyaniline (10.9 g, 58.8 mmol) in 100 mL of cyclohexane was added solid NaH (60% in mineral oil, 1.96 g, 49 mmol). Then 3-trifluoromethoxybenzyl bromide (10.0 g, 39.2 mmol) was added dropwise under a nitrogen atmosphere, and the mixture was heated to reflux for 18 h, at which time TLC analysis indicated that no 3-trifluoromethoxybenzyl bromide remained. The reaction mixture was cooled to room temperature and quenched with water, then extracted with ether. The ether layer was washed with water and brine, then dried over MgSO$_4$, and evaporated to give crude product. The crude product was purified by flash column chromatography on silica gel eluting with 1:7:0.01 of ethyl acetate:hexane:ammonium hydroxide to give the desired N-benzylaniline product, which contained a small portion of dibenzylated amine. This product was further purified by conversion to the corresponding HCl salt to give 11.0 g (73%) of the desired N-(3-phenoxyphenyl)-N-[(3-trifluoromethoxy)phenyl]methyl]amine hydrochloride product. HRMS calcd. for $C_{20}H_{16}NO_2F_3$: 360.1211 [M+H]$^+$, found 360.1208.

The N-(3-phenoxyphenyl)-N-[(3-trifluoromethoxy)phenyl]methyl]amine hydrochloride (1.0 g, 2.5 mmol) product from EX-1671A was dissolved in 20 mL of THF under nitrogen. Solid NaNH$_2$ (50% in xylene, 0.2 g, 2.6 mmol) was added, and the mixture was stirred at room temperature. Then 1-iodo-4,4,4-trifluorobutone (1.0 g, 4.2 mmol) and additional NaNH$_2$ (50% in xylene, 0.2 g 2.6 mmol) was added. The mixture was heated at reflux for 24 h, at which time HPLC analysis indicated that no secondary amine starting material remained. The reaction was quenched with water and extracted with ether. The ether layer was washed with water and brine, then dried over MgSO$_4$. The crude product was purified by flash column chromatography on silica gel eluting with 1:4:0.01 of ethyl acetate:hexane:ammonium hydroxide to give 1.0 g (85%) of the desired N-(3-phenoxyphenyl)-N-(4,4,4-trifluorobutyl)-3-(trifluoromethoxy) benzenemethanamine product as an off-white oil. $^1$H NMR (CDCl$_3$) δ 7.29 (m, 3H), 7.09 (m, 4H), 7.01 (s, 1H), 6.95 (d, 2H), 6.43 (d, 1H), 6.36 (d, 1H), 6.31 (s, 1H), 4.49 (s, 2H), 3.41 (t, 2H), 2.08 (m, 2H), 1.89 (q, 2H). $^{19}$F NMR (CDCl$_3$) δ −58.18 (s, 3F), −66.44 (t, 3F). Anal. calcd. for $C_{24}H_{21}NO_2F_6$: C, 61.41; H, 4.51; N, 2.98. Found: C, 61.16; H. 4.53; N, 2.92. HRMS calcd. 470.1555 [M+H]$^+$, found: 470.1565.

EXAMPLE 1672

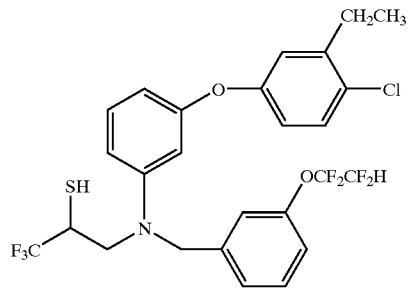

3-[[3-(4-chloro-3-ethylphenoxy)phenyl]-[[3-(1,1,2,2-tetrafluoroethoxy)phenyl] methyl]amino]-1,1,1-trifluoro-2-propanthiol EX-1672A) A solution of 3-(4chloro-3-ethylphenoxy) aniline (3.72 g, 15 mmol) and 3-(1,1,2,2-tetrafluoroethoxy)benzaldehyde (3.33 g, 15 mmol) is prepared in 60 mL of dichloroethane. Acetic acid (0.92 mL, 16.05 mmol) and solid NaBH(OAc)$_3$ (4.13 g, 19.5 mmol) are added. The mixture is stirred at room temperature for 3 hours, then is acidified with 1 N aqueous HCl. After neutralizing to pH 7.5 with 2.5 N sodium hydroxide, the mixture is extracted with methylene chloride. The organic layer is washed with brine and water, then dried over anhydrous MgSO$_4$, and evaporated to give 5.00 g (85%) of the desired N-(3-(4chloro-3-ethylphenoxy)phenyl)-[[3-(1,1,2,2-tetrafluoroethoxy)-phenyl]methyl]amine product.

Amine product EX-1672A (8 mmol) and 3,3,3-trifluoromethylthiirane (1.54 g, 12 mmol) are dissolved in 1.5 mL of acetonitrile. Ytterbium (III) trifluoromethanesulfonate (0.25 g, 0.4 mmol) is added, and the stirred solution is warmed to 50° C. under an atmosphere of nitrogen until completion of reaction as is indicated by HPLC analysis showing that no secondary amine starting material remains. The reaction is quenched with water and extracted with ether. The ether layer is washed with water and brine, then is dried over MgSO$_4$. The crude product is purified by flash column chromatography on silica gel with a solvent mixture to give the desired aminopropanethiol product.

EXAMPLE 1673

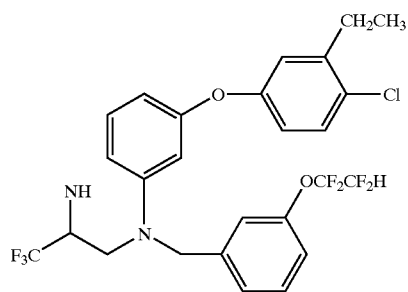

3-[[3-(4-chloro-3-ethylphenoxy)phenyl]-[[3-(1,1,2,2-tetrafluoro-ethoxy)phenyl] methyl]amino]-1,1,1-trifluoro-2-propanamine Amine product EX-1672A (8 mmol) and 3,3,3-trifluoromethylaziridine (1.33 g, 12 mmol) are dissolved in 1.5 mL of acetonitrile. Ytterbium (III) trifluoromethanesulfonate (0.25 g, 0.4 mmol) is added, and the stirred solution is warmed to 50° C. under an atmosphere of nitrogen until completion of reaction as is indicated by HPLC analysis showing that no secondary amine starting material remains. The reaction is quenched with water, the pH is adjusted to 9.5 with 2.5 N sodium hydroxide, and it is extracted with ether. The ether layer is washed with water and brine, then is dried over Na$_2$CO$_3$. The crude product is purified by flash column chromatography on silica gel with a solvent mixture to give the desired propanediamine product.

Bioassays
CETP Activity in Vitro
Assay of CETP Inhibition Using Purified Components (Reconstituted Buffer Assay)

The ability of compounds to inhibit CERP activity was assessed using an in vitro assay that measured the rate of transfer of radiolabeled cholesteryl ester ([$^3$H]CE) from HDL donor particles to LDL acceptor particles. Details of the assay are provided by Glenn, K. C. et al. (Glenn and Melton, "Quantification of Cholesteryl Ester Transfer Protein (CETP): A) CETP Activity and B) Immunochemical Assay of CETP Protein," Meth. Enzymol., 263, 339–351 (1996)). Human recombinant CETP can be obtained from the serum-free conditioned medium of CHO cells transfected with a cDNA for CETP and purified as described by Wang, S. et al. (J. Biol. Chem. 267, 17487–17490 (1992)). To measure CETP activity, [$^3$H]CE-labeled-HDL, LDL, CEIPP and assay buffer (50 mM tris(hydroxymethyl) aminomethane, pH 7.4; 150 mM sodium chloride; 2 mM ethylenediamine-tetraacetic acid (EDTA); 1% bovine serum albumin) were incubated in a final volume of 200 µL, for 2 hours at 37° C. in 96 well plates. Inhibitors were included in the assay by diluting from a 10 mM DMSO stock solution into 16% (v/v) aqueous DMSO so that the final concentration of inhibitor was 800 µM. The inhibitors were then diluted 1:1 with CETP in assay buffer, and then 25 µL of that solution was mixed with 175 µL of lipoprotein pool for assay. Following incubation, LDL was differentially precipitated by the addition of 50 µL of 1% (w/v) dextran sulfate/0.5 M magnesium chloride, mixed by vortex, and incubated at room temperature for 10 minutes. A potion of the solution (200 µL) was transferred to a filter plate (Millipore). After filtration, the radioactivity present in the precipitated LDL was measured by liquid scintillation counting. Correction for non-specific transfer or precipitation was made by including samples that do not contain CETP. The rate of [$^3$H]CE transfer using this assay was linear with respect to time and CETP concentration, up to 25–30% of [$^3$H]CE transferred.

The potency of test compounds was determined by performing the above described assay in the presence of varying concentrations of the test compounds and determining the concentration required for 50% inhibition of transfer of [$^3$H]CE from HDL to LDL. This value was defined as the IC$_{50}$. The IC$_{50}$ values determined from this assay are accurate when the IC$_{50}$ is greater than 10 nM. In the case where compounds have greater inhibitory potency, accurate measurements of IC$_{50}$ may be determined using longer incubation times (up to 18 hours) and lower final concentrations of CETP (<50 nM).

Examples of IC$_{50}$ values determined by these methods are specified in Table 9.

Assay of CETP Inhibition in Human Plasma

Blood was obtained from healthy volunteers, recruited from the personnel of Monsanto Company, Saint Louis, Mo. Blood was collected in tubes containing EDTA (EUSA plasma pool). The EDTA human plasma pool, previously stored at −20° C., was thawed at room temperature and centrifuged for 5 minutes to remove any particulate matter. Tritiated HDL, radiolabeled in the cholesteryl ester moiety ([$^3$H]CE-HDL) as described by Morton and Zilversmit (J. Biol. Chem., 256, 11992–95 (1981)), was added to the plasma to a final concentration of 25 µg/mL cholesterol. Equal volumes (396 µL) of the plasma containing the [$^3$H]CE-HDL were added by pipette into micro tubes (Titertube®, Bio-Rad laboratories, Hercules, Calif.). Inhibitor compounds, dissolved as 20–50 mM stock solutions in DMSO, were serially diluted in DMSO (or an alternative solvent in some cases, such as dimethylformamide or ethanol). Four µL of each of the serial dilutions of inhibitor compounds or DMSO alone were then added to each of the tubes containing plasma (396 µL). After mixing, triplicate aliquots (100 µL) from each plasma tube were then transferred to wells of 96-well round-bottomed polystyrene microtiter plates (Corning, Corning, N.Y.). Plates were sealed with plastic film and incubated at 37° C. for 4 hours. "Test" samples contained plasma with dilutions of inhibitor compounds. "Control" samples contained plasma with DMSO diluted to the same concentration as the test samples, but without inhibitor. "Blank" samples were prepared as "control" samples, but were left in the micro tubes at 4° C. for the 4 hour incubation and were then added to the microtiter wells at the end of the incubation period. VLDL and LDL were precipitated by the addition of 10 μL of precipitating reagent (1% (w/v) dextran sulfate (Dextralip50)/0.5 M magnesium chloride, pH 7.4) to all wells. The wells were mixed on a plate mixer and then incubated at ambient temperature for 10 min. The plates were then centrifuged at 1000×g for 30 min at 10° C. The supernatants (50 μL) from each well were then transferred to Picoplate™ 96 plate wells (Packard, Meriden, Conn.) containing Microscint™-40 (Packard, Meriden, Conn.). The plates were heat-sealed (TopSeal™-P, Packard, Meriden, Conn.) according to the manufacturer's directions and mixed for 30 min. Radioactivity was measured on a microplate scintillation counter (TopCount, Packard, Meriden, Conn.). The maximum percentage transfer in the control wells (% transfer) was determined using the following equation:

$$\% \text{ Transfer} = \frac{[dpm_{blank} - dpm_{control}] \times 100}{dpm_{blank}}$$

The percentage of transfer relative to the control (% control) was determined in the wells containing inhibitor compounds was determined as follows:

$$\% \text{ Control} = \frac{[dpm_{blank} - dpm_{test}] \times 100}{dpm_{blank} - dpm_{control}}$$

$IC_{50}$ values were then calculated from plots of % control versus concentration of inhibitor compound. $IC_{50}$ values were determined as the concentration of inhibitor compound inhibiting transfer of [$^3$H]CE from the supernatant [$^3$H]CE-HDL to the precipitated VLDL and LDL by 50% compared to the transfer obtained in the control wells.

Examples of $IC_{50}$ values determined by this method are specified in Table 10.

TABLE 9

Inhibition of CETP Activity by Examples in Reconstituted Buffer Assay.

| Ex. No. | IC$_{50}$ (μM) | Ex. No. | IC$_{50}$ (μM) | Ex. No. | IC$_{50}$ (μM) |
|---|---|---|---|---|---|
| 249 | 0.020 | 419 | 0.19 | 425 | 0.34 |
| 244 | 0.029 | 230 | 0.20 | 514 | 0.34 |
| 634 | 0.032 | 248 | 0.20 | 237 | 0.35 |
| 221 | 0.034 | 266 | 0.20 | 399 | 0.35 |
| 229 | 0.034 | 378 | 0.20 | 645 | 0.35 |
| 660 | 0.040 | 488 | 0.20 | 225 | 0.37 |
| 630 | 0.050 | 241 | 0.21 | 247 | 0.37 |
| 629 | 0.054 | 245 | 0.21 | 473 | 0.37 |
| 372 | 0.062 | 400 | 0.21 | 216 | 0.39 |
| 233 | 0.063 | 639 | 0.21 | 243 | 0.39 |
| 234 | 0.069 | 226 | 0.22 | 636 | 0.39 |
| 252 | 0.075 | 373 | 0.22 | 650 | 0.41 |
| 242 | 0.076 | 377 | 0.23 | 385 | 0.42 |
| 277 | 0.076 | 253 | 0.24 | 427 | 0.42 |
| 256 | 0.079 | 411 | 0.25 | 436 | 0.42 |
| 232 | 0.080 | 638 | 0.26 | 509 | 0.42 |
| 278 | 0.098 | 222 | 0.27 | 619 | 0.42 |
| 379 | 0.098 | 240 | 0.27 | 521 | 0.43 |
| 258 | 0.099 | 374 | 0.27 | 250 | 0.44 |
| 238 | 0.12 | 420 | 0.27 | 429 | 0.44 |
| 227 | 0.13 | 223 | 0.29 | 658 | 0.44 |
| 423 | 0.13 | 415 | 0.29 | 637 | 0.47 |
| 656 | 0.13 | 235 | 0.31 | 592 | 0.48 |
| 214 | 0.14 | 607 | 0.31 | 251 | 0.49 |
| 628 | 0.14 | 265 | 0.33 | 421 | 0.49 |
| 281 | 0.14 | 402 | 0.33 | 271 | 0.50 |
| 224 | 0.16 | 489 | 0.33 | 287 | 0.50 |
| 279 | 0.16 | 231 | 0.34 | 550 | 0.50 |
| 401 | 0.18 | 275 | 0.34 | 416 | 0.51 |
| 410 | 0.19 | 390 | 0.34 | 438 | 0.52 |
| 647 | 0.52 | 518 | 0.79 | 442 | 1.1 |
| 598 | 0.54 | 397 | 0.81 | 595 | 1.1 |
| 567 | 0.55 | 393 | 0.82 | 642 | 1.1 |
| 391 | 0.56 | 499 | 0.83 | 450B | 1.1 |
| 559 | 0.56 | 648 | 0.83 | 71 | 1.2 |
| 246 | 0.57 | 282 | 0.84 | 305 | 1.2 |
| 268 | 0.58 | 396 | 0.86 | 381 | 1.2 |
| 527 | 0.58 | 581 | 0.87 | 441 | 1.2 |
| 269 | 0.59 | 294 | 0.88 | 446 | 1.2 |
| 292 | 0.59 | 557 | 0.88 | 492 | 1.2 |
| 405 | 0.60 | 218 | 0.91 | 496 | 1.2 |
| 409 | 0.61 | 601 | 0.91 | 524 | 1.2 |
| 475 | 0.64 | 653 | 0.91 | 569 | 1.2 |
| 254 | 0.65 | 422 | 0.92 | 693 | 1.2 |
| 450A | 0.66 | 556 | 0.92 | 286 | 1.3 |
| 654 | 0.67 | 506 | 0.97 | 296 | 1.3 |
| 558 | 0.69 | 541 | 0.97 | 655B | 1.3 |
| 389 | 0.70 | 274 | 0.99 | 264 | 1.4 |
| 412 | 0.71 | 651 | 0.99 | 392 | 1.4 |
| 408 | 0.75 | 77 | 1.0 | 406 | 1.4 |
| 554 | 0.75 | 267 | 1.0 | 522 | 1.4 |
| 280 | 0.76 | 293 | 1.0 | 526 | 1.4 |
| 525 | 0.76 | 439 | 1.0 | 568 | 1.4 |
| 578 | 0.76 | 560 | 1.0 | 582 | 1.4 |
| 440 | 0.77 | 657 | 1.0 | 74 | 1.5 |
| 523 | 0.77 | 659 | 1.0 | 79 | 1.5 |
| 646 | 0.77 | 599 | 1.0 | 403 | 1.5 |
| 166 | 0.78 | 285 | 1.1 | 407 | 1.5 |
| 424 | 0.78 | 395 | 1.1 | 444 | 1.5 |
| 593 | 0.78 | 398 | 1.1 | 495 | 1.5 |
| 456B | 1.5 | 167 | 2.0 | 302 | 2.5 |
| 565 | 1.5 | 307 | 2.0 | 426 | 2.5 |
| 652 | 1.5 | 597 | 2.0 | 519 | 2.5 |
| 699 | 1.5 | 315 | 2.1 | 555 | 2.5 |
| 91 | 1.6 | 404 | 2.1 | 564 | 2.5 |
| 140 | 1.6 | 418 | 2.1 | 688 | 2.5 |
| 149 | 1.6 | 503 | 2.1 | 690 | 2.5 |
| 255 | 1.6 | 508 | 2.1 | 309 | 2.6 |
| 384 | 1.6 | 513 | 2.1 | 311 | 2.6 |
| 517 | 1.6 | 562 | 2.1 | 494 | 2.6 |
| 571 | 1.6 | 643 | 2.1 | 44 | 2.7 |
| 644 | 1.6 | 257 | 2.2 | 452 | 2.7 |
| 150 | 1.7 | 387 | 2.2 | 543 | 2.7 |
| 261 | 1.7 | 437 | 2.2 | 566 | 2.7 |
| 432 | 1.7 | 483 | 2.2 | 445 | 2.8 |
| 505 | 1.7 | 490 | 2.2 | 73 | 3.0 |
| 584 | 1.7 | 89 | 2.3 | 104 | 3.0 |
| 1670 | 1.8 | 299 | 2.3 | 115 | 3.0 |
| 212 | 1.8 | 318 | 2.3 | 220B | 3.0 |
| 289 | 1.8 | 382 | 2.3 | 322 | 3.0 |
| 312 | 1.8 | 383 | 2.3 | 388 | 3.0 |
| 478 | 1.8 | 507 | 2.3 | 460 | 3.0 |
| 493 | 1.8 | 544 | 2.3 | 464 | 3.0 |
| 515 | 1.8 | 580 | 2.3 | 516 | 3.0 |
| 561 | 1.8 | 608 | 2.3 | 691 | 3.0 |
| 570 | 1.8 | 128 | 2.4 | 316 | 3.1 |
| 579 | 1.8 | 542 | 2.4 | 394 | 3.1 |
| 304 | 1.9 | 168 | 2.5 | 633 | 3.1 |
| 480 | 1.9 | 259 | 2.5 | 386 | 3.2 |
| 70 | 2.0 | 260 | 2.5 | 376 | 3.3 |
| 459 | 3.3 | 595B | 4.5 | 310 | 6.6 |
| 317 | 3.4 | 701 | 4.5 | 514C | 6.6 |
| 63 | 3.5 | 414 | 4.6 | 603 | 6.7 |

TABLE 9-continued

Inhibition of CETP Activity by Examples in Reconstituted Buffer Assay.

| Ex. No. | IC$_{50}$ ($\mu$M) | Ex. No. | IC$_{50}$ ($\mu$M) | Ex. No. | IC$_{50}$ ($\mu$M) | Ex. No. | IC$_{50}$ ($\mu$M) | Ex. No. | IC$_{50}$ ($\mu$M) | Ex. No. | IC$_{50}$ ($\mu$M) |
|---|---|---|---|---|---|---|---|---|---|---|---|
| 159 | 3.5 | 454 | 4.6 | 428 | 6.8 | 683 | 20 | 1 | 38 | 3 | 60 |
| 204 | 3.5 | 319 | 4.7 | 602 | 6.8 | 30 | 22 | 94 | 40 | 4 | 60 |
| 609 | 3.5 | 482 | 4.8 | 632 | 6.8 | 455 | 22 | 114 | 40 | 14 | 60 |
| 622 | 3.5 | 553 | 4.8 | 42 | 7.0 | 61 | 23 | 116 | 40 | 16 | 60 |
| 210 | 3.6 | 273 | 4.9 | 52 | 7.0 | 192 | 23 | 142 | 40 | 18 | 60 |
| 501 | 3.6 | 649 | 4.9 | 59 | 7.0 | 587 | 23 | 156 | 40 | 95 | 60 |
| 655 | 3.6 | 84 | 5.0 | 75 | 7.0 | 298 | 24 | 196 | 40 | 102 | 60 |
| 262 | 3.7 | 141 | 5.0 | 127 | 7.0 | 620A | 24.6 | 335 | 40 | 108 | 60 |
| 371 | 3.9 | 321 | 5.0 | 162 | 7.0 | 109 | 25 | 357 | 40 | 110 | 60 |
| 449 | 3.9 | 620 | 5.0 | 172 | 7.0 | 117 | 25 | 363 | 40 | 203 | 60 |
| 36 | 4.0 | 689 | 5.0 | 194 | 7.0 | 125 | 25 | 497 | 42 | 685 | 60 |
| 43 | 4.0 | 60 | 5.5 | 346 | 7.7 | 132 | 25 | 473B | 42 | 111 | 65 |
| 66 | 4.0 | 433 | 5.6 | 617 | 7.9 | 133 | 25 | 528C | 42 | 119 | 70 |
| 87 | 4.0 | 502 | 5.7 | 26 | 8.0 | 306 | 25 | 528 | 43 | 342 | 70 |
| 126 | 4.0 | 585 | 5.8 | 82 | 8.0 | 353 | 70 | 435 | >50 | 263 | >50 |
| 153 | 4.0 | 76 | 6.0 | 122 | 8.0 | 664 | 70 | 435B | >50 | 284 | >50 |
| 201 | 4.0 | 101 | 6.0 | 124 | 8.0 | 28 | 75 | 443 | >50 | 430 | >50 |
| 588 | 4.1 | 134 | 6.0 | 139 | 8.0 | 88 | 75 | 465 | >50 | 434 | >50 |
| 627 | 4.1 | 208 | 6.0 | 147 | 8.0 | 107 | 75 | 467 | >50 | 563 | >50 |
| 594 | 4.2 | 474 | 6.0 | 152 | 8.0 | 355 | 75 | 469 | >50 | 573 | >50 |
| 606 | 4.2 | 239 | 6.1 | 453 | 8.0 | 85 | 80 | 470 | >50 | 575 | >50 |
| 448 | 4.3 | 512 | 6.1 | 290 | 8.1 | 130 | 80 | 476 | >50 | 577 | >50 |
| 640 | 4.3 | 591 | 6.2 | 625 | 8.3 | 143 | 80 | 479 | >50 | 586 | >50 |
| 297 | 4.4 | 576 | 6.4 | 291 | 8.4 | 332 | 80 | 484 | >50 | 632A | >50 |
| 491 | 4.4 | 583 | 6.4 | 90 | 9.0 | 366 | 80 | 487 | >50 | 5 | >100 |
| 209 | 4.5 | 434B | 6.4 | 112 | 9.0 | 635 | 80 | 498 | >50 | 6 | >100 |
| 375 | 4.5 | 270 | 6.5 | 129 | 9.0 | 665 | 80 | 500 | >50 | 7 | >100 |
| 323 | 9.0 | 136 | 12 | 67 | 15 | 97 | 90 | 511 | >50 | 8 | >100 |
| 215 | 9.2 | 158 | 12 | 68 | 15 | 100 | 90 | 530 | >50 | 9 | >100 |
| 456 | 9.2 | 288 | 12 | 98 | 15 | 123 | 90 | 531 | >50 | 10 | >100 |
| 621 | 9.3 | 431 | 12 | 145 | 15 | 165 | 90 | 532 | >50 | 11 | >100 |
| 447 | 9.8 | 462 | 12 | 148 | 15 | 207 | 90 | 533 | >50 | 12 | >100 |
| 25 | 10 | 466 | 12 | 185 | 15 | 2 | 100 | 534 | >50 | 13 | >100 |
| 47 | 10 | 605 | 12 | 186 | 15 | 45 | 100 | 535 | >50 | 15 | >100 |
| 72 | 10 | 611 | 12 | 198 | 15 | 144 | 100 | 536 | >50 | 20 | >100 |
| 78 | 10 | 687 | 12 | 200 | 15 | 333 | 100 | 537 | >50 | 21 | >100 |
| 131 | 10 | 38 | 13 | 308 | 15 | 334 | 100 | 538 | >50 | 24 | >100 |
| 146 | 10 | 451 | 13 | 347 | 15 | 340 | 100 | 539 | >50 | 27 | >100 |
| 163 | 10 | 457 | 13 | 589 | 15 | 343 | 100 | 540 | >50 | 29 | >100 |
| 193 | 10 | 458 | 13 | 661 | 15 | 618 | 100 | 545 | >50 | 32 | >100 |
| 199 | 10 | 461 | 13 | 686 | 15 | 663 | 100 | 546 | >50 | 37 | >100 |
| 236 | 10 | 463 | 13 | 694 | 15 | 672 | 100 | 547 | >50 | 40 | >100 |
| 486 | 10 | 596 | 13 | 695 | 15 | 696 | 100 | 548 | >50 | 46 | >100 |
| 551 | 10 | 211 | 14 | 514D | 15 | 698 | 100 | 549 | >50 | 48 | >100 |
| 572 | 10 | 314 | 14 | 35 | 16 | 49 | >100 | 325 | >100 | 588B | >100 |
| 613 | 10 | 504 | 14 | 692 | 16 | 81 | >100 | 326 | >100 | 614 | >100 |
| 213 | 11 | 590 | 14 | 612A | 16 | 99 | >100 | 327 | >100 | 615 | >100 |
| 301 | 11 | 19 | 15 | 276 | 17 | 121 | >100 | 328 | >100 | 631 | >100 |
| 380 | 11 | 23 | 15 | 295 | 17 | 161 | >100 | 329 | >100 | 634C | >100 |
| 472 | 11 | 39 | 15 | 413 | 17 | 164 | >100 | 330 | >100 | 667 | >100 |
| 477 | 11 | 50 | 15 | 417 | 17 | 169 | >100 | 331 | >100 | 668 | >100 |
| 641 | 11 | 53 | 15 | 1669 | 17 | 170 | >100 | 336 | >100 | 669 | >100 |
| 528B | 11 | 54 | 15 | 62 | 18 | 171 | >100 | 337 | >100 | 670 | >100 |
| 1671 | 11 | 57 | 15 | 197 | 18 | 174 | >100 | 338 | >100 | 671 | >100 |
| 31 | 12 | 58 | 15 | 220 | 18 | 175 | >100 | 339 | >100 | 673 | >100 |
| 41 | 12 | 64 | 15 | 574 | 18 | 176 | >100 | 341 | >100 | 674 | >100 |
| 92 | 12 | 33 | 15 | 616 | 18 | 177 | >100 | 344 | >100 | 675 | >100 |
| 51 | 20 | 106 | 30 | 17 | 45 | 178 | >100 | 349 | >100 | 676 | >100 |
| 55 | 20 | 138 | 30 | 118 | 45 | 179 | >100 | 354 | >100 | 677 | >100 |
| 56 | 20 | 195 | 30 | 345 | 45 | 180 | >100 | 356 | >100 | 678 | >100 |
| 65 | 20 | 520 | 30 | 362 | 45 | 181 | >100 | 358 | >100 | 679 | >100 |
| 69 | 20 | 626 | 30 | 604 | 46 | 182 | >100 | 359 | >100 | 680 | >100 |
| 80 | 20 | 300 | 31 | 529 | 49 | 183 | >100 | 360 | >100 | 681 | >100 |
| 83 | 20 | 217 | 32 | 22 | 50 | 184 | >100 | 361 | >100 | 682 | >100 |
| 86 | 20 | 320 | 32 | 34 | 50 | 187 | >100 | 364 | >100 | 684 | >100 |
| 113 | 20 | 303 | 33 | 93 | 50 | 188 | >100 | 365 | >100 | | |
| 135 | 20 | 103 | 35 | 96 | 50 | 189 | >100 | 367 | >100 | | |
| 137 | 20 | 105 | 35 | 120 | 50 | 190 | >100 | 368 | >100 | | |
| 160 | 20 | 348 | 35 | 350 | 50 | 191 | >100 | 369 | >100 | | |
| 173 | 20 | 352 | 35 | 351 | 50 | 202 | >100 | 370 | >100 | | |
| 313 | 20 | 468 | 35 | 471 | 50 | 205 | >100 | 151 | >100 | | |
| 324 | 20 | 612 | 35 | 662 | 50 | | | | | | |
| 610 | 20 | 702 | 35 | 697 | 55 | | | | | | |

TABLE 9-continued

Inhibition of CETP Activity by Examples in Reconstituted Buffer Assay.

| Ex. No. | IC$_{50}$ ($\mu$M) | Ex. No. | IC$_{50}$ ($\mu$M) | Ex. No. | IC$_{50}$ ($\mu$M) |
|---|---|---|---|---|---|
| 206 | >100 | 154 | >100 | | |
| 219 | >100 | 155 | >100 | | |
| 283 | >100 | 157 | >100 | | |

TABLE 10

Inhibition of CETP Activity by Examples in Human Plasma Assay.

| Ex. No. | IC$_{50}$ ($\mu$M) | Ex. No. | IC$_{50}$ ($\mu$M) | Ex. No. | IC$_{50}$ ($\mu$M) |
|---|---|---|---|---|---|
| 229 | 0.56 | 256 | 7.8 | 554 | 18 |
| 221 | 0.88 | 559 | 8.0 | 266 | 21 |
| 233 | 1.0 | 637 | 8.0 | 645 | 21 |
| 234 | 1.0 | 245 | 8.4 | 269 | 22 |
| 660 | 1.1 | 489 | 8.8 | 287 | 22 |
| 630 | 1.8 | 450A | 9.0 | 280 | 23 |
| 249 | 2.3 | 265 | 9.6 | 216 | 24 |
| 402 | 2.9 | 240 | 9.7 | 377 | 24 |
| 242 | 3.1 | 248 | 10 | 390 | 24 |
| 399 | 3.4 | 275 | 10 | 440 | 24 |
| 232 | 3.4 | 395 | 10 | 657 | 24 |
| 629 | 3.4 | 396 | 10 | 391 | 25 |
| 244 | 3.8 | 397 | 10 | 251 | 26 |
| 252 | 3.9 | 281 | 11 | 253 | 27 |
| 634 | 4.1 | 560 | 11 | 267 | 27 |
| 401 | 4.2 | 638 | 11 | 385 | 29 |
| 488 | 4.3 | 241 | 12 | 438 | 29 |
| 429 | 4.4 | 282 | 12 | 166 | 30 |
| 619 | 4.9 | 373 | 12 | 294 | 30 |
| 393 | 5.0 | 378 | 12 | 550 | 30 |
| 639 | 5.0 | 654 | 12 | 650 | 30 |
| 258 | 5.2 | 246 | 13 | 658 | 30 |
| 214 | 5.7 | 278 | 13 | 218 | 31 |
| 628 | 5.7 | 439 | 13 | 250 | 31 |
| 372 | 5.7 | 647 | 13 | 243 | 34 |
| 405 | 6.2 | 436 | 14 | 271 | 34 |
| 400 | 6.3 | 279 | 15 | 499 | 34 |
| 277 | 6.5 | 274 | 16 | 557 | 34 |
| 656 | 6.9 | 473 | 16 | 128 | 35 |
| 379 | 7.7 | 247 | 17 | 71 | 36 |
| 268 | 37 | 42 | 80 | 299 | >100 |
| 475 | 37 | 140 | 80 | 302 | >100 |
| 292 | 38 | 150 | 80 | 309 | >100 |
| 558 | 38 | 307 | 81 | 311 | >100 |
| 653 | 38 | 601 | 83 | 315 | >100 |
| 374 | 39 | 296 | 86 | 316 | >100 |
| 77 | 40 | 59 | 100 | 317 | >100 |
| 293 | 42 | 73 | 100 | 321 | >100 |
| 595 | 42 | 43 | 110 | 322 | >100 |
| 126 | 45 | 201 | 110 | 346 | >100 |
| 74 | 48 | 60 | 120 | 600 | >100 |
| 655 | 48 | 63 | 120 | 649 | >100 |
| 556 | 49 | 66 | 120 | 686 | >100 |
| 593 | 49 | 75 | 200 | 688 | >100 |
| 642 | 50 | 389 | >50 | 691 | >100 |
| 592 | 52 | 447 | >50 | 220B | >100 |
| 699 | 55 | 104 | >100 | 595B | >100 |
| 79 | 60 | 115 | >100 | 35 | >200 |
| 87 | 60 | 127 | >100 | 36 | >200 |
| 89 | 60 | 131 | >100 | 76 | >200 |
| 655B | 63 | 141 | >100 | 661 | >200 |
| 70 | 65 | 149 | >100 | 664 | >200 |
| 312 | 65 | 168 | >100 | 33 | 500 |
| 659 | 65 | 204 | >100 | | |
| 84 | 70 | 208 | >100 | | |
| 91 | 70 | 209 | >100 | | |
| 690 | 75 | 210 | >100 | | |
| 304 | 76 | 219 | >100 | | |

TABLE 10-continued

Inhibition of CETP Activity by Examples in Human Plasma Assay.

| Ex. No. | IC$_{50}$ ($\mu$M) | Ex. No. | IC$_{50}$ ($\mu$M) | Ex. No. | IC$_{50}$ ($\mu$M) |
|---|---|---|---|---|---|
| 305 | 76 | 273 | >100 | | |
| 254 | 77 | 297 | >100 | | |

What we claim is:

1. A compound of Formula I:

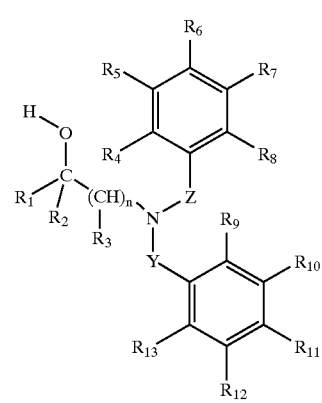

(I)

or a pharmaceutically acceptable salt thereof, wherein;

n is 1 or 2;

$R_1$ is haloalkyl or haloalkoxyalkyl;

$R_2$ is selected from the group consisting of hydrogen, hydroxyalkyl, aryl, aralkyl, alkyl, alkenyl, alkynyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, haloalkyl, perhaloaryl, perhaloaralkyl, perhaloaryloxyalkyl, heteroaryl, and heteroaralkyl;

$R_3$ is selected from the group consisting of hydrogen, alkyl, alkenyl, alkoxyalkyl, aryl, aralkyl, heteroaryl, heteroaralkyl, alkenyloxyalkyl, haloalkyl, haloalkenyl, haloalkoxy, haloalkoxyalkyl, cycloalkyl, cycloalkylalkyl, cycloalkenyl, and cycloalkenylalkyl;

Y is selected from the group consisting of a bond, $C(R_{14})_2$, O, C(O), and $N(R_{14})$ with the proviso that Y is O, C(O), or $N(R_{14})$ when Z is a bond or $C(R_{15})_2$;

$R_{14}$ and $R_{15}$ are independently hydrogen or alkyl;

Z is selected from the group consisting of a bond, $C(R_{15})_2$, O, C(O), and $N(R_{15})$ with the proviso that Z is O, C(O), or $N(R_{15})$ when Y is a bond or $C(R_{14})_2$;

$R_4$, $R_8$, $R_9$, and $R_{13}$ are independently selected from the group consisting of hydrogen, halo, halo alkyl, and alkyl;

$R_5$, $R_6$, $R_7$, $R_{10}$, $R_{11}$, and $R_{12}$ are independently selected from the group consisting of hydrogen, perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, alkylamino, alkylthio, arylamino, aralkylamino, arylthio, arylthioalkyl, alkylsulfonyl, alkylsulfonamido, monoarylamidosulfonyl, arylsulfonyl, heteroarylthio, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

with the proviso that at least one of $R_4$, $R_5$, $R_6$, $R_7$, and $R_8$ is not hydrogen or with the proviso that at least one of $R_9$, $R_{10}$, $R_{11}$, $R_{12}$, and $R_{13}$ is not hydrogen.

2. Compound of claim 1 or a pharmaceutically acceptable salt thereof, wherein at least one of $R_4$, $R_5$, $R_6$, $R_7$, and $R_8$ is not hydrogen and at least one of $R_9$, $R_{10}$, $R_{11}$, $R_{12}$, and $R_{13}$ is not hydrogen.

3. Compound of claim 2 or a pharmaceutically acceptable salt thereof, wherein;

n is 1 or 2;

$R_1$ is haloalkoxyalkyl or haloalkyl with the proviso that said haloalkyl has two or more halo substituents;

$R_2$ is hydrogen;

$R_3$ is hydrogen;

Y is selected from the group consisting of a NH, O, and C(O);

Z is a bond;

$R_4$, $R_8$, $R_9$, and $R_{13}$ are independently hydrogen or halo;

$R_5$, $R_6$, $R_7$, $R_{10}$, $R_{11}$, and $R_{12}$ are independently selected from the group consisting of hydrogen, perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, heteroaralkoxy, heterocyclyloxy, aralkylaryl, aralkyl, haloalkylthio, alkoxy, cycloalkoxy, cycloalkylalkoxy, alkylamino, alkylthio, arylamino, arylthio, arylsulfonyl, heteroarylthio, heteroarylsulfonyl, aroyl, alkyl, cycloalkyl, cycloalkylalkanoyl, halo, haloalkyl, haloalkoxy, hydroxyhaloalkyl, aryl, aryloxy, aralkoxy, saturated heterocyclyl, heteroaryl, heteroaryloxyalkyl, and heteroaryloxy;

with the proviso that at least one of $R_4$, $R_5$, $R_6$, $R_7$, and $R_8$ is not hydrogen and with the further proviso that at least one of $R_9$, $R_{10}$, $R_{11}$, $R_{12}$, and $R_{13}$ is not hydrogen.

4. Compound of claim 3 or a pharmaceutically acceptable salt thereof, wherein;

n is 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is hydrogen;

$R_3$ is hydrogen;

Y is NH or O;

Z is a bond;

$R_4$, $R_8$, $R_9$, and $R_{13}$ are independently hydrogen or fluoro;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, difluoromethoxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrogen, pentafluoroethyl, 1,1,2,2-tetrafluoroethoxy, trifluoromethyl, and trifluoromethoxy;

$R_7$ and $R_{12}$ are independently selected from the group consisting of hydrogen, fluoro, and trifluoromethyl.

5. Compound of claim 4 or a pharmaceutically acceptable salt thereof, wherein;

n is 1;

$R_1$ is selected from the group consisting of trifluoromethyl, difluoromethyl, chlorodifluoromethyl, and pentafluoroethyl;

$R_2$ is hydrogen;

$R_3$ is hydrogen;

Y is O;

Z is a bond;

$R_4$, $R_8$, $R_9$, and $R_{13}$ are independently hydrogen or fluoro;

$R_5$ and $R_{10}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 4-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 4-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrogen, pentafluoroethyl, 1,1,2,2-tetrafluoroethoxy, and trifluoromethyl;

$R_7$ and $R_{12}$ are independently selected from the group consisting of hydrogen, fluoro, and trifluoromethyl.

6. Compound of claim 3 of Formula II:

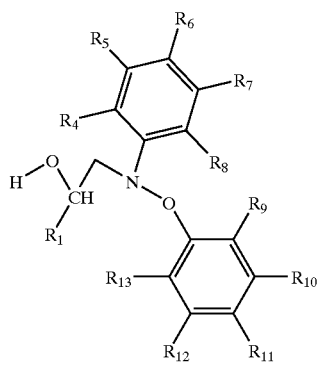

(II)

or a pharmaceutically acceptable salt thereof, wherein;

$R_1$ is haloalkyl;

$R_4$, $R_8$, $R_9$, and $R_{13}$ are independently hydrogen or halo;

$R_5$, $R_6$, $R_7$, $R_{10}$, $R_{11}$, and $R_{12}$ are independently selected from the group consisting of hydrogen, perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, heteroaralkoxy, aralkyl, haloalkylthio, alkoxy, cycloalkoxy, cycloalkylalkoxy, alkylthio, arylamino, arylthio, arylsulfonyl, aroyl, alkyl, cycloalkyl, cycloalkylalkanoyl, halo, haloalkyl, haloalkoxy, hydroxyhaloalkyl, aryl, aryloxy, aralkoxy, heteroaryl, heteroaryloxyalkyl, and heteroaryloxy;

with the proviso that at least one of $R_4$, $R_5$, $R_6$, $R_7$, and $R_8$ is not hydrogen and with the further proviso that at least one of $R_9$, $R_{10}$, $R_{11}$, $R_{12}$, and $R_{13}$ is not hydrogen.

7. Compound of claim 6 or a pharmaceutically acceptable salt thereof, wherein;

$R_1$ is trifluoromethyl;

$R_4$, $R_8$, $R_9$, and $R_{13}$ are independently hydrogen or fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$, $R_7$, $R_{11}$, and $R_{12}$ are independently hydrogen or fluoro.

8. Compound of claim 7 or a pharmaceutically acceptable salt thereof, wherein;

$R_1$ is trifluoromethyl;

$R_4$, $R_8$, $R_9$, and $R_{13}$ are independently hydrogen or fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of 1,1,2,2-tetrafluoroethoxy, pentafluoroethyl, and trifluoromethyl;

$R_6$, $R_7$, $R_{11}$, and $R_{12}$ are independently hydrogen or fluoro.

9. Compound of claim 1 or a pharmaceutically acceptable salt thereof, wherein said compound is a compound of Formula III:

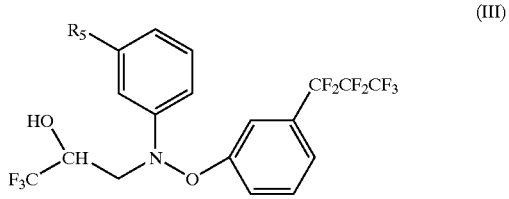

(III)

wherein $R_5$ selected to form a compound selected from the group consisting of;

$R_5$ is 3-isopropylphenoxy;

$R_5$ is 2,3-dichlorophenoxy;

$R_5$ is 3-trifluoromethoxyphenoxy;

$R_5$ is 4-fluorophenoxy;

$R_5$ is 4-methylphenoxy;

$R_5$ is 2-fluoro-5-bromophenoxy;

$R_5$ is 4-chloro-3-ethylphenoxy;

$R_5$ is 3-ethylphenoxy;

$R_5$ is 3,5-dimethylphenoxy;

$R_5$ is 3-t-butylphenoxy;

$R_5$ is 4-fluoro-3-methylphenoxy;

$R_5$ is 3,4-dichlorophenoxy;

$R_5$ is 5,6,7,8-tetrahydronaphthyl-2-oxyphenoxy;

$R_5$ is 3-(1,1,2,2-tetrafluoroethoxy)phenoxy;

$R_5$ is 3-difluoromethoxyphenoxy;

$R_5$ is 3-dimethylaminophenoxy;

$R_5$ is 3-cyclopropylphenoxy;

$R_5$ is 3-(2-furyl)phenoxy;

$R_5$ is 3-pentafluoroethylphenoxy;

$R_5$ is 4-aminophenoxy;

$R_5$ is 3,4,5-trimethylphenoxy;

$R_5$ is 4-propoxyphenoxy;

$R_5$ is 2-nitrophenoxy;

$R_5$ is 3-trifluoromethoxybenzyloxy;

$R_5$ is 3-trifluoromethylbenzyloxy;

$R_5$ is 3,5-difluorobenzyloxy;

$R_5$ is cyclohexylmethyleneoxy;

$R_5$ is benzyloxy;

$R_5$ is 3,5-ditrifluoromethylbenzyloxy;

$R_5$ is 4-trifluoromethoxybenzyloxy;
$R_5$ is 4-ethylbenzyloxy;
$R_5$ is isopropoxy;
$R_5$ is 3-trifluoromethylbenzyl;
$R_5$ is isopropylthio;
$R_5$ is cyclopentoxy;
$R_5$ is 3-chloro-5-pyridinyloxy;
$R_5$ is 3-trifluoromethylthiobenzyloxy;
$R_5$ is 3,4-dimethylbenzyloxy;
$R_5$ is 2-fluoro-3-trifluoromethylbenzyloxy;
$R_5$ is 3-fluoro-5-trifluoromethylbenzyloxy;
$R_5$ is 4-isopropylbenzyloxy;
$R_5$ is 1-phenylethoxy;
$R_5$ is 4-fluoro-3-methylbenzoyl;
$R_5$ is 3-trifluoromethylphenyl;
$R_5$ is 4-methoxyphenylamino; and
$R_5$ is 4-nitrophenylthio.

10. A pharmaceutical composition comprising a therapeutically effective amount of a compound or a pharmaceutically acceptable salt thereof, together with a pharmaceutically acceptable carrier, said compound being of Formula I:

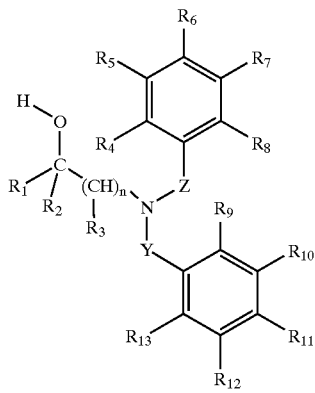

wherein;
n is 1 or 2;
$R_1$ is haloalkyl or haloalkoxyalkyl;
$R_2$ is selected from the group consisting of hydrogen, hydroxyalkyl, aryl, aralkyl, alkyl, alkenyl, alkynyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, haloalkyl, perhaloaryl, perhaloaralkyl, perhaloaryloxyalkyl, heteroaryl, and heteroaralkyl;
$R_3$ is selected from the group consisting of hydrogen, alkyl, alkenyl, alkoxyalkyl, aryl, aralkyl, heteroaryl, heteroaralkyl, alkenyloxyalkyl, haloalkyl, haloalkenyl, haloalkoxy, haloalkoxyalkyl, cycloalkyl, cycloalkylalkyl, cycloalkenyl, and cycloalkenylalkyl;
Y is selected from the group consisting of a bond, $C(R_{14})_2$, O, C(O), and $N(R_{14})$ with the proviso that Y is O, C(O), or $N(R_{14})$ when Z is a bond or $C(R_{15})_2$;
$R_{14}$ and $R_{15}$ are independently hydrogen or alkyl;
Z is selected from the group consisting of a bond, $C(R_{15})_2$, O, C(O), and $N(R_{15})$ with the proviso that Z is O, C(O), or $N(R_{15})$ when Y is a bond or $C(R_{14})_2$;
$R_4$, $R_8$, $R_9$, and $R_{13}$ are independently selected from the group consisting of hydrogen, halo, haloalkyl, and alkyl;

$R_5$, $R_6$, $R_7$, $R_{10}$, $R_{11}$, and $R_{12}$ are independently selected from the group consisting of hydrogen, perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, alkylamino, alkylthio, arylamino, aralkylamino, arylthio, arylthioalkyl, alkylsulfonyl, alkylsulfonamido, monoarylamidosulfonyl, arylsulfonyl, heteroarylthio, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

with the proviso that at least one of $R_4$, $R_5$, $R_6$, $R_7$, and $R_8$ is not hydrogen or with the proviso that at least one of $R_9$, $R_{10}$, $R_{11}$, $R_{12}$, and $R_{13}$ is not hydrogen.

11. The pharmaceutical composition of claim 10, wherein said compound is of Formula I, wherein at least one of $R_4$, $R_5$, $R_6$, $R_7$, and $R_8$ is not hydrogen and at least one of $R_9$, $R_{10}$, $R_{11}$, $R_{12}$, and $R_{13}$ is not hydrogen.

12. The pharmaceutical composition of claim 11, wherein said compound is of Formula I, wherein;
n is 1 or 2;
$R_1$ is haloalkyl or haloalkoxyalkyl;
$R_2$ is hydrogen;
$R_3$ is hydrogen;
Y is selected from the group consisting of a NH, O, and C(O);
Z is a bond;
$R_4$, $R_8$, $R_9$, and $R_{13}$ are independently hydrogen or halo;
$R_5$, $R_6$, $R_7$, $R_{10}$, $R_{11}$, and $R_{12}$ are independently selected from the group consisting of hydrogen, perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, heteroaralkoxy, heterocyclyloxy, aralkylaryl, aralkyl, haloalkylthio, alkoxy, cycloalkoxy, cycloalkylalkoxy, alkylamino, alkylthio, arylamino, arylthio, arylsulfonyl, heteroarylthio, heteroarylsulfonyl, aroyl, alkyl, cycloalkyl, cycloalkylalkanoyl, halo, haloalkyl, haloalkoxy, hydroxyhaloalkyl, aryl, aryloxy, aralkoxy, saturated heterocyclyl, heteroaryl, heteroaryloxyalkyl, and heteroaryloxy;

with the proviso that at least one of $R_4$, $R_5$, $R_6$, $R_7$, and $R_8$ is not hydrogen and with the further proviso that at least one of $R_9$, $R_{10}$, $R_{11}$, $R_{12}$, and $R_{13}$ is not hydrogen.

13. The pharmaceutical composition of claim 12, wherein said compound is of Formula I, wherein;

n is 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is hydrogen;

$R_3$ is hydrogen;

Y is NH or O;

Z is a bond;

$R_4$, $R_8$, $R_9$, and $R_{13}$ are independently hydrogen or fluoro;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, difluoromethoxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrogen, pentafluoroethyl, 1,1,2,2-tetrafluoroethoxy, trifluoromethyl, and trifluoromethoxy;

$R_7$ and $R_{12}$ are independently selected from the group consisting of hydrogen, fluoro, and trifluoromethyl.

14. The pharmaceutical composition of claim 13, wherein said compound is of Formula I, wherein;

n is 1;

$R_1$ is selected from the group consisting of trifluoromethyl, difluoromethyl, chlorodifluoromethyl, and pentafluoroethyl;

$R_2$ is hydrogen;

$R_3$ is hydrogen;

Y is O;

Z is a bond;

$R_4$, $R_8$, $R_9$, and $R_{13}$ are independently hydrogen or fluoro;

$R_5$ and $R_{10}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3- ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 4-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 4-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are in dependently selected from the group consisting of chloro, fluoro, hydrogen, pentafluoroethyl, 1,1,2,2-tetrafluoroethoxy, and trifluoromethyl;

$R_7$ and $R_{12}$ are independently selected from the group consisting of hydrogen, fluoro, and trifluoromethyl.

15. The pharmaceutical composition of claim 12, wherein said compound is of Formula II:

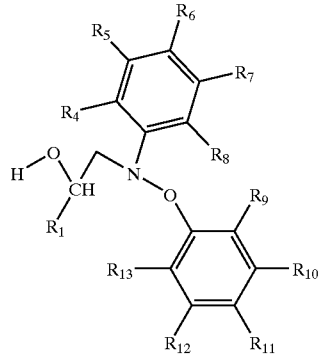

(II)

wherein;

$R_1$ is haloalkyl;

$R_4$, $R_8$, $R_9$, and $R_{13}$ are independently hydrogen or halo;

$R_5$, $R_6$, $R_7$, $R_{10}$, $R_{11}$, and $R_{12}$ are independently selected from the group consisting of hydrogen, perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, heteroaralkoxy, aralkyl, haloalkylthio, alkoxy, cycloalkoxy, cycloalkylalkoxy, alkylthio, arylamino, arylthio, arylsulfonyl, aroyl, alkyl, cycloalkyl, cycloalkylalkanoyl, halo, haloalkyl, haloalkoxy, hydroxyhaloalkyl, aryl, aryloxy, aralkoxy, heteroaryl, heteroaryloxyalkyl, and heteroaryloxy;

with the proviso that at least one of $R_4$, $R_5$, $R_6$, $R_7$, and $R_8$ is not hydrogen and with the further proviso that at least one of $R_9$, $R_{10}$, $R_{11}$, $R_{12}$, and $R_{13}$ is not hydrogen.

16. The pharmaceutical composition of claim 15, wherein said compound is of Formula II, wherein;

$R_1$ is trifluoromethyl;

$R_4$, $R_8$, $R_9$, and $R_{13}$ are independently hydrogen or fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$, $R_7$, $R_{11}$, and $R_{12}$ are independently hydrogen or fluoro.

17. The pharmaceutical composition of claim 16, wherein said compound is of Formula II, wherein;

$R_1$ is trifluoromethyl;

$R_4$, $R_8$, $R_9$, and $R_{13}$ are independently hydrogen or fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of 1,1,2,2-tetrafluoroethoxy, pentafluoroethyl, and trifluoromethyl;

$R_6$, $R_7$, $R_{11}$, and $R_{12}$ are independently hydrogen or fluoro.

18. The pharmaceutical composition of claim 10, wherein said compound is a compound of Formula III:

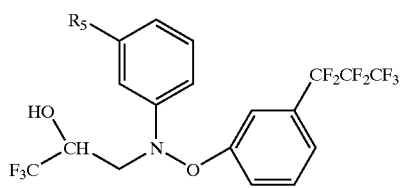

(III)

wherein $R_5$ selected to form a compound selected from the group consisting of;

$R_5$ is 3-isopropylphenoxy;
$R_5$ is 2,3-dichlorophenoxy;
$R_5$ is 3-trifluoromethoxyphenoxy;
$R_5$ is 4-fluorophenoxy;
$R_5$ is 4-methylphenoxy;
$R_5$ is 2-fluoro-5-bromophenoxy;
$R_5$ is 4-chloro-3-ethylphenoxy;
$R_5$ is 3-ethylphenoxy;
$R_5$ is 3,5-dimethylphenoxy;
$R_5$ is 3-t-butylphenoxy;
$R_5$ is 4-fluoro-3-methylphenoxy;
$R_5$ is 3,4-dichlorophenoxy;
$R_5$ is 5,6,7,8-tetrahydronaphthyl-2-oxyphenoxy
$R_5$ is 3-(1,1,2,2-tetrafluoroethoxy)phenoxy;
$R_5$ is 3-difluoromethoxyphenoxy;
$R_5$ is 3-dimethylaminophenoxy;
$R_5$ is 3-cyclopropylphenoxy;
$R_5$ is 3-(2-furyl)phenoxy;
$R_5$ is 3-pentafluoroethylphenoxy;
$R_5$ is 4-aminophenoxy;
$R_5$ is 3,4,5-trimethylphenoxy;
$R_5$ is 4-propoxyphenoxy;
$R_5$ is 2-nitrophenoxy;
$R_5$ is 3-trifluoromethoxybenzyloxy
$R_5$ is 3-trifluoromethylbenzyloxy;
$R_5$ is 3,5-difluorobenzyloxy;
$R_5$ is cyclohexylmethyleneoxy;
$R_5$ is benzyloxy;
$R_5$ is 3,5-ditrifluoromethylbenzyloxy
$R_5$ is 4-trifluoromethoxybenzyloxy;
$R_5$ is 4-ethylbenzyloxy;
$R_5$ is isopropoxy;
$R_5$ is 3-trifluoromethylbenzyl;
$R_5$ is isopropylthio;
$R_5$ is cyclopentoxy;
$R_5$ is 3-chloro-5-pyridinyloxy;
$R_5$ is 3-trifluoromethylthiobenzyloxy;
$R_5$ is 3,4-dimethylbenzyloxy;
$R_5$ is 2-fluoro-3-trifluoromethylbenzyloxy
$R_5$ is 3-fluoro-5-trifluoromethylbenzyloxy;
$R_5$ is 4-isopropylbenzyloxy;
$R_5$ is 1-phenylethoxy;
$R_5$ is 4-fluoro-3-methylbenzoyl;
$R_5$ is 3-trifluoromethylphenyl;
$R_5$ is 4-methoxyphenylamino; and
$R_5$ is 4-nitrophenylthio.

* * * * *